United States Patent
Bozung et al.

(10) Patent No.: US 12,232,744 B2
(45) Date of Patent: Feb. 25, 2025

(54) ROBOTIC HAND-HELD SURGICAL INSTRUMENT SYSTEMS AND METHODS

(71) Applicant: MAKO Surgical Corp., Weston, FL (US)

(72) Inventors: Timothy J. Bozung, Scotts, MI (US); Stephen J. Reasoner, Kalamazoo, MI (US); Jeffrey Timmer, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 631 days.

(21) Appl. No.: 17/627,208

(22) PCT Filed: Jul. 15, 2020

(86) PCT No.: PCT/US2020/042128
§ 371 (c)(1),
(2) Date: Jan. 14, 2022

(87) PCT Pub. No.: WO2021/011646
PCT Pub. Date: Jan. 21, 2021

(65) Prior Publication Data
US 2022/0273396 A1    Sep. 1, 2022

Related U.S. Application Data

(60) Provisional application No. 63/015,184, filed on Apr. 24, 2020, provisional application No. 62/874,107, filed on Jul. 15, 2019.

(51) Int. Cl.
*A61B 17/14* (2006.01)
*A61B 34/20* (2016.01)
(Continued)

(52) U.S. Cl.
CPC ............ *A61B 17/142* (2016.11); *A61B 34/20* (2016.02); *A61B 34/30* (2016.02); *A61B 90/57* (2016.02);
(Continued)

(58) Field of Classification Search
CPC ........................... A61B 17/1622; A61B 17/14
See application file for complete search history.

(56) References Cited

U.S. PATENT DOCUMENTS

| 3,776,315 A | 12/1973 | Gill et al. |
| 4,150,326 A | 4/1979 | Engelberger et al. |

(Continued)

FOREIGN PATENT DOCUMENTS

| CN | 105636541 A | 6/2016 |
| DE | 20205006 U1 | 7/2002 |

(Continued)

OTHER PUBLICATIONS

English language abstract for JPH 09-29681 A extracted from espacenet.com database on Mar. 8, 2024, 2 pages.
(Continued)

*Primary Examiner* — Andrew Yang
(74) *Attorney, Agent, or Firm* — Howard & Howard Attorneys PLLC

(57) ABSTRACT

A system is provided comprising a robotic instrument for use with a tool. In some versions, the robotic instrument comprises a hand-held portion to be held by a user and a tool support movably coupled to the hand-held portion to support the tool. A plurality of actuators operatively interconnect the tool support and the hand-held portion to move the tool support in three degrees of freedom relative to the hand-held portion. An optional constraint assembly may operatively interconnect the tool support and the hand-held portion to constrain movement of the tool support relative to the
(Continued)

hand-held portion in three degrees of freedom. A guidance array assists users in positioning the tool and/or portions of the instrument.

23 Claims, 62 Drawing Sheets

(51) Int. Cl.
*A61B 34/30* (2016.01)
*A61B 90/57* (2016.01)
*A61B 17/00* (2006.01)

(52) U.S. Cl.
CPC .............. *A61B 2017/00398* (2013.01); *A61B 2017/0046* (2013.01)

(56) References Cited

U.S. PATENT DOCUMENTS

| | | |
|---|---|---|
| 4,442,493 A | 4/1984 | Wakai et al. |
| 4,667,371 A | 5/1987 | Vogt |
| 4,711,238 A | 12/1987 | Cunningham |
| 4,736,742 A | 4/1988 | Alexson et al. |
| 4,791,583 A | 12/1988 | Colburn |
| 4,834,092 A | 5/1989 | Alexson et al. |
| 4,979,949 A | 12/1990 | Matsen, III et al. |
| 4,985,856 A | 1/1991 | Kaufman et al. |
| 5,017,139 A | 5/1991 | Mushabac |
| 5,078,140 A | 1/1992 | Kwoh |
| 5,086,401 A | 2/1992 | Glassman et al. |
| 5,091,861 A | 2/1992 | Geller et al. |
| 5,189,626 A | 2/1993 | Colburn |
| 5,279,309 A | 1/1994 | Taylor et al. |
| 5,281,136 A | 1/1994 | Giannella et al. |
| 5,343,391 A | 8/1994 | Mushabac |
| 5,381,518 A | 1/1995 | Drebin et al. |
| 5,399,951 A | 3/1995 | Lavallee et al. |
| 5,405,344 A | 4/1995 | Williamson et al. |
| 5,408,409 A | 4/1995 | Glassman et al. |
| 5,454,827 A | 10/1995 | Aust et al. |
| 5,458,206 A | 10/1995 | Bourner et al. |
| 5,464,144 A | 11/1995 | Guy et al. |
| 5,497,934 A | 3/1996 | Brady et al. |
| 5,499,984 A | 3/1996 | Steiner et al. |
| 5,503,320 A | 4/1996 | Webster et al. |
| 5,520,678 A | 5/1996 | Heckele et al. |
| 5,546,942 A | 8/1996 | Zhang |
| 5,558,619 A | 9/1996 | Kami et al. |
| 5,562,448 A | 10/1996 | Mushabac |
| 5,569,578 A | 10/1996 | Mushabac |
| 5,591,170 A | 1/1997 | Spievack et al. |
| 5,618,294 A | 4/1997 | Aust et al. |
| 5,628,748 A | 5/1997 | Vicari |
| 5,630,431 A | 5/1997 | Taylor |
| 5,682,886 A | 11/1997 | Delp et al. |
| 5,704,791 A | 1/1998 | Gillio |
| 5,711,299 A | 1/1998 | Manwaring et al. |
| 5,740,699 A | 4/1998 | Ballantyne et al. |
| 5,748,767 A | 5/1998 | Raab |
| 5,769,092 A | 6/1998 | Williamson, Jr. |
| 5,776,136 A | 7/1998 | Sahay et al. |
| 5,784,542 A | 7/1998 | Ohm et al. |
| 5,823,066 A | 10/1998 | Huitema et al. |
| 5,824,085 A | 10/1998 | Sahay et al. |
| 5,851,208 A | 12/1998 | Trott |
| 5,865,063 A | 2/1999 | Sheldon |
| 5,880,976 A | 3/1999 | DiGioia III et al. |
| 5,882,206 A | 3/1999 | Gillio |
| 5,899,914 A | 5/1999 | Zirps et al. |
| 5,906,591 A | 5/1999 | Dario et al. |
| 5,921,992 A | 7/1999 | Costales et al. |
| 5,938,678 A | 8/1999 | Zirps et al. |
| 5,950,629 A | 9/1999 | Taylor et al. |
| 5,976,121 A | 11/1999 | Matern et al. |
| 5,997,528 A | 12/1999 | Bisch et al. |
| 6,021,343 A | 2/2000 | Foley et al. |
| 6,117,126 A | 9/2000 | Appelbaum et al. |
| 6,126,633 A | 10/2000 | Kaji et al. |
| 6,126,667 A | 10/2000 | Barry et al. |
| 6,157,873 A | 12/2000 | DeCamp et al. |
| 6,167,145 A | 12/2000 | Foley et al. |
| 6,200,321 B1 | 3/2001 | Orbay et al. |
| 6,228,089 B1 | 5/2001 | Wahrburg |
| 6,236,875 B1 | 5/2001 | Bucholz et al. |
| 6,238,384 B1 | 5/2001 | Peer |
| 6,238,875 B1 | 5/2001 | Altieri |
| 6,282,437 B1 | 8/2001 | Franck et al. |
| 6,285,902 B1 | 9/2001 | Kienzle, III et al. |
| 6,311,100 B1 | 10/2001 | Sarma et al. |
| 6,322,567 B1 | 11/2001 | Mittelstadt et al. |
| 6,330,837 B1 | 12/2001 | Charles et al. |
| 6,351,659 B1 | 2/2002 | Vilsmeier |
| 6,368,330 B1 | 4/2002 | Hynes et al. |
| 6,377,839 B1 | 4/2002 | Kalfas et al. |
| 6,408,253 B2 | 6/2002 | Rosenberg et al. |
| 6,413,264 B1 | 7/2002 | Jensen et al. |
| 6,414,711 B2 | 7/2002 | Arimatsu et al. |
| 6,418,811 B1 | 7/2002 | Rosheim |
| 6,421,048 B1 | 7/2002 | Shih et al. |
| 6,423,077 B2 | 7/2002 | Carol et al. |
| 6,432,112 B2 | 8/2002 | Brock et al. |
| 6,436,107 B1 | 8/2002 | Wang et al. |
| 6,450,978 B1 | 9/2002 | Brosseau et al. |
| 6,461,372 B1 | 10/2002 | Jensen et al. |
| 6,466,815 B1 | 10/2002 | Saito et al. |
| 6,494,882 B1 | 12/2002 | Lebouitz et al. |
| 6,514,082 B2 | 2/2003 | Kaufman et al. |
| 6,522,906 B1 | 2/2003 | Salisbury, Jr. et al. |
| 6,533,737 B1 | 3/2003 | Brosseau et al. |
| 6,535,756 B1 | 3/2003 | Simon et al. |
| 6,542,770 B2 | 4/2003 | Zylka et al. |
| 6,554,837 B1 | 4/2003 | Hauri et al. |
| 6,556,199 B1 | 4/2003 | Fang et al. |
| 6,611,141 B1 | 8/2003 | Schulz et al. |
| 6,620,174 B2 | 9/2003 | Jensen et al. |
| 6,665,554 B1 | 12/2003 | Charles et al. |
| 6,676,669 B2 | 1/2004 | Charles et al. |
| 6,676,706 B1 | 1/2004 | Mears et al. |
| 6,678,545 B2 | 1/2004 | Bucholz |
| 6,687,531 B1 | 2/2004 | Ferre et al. |
| 6,697,664 B2 | 2/2004 | Kienzle, III et al. |
| 6,699,177 B1 | 3/2004 | Wang et al. |
| 6,704,694 B1 | 3/2004 | Basdogan et al. |
| 6,711,432 B1 | 3/2004 | Krause et al. |
| 6,720,966 B2 | 4/2004 | Barth et al. |
| 6,723,106 B1 | 4/2004 | Charles et al. |
| 6,725,080 B2 | 4/2004 | Melkent et al. |
| 6,728,599 B2 | 4/2004 | Wang et al. |
| 6,738,656 B1 | 5/2004 | Ferre et al. |
| 6,757,557 B1 | 6/2004 | Bladen et al. |
| 6,757,582 B2 | 6/2004 | Brisson et al. |
| 6,778,867 B1 | 8/2004 | Ziegler et al. |
| 6,782,287 B2 | 8/2004 | Grzeszczuk et al. |
| 6,785,572 B2 | 8/2004 | Yanof et al. |
| 6,785,593 B2 | 8/2004 | Wang et al. |
| 6,788,999 B2 | 9/2004 | Green |
| 6,793,653 B2 | 9/2004 | Sanchez et al. |
| 6,804,547 B2 | 10/2004 | Pelzer et al. |
| 6,827,723 B2 | 12/2004 | Carson |
| 6,831,640 B2 | 12/2004 | Shih et al. |
| 6,837,892 B2 | 1/2005 | Shoham |
| 6,850,794 B2 | 2/2005 | Shahidi |
| 6,856,827 B2 | 2/2005 | Seeley et al. |
| 6,857,943 B2 | 2/2005 | Kapgan |
| 6,859,661 B2 | 2/2005 | Tuke |
| 6,871,117 B2 | 3/2005 | Wang et al. |
| 6,887,245 B2 | 5/2005 | Kienzle, III et al. |
| 6,892,112 B2 | 5/2005 | Wang et al. |
| 6,901,310 B2 | 5/2005 | Kobbelt et al. |
| 6,917,827 B2 | 7/2005 | Kienzle, III |
| 6,920,347 B2 | 7/2005 | Simon et al. |
| 6,923,817 B2 | 8/2005 | Carson et al. |
| 6,929,481 B1 | 8/2005 | Alexander et al. |
| 6,934,575 B2 | 8/2005 | Ferre et al. |

(56) References Cited

U.S. PATENT DOCUMENTS

| | | |
|---|---|---|
| 6,945,149 B2 | 9/2005 | Gass et al. |
| 6,947,786 B2 | 9/2005 | Simon et al. |
| 6,963,792 B1 | 11/2005 | Green |
| 6,973,202 B2 | 12/2005 | Mostafavi |
| 6,978,166 B2 | 12/2005 | Foley et al. |
| 6,991,656 B2 | 1/2006 | Mears |
| 6,999,852 B2 | 2/2006 | Green |
| 7,006,895 B2 | 2/2006 | Green |
| 7,008,430 B2 | 3/2006 | Dong et al. |
| 7,022,123 B2 | 4/2006 | Heldreth |
| 7,035,716 B2 | 4/2006 | Harris et al. |
| RE39,133 E | 6/2006 | Clayton et al. |
| 7,055,789 B2 | 6/2006 | Libbey et al. |
| 7,056,123 B2 | 6/2006 | Gregorio et al. |
| 7,072,707 B2 | 7/2006 | Galloway, Jr. et al. |
| 7,090,637 B2 | 8/2006 | Danitz et al. |
| 7,090,677 B2 | 8/2006 | Fallin et al. |
| 7,090,683 B2 | 8/2006 | Brock et al. |
| 7,092,787 B2 | 8/2006 | Kuhnert |
| 7,097,640 B2 | 8/2006 | Wang et al. |
| 7,118,574 B2 | 10/2006 | Patel et al. |
| 7,121,832 B2 | 10/2006 | Hsieh et al. |
| 7,139,601 B2 | 11/2006 | Bucholz et al. |
| 7,147,650 B2 | 12/2006 | Lee |
| 7,155,316 B2 | 12/2006 | Sutherland et al. |
| 7,166,114 B2 | 1/2007 | Moctezuma De La Barrera et al. |
| 7,174,202 B2 | 2/2007 | Bladen et al. |
| 7,181,315 B2 | 2/2007 | Watanabe et al. |
| 7,194,117 B2 | 3/2007 | Kaufman et al. |
| 7,194,120 B2 | 3/2007 | Wicker et al. |
| 7,204,844 B2 | 4/2007 | Jensen et al. |
| 7,206,626 B2 | 4/2007 | Quaid, III |
| 7,206,627 B2 | 4/2007 | Abovitz et al. |
| 7,213,598 B2 | 5/2007 | Zeiss et al. |
| 7,215,326 B2 | 5/2007 | Rosenberg |
| 7,217,276 B2 | 5/2007 | Henderson et al. |
| 7,226,456 B2 | 6/2007 | O'Neil et al. |
| 7,226,465 B1 | 6/2007 | Farin |
| 7,237,708 B1 | 7/2007 | Guy et al. |
| 7,239,940 B2 | 7/2007 | Wang et al. |
| 7,241,289 B2 | 7/2007 | Braun |
| 7,245,977 B1 | 7/2007 | Simkins |
| 7,246,030 B2 | 7/2007 | Raab et al. |
| 7,249,951 B2 | 7/2007 | Bevirt et al. |
| 7,252,660 B2 | 8/2007 | Kunz |
| 7,255,561 B2 | 8/2007 | Tricca et al. |
| 7,277,594 B2 | 10/2007 | Hofstetter et al. |
| 7,297,142 B2 | 11/2007 | Brock |
| 7,302,288 B1 | 11/2007 | Schellengberg |
| 7,331,967 B2 | 2/2008 | Lee et al. |
| 7,346,417 B2 | 3/2008 | Luth et al. |
| 7,347,862 B2 | 3/2008 | Layer |
| 7,356,367 B2 | 4/2008 | Liang et al. |
| 7,359,174 B2 | 4/2008 | Gass |
| 7,366,562 B2 | 4/2008 | Dukesherer et al. |
| 7,371,210 B2 | 5/2008 | Brock et al. |
| 7,373,863 B2 | 5/2008 | O'Banion et al. |
| 7,377,924 B2 | 5/2008 | Raistrick et al. |
| 7,383,198 B1 | 6/2008 | Sepe |
| 7,387,511 B2 | 6/2008 | Marshall |
| 7,404,716 B2 | 7/2008 | Gregorio et al. |
| 7,422,582 B2 | 9/2008 | Malackowski et al. |
| 7,427,272 B2 | 9/2008 | Richard et al. |
| 7,454,268 B2 | 11/2008 | Jinno |
| 7,457,443 B2 | 11/2008 | Persky |
| 7,466,303 B2 | 12/2008 | Yi et al. |
| 7,468,594 B2 | 12/2008 | Svensson et al. |
| 7,471,892 B2 | 12/2008 | Spaulding et al. |
| 7,486,811 B2 | 2/2009 | Kaufman et al. |
| 7,492,470 B2 | 2/2009 | Buchler et al. |
| 7,493,153 B2 | 2/2009 | Ahmed et al. |
| 7,498,811 B2 | 3/2009 | MacFarlane et al. |
| 7,524,320 B2 | 4/2009 | Tierney et al. |
| 7,532,949 B2 | 5/2009 | Ban et al. |
| 7,534,965 B1 | 5/2009 | Thompson |
| 7,535,411 B2 | 5/2009 | Falco |
| 7,540,867 B2 | 6/2009 | Jinno et al. |
| 7,540,875 B2 | 6/2009 | Jessen |
| 7,542,791 B2 | 6/2009 | Mire et al. |
| 7,543,588 B2 | 6/2009 | Wang et al. |
| 7,549,204 B1 | 6/2009 | Vangal-Ramamurthy et al. |
| 7,549,998 B2 | 6/2009 | Braun |
| RE40,852 E | 7/2009 | Martinelli et al. |
| 7,559,931 B2 | 7/2009 | Stone |
| 7,567,834 B2 | 7/2009 | Clayton et al. |
| 7,570,791 B2 | 8/2009 | Frank et al. |
| 7,573,461 B2 | 8/2009 | Rosenberg |
| 7,582,058 B1 | 9/2009 | Miles et al. |
| 7,600,455 B2 | 10/2009 | Gass et al. |
| 7,608,083 B2 | 10/2009 | Lee et al. |
| 7,618,428 B2 | 11/2009 | O'Quinn et al. |
| RE41,066 E | 12/2009 | Martinelli et al. |
| 7,625,383 B2 | 12/2009 | Charles et al. |
| 7,630,750 B2 | 12/2009 | Liang et al. |
| 7,630,753 B2 | 12/2009 | Simon et al. |
| 7,636,595 B2 | 12/2009 | Marquart et al. |
| 7,641,660 B2 | 1/2010 | Lakin et al. |
| 7,648,513 B2 | 1/2010 | Green et al. |
| 7,654,431 B2 | 2/2010 | Hueil et al. |
| 7,660,623 B2 | 2/2010 | Hunter et al. |
| 7,674,255 B2 | 3/2010 | Braun |
| 7,683,565 B2 | 3/2010 | Quaid et al. |
| 7,721,934 B2 | 5/2010 | Shelton, IV et al. |
| 7,727,185 B2 | 6/2010 | Weitzner et al. |
| 7,741,802 B2 | 6/2010 | Prisco et al. |
| 7,742,801 B2 | 6/2010 | Neubauer et al. |
| 7,744,608 B2 | 6/2010 | Lee et al. |
| 7,744,622 B2 | 6/2010 | Brock et al. |
| 7,747,055 B1 | 6/2010 | Vining et al. |
| 7,747,311 B2 | 6/2010 | Quaid, III |
| 7,758,569 B2 | 7/2010 | Brock |
| 7,763,035 B2 | 7/2010 | Melkent et al. |
| 7,766,894 B2 | 8/2010 | Weitzner et al. |
| 7,775,972 B2 | 8/2010 | Brock et al. |
| 7,780,054 B2 | 8/2010 | Wales |
| 7,780,681 B2 | 8/2010 | Sarin et al. |
| 7,784,662 B2 | 8/2010 | Wales et al. |
| 7,785,320 B2 | 8/2010 | Wang et al. |
| 7,787,131 B1 | 8/2010 | Moran |
| 7,789,875 B2 | 9/2010 | Brock et al. |
| 7,810,693 B2 | 10/2010 | Broehl et al. |
| 7,813,838 B2 | 10/2010 | Sommer |
| 7,818,044 B2 | 10/2010 | Dukesherer et al. |
| 7,819,884 B2 | 10/2010 | Lee et al. |
| 7,824,424 B2 | 11/2010 | Jensen et al. |
| 7,831,082 B2 | 11/2010 | Holsing et al. |
| 7,831,292 B2 | 11/2010 | Quaid et al. |
| 7,833,275 B2 | 11/2010 | Mears et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,854,738 B2 | 12/2010 | Lee et al. |
| RE42,055 E | 1/2011 | Raab et al. |
| 7,864,173 B2 | 1/2011 | Handley et al. |
| 7,867,241 B2 | 1/2011 | Brock et al. |
| RE42,082 E | 2/2011 | Raab et al. |
| 7,892,243 B2 | 2/2011 | Stuart |
| RE42,194 E | 3/2011 | Foley et al. |
| RE42,226 E | 3/2011 | Foley et al. |
| 7,899,512 B2 | 3/2011 | Labadie et al. |
| 7,901,399 B2 | 3/2011 | Brock |
| 7,901,404 B2 | 3/2011 | Reay-Young |
| 7,905,828 B2 | 3/2011 | Brock et al. |
| 7,914,522 B2 | 3/2011 | Morley et al. |
| 7,918,861 B2 | 4/2011 | Brock et al. |
| 7,931,470 B2 | 4/2011 | Alexander et al. |
| 7,931,586 B2 | 4/2011 | Brock et al. |
| 7,947,050 B2 | 5/2011 | Lee et al. |
| 7,947,051 B2 | 5/2011 | Lee et al. |
| 7,949,386 B2 | 5/2011 | Buly et al. |

(56) References Cited

U.S. PATENT DOCUMENTS

| | | |
|---|---|---|
| 7,950,306 B2 | 5/2011 | Stuart |
| 7,955,316 B2 | 6/2011 | Weitzner et al. |
| 7,959,557 B2 | 6/2011 | Weitzner et al. |
| 7,963,433 B2 | 6/2011 | Whitman et al. |
| 7,984,663 B2 | 7/2011 | Dent |
| 8,002,839 B2 | 8/2011 | Rochetin et al. |
| 8,010,180 B2 | 8/2011 | Quaid et al. |
| 8,021,368 B2 | 9/2011 | Haines |
| 8,095,200 B2 | 1/2012 | Quaid |
| 8,114,086 B2 | 2/2012 | Claypool et al. |
| 8,126,533 B2 | 2/2012 | Lavallee |
| 8,196,796 B2 | 6/2012 | Shelton, IV et al. |
| 8,231,634 B2 | 7/2012 | Mahfouz et al. |
| 8,257,360 B2 | 9/2012 | Richard et al. |
| 8,265,949 B2 | 9/2012 | Haddad |
| 8,272,554 B2 | 9/2012 | Whitman et al. |
| 8,282,685 B2 | 10/2012 | Rochetin et al. |
| 8,292,150 B2 | 10/2012 | Bryant |
| 8,296,094 B2 | 10/2012 | Harrison et al. |
| 8,303,575 B2 | 11/2012 | Rodriguez Y Baena |
| 8,308,043 B2 | 11/2012 | Bindra et al. |
| 8,308,663 B2 | 11/2012 | Tuma et al. |
| 8,342,379 B2 | 1/2013 | Whitman et al. |
| 8,391,954 B2 | 3/2013 | Quaid, III |
| 8,442,677 B2 | 5/2013 | Shoham |
| 8,498,744 B2 | 7/2013 | Odermatt et al. |
| 8,500,721 B2 | 8/2013 | Jinno |
| 8,560,047 B2 | 10/2013 | Haider et al. |
| 8,571,628 B2 | 10/2013 | Kang et al. |
| 8,573,465 B2 | 11/2013 | Shelton, IV |
| 8,594,397 B2 | 11/2013 | Haimerl et al. |
| 8,616,431 B2 | 12/2013 | Timm et al. |
| 8,626,267 B2 | 1/2014 | Lavallee |
| 8,652,148 B2 | 2/2014 | Zuhars |
| 8,679,125 B2 | 3/2014 | Smith et al. |
| 8,696,675 B2 | 4/2014 | Boutin et al. |
| 8,702,712 B2 | 4/2014 | Jordan et al. |
| 8,709,016 B2 | 4/2014 | Park et al. |
| 8,752,749 B2 | 6/2014 | Moore et al. |
| 8,753,346 B2 | 6/2014 | Suarez et al. |
| 8,774,900 B2 | 7/2014 | Buly et al. |
| 8,831,302 B2 | 9/2014 | Mahfouz |
| 8,834,490 B2 | 9/2014 | Bonutti |
| 8,876,830 B2 | 11/2014 | Hodorek et al. |
| 8,880,152 B2 | 11/2014 | Lavallee |
| 8,888,782 B2 | 11/2014 | Smith et al. |
| 8,894,654 B2 | 11/2014 | Anderson |
| 8,898,043 B2 | 11/2014 | Ashby et al. |
| 8,903,546 B2 | 12/2014 | Diolaiti et al. |
| 8,908,937 B2 | 12/2014 | Beck |
| 8,911,499 B2 | 12/2014 | Quaid et al. |
| 8,931,682 B2 | 1/2015 | Timm et al. |
| 8,961,536 B2 | 2/2015 | Nikou et al. |
| 8,968,276 B2 | 3/2015 | Zemlok et al. |
| 8,990,052 B2 | 3/2015 | Lavallee et al. |
| 8,991,677 B2 | 3/2015 | Moore et al. |
| 8,992,542 B2 | 3/2015 | Hagag et al. |
| 8,996,169 B2 | 3/2015 | Lightcap et al. |
| 8,998,058 B2 | 4/2015 | Moore et al. |
| 9,002,426 B2 | 4/2015 | Quaid et al. |
| 9,008,757 B2 | 4/2015 | Wu |
| 9,017,371 B2 | 4/2015 | Whitman et al. |
| 9,023,014 B2 | 5/2015 | Chowaniec et al. |
| 9,028,494 B2 | 5/2015 | Shelton, IV et al. |
| 9,037,295 B2 | 5/2015 | Hodgson et al. |
| 9,043,027 B2 | 5/2015 | Durant et al. |
| 9,050,132 B2 | 6/2015 | Lavallee |
| 9,055,943 B2 | 6/2015 | Zemlok et al. |
| 9,060,794 B2 | 6/2015 | Kang et al. |
| 9,060,796 B2 | 6/2015 | Seo |
| 9,078,671 B2 | 7/2015 | Beale et al. |
| 9,084,601 B2 | 7/2015 | Moore et al. |
| 9,084,613 B2 | 7/2015 | Qutub |
| 9,095,339 B2 | 8/2015 | Moore et al. |
| 9,101,393 B2 | 8/2015 | Jordan et al. |
| 9,119,638 B2 | 9/2015 | Schwarz et al. |
| 9,161,760 B2 | 10/2015 | Suarez et al. |
| 9,186,143 B2 | 11/2015 | Timm et al. |
| 9,220,510 B2 | 12/2015 | Cheal et al. |
| 9,220,571 B2 | 12/2015 | Lavallee |
| 9,248,001 B2 | 2/2016 | Colombet et al. |
| 9,259,280 B2 | 2/2016 | Au et al. |
| 9,265,581 B2 | 2/2016 | Navve et al. |
| 9,271,797 B2 | 3/2016 | Adler et al. |
| 9,272,416 B2 | 3/2016 | Hourtash et al. |
| 9,282,961 B2 | 3/2016 | Whitman et al. |
| 9,282,963 B2 | 3/2016 | Bryant |
| 9,342,632 B2 | 5/2016 | Zoran et al. |
| 9,399,298 B2 | 7/2016 | Kang |
| 9,408,698 B2 | 8/2016 | Miles et al. |
| 9,421,003 B2 | 8/2016 | Williams et al. |
| 9,433,471 B2 | 9/2016 | Zuhars |
| 9,463,030 B2 | 10/2016 | Uthgenannt |
| 9,463,031 B2 | 10/2016 | Radermacher et al. |
| 9,468,438 B2 | 10/2016 | Baber et al. |
| 9,498,219 B2 | 11/2016 | Moore et al. |
| 9,498,231 B2 | 11/2016 | Haider et al. |
| 9,504,579 B2 | 11/2016 | Mahfouz et al. |
| 9,514,533 B2 | 12/2016 | Chabanas et al. |
| 9,532,788 B2 | 1/2017 | Jordan et al. |
| 9,532,794 B2 | 1/2017 | Jinno |
| 9,554,812 B2 | 1/2017 | Inkpen et al. |
| 9,561,082 B2 | 2/2017 | Yen et al. |
| 9,563,186 B2 | 2/2017 | Steinle et al. |
| 9,582,079 B2 | 2/2017 | Bock-Krausen et al. |
| 9,585,658 B2 | 3/2017 | Shelton, IV |
| 9,597,104 B2 | 3/2017 | Nicholas et al. |
| 9,597,157 B2 | 3/2017 | Hagag et al. |
| 9,649,096 B2 | 5/2017 | Sholev |
| 9,649,164 B2 | 5/2017 | Kim et al. |
| 9,684,768 B2 | 6/2017 | Lavallee et al. |
| 9,707,043 B2 | 7/2017 | Bozung |
| 9,713,466 B2 | 7/2017 | Kostrzewski |
| 9,724,167 B2 | 8/2017 | Ziaei et al. |
| 9,734,632 B2 | 8/2017 | Thomas et al. |
| 9,750,498 B2 | 9/2017 | Timm et al. |
| 9,757,859 B1 | 9/2017 | Kolb et al. |
| 9,770,306 B2 | 9/2017 | Hagag et al. |
| 9,775,681 B2 | 10/2017 | Quaid et al. |
| 9,782,169 B2 | 10/2017 | Kimsey et al. |
| 9,788,904 B2 | 10/2017 | Boutin et al. |
| 9,795,381 B2 | 10/2017 | Shelton, IV |
| 9,801,686 B2 | 10/2017 | Lightcap et al. |
| 9,812,035 B2 | 11/2017 | Stuart et al. |
| 9,820,740 B2 | 11/2017 | Zemlok et al. |
| 9,820,753 B2 | 11/2017 | Walen et al. |
| 9,820,768 B2 | 11/2017 | Gee et al. |
| 9,820,818 B2 | 11/2017 | Malackowski et al. |
| 9,839,481 B2 | 12/2017 | Blumenkranz et al. |
| 9,852,268 B2 | 12/2017 | Gotte |
| 9,861,447 B2 | 1/2018 | Hourtash et al. |
| 9,865,095 B2 | 1/2018 | Gotte et al. |
| 9,877,734 B2 | 1/2018 | Anderson |
| 9,883,860 B2 | 2/2018 | Leimbach et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,356 B2 | 2/2018 | Shen et al. |
| 9,937,014 B2 | 4/2018 | Bowling et al. |
| 9,980,729 B2 | 5/2018 | Moore et al. |
| 9,987,003 B2 | 6/2018 | Timm et al. |
| 9,999,426 B2 | 6/2018 | Moore et al. |
| 10,004,504 B2 | 6/2018 | Bryant |
| 10,004,505 B2 | 6/2018 | Moore et al. |
| 10,005,312 B2 | 6/2018 | Zoran et al. |
| 10,022,123 B2 | 7/2018 | Williams et al. |
| 10,052,166 B2 | 8/2018 | Ziaei et al. |
| 10,080,617 B2 | 9/2018 | Haider et al. |
| 10,085,811 B2 | 10/2018 | Weir et al. |
| 10,092,365 B2 | 10/2018 | Seeber |
| 10,098,704 B2 | 10/2018 | Bowling et al. |
| 10,102,309 B2 | 10/2018 | McKinnon et al. |
| 10,105,149 B2 | 10/2018 | Haider et al. |
| 10,117,713 B2 | 11/2018 | Moctezuma de la Barrera et al. |

(56) References Cited

U.S. PATENT DOCUMENTS

| | | |
|---|---|---|
| 10,136,950 B2 | 11/2018 | Schoenefeld |
| 10,149,686 B2 | 12/2018 | Anderson |
| 10,166,075 B2 | 1/2019 | Jeong et al. |
| 10,182,875 B2 | 1/2019 | Yates et al. |
| 10,206,750 B2 | 2/2019 | Hagag et al. |
| 10,226,249 B2 | 3/2019 | Jaworek et al. |
| 10,231,785 B2 | 3/2019 | Dohmen et al. |
| 10,231,790 B2 | 3/2019 | Quaid et al. |
| 10,231,792 B2 | 3/2019 | Shiels et al. |
| 10,251,644 B2 | 4/2019 | Williams et al. |
| 10,265,854 B2 | 4/2019 | Chen et al. |
| 10,299,772 B2 | 5/2019 | Williams et al. |
| 10,299,787 B2 | 5/2019 | Shelton, IV |
| 10,307,163 B2 | 6/2019 | Moore et al. |
| 10,327,765 B2 | 6/2019 | Timm et al. |
| 10,327,849 B2 | 6/2019 | Post |
| 10,350,014 B2 | 7/2019 | Beelen et al. |
| 10,363,033 B2 | 7/2019 | Timm et al. |
| 10,368,863 B2 | 8/2019 | Timm et al. |
| 10,368,878 B2 | 8/2019 | Lavallee et al. |
| 10,369,708 B2 | 8/2019 | Kang |
| 10,405,936 B2 | 9/2019 | Awtar et al. |
| 10,410,746 B2 | 9/2019 | Moctezuma de la Barrera et al. |
| 10,413,294 B2 | 9/2019 | Shelton, IV et al. |
| 10,420,548 B2 | 9/2019 | Whitman et al. |
| 10,420,555 B2 | 9/2019 | Shelton, IV et al. |
| 10,441,280 B2 | 10/2019 | Timm et al. |
| 10,441,294 B2 | 10/2019 | Lavallee et al. |
| 10,441,434 B2 | 10/2019 | Miller et al. |
| 10,441,437 B2 | 10/2019 | Lavallee |
| 10,492,870 B2 | 12/2019 | Shalayev et al. |
| 10,492,875 B2 | 12/2019 | Janik et al. |
| 10,500,005 B2 | 12/2019 | Weir et al. |
| 10,500,312 B2 | 12/2019 | Bagga et al. |
| 10,555,774 B1 | 2/2020 | Mirdo et al. |
| 10,595,948 B2 | 3/2020 | Solomon et al. |
| 10,603,119 B2 | 3/2020 | Ross et al. |
| 10,631,932 B2 | 4/2020 | Mckinnon et al. |
| 10,631,940 B2 | 4/2020 | Lee et al. |
| 10,660,711 B2 | 5/2020 | Moctezuma de la Barrera et al. |
| 10,660,712 B2 | 5/2020 | Kostrzewski et al. |
| 10,660,715 B2 | 5/2020 | Dozeman |
| 10,687,823 B2 | 6/2020 | Mac an Tuile et al. |
| 10,687,899 B1 | 6/2020 | Hu et al. |
| 10,739,963 B2 | 8/2020 | Nikou et al. |
| 10,779,899 B2 | 9/2020 | Griffiths et al. |
| 10,786,307 B2 | 9/2020 | Schoenfeld |
| 10,792,105 B2 | 10/2020 | Gotte |
| 10,792,150 B2 | 10/2020 | Nguyen et al. |
| 10,806,617 B2 | 10/2020 | Kanjickal et al. |
| 10,807,242 B2 | 10/2020 | Zhou et al. |
| 10,813,574 B2 | 10/2020 | Fleig et al. |
| 10,828,786 B2 | 11/2020 | Shoham |
| 10,835,288 B2 | 11/2020 | Steger et al. |
| 10,864,047 B2 | 12/2020 | Hagag et al. |
| 10,881,462 B2 | 1/2021 | Heavener et al. |
| 10,888,337 B2 | 1/2021 | Shen et al. |
| 10,899,729 B2 | 1/2021 | Moriguchi et al. |
| 10,921,150 B2 | 2/2021 | Scarr et al. |
| 10,932,855 B2 | 3/2021 | Shupe et al. |
| 10,932,873 B2 | 3/2021 | Griffiths et al. |
| 10,939,969 B2 | 3/2021 | Swarup et al. |
| 10,952,801 B2 | 3/2021 | Miller et al. |
| 10,967,525 B2 | 4/2021 | Kang |
| 10,973,519 B2 | 4/2021 | Weir et al. |
| 11,045,264 B2 | 6/2021 | Yen et al. |
| 11,055,648 B2 | 7/2021 | DiSilvestro et al. |
| 11,068,822 B2 | 7/2021 | DiSilvestro et al. |
| 11,076,918 B2 | 8/2021 | Quaid, III |
| 11,090,120 B2 | 8/2021 | McKinnon et al. |
| 11,116,574 B2 | 9/2021 | Haider et al. |
| 11,116,584 B2 | 9/2021 | Dekel et al. |
| 11,123,881 B2 | 9/2021 | Kang |
| 11,185,378 B2 | 11/2021 | Weir et al. |
| 11,185,380 B2 | 11/2021 | Burbank et al. |
| 11,213,360 B2 | 1/2022 | Hourtash et al. |
| 11,253,329 B2 | 2/2022 | Bowling |
| 11,278,363 B2 | 3/2022 | Ross et al. |
| 11,369,438 B2 | 6/2022 | Malackowski et al. |
| 2001/0012932 A1 | 8/2001 | Peer |
| 2002/0133173 A1 | 9/2002 | Brock |
| 2002/0156497 A1 | 10/2002 | Nagase et al. |
| 2002/0170399 A1 | 11/2002 | Gass et al. |
| 2003/0050649 A1 | 3/2003 | Brock et al. |
| 2003/0135204 A1 | 7/2003 | Lee |
| 2003/0229279 A1 | 12/2003 | Amstutz et al. |
| 2004/0077939 A1 | 4/2004 | Graumann |
| 2004/0102866 A1 | 5/2004 | Harris et al. |
| 2004/0106916 A1 | 6/2004 | Quaid et al. |
| 2004/0138555 A1 | 7/2004 | Krag et al. |
| 2004/0147830 A1 | 7/2004 | Parker et al. |
| 2004/0147934 A1 | 7/2004 | Kiester |
| 2004/0157188 A1 | 8/2004 | Luth et al. |
| 2004/0171924 A1 | 9/2004 | Mire et al. |
| 2004/0171929 A1 | 9/2004 | Leitner et al. |
| 2004/0171930 A1 | 9/2004 | Grimm et al. |
| 2004/0176751 A1 | 9/2004 | Weitzner et al. |
| 2004/0186612 A1 | 9/2004 | Edwards et al. |
| 2004/0193146 A1 | 9/2004 | Lee et al. |
| 2004/0236316 A1 | 11/2004 | Danitz et al. |
| 2004/0254454 A1 | 12/2004 | Kockro |
| 2004/0267267 A1 | 12/2004 | Daniels et al. |
| 2005/0015005 A1 | 1/2005 | Kockro |
| 2005/0020909 A1 | 1/2005 | Moctezuma de la Barrera et al. |
| 2005/0049580 A1 | 3/2005 | Brock et al. |
| 2005/0059883 A1 | 3/2005 | Peterson |
| 2005/0090733 A1 | 4/2005 | Van Der Lugt et al. |
| 2005/0101970 A1 | 5/2005 | Rosenberg |
| 2005/0107667 A1 | 5/2005 | Danitz et al. |
| 2005/0148843 A1 | 7/2005 | Roose |
| 2005/0149091 A1 | 7/2005 | Tanamal et al. |
| 2005/0154296 A1 | 7/2005 | Lechner et al. |
| 2005/0159759 A1 | 7/2005 | Harbaugh et al. |
| 2005/0171553 A1 | 8/2005 | Schwarz et al. |
| 2005/0228440 A1 | 10/2005 | Brock et al. |
| 2005/0245935 A1 | 11/2005 | Casey et al. |
| 2005/0251112 A1 | 11/2005 | Danitz et al. |
| 2006/0109266 A1 | 5/2006 | Itkowitz et al. |
| 2006/0142657 A1 | 6/2006 | Quaid et al. |
| 2006/0155262 A1 | 7/2006 | Kishi et al. |
| 2006/0225551 A1 | 10/2006 | Gass |
| 2006/0271056 A1 | 11/2006 | Terrill-Grisoni |
| 2006/0293557 A1 | 12/2006 | Chuanggui et al. |
| 2007/0038223 A1 | 2/2007 | Marquart et al. |
| 2007/0049819 A1 | 3/2007 | Stifter et al. |
| 2007/0073136 A1 | 3/2007 | Metzger |
| 2007/0129626 A1 | 6/2007 | Mahesh et al. |
| 2007/0142825 A1 | 6/2007 | Prisco et al. |
| 2007/0198022 A1 | 8/2007 | Lang et al. |
| 2007/0213692 A1 | 9/2007 | Neubauer et al. |
| 2007/0233052 A1 | 10/2007 | Brock |
| 2007/0249899 A1 | 10/2007 | Seifert |
| 2007/0260394 A1 | 11/2007 | Dean |
| 2007/0265527 A1 | 11/2007 | Wohlgemuth |
| 2007/0270685 A1 | 11/2007 | Kang et al. |
| 2007/0276391 A1 | 11/2007 | Graves et al. |
| 2007/0282345 A1 | 12/2007 | Yedlicka et al. |
| 2007/0287911 A1 | 12/2007 | Haid et al. |
| 2008/0009697 A1 | 1/2008 | Haider et al. |
| 2008/0027448 A1 | 1/2008 | Raus et al. |
| 2008/0058776 A1 | 3/2008 | Jo et al. |
| 2008/0221520 A1 | 9/2008 | Nagel et al. |
| 2008/0262480 A1 | 10/2008 | Stahler et al. |
| 2008/0269596 A1 | 10/2008 | Revie et al. |
| 2009/0003975 A1 | 1/2009 | Kuduvalli et al. |
| 2009/0023988 A1 | 1/2009 | Korner et al. |
| 2009/0063118 A1 | 3/2009 | Dachille et al. |
| 2009/0163923 A1 | 6/2009 | Flett et al. |
| 2009/0228145 A1 | 9/2009 | Hodgson et al. |
| 2009/0234217 A1 | 9/2009 | Mire et al. |
| 2009/0264729 A1 | 10/2009 | Gilboa |
| 2009/0281566 A1 | 11/2009 | Edwards et al. |
| 2010/0041004 A1 | 2/2010 | Meglan |
| 2010/0041985 A1 | 2/2010 | Simon et al. |

(56) References Cited

U.S. PATENT DOCUMENTS

| | | |
|---|---|---|
| 2010/0057087 A1 | 3/2010 | Cha |
| 2010/0099983 A1 | 4/2010 | Moctezuma De La Barrera et al. |
| 2010/0133317 A1 | 6/2010 | Shelton, IV et al. |
| 2010/0168722 A1 | 7/2010 | Lee et al. |
| 2010/0168747 A1 | 7/2010 | Lynch et al. |
| 2010/0215150 A1 | 8/2010 | Vallee et al. |
| 2010/0228235 A1 | 9/2010 | Lee et al. |
| 2010/0262127 A1 | 10/2010 | Schmied et al. |
| 2010/0268068 A1 | 10/2010 | Vass et al. |
| 2010/0292701 A1 | 11/2010 | Fisher et al. |
| 2010/0298832 A1 | 11/2010 | Lau et al. |
| 2010/0305552 A1 | 12/2010 | Shelton, IV et al. |
| 2010/0331855 A1 | 12/2010 | Zhao et al. |
| 2011/0113270 A1 | 5/2011 | Carter et al. |
| 2011/0315413 A1 | 12/2011 | Fisher et al. |
| 2012/0059378 A1 | 3/2012 | Farrell |
| 2012/0143084 A1 | 6/2012 | Shoham |
| 2013/0060278 A1 | 3/2013 | Bozung et al. |
| 2013/0096373 A1 | 4/2013 | Chabanas et al. |
| 2013/0096574 A1 | 4/2013 | Kang et al. |
| 2013/0172905 A1 | 7/2013 | Iorgulescu et al. |
| 2014/0012236 A1 | 1/2014 | Williams et al. |
| 2014/0135791 A1 | 5/2014 | Nikou et al. |
| 2014/0148808 A1 | 5/2014 | Inkpen et al. |
| 2014/0246475 A1 | 9/2014 | Hall et al. |
| 2014/0276937 A1 | 9/2014 | Wong et al. |
| 2014/0350569 A1 | 11/2014 | Jeong et al. |
| 2015/0080966 A1 | 3/2015 | Anderson |
| 2015/0182285 A1 | 7/2015 | Yen et al. |
| 2015/0201918 A1 | 7/2015 | Kumar et al. |
| 2015/0305828 A1 | 10/2015 | Park et al. |
| 2015/0342588 A1 | 12/2015 | Bechtold et al. |
| 2015/0342601 A1 | 12/2015 | Williams et al. |
| 2016/0022374 A1 | 1/2016 | Haider |
| 2016/0074123 A1 | 3/2016 | Bly et al. |
| 2016/0095585 A1 | 4/2016 | Zergiebel et al. |
| 2016/0113720 A1 | 4/2016 | Lavallee et al. |
| 2016/0135816 A1 | 5/2016 | Lavallee et al. |
| 2016/0206375 A1 | 7/2016 | Abbasi et al. |
| 2016/0206376 A1 | 7/2016 | Haider et al. |
| 2016/0256232 A1 | 9/2016 | Awtar et al. |
| 2017/0007254 A1 | 1/2017 | Jaworek et al. |
| 2017/0007255 A1 | 1/2017 | Jaworek et al. |
| 2017/0007327 A1 | 1/2017 | Haider et al. |
| 2017/0026591 A1 | 1/2017 | Yuki |
| 2017/0055940 A1 | 3/2017 | Shoham |
| 2017/0056116 A1 | 3/2017 | Kostrzewski, Phd |
| 2017/0084027 A1 | 3/2017 | Mintz et al. |
| 2017/0086831 A1 | 3/2017 | Shelton, IV et al. |
| 2017/0105757 A1 | 4/2017 | Weir et al. |
| 2017/0112579 A1 | 4/2017 | Yen et al. |
| 2017/0135695 A1 | 5/2017 | Shelton, IV et al. |
| 2017/0172576 A1 | 6/2017 | Nicholas et al. |
| 2017/0215881 A1 | 8/2017 | Shelton, IV et al. |
| 2017/0224428 A1 | 8/2017 | Kopp |
| 2017/0231718 A1 | 8/2017 | Wohrle et al. |
| 2017/0258467 A1 | 9/2017 | Williams et al. |
| 2017/0258532 A1 | 9/2017 | Shalayev et al. |
| 2017/0265879 A1 | 9/2017 | Washburn, II et al. |
| 2017/0265947 A1 | 9/2017 | Dyer et al. |
| 2017/0265951 A1 | 9/2017 | Grover et al. |
| 2017/0281280 A1 | 10/2017 | Haider et al. |
| 2017/0290585 A1 | 10/2017 | Shelton, IV et al. |
| 2017/0296167 A1 | 10/2017 | Kostrzewski |
| 2017/0319141 A1 | 11/2017 | Revie et al. |
| 2018/0008270 A1 | 1/2018 | Moore et al. |
| 2018/0008271 A1 | 1/2018 | Moore et al. |
| 2018/0008358 A1 | 1/2018 | Kostrzewski et al. |
| 2018/0014891 A1 | 1/2018 | Krebs et al. |
| 2018/0049767 A1 | 2/2018 | Gee et al. |
| 2018/0070941 A1 | 3/2018 | Zemlok et al. |
| 2018/0070942 A1 | 3/2018 | Shelton, IV et al. |
| 2018/0104439 A1 | 4/2018 | Tzvieli et al. |
| 2018/0116662 A1 | 5/2018 | Shelton, IV et al. |
| 2018/0116739 A1 | 5/2018 | Gogarty et al. |
| 2018/0116740 A1 | 5/2018 | Gogarty et al. |
| 2018/0125580 A1 | 5/2018 | Boutin et al. |
| 2018/0132941 A1 | 5/2018 | Haider et al. |
| 2018/0132949 A1 | 5/2018 | Merette et al. |
| 2018/0140426 A1 | 5/2018 | Belcher et al. |
| 2018/0157238 A1 | 6/2018 | Gogarty et al. |
| 2018/0228501 A1 | 8/2018 | Shen et al. |
| 2018/0280065 A1 | 10/2018 | Babic et al. |
| 2018/0280159 A1 | 10/2018 | Hunter et al. |
| 2018/0296211 A1 | 10/2018 | Timm et al. |
| 2018/0296217 A1 | 10/2018 | Moore et al. |
| 2018/0303485 A1 | 10/2018 | Bryant |
| 2018/0325526 A1 | 11/2018 | Haddad |
| 2018/0333207 A1 | 11/2018 | Moctezuma De La Barrera |
| 2018/0344409 A1 | 12/2018 | Bonny et al. |
| 2018/0353245 A1 | 12/2018 | Mccloud et al. |
| 2019/0021937 A1 | 1/2019 | Swift et al. |
| 2019/0070731 A1 | 3/2019 | Bowling et al. |
| 2019/0076198 A1 | 3/2019 | Berend et al. |
| 2019/0090952 A1 | 3/2019 | Bonny et al. |
| 2019/0090959 A1 | 3/2019 | Haider et al. |
| 2019/0105044 A1 | 4/2019 | Shelton, IV et al. |
| 2019/0105049 A1 | 4/2019 | Moore et al. |
| 2019/0117225 A1 | 4/2019 | Moore et al. |
| 2019/0133695 A1 | 5/2019 | Hladio et al. |
| 2019/0183491 A1 | 6/2019 | Shelton, IV et al. |
| 2019/0192234 A1 | 6/2019 | Gadda et al. |
| 2019/0201214 A1 | 7/2019 | Miller et al. |
| 2019/0223957 A1 | 7/2019 | Dekel et al. |
| 2019/0223962 A1 | 7/2019 | Roldan et al. |
| 2019/0290390 A1 | 9/2019 | Davies |
| 2019/0336139 A1 | 11/2019 | Guzman et al. |
| 2019/0365391 A1 | 12/2019 | Nikou et al. |
| 2019/0388099 A1 | 12/2019 | Zuhars et al. |
| 2020/0001494 A1 | 1/2020 | Gisler et al. |
| 2020/0008884 A1 | 1/2020 | Lavallee et al. |
| 2020/0008889 A1 | 1/2020 | Ho et al. |
| 2020/0028356 A1 | 1/2020 | Bultitude et al. |
| 2020/0033568 A1 | 1/2020 | Liu |
| 2020/0036798 A1 | 1/2020 | Dierckens et al. |
| 2020/0037308 A1 | 1/2020 | Liu et al. |
| 2020/0038108 A1 | 2/2020 | Chou et al. |
| 2020/0046438 A1 | 2/2020 | Shalayev et al. |
| 2020/0069372 A1 | 3/2020 | Dufour et al. |
| 2020/0069373 A1 | 3/2020 | Yu et al. |
| 2020/0069377 A1 | 3/2020 | Finley et al. |
| 2020/0093500 A1 | 3/2020 | Lavallee et al. |
| 2020/0100848 A1 | 4/2020 | Zuhars et al. |
| 2020/0121400 A1 | 4/2020 | Girardeau-Montaut et al. |
| 2020/0197185 A1 | 6/2020 | Mahfouz |
| 2020/0197191 A1 | 6/2020 | Akhlaghpour et al. |
| 2020/0268461 A1 | 8/2020 | Forstein et al. |
| 2020/0275943 A1 | 9/2020 | Keppler et al. |
| 2020/0305978 A1 | 10/2020 | Tan et al. |
| 2020/0323540 A1 | 10/2020 | Kang et al. |
| 2020/0345433 A1 | 11/2020 | Peine |
| 2020/0375670 A1 | 12/2020 | Bonny et al. |
| 2020/0390501 A1 | 12/2020 | Brown et al. |
| 2020/0390506 A1 | 12/2020 | Bonny |
| 2020/0406480 A1 | 12/2020 | Shoham |
| 2021/0029846 A1 | 1/2021 | Revankar et al. |
| 2021/0059656 A1 | 3/2021 | Otto et al. |
| 2021/0059771 A1 | 3/2021 | Hagag et al. |
| 2021/0059781 A1 | 3/2021 | Peine et al. |
| 2021/0068845 A1 | 3/2021 | Schers et al. |
| 2021/0093400 A1 | 4/2021 | Quaid et al. |
| 2021/0100629 A1 | 4/2021 | Urvoy et al. |
| 2021/0113215 A1 | 4/2021 | Gisler |
| 2021/0113270 A1 | 4/2021 | Lavallee et al. |
| 2021/0128252 A1 | 5/2021 | Zuhars et al. |
| 2021/0153957 A1 | 5/2021 | Demanget et al. |
| 2021/0153960 A1 | 5/2021 | Griffiths et al. |
| 2021/0153973 A1 | 5/2021 | Kapadia et al. |
| 2021/0169596 A1 | 6/2021 | Urvoy et al. |
| 2021/0177535 A1 | 6/2021 | Miller et al. |
| 2021/0186632 A1 | 6/2021 | Quaid et al. |
| 2021/0196270 A1 | 7/2021 | Shelton, IV et al. |
| 2021/0204963 A1 | 7/2021 | Mitra et al. |
| 2021/0205033 A1 | 7/2021 | Lavallee et al. |

(56) References Cited

U.S. PATENT DOCUMENTS

| | | |
|---|---|---|
| 2021/0205040 A1 | 7/2021 | Hassan et al. |
| 2021/0220064 A1 | 7/2021 | Kottenstette et al. |
| 2021/0321855 A1 | 10/2021 | Yu et al. |
| 2021/0369349 A1 | 12/2021 | Haider et al. |
| 2021/0369370 A1 | 12/2021 | Malanowski |
| 2021/0402603 A1 | 12/2021 | Murphy et al. |
| 2022/0022986 A1 | 1/2022 | Gilhooley et al. |
| 2022/0233251 A1 | 7/2022 | Bowling et al. |

FOREIGN PATENT DOCUMENTS

| | | |
|---|---|---|
| DE | 20205007 U1 | 7/2002 |
| DE | 10239673 A1 | 3/2004 |
| DE | 102008024261 B4 | 12/2010 |
| EP | 1524626 A2 | 4/2005 |
| EP | 1355765 B1 | 5/2008 |
| EP | 1531744 B1 | 10/2009 |
| EP | 2754383 A2 | 7/2014 |
| EP | 3007636 B1 | 9/2017 |
| EP | 3007637 B1 | 11/2017 |
| EP | 3443924 A1 | 2/2019 |
| EP | 3569159 A1 | 11/2019 |
| EP | 2467798 B1 | 4/2020 |
| JP | H0929681 A | 2/1997 |
| JP | H11137755 A | 5/1999 |
| KR | 20120068597 A | 6/2012 |
| KR | 20130015437 A | 2/2013 |
| KR | 101480251 B1 | 1/2015 |
| KR | 20150007020 A | 1/2015 |
| KR | 20150125069 A | 11/2015 |
| KR | 20190000940 A | 1/2019 |
| KR | 20190030414 A | 3/2019 |
| WO | 1998038919 A2 | 9/1998 |
| WO | 99037220 A1 | 7/1999 |
| WO | 0021450 A1 | 4/2000 |
| WO | 0035366 A1 | 6/2000 |
| WO | 0059397 A1 | 10/2000 |
| WO | 0060571 A1 | 10/2000 |
| WO | 200064367 A1 | 11/2000 |
| WO | 2001087136 A2 | 11/2001 |
| WO | 200200131 A1 | 1/2002 |
| WO | 2002000093 A2 | 1/2002 |
| WO | 0224051 A2 | 3/2002 |
| WO | 02060653 A2 | 8/2002 |
| WO | 03094108 A2 | 11/2003 |
| WO | 2004001569 A2 | 12/2003 |
| WO | 2004014244 A2 | 2/2004 |
| WO | 2004019785 A2 | 3/2004 |
| WO | 2004069036 A2 | 8/2004 |
| WO | 2005009215 A2 | 2/2005 |
| WO | 2005048852 A1 | 6/2005 |
| WO | 2005079492 A2 | 9/2005 |
| WO | 2007045993 A2 | 4/2007 |
| WO | 2007111749 A2 | 10/2007 |
| WO | 2007117297 A2 | 10/2007 |
| WO | 2007136739 A2 | 11/2007 |
| WO | 2007136768 A2 | 11/2007 |
| WO | 2007136769 A2 | 11/2007 |
| WO | 2007136771 A2 | 11/2007 |
| WO | 2008091917 A2 | 7/2008 |
| WO | 2009059330 A2 | 5/2009 |
| WO | 2011021192 A1 | 2/2011 |
| WO | 2012131660 A1 | 10/2012 |
| WO | 2014139023 A1 | 9/2014 |
| WO | 2015006721 A1 | 1/2015 |
| WO | 2015166487 A1 | 11/2015 |
| WO | 2016049180 A1 | 3/2016 |
| WO | 2017114855 A1 | 7/2017 |
| WO | 2017127202 A1 | 7/2017 |
| WO | 2017151863 A1 | 9/2017 |
| WO | 2017204832 A1 | 11/2017 |
| WO | 201803945 A1 | 1/2018 |
| WO | 201804439 A1 | 1/2018 |
| WO | 2018103945 A1 | 6/2018 |
| WO | 2018104439 A1 | 6/2018 |
| WO | 2018104523 A1 | 6/2018 |
| WO | 2019050829 A1 | 3/2019 |
| WO | 2019050878 A2 | 3/2019 |
| WO | 2019140533 A1 | 7/2019 |
| WO | 2019219348 A1 | 11/2019 |
| WO | 2020028356 A1 | 2/2020 |
| WO | 2020113030 A1 | 6/2020 |
| WO | 2020198027 A1 | 10/2020 |
| WO | 2021113227 A1 | 6/2021 |
| WO | 2021126786 A1 | 6/2021 |
| WO | 2021137051 A1 | 7/2021 |
| WO | 2021138096 A1 | 7/2021 |
| WO | 2021194903 A1 | 9/2021 |

OTHER PUBLICATIONS

English language abstract and machine-assisted English translation for JPH 11-137755 A extracted from espacenet.com database on Mar. 8, 2024, 14 pages.

United States Non-Provisional U.S. Appl. No. 18/072,715, filed Dec. 2, 2022.

American Heritage, "College Edition Dictionary—Freebie to Free World; Meaningful to Mechanism; and Supplicant to Surcharge", Second College Edition, 1982, 5 pages.

Burghart, Catherina et al., "Robot Controlled Osteotomy in Craniofacial Surgery", First International Workshop on Haptic Devices in Medical Applications, 1999, 11 pages.

D'Attansio, S. et al., A Semi-Automatic Handheld Mechatronic Endoscope with Collision-Avoidance Capabilities, IEEE International Conference on Robotics and Automation, Apr. 2000, 6 pages.

Davies, Brian, "Computer-Assisted and Roboticcs Surgery", New Horizons in High Technology Medicine, 1997, 12 pages.

Digioia III, Anthony M. et al., "An Integrated Approach to Medical Roboticcs and Computer Assisted Surgery in Orthopaedics", Center for Orthopaedic Research, Jan. 1995, 6 pages.

English language abstract and machine-assisted English translation for DE 10 2008 024 261 B4 extracted from espacenet.com database on Mar. 31, 2022, 6 pages.

English language abstract and machine-assisted English translation for DE 20 205 006 U1 extracted from espacenet.com database on Mar. 31, 2022, 9 pages.

English language abstract and machine-assisted English translation for DE 20 205 007 U1 extracted from espacenet.com database on Mar. 31, 2022, 6 pages.

English language abstract and machine-assisted English translation for KR 101480251 B1 extracted from espacenet.com database on Mar. 31, 2022, 25 pages.

English language abstract and machine-assisted English translation for KR 2013-0015437 A extracted from espacenet.com database on Mar. 31, 2022, 16 pages.

English language abstract and machine-assisted English translation for KR 2019-0030414 A extracted from espacenet.com database on Mar. 31, 2022, 11 pages.

English language abstract and machine-assisted English translation for WO 00/21450 A1 extracted from espacenet.com database on Mar. 31, 2022, 9 pages.

English language abstract and machine-assisted English translation for WO 00/59397 A1 extracted from espacenet.com database on Mar. 31, 2022, 8 pages.

English language abstract and machine-assisted English translation for WO 2005/048852 A1 extracted from espacenet.com database on Mar. 31, 2022, 9 pages.

English language abstract for CN 105636541 A1 extracted from espacenet.com database on Mar. 31, 2022, 2 pages.

English language abstract for DE 10 239 673 A1 extracted from espacenet.com database on Mar. 31, 2022, 2 pages.

English language abstract for EP 1 531 744 B1 extracted from espacenet.com database on Feb. 7, 2022, 2 pages.

English language abstract for KR 2015-0007020 A extracted from espacenet.com database on Mar. 31, 2022, 1 page.

English language abstract for KR 2012-0068597 A and machine-assissted English translation for equivalent CN 106214262 B extracted from espacenet.com database on Mar. 31, 2022, 39 pages.

(56) References Cited

OTHER PUBLICATIONS

English language abstract for KR 2015-025019 A extracted from espacenet.com database on Mar. 31, 2022, 2 pages.
English language abstract for KR 2019-0000940 A extracted from espacenet.com database on Mar. 31, 2022, 2 pages.
English language abstract for WO 2004/019785 A2 extracted from espacenet.com database on Feb. 7, 2022, 2 pages.
English language abstract for WO 2018/003945 A1 extracted from espacenet.com database on Feb. 7, 2022, 1 page.
Faro, "Faro Arm Caliper 3D Version 2.42 Instruction Book", Feb. 1999, 116 pages.
Glossop, Ph.D, Neil et al., "Assessment of Vertebral Body Motion During Spine Surgery", vol. 22, No. 8, 1997, pp. 903-909.
Haidegger, T. et al., "The Importance of Accuracy Measurement Standards for Computer-Integrated Interventional Systems", Computer Science, 2010, 6 pages.
Harris, S.J. et al., "Experiences With Roboticc Systems for Knee Surgery", Mechatronics in Medicine, Department of Mechanical Engineering, Imperial College of Science, Technology and Medicine, London, 1997, 10 pages.
Harris, S.J. et al., "The Probot-An Active Robot for Prostate Resection", Proc. Instn. Mech. Engrs., vol. 211, Part H, 1997, 9 pages.
Hashim BDS, Hayder Abdullah et al., "Tooth Width and Arch Dimensions in Normal and Malocclusion Samples: An Odontometric Study", The Journal of Contemporary Dental Practice, vol. 6, No. 2, May 15, 2005, 13 pages.
Heck Md, David A. et al., "Six Sigma Analysis of Minimally Invasive Acetabluar Arthroplasty", Clin. Orthop. Relat. Res., vol. 467, 2009, pp. 2025-2031.
Hein, Andreas et al., "Image-Based Control of Interactive Systems", MICCAI, 1999, 8 pages.
Hinsche, A.F. et al., "Surgical Techniques: Image-Guided Surgery", Current Orthopaedics, vol. 15, 2001, pp. 296-303.
Howe, Robert D. et al., "Roboticcs for Surgery", Annu. Rev. Biomed. Eng., 1999, pp. 211-240.
International Search Report for Application No. PCT/US2020/042128 dated Feb. 24, 2021, 4 pages.
Jones, C.T. et al., "Patrick-Turner's Industrial Automation Dictionary-Emulate to Encoder Ambiguity", First Edition, 1996, 4 page.s.
Kazanzides, Peter et al., "An Integrated System for Cementless Hip Replacement" IEEE Engineering in Medicine and Biology, 1995, 7 pages.
Klimek, Md, Ludger et al., "A Passive-Marker-Based Optical System for Computer-Aided surgery in Otorhinolaryngology: Development and First Clinical Experiences", The Laryngoscope, 1999, 7 pages.
Laplante, Phillip A., "Dictionary of Computer Science, Engineering, and Technology—Degree to Delimiter", 2001, 4 pages.
Madison, Michael et al., Operative Orthopaedics Textbook—Chapter 135, Unicompartmental Arthrosplasty of the Knee, 2nd Edition, 1993. 13 pages.
Merriam-Webster, "Collegiate Dictionary—Free to Free Throw; Measurability to Medea; and Supersonic to Supportable", Tenth Edition, 2001, 5 pages.
Nayler, G.H.F., "Dictionary of Mechanical Engeering—Keyway Tool to Kinematic Pair", Fourth Edition, 1996, 3 pages.
Partial International Search Report for Application No. PCT/US2020/042128 dated Oct. 21, 2020, 3 pages.
Taylor, Russell H. et al., "An Image-Directed Roboticc System fo Precise Orthopaedic Surgery", IEEE Transactions on Roboticcs and Automation, vol. 10, No. 3, Jun. 1994, 15 pages.
Taylor, Russell H. et al., "Computer-Integrated Surgery Technology and Clinical Applications—Chapter 19: A Discussion of Safety Issues for Medical Robots", 1996, 12 pages.
Traxtal Technologies, "Optically and Magnetically Tracked Tools and Instrumentation Website", 2000-2002, 2 pages.
Vossel, Manuel et al., "Minaro HD: Control and Evaluation of a Handheld, Highly Dynamic Surgical Robot", International Journal of Computer Assisted Radiology and Surgery, Janary 23, 2021, 8 pages.

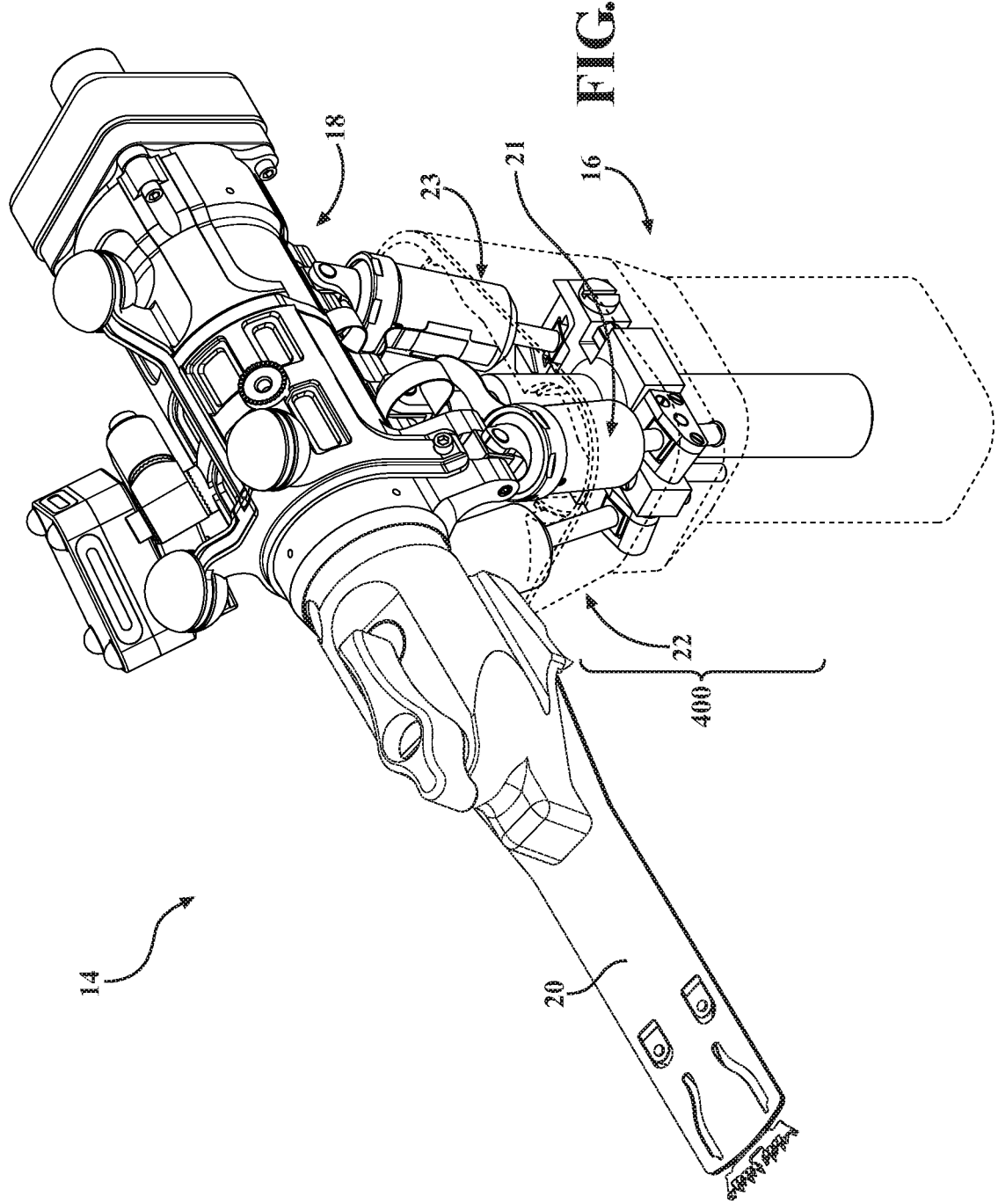

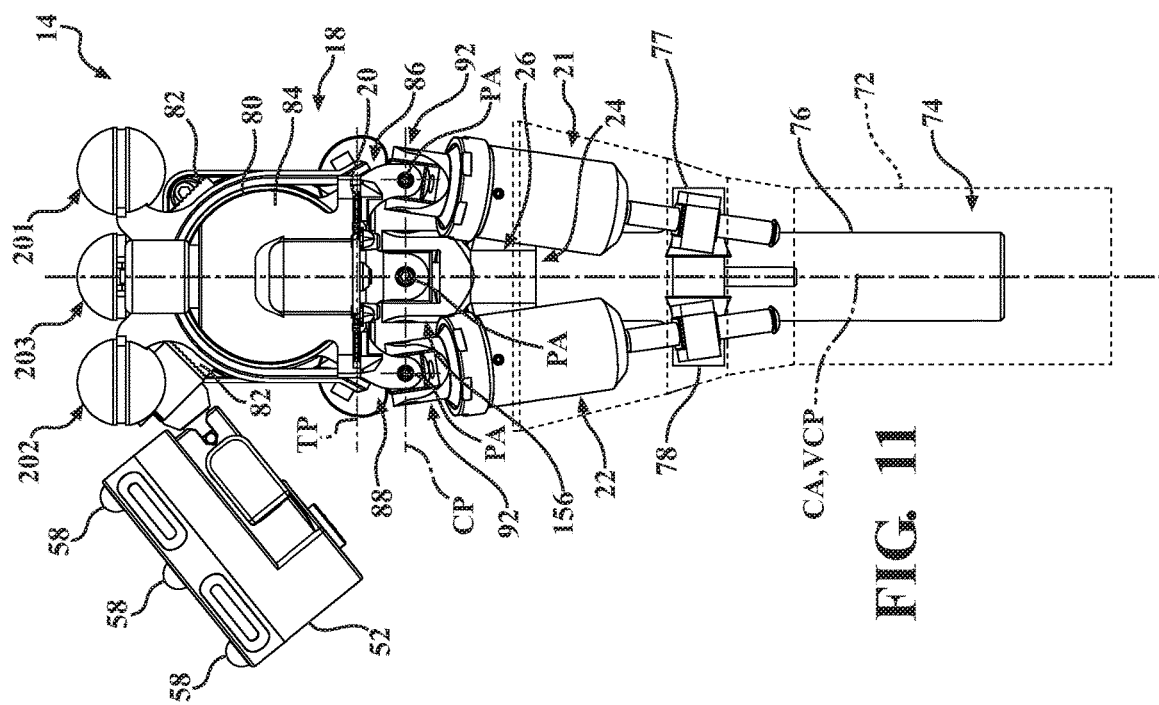
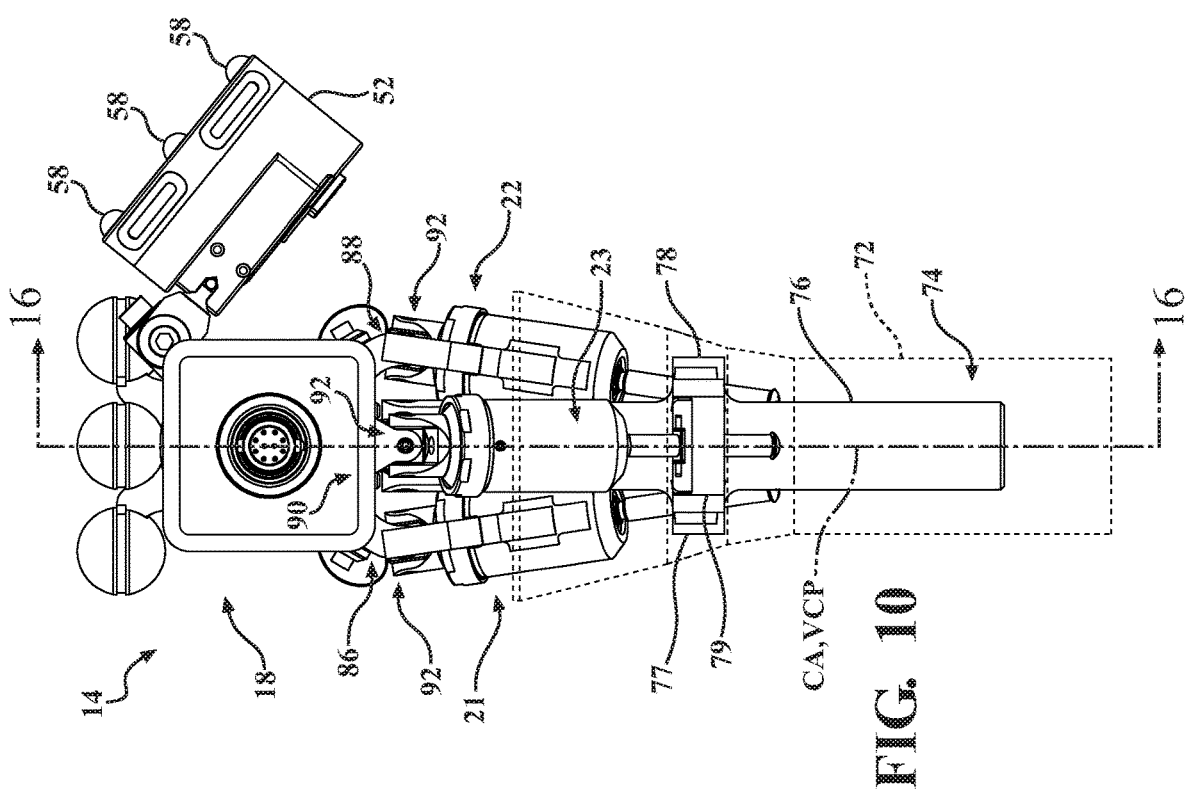
FIG. 11
FIG. 10

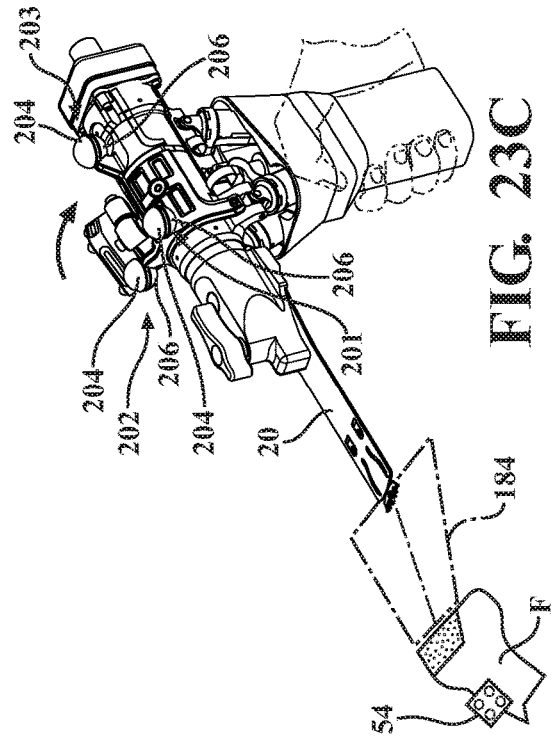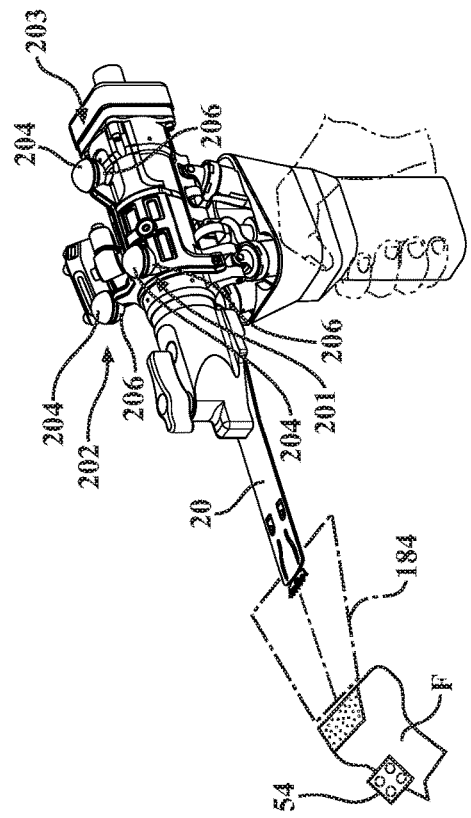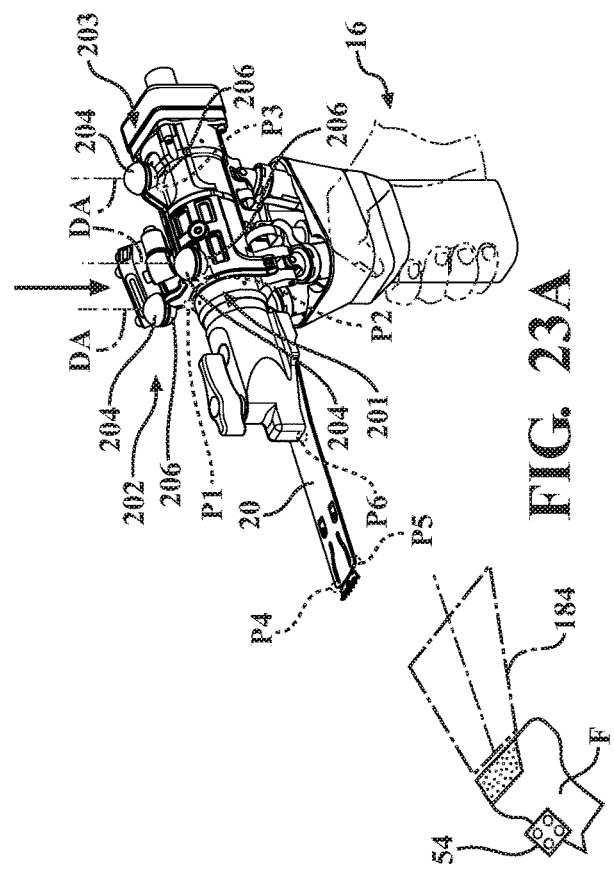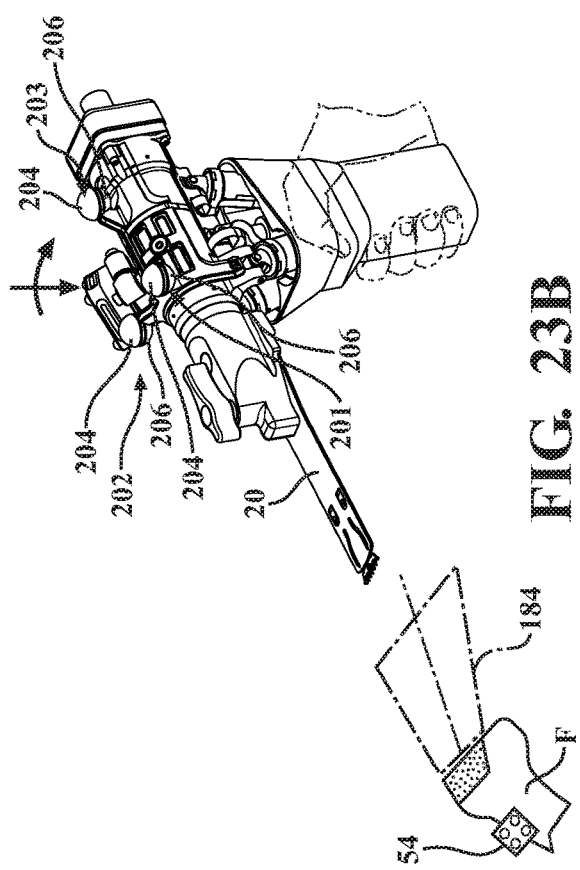

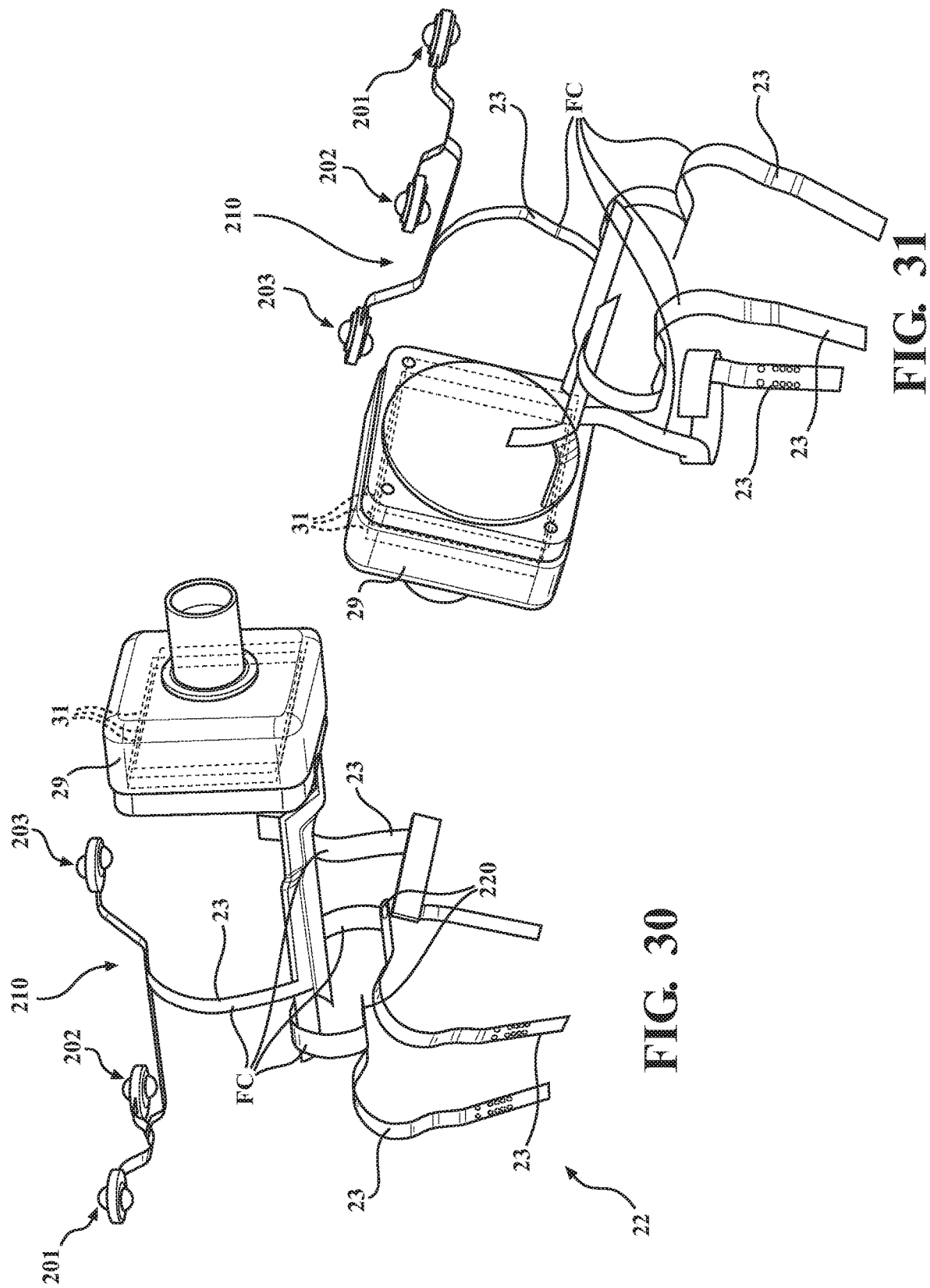

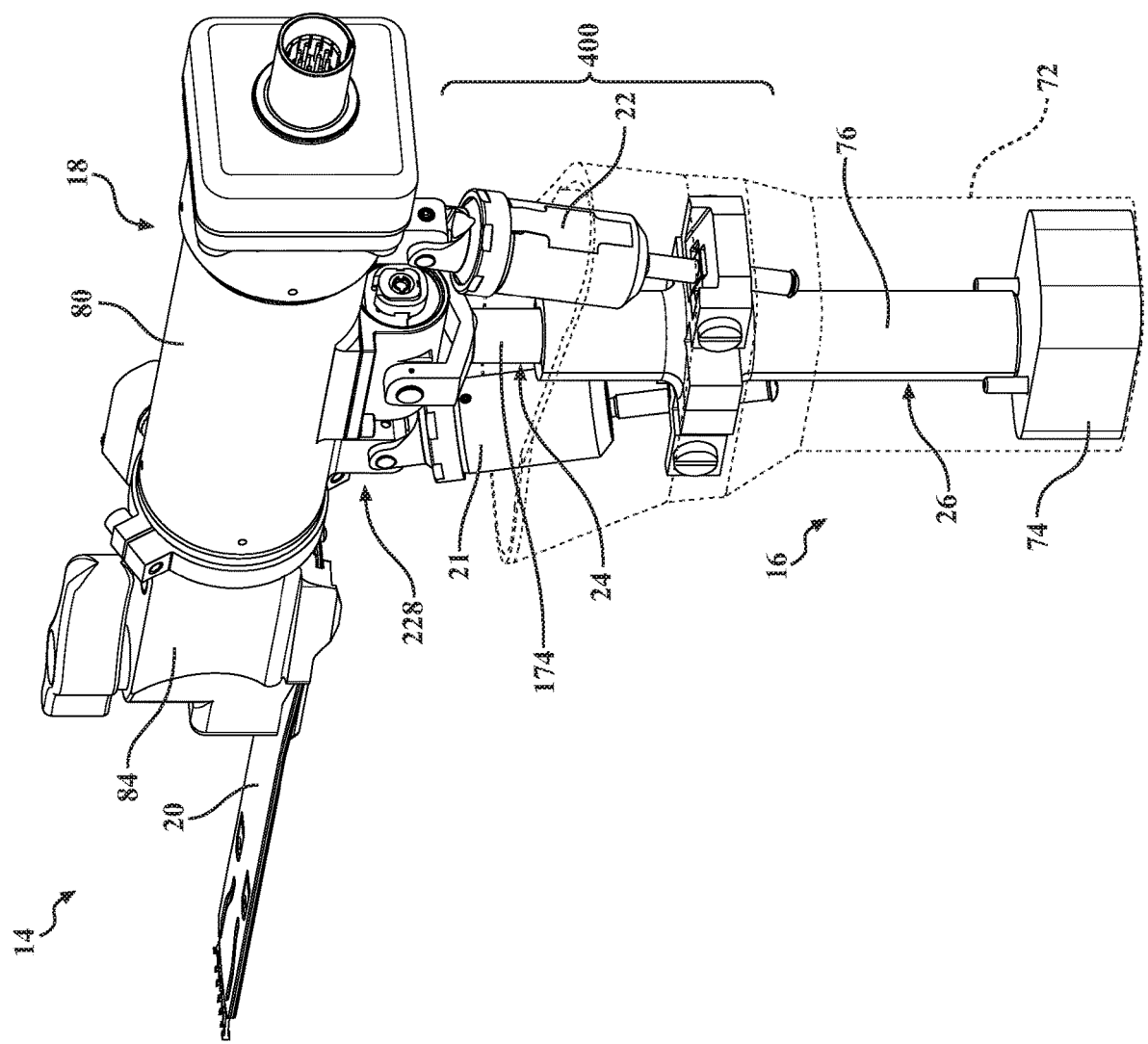

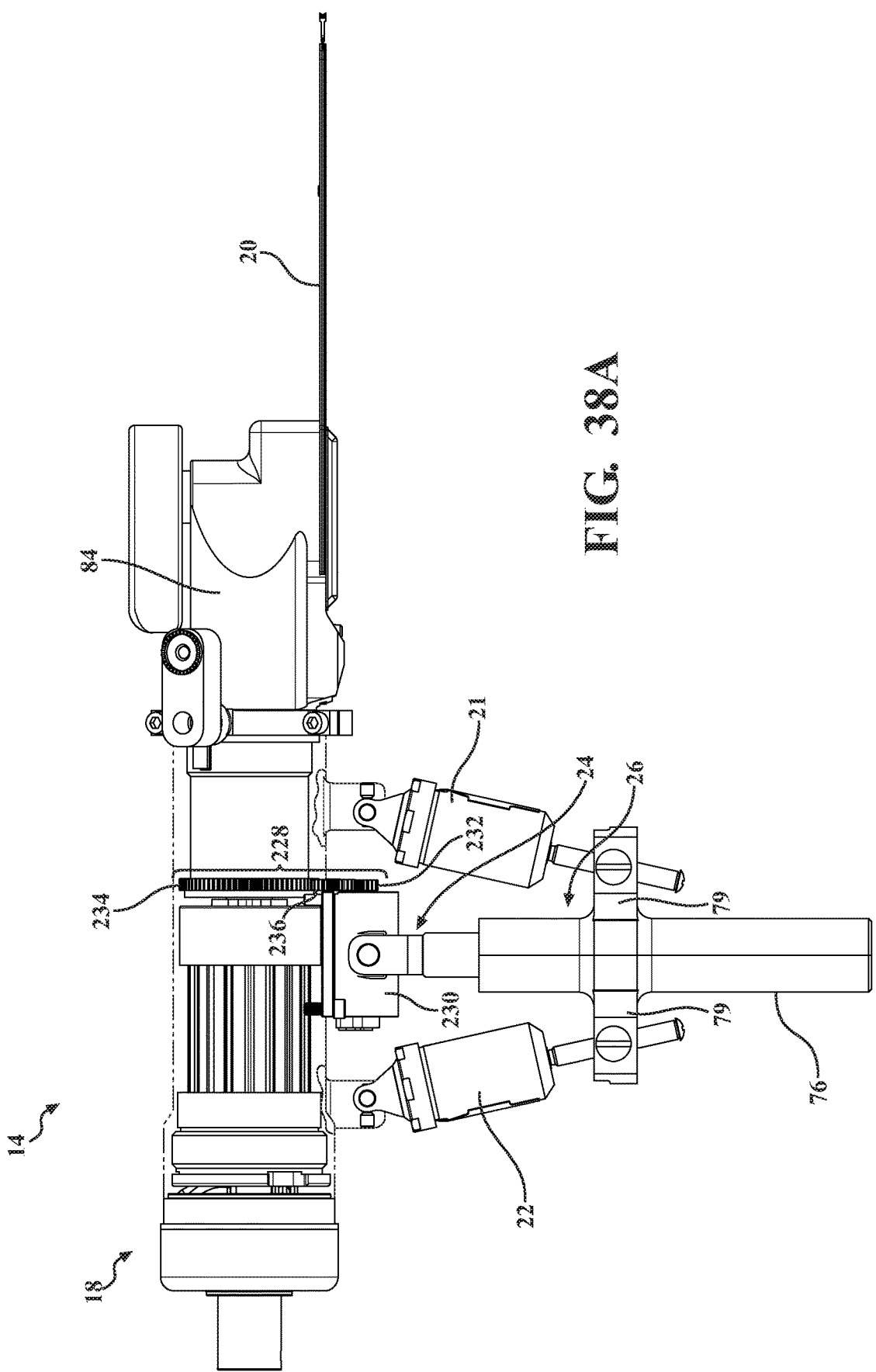

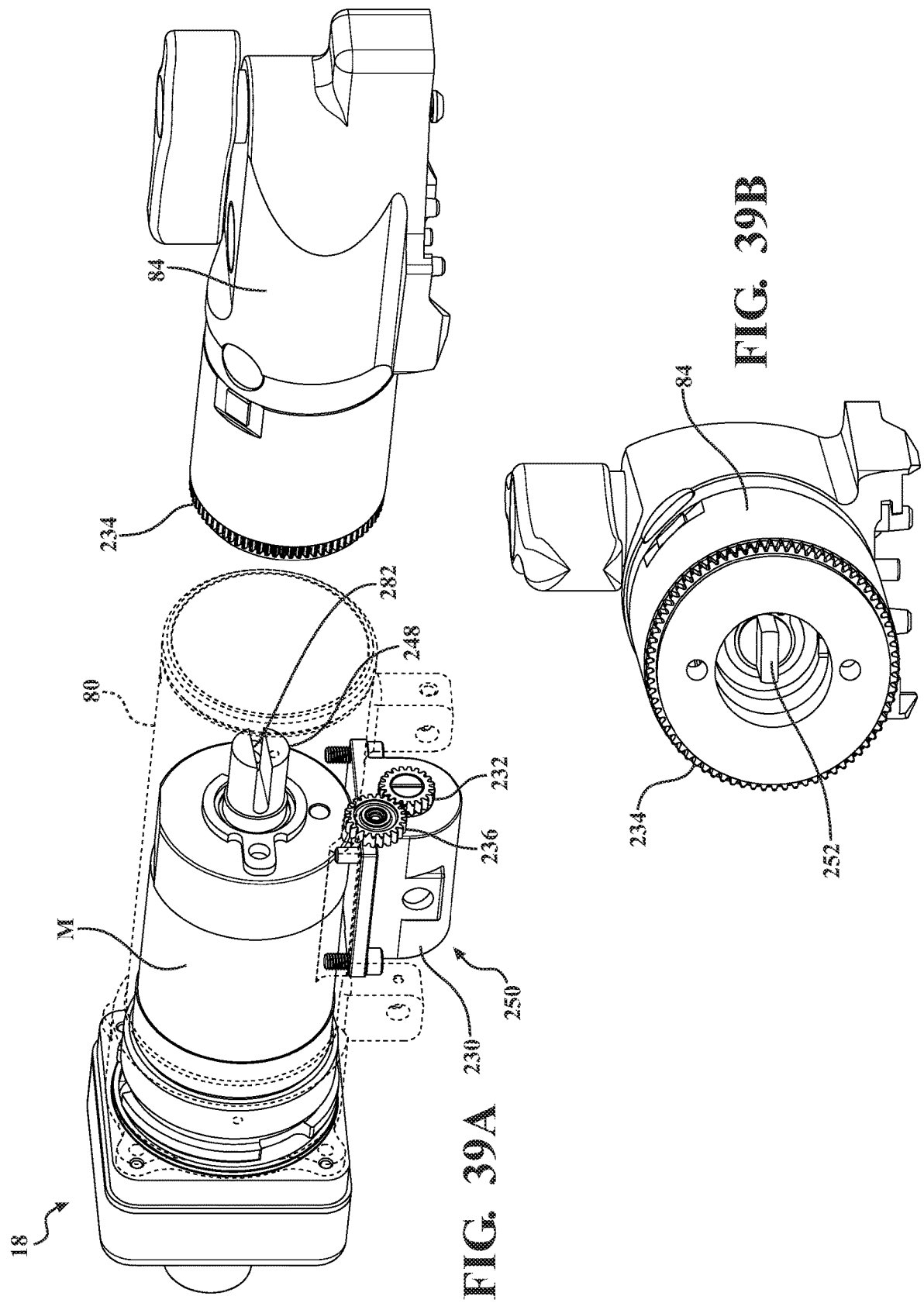

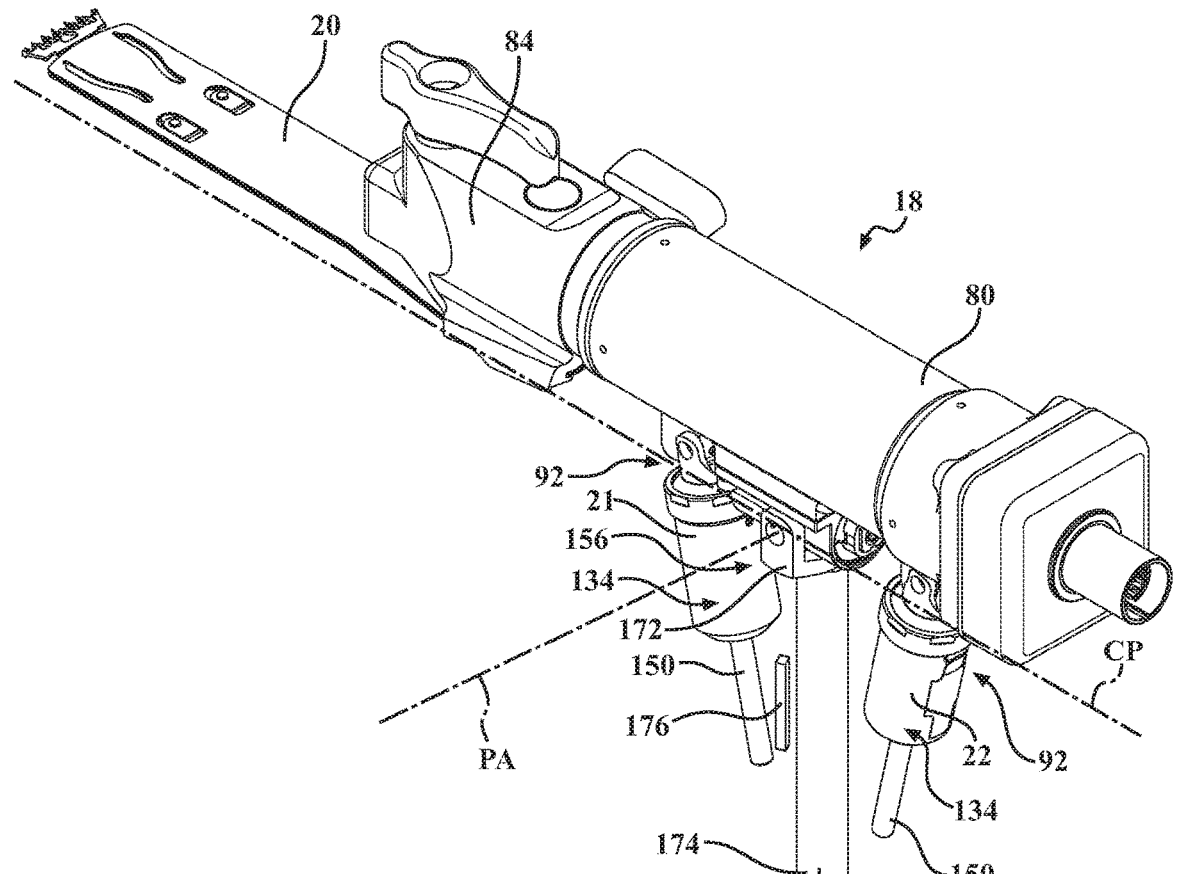
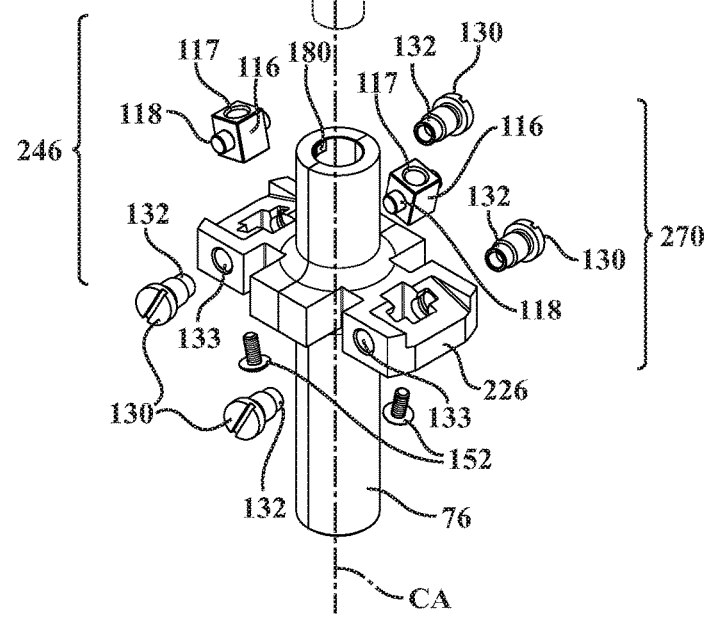
FIG. 42

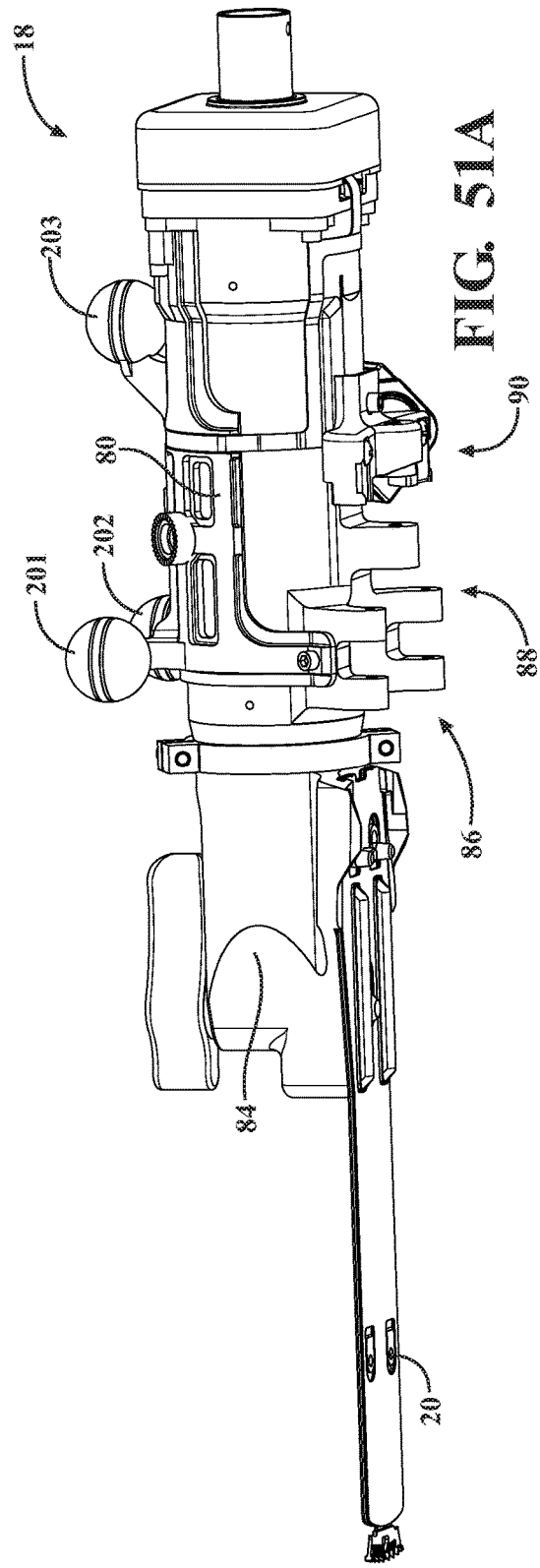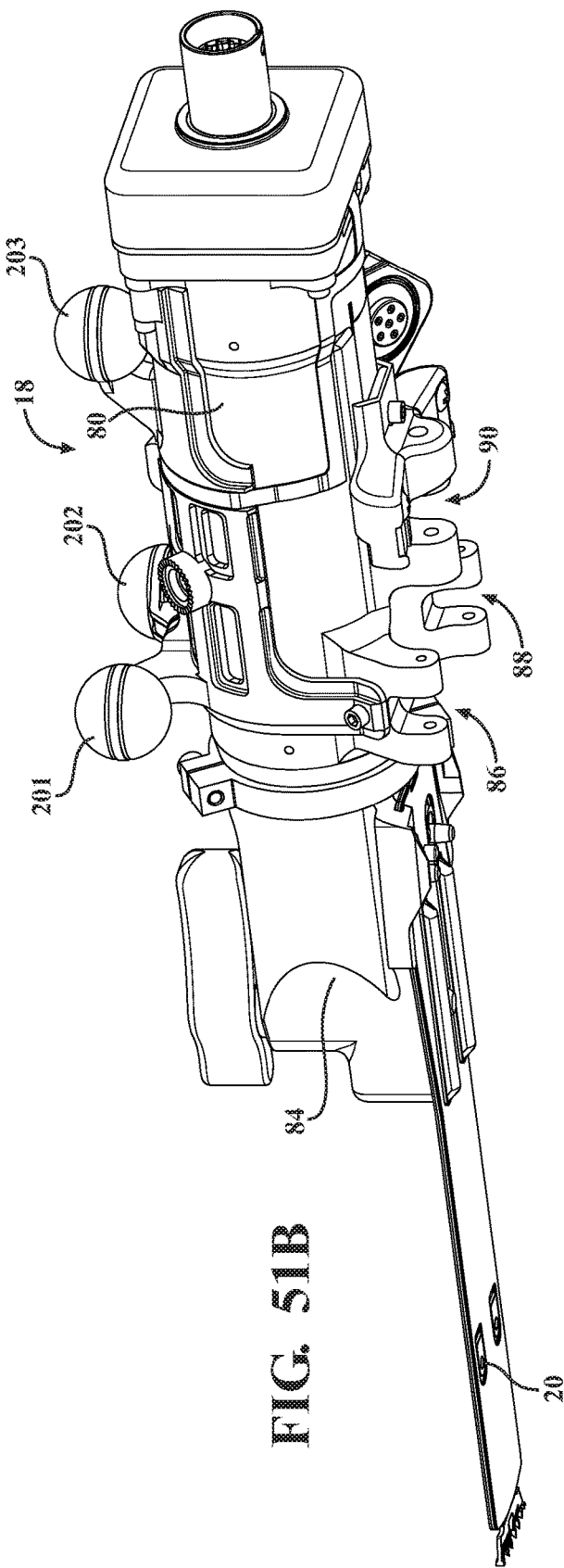

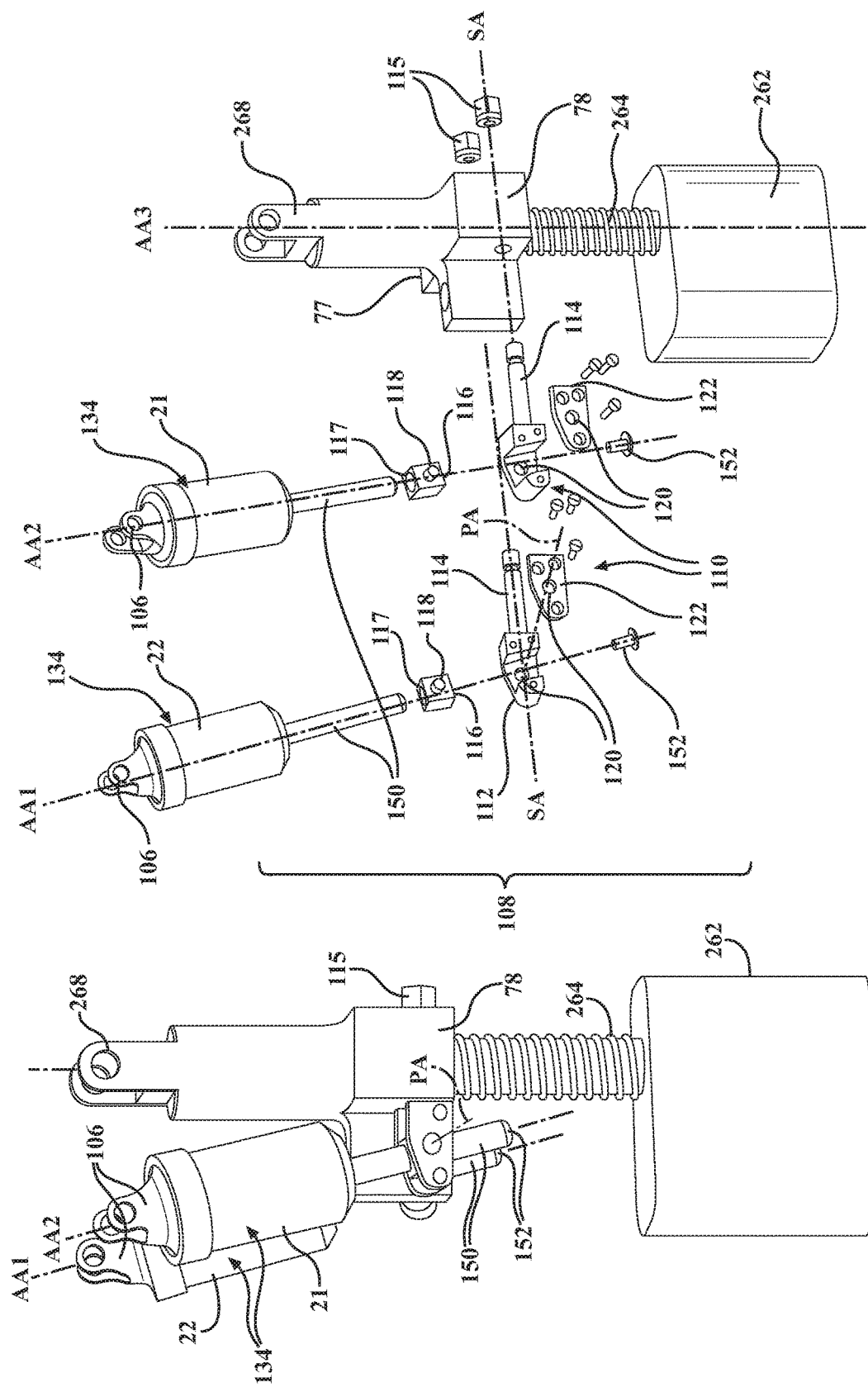

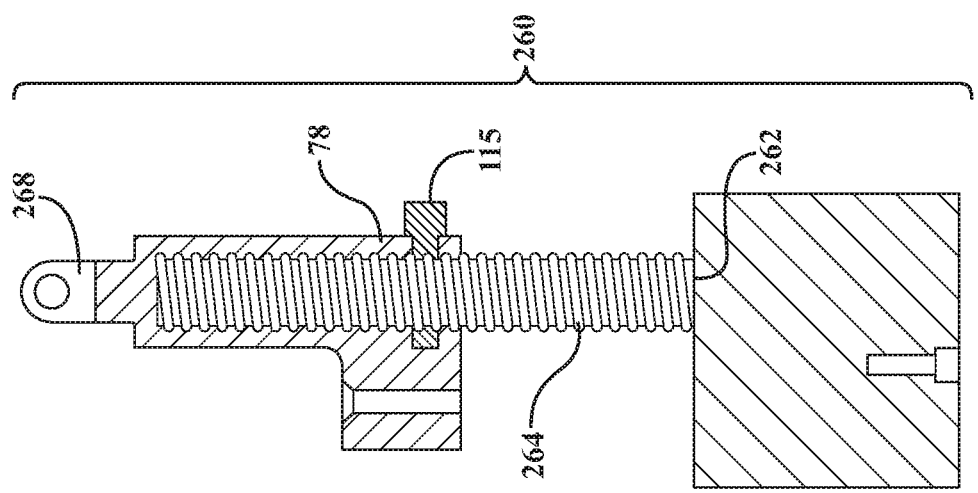
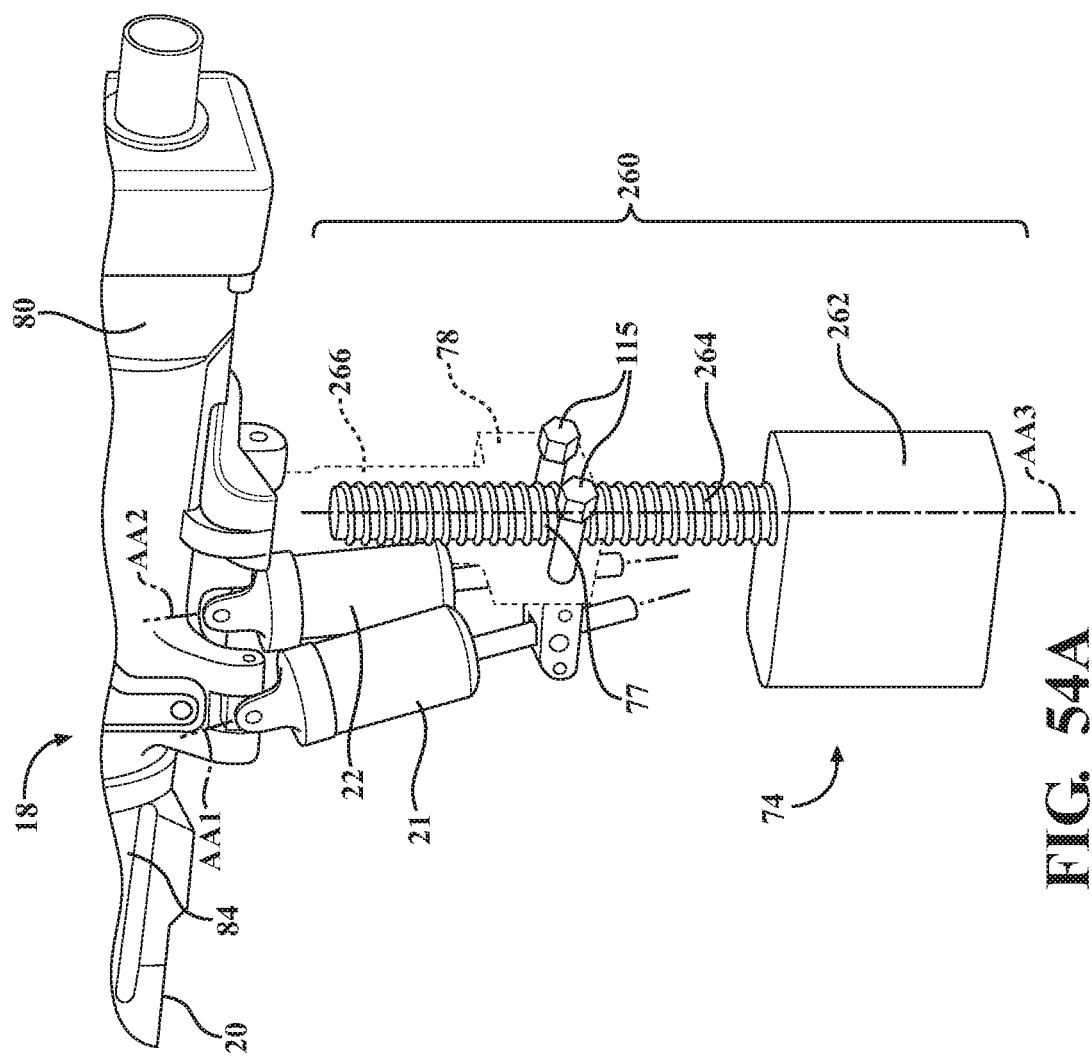

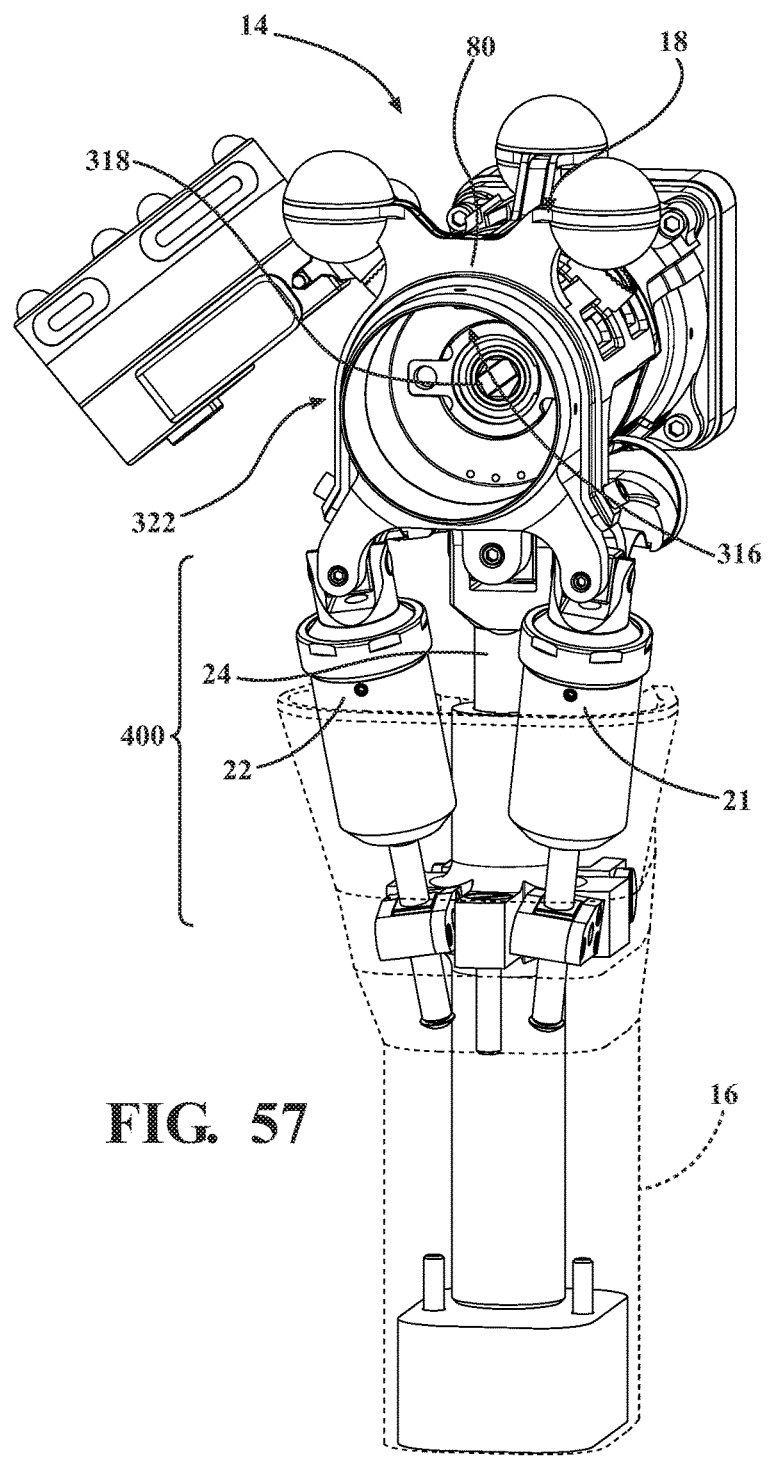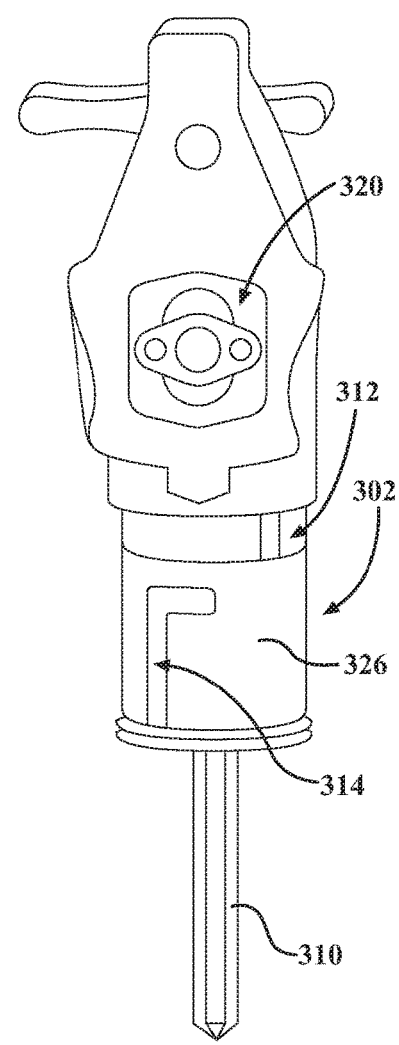
FIG. 57
FIG. 58A

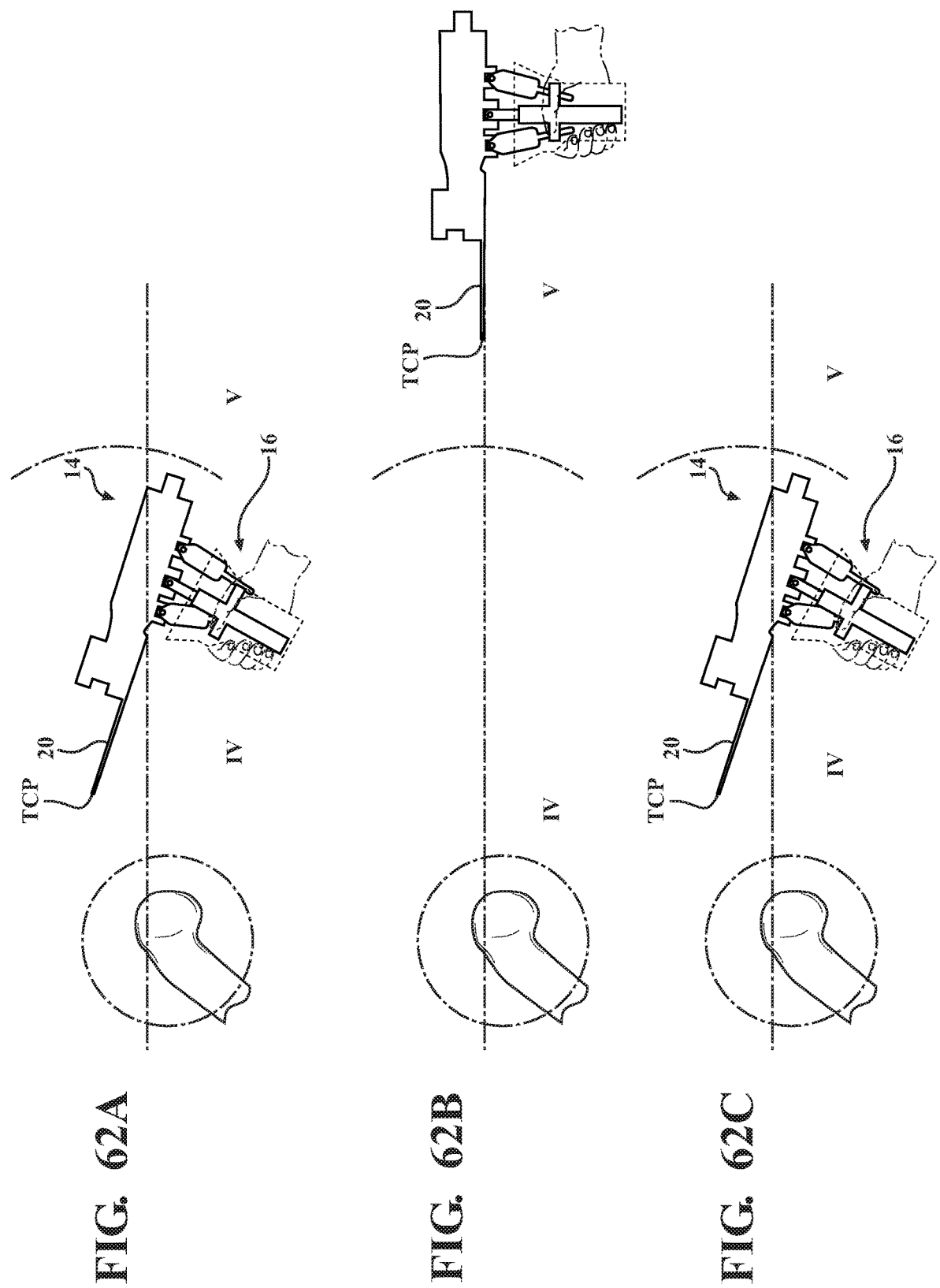

ROBOTIC HAND-HELD SURGICAL INSTRUMENT SYSTEMS AND METHODS

The subject patent application is a national entry of International Application No. PCT/US2020/042128, filed Jul. 15, 2020, which claims priority to and all the benefits of U.S. Provisional Application No. 62/874,107, filed Jul. 15, 2019, and U.S. Provisional Application No. 63/015,184, filed Apr. 24, 2020 the entire contents of each are incorporated herein by reference.

TECHNICAL FIELD

The present disclosure relates generally to surgical robotic hand-held instrument systems and methods of use.

BACKGROUND

Physical cutting guides are used to constrain surgical tools when resecting tissue from a patient. In some cases, physical cutting guides constrain such surgical tools for the purpose of preparing joints to accept replacement implants. The time required to position and secure a physical cutting guide to the patient can represent a significant portion of the overall time required to perform a surgical procedure.

Navigation systems (also referred to as tracking systems) can be used to properly align and secure jigs, as well as track a position and/or orientation of a surgical tool used to resect tissue from a patient. Tracking systems typically employ one or more trackers associated with the tool and the tissue being resected. A display can then be viewed by a user to determine a current position of the tool relative to a desired cut path of tissue to be removed. The display may be arranged in a manner that requires the user to look away from the tissue and surgical site to visualize the tool's progress. This can distract the user from focusing on the surgical site. Also, it may be difficult for the user to place the tool in a desired manner.

Robotically assisted surgery typically relies on large robots with robotic arms that can move in six degrees of freedom (DOF). These large robots may be cumbersome to operate and maneuver in the operating room.

There is a need for systems and methods to address one or more of these challenges.

SUMMARY

A robotic instrument is provided for use with a tool. The robotic instrument comprises a hand-held portion to be held by a user. A tool support is movably coupled to the hand-held portion to support the tool. A plurality of actuators operatively interconnect the tool support and the hand-held portion to move the tool support in three degrees of freedom relative to the hand-held portion. Each of the plurality of actuators is actively adjustable. A constraint assembly has a passive linkage that operatively interconnects the tool support and the hand-held portion. The passive linkage is coupled to the tool support and the hand-held portion in a manner configured to constrain movement of the tool support relative to the hand-held portion in three degrees of freedom.

Another robotic instrument is provided for use with a saw blade. The robotic instrument comprises a hand-held portion to be held by a user. A blade support is movably coupled to the hand-held portion to support the saw blade. A plurality of actuators operatively interconnect the blade support and the hand-held portion to move the blade support in three degrees of freedom relative to the hand-held portion. A constraint assembly operatively interconnects the blade support and the hand-held portion to constrain movement of the blade support relative to the hand-held portion in three degrees of freedom. A controller is coupled to the plurality of actuators to control adjustment of the plurality of actuators to define a virtual saw cutting guide.

Another system is provided for use with a tool. The system comprises an instrument having a hand-held portion to be held by a user and a tool support coupled to the hand-held portion to support the tool. A guidance array is coupled to the instrument and controllable to visually indicate to the user desired changes in pitch orientation, roll orientation, and translation of the hand-held portion to achieve a desired pose of the tool. A controller is coupled to the guidance array and configured to automatically adjust the guidance array to visually indicate the desired changes in pitch orientation, roll orientation, and translation while the user moves the hand-held portion of the instrument.

Another system is provided for use with a tool. The system comprises an instrument having a hand-held portion to be held by a user and a tool support coupled to the hand-held portion to support the tool. A guidance array is coupled to the instrument and controllable to visually indicate to the user desired changes in pitch orientation, roll orientation, and translation of the tool to achieve a desired pose. The guidance array is arranged to represent a plane of the tool. A controller is coupled to the guidance array and configured to automatically adjust the guidance array to visually indicate the desired changes in pitch orientation, roll orientation, and translation while the user moves the tool.

Another robotic system is provided for use with a tool. The robotic system comprises a hand-held portion to be held and supported by a user. A tool support is movably coupled to the hand-held portion to support the tool. A plurality of actuators operatively interconnect the tool support and the hand-held portion to move the tool support in three degrees of freedom relative to the hand-held portion to place the tool on a desired trajectory or plane. Each of the plurality of actuators is adjustable between maximum and minimum positions and has a home position between the maximum and minimum positions. Visual indicators are associated with the plurality of actuators to indicate desired movement of the hand-held portion. A controller is coupled to the visual indicators to control operation of the visual indicators to indicate the desired movement of the hand-held portion.

Another robotic system is provided. The robotic system comprises a hand-held portion to be held by a user. A tool support is movably coupled to the hand-held portion to support the tool. A plurality of actuators operatively interconnect the tool support and the hand-held portion to move the tool support in three degrees of freedom relative to the hand-held portion to place the tool on a desired trajectory or plane. Each of the plurality of actuators is adjustable between maximum and minimum positions and has a home position between the maximum and minimum positions. Visual indicators are associated with the plurality of actuators to indicate desired movement of the hand-held portion. A controller is coupled to the plurality of actuators and the visual indicators to control operation in a plurality of modes including a home mode in which the controller automatically adjusts each of the plurality of actuators to their home position, an approach mode in which the controller indicates the desired movement of the tool to place the tool on the desired trajectory or plane while the plurality of actuators are at their home positions, and an on-target mode in which the tool is generally located on the desired trajectory or plane and the controller indicates the desired movement of the hand-held portion to maintain the tool on the desired trajectory or plane.

A method is provided for using a robotic instrument with a tool, the robotic instrument comprising a hand-held portion to be held by a user, a tool support movably coupled to the hand-held portion to support the tool, a plurality of actuators operatively interconnecting the tool support and the hand-held portion, and a constraint assembly having a passive linkage operatively interconnecting the tool support and the hand-held portion. The method comprises moving the tool support in three degrees of freedom relative to the hand-held portion by actively adjusting one or more effective lengths of the plurality of actuators and constraining movement of the tool support relative to the hand-held portion in three degrees of freedom.

A method is provided for guiding movement of an instrument having a hand-held portion to be held by a user, a tool support coupled to the hand-held portion to support a tool, and a guidance array coupled to the instrument and arranged to represent a plane of the tool. The method comprises visually indicating to the user desired changes in pitch orientation, roll orientation, and translation of the tool to achieve a desired pose.

Another method is provided for guiding movement of a robotic instrument, the robotic instrument having a hand-held portion to be held and supported by a user, a tool support movably coupled to the hand-held portion to support a tool, a plurality of actuators operatively interconnecting the tool support and the hand-held portion to move the tool support in three degrees of freedom relative to the hand-held portion to place the tool on a desired trajectory or plane, and visual indicators associated with the plurality of actuators. The method comprises adjusting each of the plurality of actuators to a home position between maximum and minimum positions and indicating desired movement of the hand-held portion with the visual indicators.

Another method is provided for guiding movement of a robotic instrument, the robotic instrument having a hand-held portion to be held by a user, a tool support movably coupled to the hand-held portion to support a tool, a plurality of actuators operatively interconnecting the tool support and the hand-held portion to move the tool support in three degrees of freedom relative to the hand-held portion to place the tool on a desired trajectory or plane, and visual indicators associated with the plurality of actuators. The method comprises controlling operation of the robotic instrument in a plurality of modes including: a home mode in which the controller automatically adjusts each of the plurality of actuators to a home position between maximum and minimum positions; an approach mode in which the controller indicates the desired movement of the tool to place the tool on the desired trajectory or plane while the plurality of actuators are at their home positions; and an on-target mode in which the tool is generally located on the desired trajectory or plane and the controller indicates the desired movement of the hand-held portion to maintain the tool on the desired trajectory or plane.

In one example, a robotic surgical instrument is provided. The robotic surgical instrument comprising a hand-holdable body to be held by a user, a tool support movably coupled to the hand-holdable body, a tool coupler supported by the tool support, and a plurality of actuators to move the tool support in a plurality of degrees of freedom relative to the hand-holdable body. The plurality of actuators including a pair of linear actuators operatively interconnecting the tool support and the hand-holdable body. Each of the pair of linear actuators having a first portion connected to the hand-holdable body and a second portion connected to the tool support, arranged to control elevation and pitch of the tool support relative to the hand-holdable body. The plurality of actuators further include a rotary actuator arranged to control roll movement of the tool coupler relative to the tool support and the hand-holdable body.

In a further example, a robotic surgical instrument for use with a surgical tool is provided. The surgical instrument comprising a hand-holdable body to be held by a user, a tool support movably coupled to the hand-holdable body to support the tool, and a plurality of actuators to move the tool support in a plurality of degrees of freedom relative to the hand-holdable body. The plurality of actuators including an elevation actuator with a first portion connected to the hand-holdable body and a second portion connected to the tool support, and a pair of secondary actuators. Each of the pair of secondary actuators including an actuator portion operatively connected to the elevation actuator and a support portion operatively connected to the tool support such that each of the pair of secondary actuators is arranged to effectively operate between the elevation actuator and the tool support to move the tool support relative to the elevation actuator. The elevation actuator is arranged to move both the tool support and the secondary actuators relative to the hand-holdable body in one degree of freedom.

In another example, a robotic surgical instrument for use with a tool is provided. The surgical instrument comprising a pistol grip to be held by a user, the pistol grip having a distal end and a proximal end, a tool support movably coupled to the pistol grip to support the tool, and a plurality of actuators operatively interconnecting the tool support and the pistol grip to move the tool support in a plurality of degrees of freedom relative to the pistol grip. The plurality of actuators including: an elevation actuator comprising a motor located in the pistol grip connected to a shaft, and a carriage connected to the tool support and that translates along the shaft when the motor is activated. The plurality of actuators further including a pair of secondary actuators, each secondary actuator being coupled with the carriage and the tool support, located distal to the elevation actuator.

One general aspect includes a hand-held robotic system for use with a saw blade in performing surgery. The hand-held robotic system also includes an instrument may include a hand-held portion to be held by a user; and a blade support coupled to the hand-held portion to support the saw blade; an actuator assembly operatively interconnecting the blade support and the hand-held portion to move the blade support in three degrees of freedom relative to the hand-held portion, the actuator assembly including a plurality of actuators. The system also includes a guidance array that may include a plurality of visual indicators, the guidance array coupled to the instrument and controllable to visually indicate to the user one or more desired changes in pitch orientation, roll orientation, and translation of the hand-held portion to achieve a desired pose of the hand-held portion; and a controller configured to control adjustment of the plurality of actuators to maintain the saw blade along a desired plane. The system also includes the controller further configured to control the guidance array based on actuator information of an actuator of the plurality of actuators to visually indicate the one or more desired changes in pitch orientation, roll orientation, and translation position while the user moves the instrument.

One general aspect includes a hand-held robotic system for use with a saw blade. The hand-held robotic system also includes an instrument may include a hand-held portion to be held and supported by a user; a blade support movably coupled to the hand-held portion to support the saw blade; an actuator assembly operatively interconnecting the blade support and the hand-held portion to move the blade support in three degrees of freedom relative to the hand-held portion to place the saw blade on a desired plane, the actuator assembly including a plurality of actuators; and a visual indicator to indicate desired movement of the hand-held portion; and a controller configured to control adjustment of the plurality of actuators to maintain the saw blade along the desired plane, the controller configured to control the visual indicator to visually indicate changes in pitch orientation, roll orientation, and translation position while the user moves the instrument based on actuator information about an actuator of the plurality of actuators.

One general aspect includes a method of controlling movement. The method of controlling movement may include determining a pose of the saw blade with the tracker with the localizer; determining a desired pose of the saw blade; determine a position of each of the plurality of actuators; determine a pose of the hand-held portion based on the position of each of the plurality of actuators; determining a commanded pose of the saw blade based on the pose of the saw blade determined by the localizer, the desired pose of the saw blade, and the pose of the hand-held portion; determining a commanded position of each of the plurality of actuators based on the commanded pose and based on the position of each of the plurality of actuators; and controlling each of plurality of actuators based on the commanded position. One general aspect includes controlling each of plurality of actuators based on the commanded position. This method of controlling movement may include determining a pose of the saw blade with the first tracker using the localizer; determining a pose of the hand-held portion with the second tracker using the localizer, and controlling one or more of the plurality of actuators to move towards a desired plane based on the pose of the saw blade and the pose of the hand-held portion.

One general aspect includes a method of controlling movement of a hand-held robotic system for use with a saw blade. The method of controlling movement also includes determining a position of the saw blade using the localizer in a known coordinate system; determining a position of a reference location associated with bone in the known coordinate system. The movement also includes determining a distance parameter based on the position of the reference location and the position of the saw blade; controlling the plurality of actuators to move the saw blade towards the desired plane at a first value of a motion parameter between the saw blade and the hand-held portion; and controlling the plurality of actuators to move the saw blade towards the desired plane at a second value of the motion parameter between the saw blade and the hand-held portion, where the first value is different from the second value, the controller is operable to change operation from the first value to the second value based on the distance parameter.

One general aspect includes a hand-held robotic system for use with a saw blade. The hand-held robotic system also includes an instrument that may include a hand-held portion to be held by a user and a blade support coupled to the hand-held portion to support the saw blade; an actuator assembly operatively interconnecting the blade support and the hand-held portion to move the blade support in three degrees of freedom relative to the hand-held portion. The system also includes a guidance array that may include a plurality of visual indicators, the guidance array being coupled to the instrument and controllable to visually indicate to the user one or more desired changes in pitch orientation, roll orientation, and translation of the hand-held portion to achieve a desired pose of the hand-held portion. The system may include a controller coupled to the plurality of actuators to control adjustment of the plurality of actuators to maintain the saw blade along a desired plane based on a pose of the saw blade and the pose of the hand-held portion, the controller further coupled to the guidance array and configured to control the guidance array to visually indicate the one or more desired changes in pitch orientation, roll orientation, and translation position while the user moves the instrument based on the desired plane of the blade.

One general aspect includes a hand-held robotic system for use with a saw blade. The hand-held robotic system also includes an instrument that may include a hand-held portion to be held and supported by a user, a blade support movably coupled to the hand-held portion to support the blade; an actuator assembly operatively interconnecting the blade support and the hand-held portion to move the blade support in three degrees of freedom relative to the hand-held portion to place the saw blade on a desired plane, the actuator assembly including a plurality of actuators. The system also includes a visual indicator to indicate desired movement of the hand-held portion; and a controller coupled to the plurality of actuators to control adjustment of the plurality of actuators to maintain the saw blade along the desired plane based on a pose of the saw blade and the pose of the hand-held portion. The controller may be coupled to the visual indicator and configured to control the visual indicator to visually indicate changes in pitch orientation, roll orientation, and translation position of the hand-held portion to achieve a desired hand-held portion pose based on the desired plane of the blade.

One general aspect includes a hand-held robotic system for use with a saw blade. The hand-held robotic system also includes an instrument may include a hand-held portion to be held by a user and a blade support coupled to the hand-held portion, the blade support may include a saw drive motor to drive motion of the saw blade; an actuator assembly operatively interconnecting the blade support and the hand-held portion to move the blade support in three degrees of freedom relative to the hand-held portion to place the saw blade on a desired plane, the actuator assembly including a plurality of actuators. The system also includes a localizer configured to determine a position of the saw blade and a reference location associated with a bone in a known coordinate system; and a controller coupled to the plurality of actuators, the controller operable to control the plurality of actuators to move the saw blade towards the desired plane at a first value of a motion parameter between the saw blade and the hand-held portion, and the controller is further operable to control the plurality of actuators to move the saw blade towards the desired plane at a second value of the motion parameter between the saw blade and the hand-held portion, where the first value is different than the second value, the controller operable to change operation from the first value to the second value based on the position of the saw blade and the position of the reference location associated with bone.

One general aspect includes a hand-held robotic system for use with a saw blade. The hand-held robotic system includes an instrument that includes a hand-held portion to be held by a user and a blade support coupled to the hand-held portion, the blade support may include a saw drive motor to drive motion of the saw blade; an actuator assembly operatively interconnecting the blade support and the hand-held portion to move the blade support in three degrees of freedom relative to the hand-held portion to place the saw blade on a desired plane, the actuator assembly may include a plurality of actuators. The system also includes a localizer configured to determine a position of the saw blade and a reference location associated with a bone in a known coordinate system. The system may include a controller coupled to the plurality of actuators which is operable to control the plurality of actuators to move the saw blade towards the desired plane, and the controller is further operable to control a motor parameter of the saw drive motor at a first value and a second value, where the first value is different than the second value, the controller operable to change operation from the first value to the second value based on the position of the saw blade and the position of the reference location associated with bone.

One general aspect includes a hand-held robotic system for use with a saw blade. The hand-held robotic system includes an instrument that includes a hand-held portion to be held by a user and a blade support coupled to the hand-held portion, the blade support may include a saw drive motor to drive motion of the saw blade; an actuator assembly operatively interconnecting the blade support and the hand-held portion to move the blade support in three degrees of freedom relative to the hand-held portion to place the saw blade on a desired plane, the actuator assembly may include a plurality of actuators. The system also includes a localizer configured to determine a position of the saw blade and a reference location associated with a bone in a known coordinate system to determine a distance parameter. The system may include a controller coupled to the plurality of actuators, the controller operable to control the plurality of actuators to move the saw blade towards the desired plane, and the controller is further operable to control a motor parameter of the saw drive motor at a first value and a second value, where the first value is different than the second value, the controller operable to change operation from the first value to the second value based on the distance parameter.

One general aspect includes a hand-held robotic system for use with a saw blade. The hand-held robotic system includes an instrument that has a hand-held portion to be held by a user and a blade support coupled to the hand-held portion, the blade support may include a saw drive motor to drive motion of the saw blade; an actuator assembly operatively interconnecting the blade support and the hand-held portion to move the blade support in three degrees of freedom relative to the hand-held portion to place the saw blade on a desired plane, the actuator assembly may include a plurality of actuators. The system also includes a controller coupled to the plurality of actuators, which is operable to determine a pose of the saw blade, a desired pose of the saw blade, a position of each of the plurality of actuators, a pose of the hand-held portion based on the current position of each of the plurality of actuators, a commanded pose of the saw blade based on the pose of the saw blade, the desired pose of the saw blade, and the pose of the hand-held portion, and a commanded position for each of the plurality of actuators based on the commanded pose and based on the position. The system also includes the controller operable to control each of the plurality of actuators based on the commanded position.

One general aspect includes a hand-held robotic system for use with a saw blade. The hand-held robotic system includes an instrument that has a hand-held portion to be held by a user and a blade support coupled to the hand-held portion to support the saw blade; an actuator assembly operatively interconnecting the blade support and the hand-held portion to move the blade support in three degrees of freedom relative to the hand-held portion, the actuator assembly may include a plurality of actuators. The system also includes a guidance array which includes a plurality of visual indicators, the guidance array coupled to the instrument and controllable to visually indicate to the user one or more desired changes in pitch orientation, roll orientation, and translation of the saw blade to achieve a desired pose of the hand-held portion. The system may include a controller coupled to the guidance array and being configured to control the guidance array to visually indicate the one or more desired changes of the saw blade in pitch orientation, roll orientation, and translation position while the user moves the instrument based on actuator information about one or more of the plurality of actuators.

One general aspect includes a hand-held robotic system for use with a saw blade. The hand-held robotic system includes an instrument that has a hand-held portion to be held and supported by a user; a blade support movably coupled to the hand-held portion to support the blade; an actuator assembly operatively interconnecting the blade support and the hand-held portion to move the blade support in three degrees of freedom relative to the hand-held portion to place the saw blade on a desired plane, the actuator assembly may include a plurality of actuators. The system also includes a visual indicator to indicate desired movement of the saw blade. The system includes a controller coupled to the visual indicator and being configured to control the visual indicator to visually indicate changes in pitch orientation, roll orientation, and translation position of the saw blade while the user moves the instrument based on actuator information of the plurality of actuators.

One general aspect includes a hand-held robotic system for use with a saw blade. The hand-held robotic system also includes an instrument having a hand-held portion to be held by a user. The system also includes a blade support movably coupled to the hand-held portion to support the tool. The system also includes an actuator assembly operatively interconnecting the blade support and the hand-held portion to move the blade support in three degrees of freedom relative to the hand-held portion to place the saw blade on a desired plane, the actuator assembly may include a plurality of actuators, each of the plurality of actuators being adjustable between maximum and minimum positions and having a home position between the maximum and minimum positions. The system also includes a visual indicator to indicate desired movement of the hand-held portion. The system also includes a controller coupled to the plurality of actuators and the visual indicators to control operation in a plurality of modes including a first mode in which the controller automatically adjusts each of the plurality of actuators to their home position, and second mode in which the saw blade is generally located on the desired plane and the controller indicates the desired movement of the hand-held portion to maintain the saw blade on the desired plane.

One general aspect includes a hand-held robotic system for use with a saw blade. The hand-held robotic system includes an instrument may include; a hand-held portion to be held and supported by a user; a blade support movably coupled to the hand-held portion to support the blade; an actuator assembly operatively interconnecting the blade support and the hand-held portion to move the blade support in three degrees of freedom relative to the hand-held portion to place the saw blade on a desired plane, the actuator assembly may include a plurality of actuators. The system also includes a localizer configured to determine a position of the saw blade and a reference location associated with bone in a known coordinate system and a visual indicator. The system includes a controller that is coupled to the visual indicator, the controller being configured to control the visual indicator in a first mode to visually indicate changes in pitch orientation, roll orientation, and translation position of the saw blade while the user moves the instrument based on actuator information of the plurality of actuators, the controller further configured to control the visual indicator in a second mode to visually indicate changes in pitch orientation, roll orientation, and translation position of the hand-held portion while the user moves the instrument based on actuator information of the plurality of actuators, the controller configured to switch between the first mode and the second mode based on the position of the saw blade and the position of the reference location or based on an input signal received from an input device.

One general aspect includes a hand-held robotic system for use with a saw blade. The hand-held robotic system includes an instrument that has a hand-held portion to be held by a user and a blade support coupled to the hand-held portion to support the saw blade; an actuator assembly operatively interconnecting the blade support and the hand-held portion to move the blade support in three degrees of freedom relative to the hand-held portion, the actuator assembly may include a plurality of actuators. The system may include a localizer configured to determine a position of the saw blade and a reference location associated with bone in a known coordinate system. The system also includes a guidance array that may include a plurality of visual indicators and a controller coupled to the guidance array. The controller may be configured to control the guidance array in a first mode to visually indicate one or more desired changes of the saw blade in pitch orientation, roll orientation, and translation position while the user moves the instrument based on actuator information about one or more of the plurality of actuators, and the controller is further configured to control the guidance array in a second mode to visually indicate one or more changes in pitch orientation, roll orientation, and translation position of the hand-held portion while the user moves the instrument based on actuator information of the plurality of actuators, the controller configured to switch between the first mode and the second mode based on the position of the saw blade and the position of the reference location or based on an input signal received from an input device.

BRIEF DESCRIPTION OF THE DRAWINGS

Advantages of the present disclosure will be readily appreciated as the same becomes better understood by reference to the following detailed description when considered in connection with the accompanying drawings.

FIG. 6 is a front perspective view of the robotic instrument illustrating one particular pose of a tool support relative to a hand-held portion.

FIG. 10 is a rear elevational view of the robotic instrument.

FIG. 11 is a front elevational view of the robotic instrument.

FIGS. 23A-23D illustrate use of a guidance array.

FIGS. 30 and 31 are perspective views of flex circuits used in the robotic instrument of FIG. 28.

FIG. 37 is a rear perspective view of the alternative configuration of the robotic instrument of FIG. 35.

FIG. 38A is a side elevational view of the alternative configuration of the robotic instrument of FIG. 35 showing linear actuators and a rotary actuator assembly.

FIGS. 39A and 39B show the tool support with a motor separated from a head of the robotic instrument, the head including a ring gear.

FIG. 42 is an exploded view showing a base of the hand-held portion and associated joint connections to the plurality of actuators.

FIGS. 51A and 51B are perspective views of a tool support of the robotic instrument of FIG. 46.

FIG. 53A in a side perspective view that shows the actuator assembly including an elevation actuator and a pair of secondary actuators.

FIG. 53B shows an exploded view of the actuator assembly.

FIG. 54A is a perspective view of the actuator assembly attached with the tool support.

FIG. 54B is a cross sectional view of the elevation actuator.

FIG. 57 shows a perspective view of an alternative configuration of the robotic instrument with a modular tool system.

FIGS. 58A-58D depict perspective views of the multiple modular tool attachments for use with the robotic instrument of FIG. 57.

FIGS. 62A-62C illustrate one example of actuator control in a selected mode.

DETAILED DESCRIPTION

Overview

Figure 1:
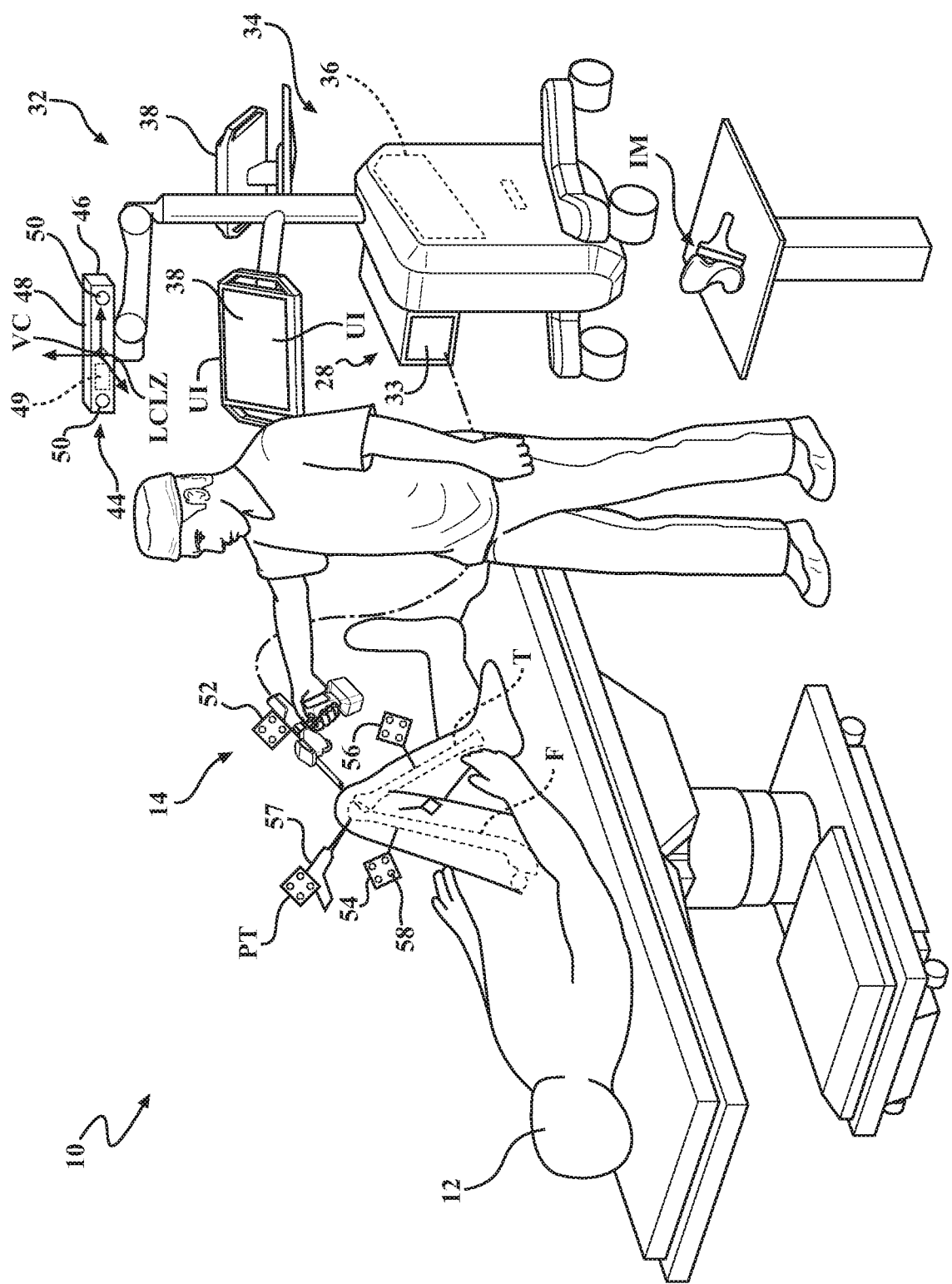
FIG. 1 is a perspective view of a robotic system.

Referring to FIG. 1, a robotic system 10 is illustrated. The robotic system 10 is shown performing a total knee procedure on a patient 12 to resect portions of a femur F and tibia T of the patient 12 so that the patient 12 can receive a total knee implant IM. The robotic system 10 may be used to perform other types of surgical procedures, including procedures that involve hard/soft tissue removal, or other forms of treatment. For example, treatment may include cutting tissue, coagulating tissue, ablating tissue, stapling tissue, suturing tissue, or the like. In some examples, the surgical procedure involves knee surgery, hip surgery, shoulder surgery, spine surgery, and/or ankle surgery, and may involve removing tissue to be replaced by surgical implants, such as knee implants, hip implants, shoulder implants, spine implants, and/or ankle implants. The robotic system 10 and techniques disclosed herein may be used to perform other procedures, surgical or non-surgical, and may be used in industrial applications or other applications where robotic systems are utilized.

Figure 2:
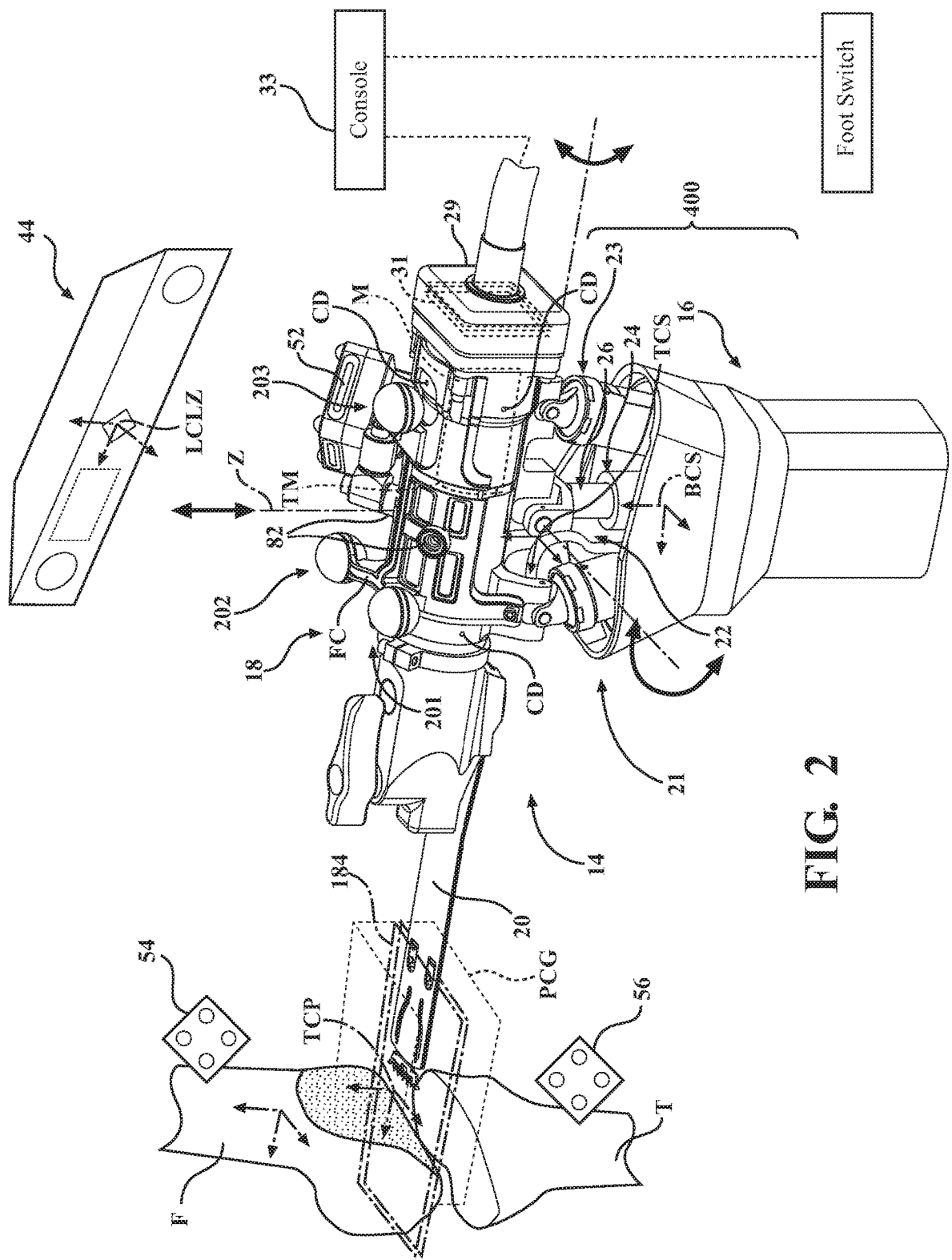
FIG. 2 is a perspective view of a robotic instrument being used to cut five planes on a femur to receive a total knee implant.
Figure 3A:
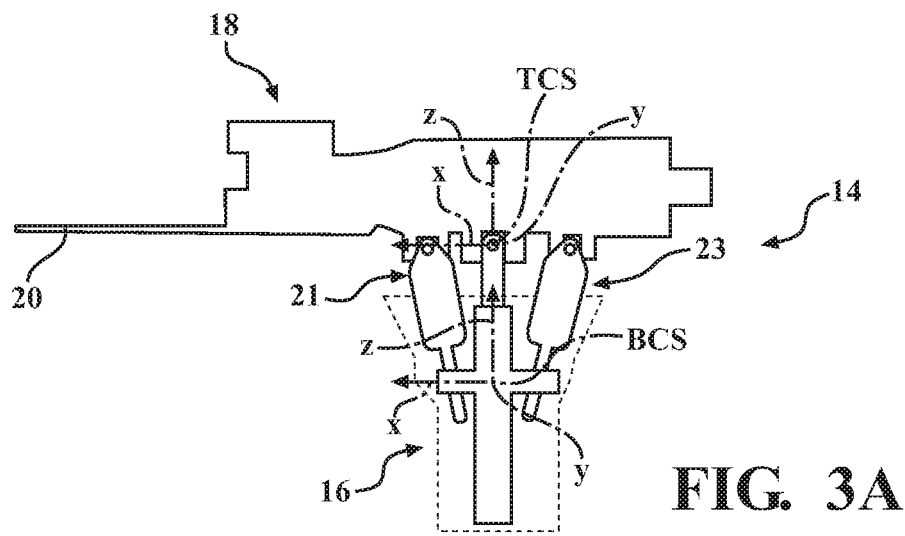
FIGS. 3A-3C are illustrations of various pitch orientations of the robotic instrument.
Figure 3B:
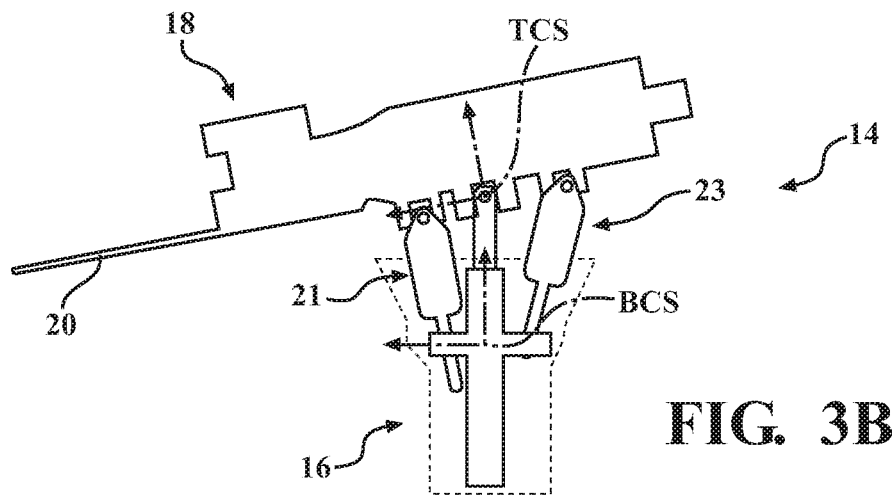
Figure 3C:
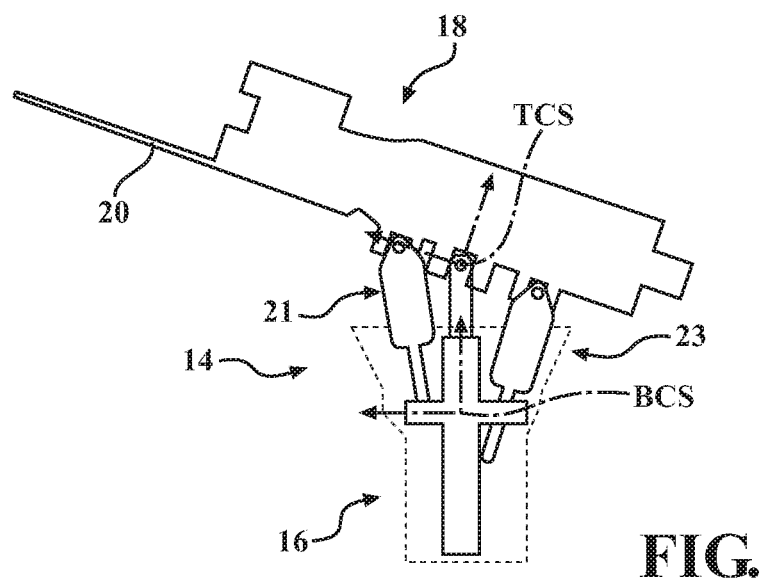
Figure 4C:
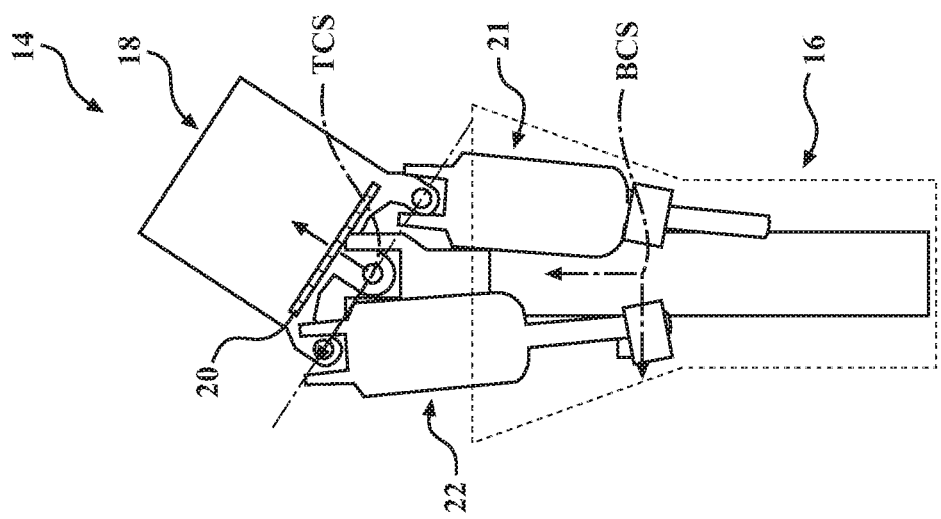
FIGS. 4A-4C are illustrations of various roll orientations of the robotic instrument.
Figure 4B:
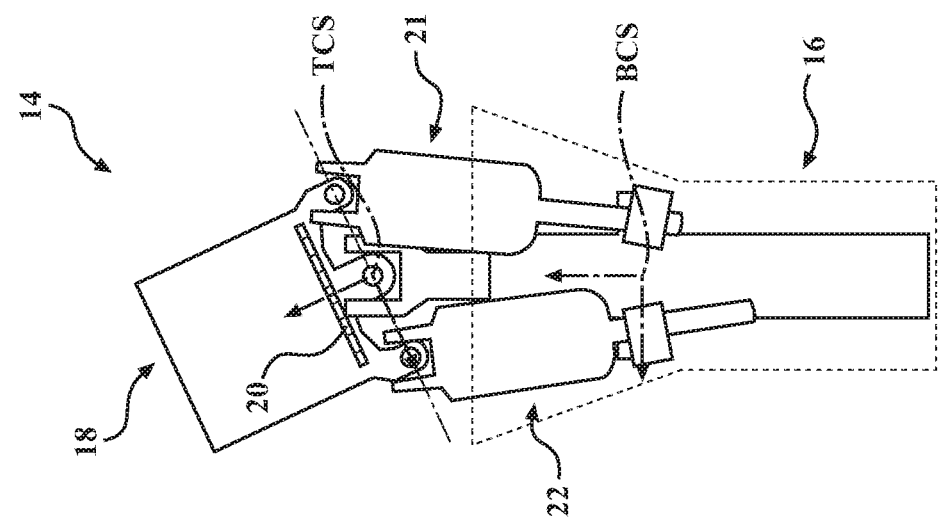
Figure 4A:
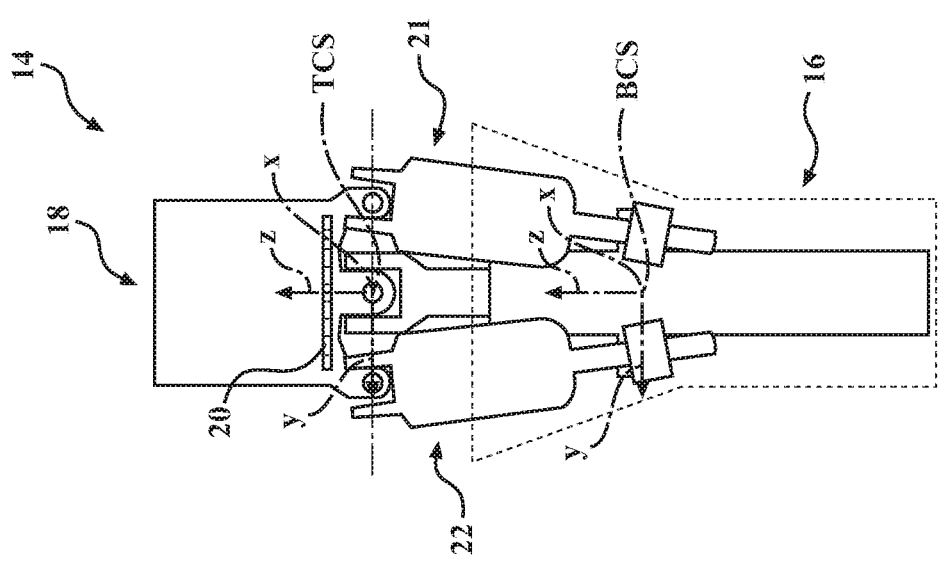
Figure 5A:
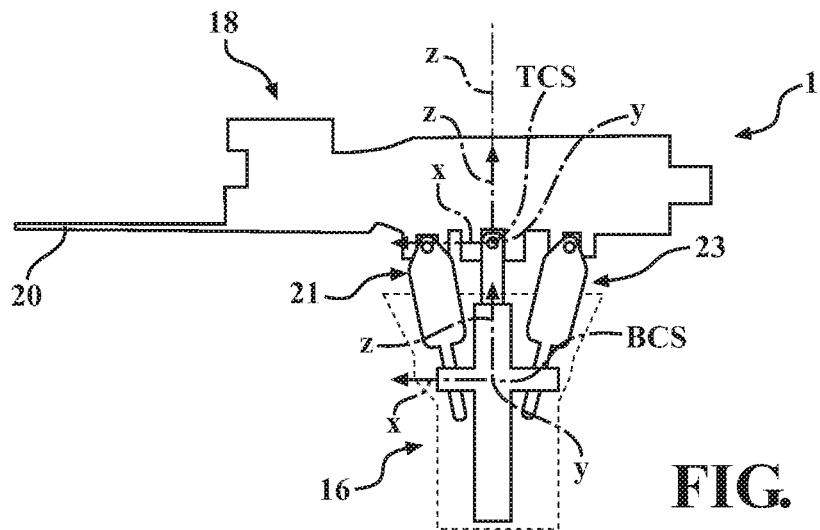
FIGS. 5A-5C are illustrations of various z-axis translation positions of the robotic instrument.
Figure 5B:
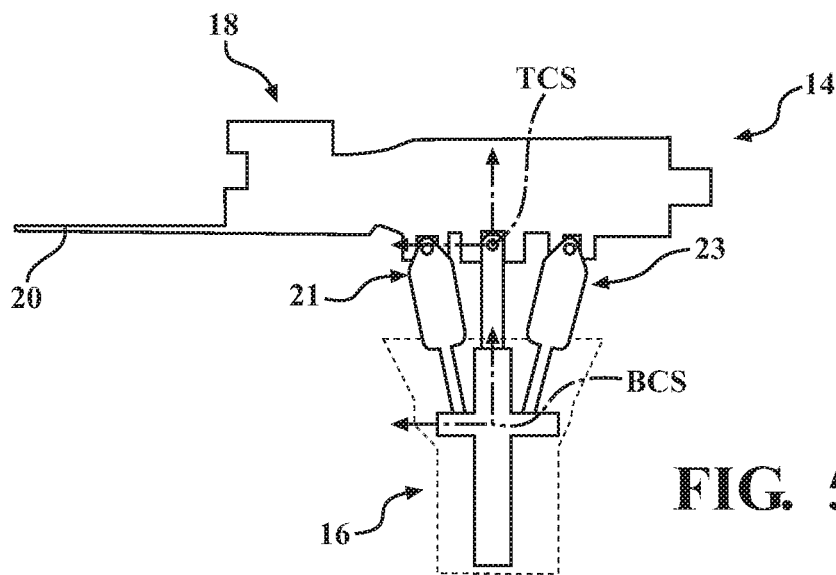
Figure 5C:
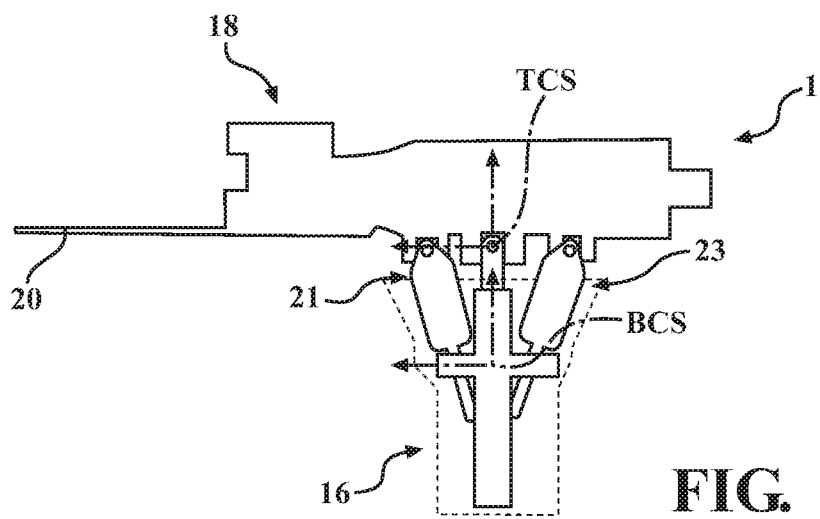
Figure 70:
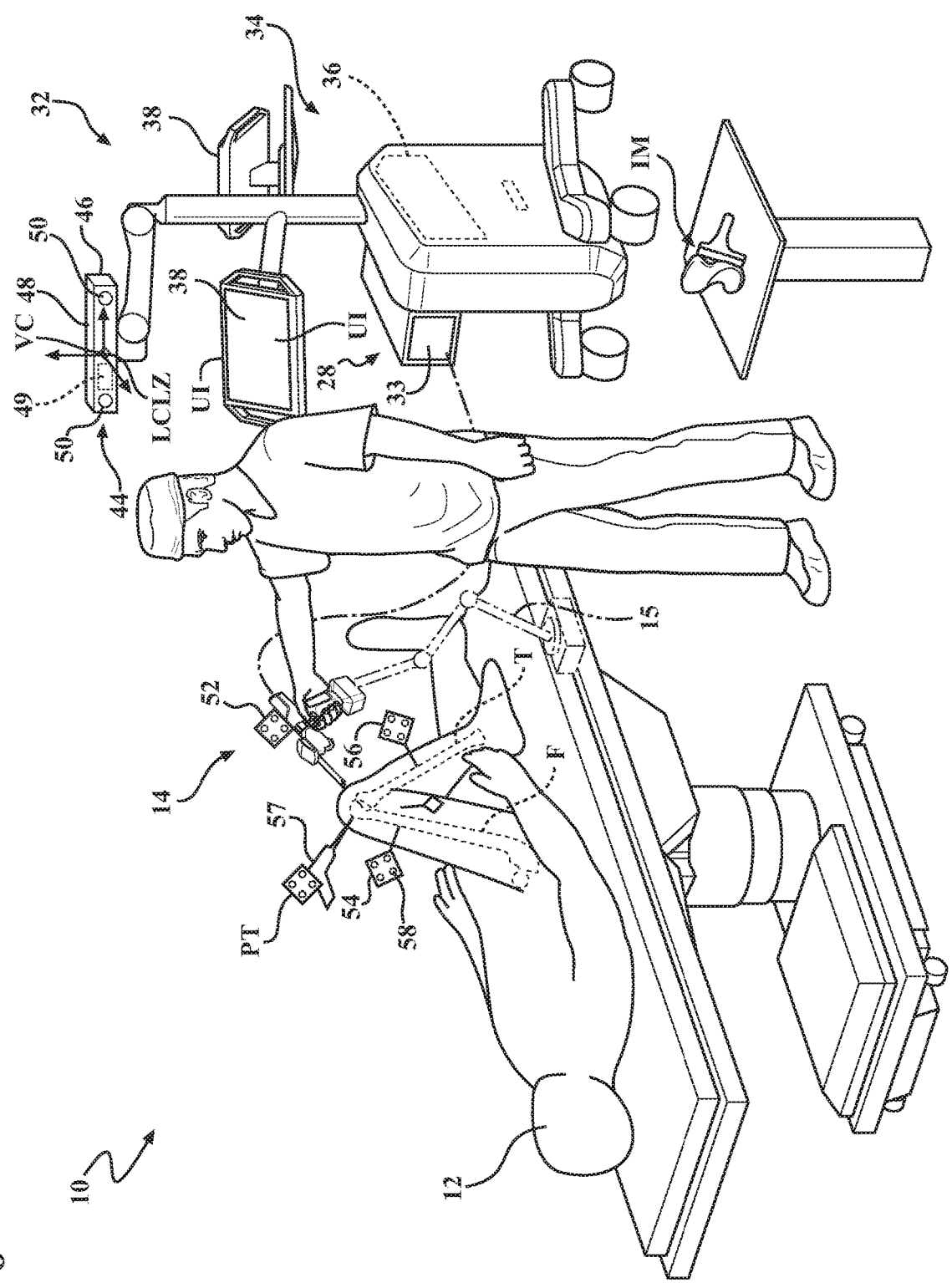
FIG. 70 is perspective view of an alternative configuration of the robotic system.

Referring to FIGS. 1 and 2, the robotic system 10 includes a robotic instrument 14. In some examples, a user manually holds and supports the instrument 14 (as shown in FIG. 1). In some examples, referring to FIG. 70, the user may manually hold the instrument 14 while the instrument is being at least partially, or fully, supported by an assistive device, such as a passive arm (e.g., linkage arm with locking joints), an active arm, and/or the like (see, e.g., passive arm 15 shown by hidden lines in FIG. 70). As best shown in FIGS. 1 and 2, the instrument 14 comprises a hand-held portion 16 for being manually grasped and/or supported by the user and/or assistive device.

The instrument 14 may be freely moved and supported by a user without the aid of a guide arm, e.g., configured to be held by a human user while effecting physical removal of material such that the weight of the tool is supported solely by a hand of the user during the procedure. Put another way, the instrument 14 may be configured to be held such that the user's hand is supporting the instrument 14 against the force of gravity. The instrument 14 may weigh 8 lbs. or less, 6 lbs. or less, 5 lbs. or less, or even 3 lbs. or less. The instrument 14 may have a weight corresponding to ANSI/AAMI HE75: 2009. The instrument 14 also comprises a tool support 18 for receiving a tool 20. The method for operating the instrument 14 may include a user suspending the weight of the instrument 14 without any assistance from a passive arm or robotic arm. The passive arm and the contents of U.S. Pat. No. 9,060,794 to Kang et al. are incorporated herein by reference. The robotic system 10, in some examples, may be free from a robot arm having more than one joint in series.

The tool 20 couples to the tool support 18 to interact with the anatomy in certain operations of the robotic system 10 described further below. The tool 20 may also be referred to as an end effector. The tool 20 may be removable from the tool support 18 such that new/different tools 20 can be attached when needed. The tool 20 may also be permanently fixed to the tool support 18. The tool 20 may comprise an energy applicator designed to contact the tissue of the patient 12. In some examples, the tool 20 may be a saw blade, as shown in FIGS. 1 and 2, or other type of cutting accessory. In such instances, the tool support may be referred to as a blade support. It should be appreciated that in any instance where blade support is referred to, it may be substituted for the term 'tool support' and vice-versa. However, other tools may be contemplated, such as the contents of U.S. Pat. No. 9,707,043 to Bozung, which are incorporated herein by reference. In some examples, the tool 20 may be a drill bit, an ultrasonic vibrating tip, a bur, a stapler, or the like. The tool 20 may comprise the blade assembly shown in U.S. Pat. No. 9,820,753 to Walen et al. or U.S. Pat. No. 10,687,823, hereby incorporated herein by reference. The tool support 18 may incorporate a drive motor M and other driving components shown in U.S. Pat. No. 9,820,753 to Walen et al., to drive oscillating motion of the blade assembly. Such driving components may comprise a transmission TM coupled to the drive motor M to convert rotary motion from the drive motor M into oscillating motion of the tool 20.

An actuator assembly 400 comprising one or more actuators 21, 22, 23 move the tool support 18 in three degrees of freedom relative to the hand-held portion 16 to provide robotic motion that assists in placing the tool 20 at a desired position and/or orientation (e.g., at a desired pose relative to the femur F and/or tibia T during resection), while the user manually holds the hand-held portion 16. The actuator assembly 400 may comprise actuators 21, 22, 23 that are arranged in parallel, in series, or both. In some examples, the actuators 21, 22, 23 move the tool support 18 in three or more degrees of freedom relative to the hand-held portion 16. In some examples, the actuator assembly 400 is configured to move the tool support 18 relative to the hand-held portion 16 in at least two degrees of freedom, such as pitch and z-axis translation. In some examples, such as shown herein, the actuators 21, 22, 23 move the tool support 18 and its associated tool support coordinate system TCS in only three degrees of freedom relative to the hand-held portion 16 and its associated base coordinate system BCS. For example, the tool support 18 and its tool support coordinate system TCS may: rotate about its y-axis to provide pitch motion; rotate about its x-axis to provide roll motion; and translate along an axis Z coincident with a z-axis of the base coordinate system BCS to provide z-axis translation motion. The allowed motions in pitch, roll, and z-axis translation are shown by arrows in FIG. 2 and in the schematic illustrations of FIGS. 3A-3C, 4A-4C, and 5A-5C, respectively. FIG. 6 provides one example of a pose of the tool support 18 and a pose of the hand-held portion 16 within the range of motion of the instrument 14. In some examples, not shown in the figures, actuators may move the tool support 18 in four or more degrees of freedom relative to the hand-held portion 16.

Referring back to FIG. 2, a constraint assembly 24 having a passive linkage 26 may be used to constrain movement of the tool support 18 relative to the hand-held portion 16 in the remaining three degrees of freedom. The constraint assembly 24 may comprise any suitable linkage (e.g., one or more links having any suitable shape or configuration) to constrain motion as described herein. In the example shown in FIG. 2, the constraint assembly 24 operates to limit motion of the tool support coordinate system TCS by: constraining rotation about the z-axis of the base coordinate system BCS to constrain yaw motion; constraining translation in the x-axis direction of the base coordinate system BCS to constrain x-axis translation; and constraining translation in the y-axis direction of the base coordinate system BCS to constrain y-axis translation. The actuators 21, 22, 23 and constraint assembly 24, in certain situations described further below, are controlled to effectively mimic the function of a physical cutting guide PCG, such as a physical saw cutting guide (see hidden lines in FIG. 2).

Figure 7:
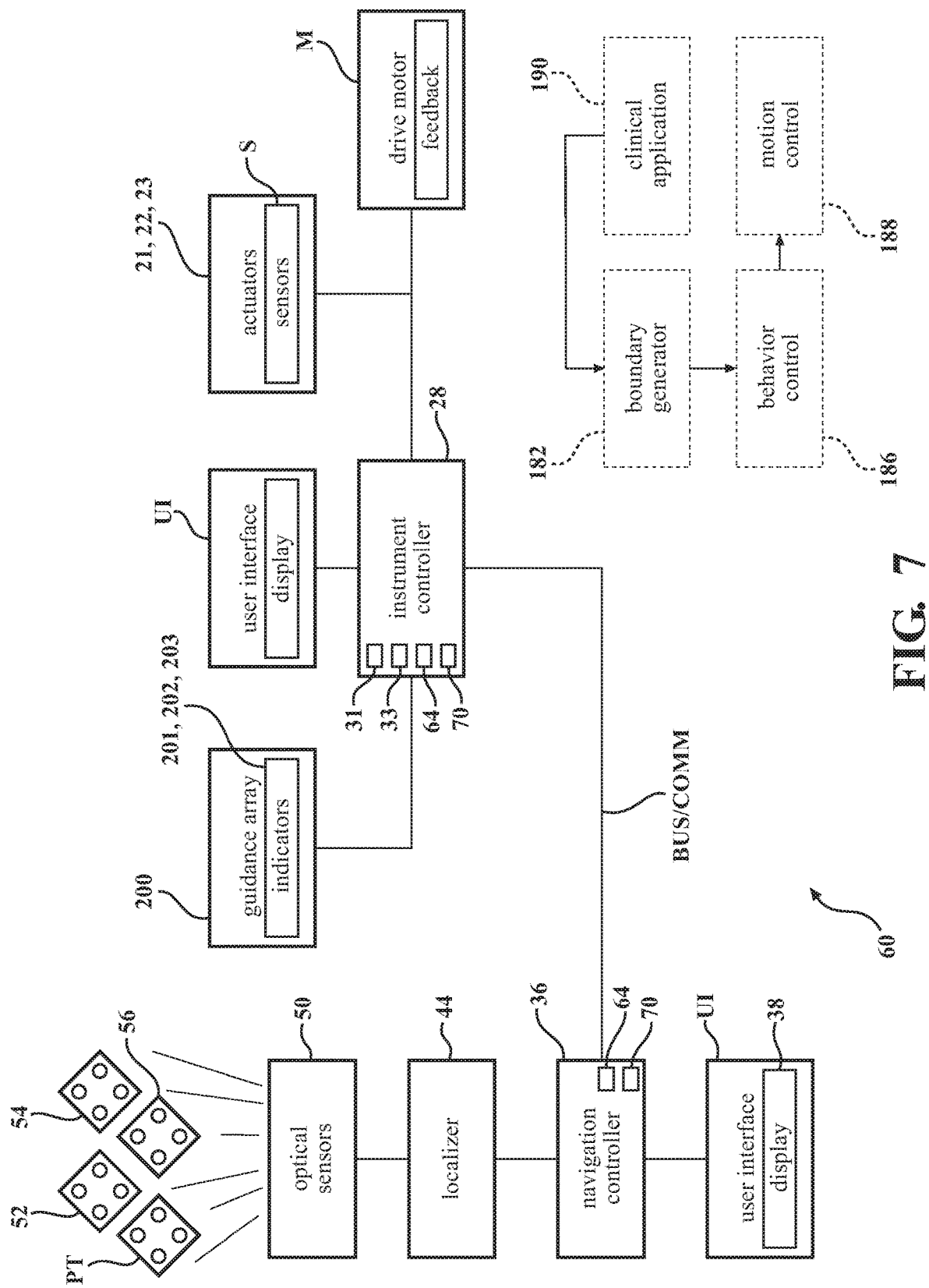
FIG. 7 is a block diagram of a control system, and also illustrates various software modules.
Figure 8:
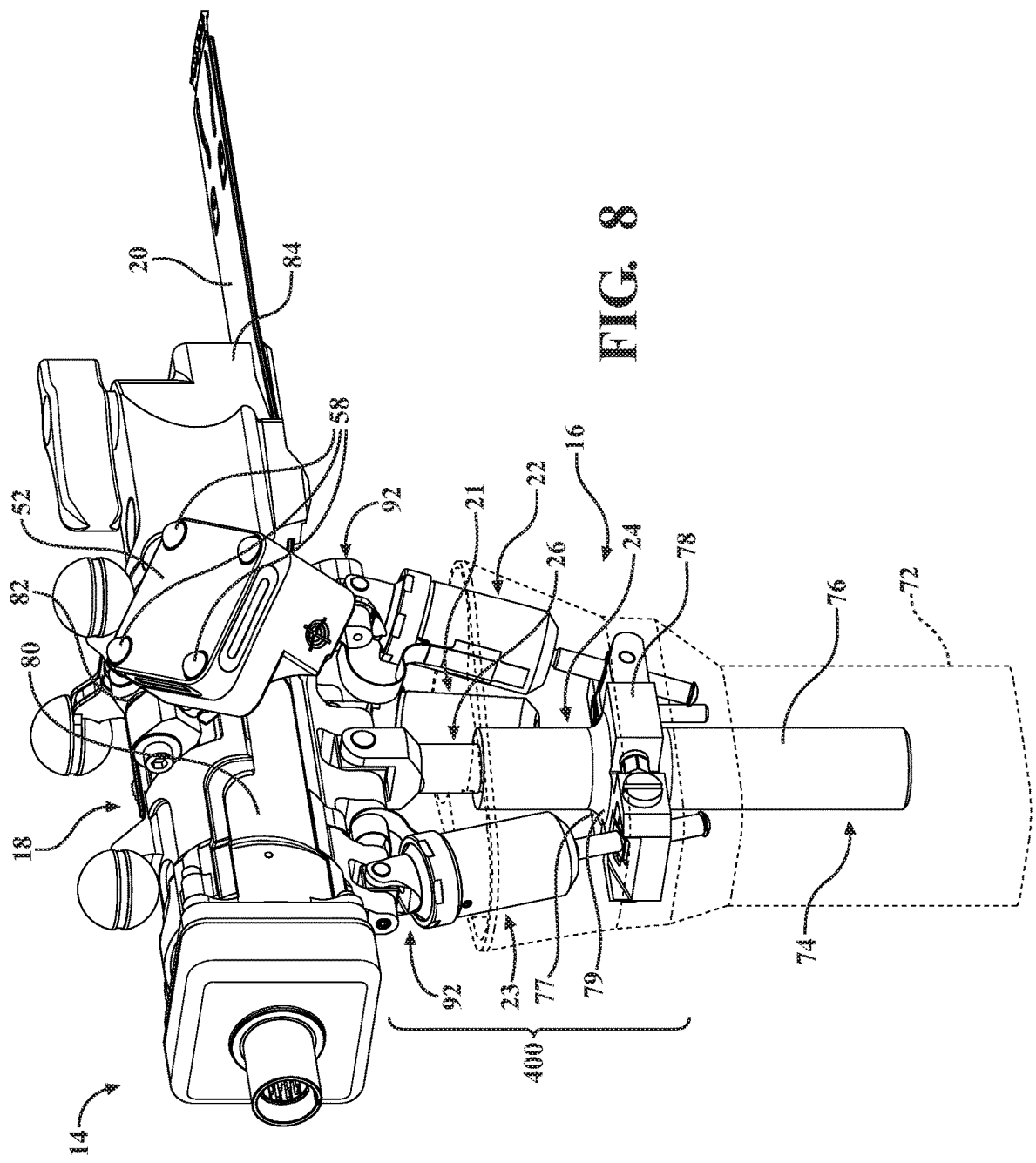
FIG. 8 is a rear perspective view of the robotic instrument.

Referring to FIG. 7, an instrument controller 28, or other type of control unit, is provided to control the instrument 14. The instrument controller 28 may comprise one or more computers, or any other suitable form of controller that directs operation of the instrument 14 and motion of the tool support 18 (and tool 20) relative to the hand-held portion 16. The instrument controller 28 may have a central processing unit (CPU) and/or other processors, memory, and storage (not shown). The instrument controller 28 is loaded with software as described below. The processors could include one or more processors to control operation of the instrument 14. The processors can be any type of microprocessor, multi-processor, and/or multi-core processing system. The instrument controller 28 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor. The instrument 14 may also comprise a user interface UI with one or more displays and/or input devices (e.g., triggers, push buttons, foot switches, keyboard, mouse, microphone (voice-activation), gesture control devices, touchscreens, etc.).

The instrument controller 28 controls operation of the tool 20, such as by controlling power to the tool 20 (e.g., to the drive motor M of the tool 20 that controls cutting motion) and controlling movement of the tool support 18 relative to the hand-held portion 16 (e.g., by controlling the actuators 21, 22, 23). The instrument controller 28 controls a state (e.g., position and/or orientation) of the tool support 18 and the tool 20 with respect to the hand-held portion 16. The instrument controller 28 can control velocity (linear or angular), acceleration, or other derivatives of motion of the tool 20 relative to the hand-held portion 16 and/or relative to the anatomy that is caused by the actuators 21, 22, 23.

As shown in FIG. 2, the instrument controller 28 may comprise a control housing 29 mounted to the tool support 18 with one or more control boards 31 (e.g., one or more printed circuit boards and associated electronic components) located inside the control housing 29. The control boards 31 may comprise microcontrollers, drivers, memory, sensors, or other electronic components for controlling the actuators 21, 22, 23 and the drive motor M (e.g., via motor controllers). The instrument controller 28 may also comprise an off-board control console 33 in data and power communication with the control boards 31. The sensors S, actuators 21, 22, 23, and/or drive motor M described herein may feed signals to the control boards 31, which transmit data signals out to the console 33 for processing, and the console 33 may feed power and/or position commands back to the control boards 31 in order to power and control positioning of the actuators 21, 22, 23 and/or the drive motor M. It is contemplated that the processing may also be performed on the control board(s) of the control housing. Of course, it is contemplated that no separate control housing is necessary.

In some versions, the console 33 may comprise a single console for powering and controlling the actuators 21, 22, 23, and the drive motor M. In some versions, the console 33 may comprise one console for powering and controlling the actuators 21, 22, 23 and a separate console for powering and controlling the drive motor M. One such console for powering and controlling the drive motor M may be like that described in U.S. Pat. No. 7,422,582, filed on Sep. 30, 2004, entitled, "Control Console to which Powered Surgical Handpieces are Connected, the Console Configured to Simultaneously Energize more than one and less than all of the Handpieces," hereby incorporated herein by reference. Flexible circuits FC, also known as flex circuits, may interconnect the actuators 21, 22, 23 and/or other components with the instrument controller 28. For example, flexible circuits FC may be provided between the actuators 21, 22, 23, and the control boards 31. Other forms of connections, wired or wireless, may additionally, or alternatively, be present between components.

Referring briefly back to FIG. 1, the robotic system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated herein by reference. The navigation system 32 tracks movement of various objects. Such objects include, for example, the instrument 14, the tool 20 and the anatomy, e.g., the femur F and tibia T. The navigation system 32 tracks these objects to gather state information of each object with respect to a (navigation) localizer coordinate system LCLZ. As used herein, the state of an object includes, but is not limited to, data that defines the position and/or orientation of the tracked object (e.g., coordinate systems thereof) or equivalents/derivatives of the position and/or orientation. For example, the state may be a pose of the object, and/or may include linear velocity data, angular velocity data, and the like.

The navigation system 32 may include a cart assembly 34 that houses a navigation controller 36, and/or other types of control units. A navigation user interface UI is in operative communication with the navigation controller 36. The navigation user interface UI includes one or more displays 38. The navigation system 32 is capable of displaying graphical representations of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, foot switches, a keyboard, a mouse, a microphone (voice-activation), gesture control devices, and the like.

The navigation system 32 also includes a navigation localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC.

The navigation system 32 includes one or more trackers. In some examples, the trackers include a pointer tracker PT, a tool tracker 52, a first patient tracker 54, and a second patient tracker 56. In the illustrated example of FIG. 1, the tool tracker 52 is firmly attached to the instrument 14, the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The pointer tracker PT is firmly affixed to a pointer 57 used for registering the anatomy to the localizer coordinate system LCLZ and/or used for other calibration and/or registration functions.

The tool tracker 52 may be affixed to any suitable component of the instrument 14, and in some versions may be attached to the hand-held portion 16, the tool support 18, directly to the tool 20, or a combination thereof. The trackers 52, 54, 56, PT may be fixed to their respective components in any suitable manner, such as by fasteners, clamps, or the like. For example, the trackers 52, 54, 56, PT may be rigidly fixed, flexibly connected (optical fiber), or not physically connected at all (ultrasound), as long as there is a suitable (supplemental) way to determine the relationship (measurement) of that respective tracker to the associated object. Any one or more of the trackers 52, 54, 56, PT may include active markers 58. The active markers 58 may include light emitting diodes (LEDs). Alternatively, the trackers 52, 54, 56, PT may have passive markers, such as reflectors, which reflect light emitted from the camera unit 46. Printed markers, or other suitable markers not specifically described herein, may also be utilized.

Various coordinate systems may be employed for purposes of tracking the objects. For instance, the coordinate systems may comprise the localizer coordinate system LCLZ, the tool support coordinate system TCS, the base coordinate system BCS, coordinate systems associated with each of the trackers 52, 54, 56, PT, one or more coordinate systems associated with the anatomy, one or more coordinate systems associated with pre-operative and/or intra-operative images (e.g., CT images, MRI images, etc.) and/or models (e.g., 2D or 3D models) of the anatomy, and a TCP (tool center point) coordinate system. Coordinates in the various coordinate systems may be transformed to other coordinate systems using transformations upon establishing relationships between the coordinate systems, e.g., via registration, calibration, geometric relationships, measuring, etc.

As shown in FIG. 2, in some examples, the TCP is a predetermined reference point or origin of the TCP coordinate system defined at the distal end of the tool 20. The geometry of the tool 20 may be defined relative to the TCP coordinate system and/or relative to the tool support coordinate system TCS. The tool 20 may comprise one or more geometric features, e.g., perimeter, circumference, radius, diameter, width, length, height, volume, area, surface/plane, range of motion envelope (along any one or more axes), etc. defined relative to the TCP coordinate system and/or relative to the tool support coordinate system TCS and stored in the navigation system 32. In some examples, the tool 20 has a blade plane (e.g., for saw blades) that will be described for convenience and ease of illustration, but is not intended to limit the tool 20 to any particular form. Points, other primitives, meshes, other 3D models, etc., can be used to virtually represent the tool 20. The TCP coordinate system, the tool support coordinate system TCS, and the coordinate system of the tool tracker 52 may be defined in various ways depending on the configuration of the tool 20. For example, the pointer 57 may be used with calibration divots CD in the tool support 18 and/or in the tool 20 for: determining (calibrating) a pose of the tool support coordinate system TCS relative to the coordinate system of the tool tracker 52;

determining a pose of the TCP coordinate system relative to the coordinate system of the tool tracker 52; and/or determining a pose of the TCP coordinate system relative to the tool support coordinate system TCS. Other techniques could be used to measure the pose of the TCP coordinate system directly, such as by attaching and fixing one or more additional trackers/markers directly to the tool 20. In some versions, trackers/markers may also be attached and fixed to the hand-held portion 16, the tool support 18, or both.

Since the tool support 18 is movable in multiple degrees of freedom relative to the hand-held portion 16 via the actuators 21, 22, 23, the instrument 14 may employ encoders, hall-effect sensors (with analog or digital output), and/or any other position sensing method, to measure a pose of the TCP coordinate system and/or tool support coordinate system TCS relative to the base coordinate system BCS. The instrument 14 may use measurements from sensors that measure actuation of the actuators 21, 22, 23 to determine a pose of the TCP coordinate system and/or tool support coordinate system TCS relative to the base coordinate system BCS, as described further below.

The localizer 44 monitors the trackers 52, 54, 56, PT (e.g., coordinate systems thereof) to determine a state of each of the trackers 52, 54, 56, PT, which correspond respectively to the state of the object respectively attached thereto. The localizer 44 may perform known triangulation techniques to determine the states of the trackers 52, 54, 56, PT, and associated objects. The localizer 44 provides the states of the trackers 52, 54, 56, PT to the navigation controller 36. In some examples, the navigation controller 36 determines and communicates the states of the trackers 52, 54, 56, PT to the instrument controller 28.

The navigation controller 36 may comprise one or more computers, or any other suitable form of controller. Navigation controller 36 has a central processing unit (CPU) and/or other processors, memory, and storage (not shown). The processors can be any type of processor, microprocessor or multi-processor system. The navigation controller 36 is loaded with software. The software, for example, converts the signals received from the localizer 44 into data representative of the position and/or orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

Although one example of the navigation system 32 is shown that employs triangulation techniques to determine object states, the navigation system 32 may have any other suitable configuration for tracking the instrument 14, tool 20, and/or the patient 12. In another example, the navigation system 32 and/or localizer 44 are ultrasound-based. For example, the navigation system 32 may comprise an ultrasound imaging device coupled to the navigation controller 36. The ultrasound imaging device images any of the aforementioned objects, e.g., the instrument 14, the tool 20, and/or the patient 12, and generates state signals to the navigation controller 36 based on the ultrasound images. The ultrasound images may be 2D, 3D, or a combination of both. The navigation controller 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation controller 36. The instrument 14, the tool 20, and/or the patient 12 may comprise RF emitters or transponders attached thereto. The RF emitters or transponders may be passive or actively energized. The RF transceiver transmits an RF tracking signal and generates state signals to the navigation controller 36 based on RF signals received from the RF emitters. The navigation controller 36 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56, PT shown in FIG. 1.

In yet another example, the navigation system 32 and/or localizer 44 are electromagnetically based. For example, the navigation system 32 may comprise an EM transceiver coupled to the navigation controller 36. The instrument 14, the tool 20, and/or the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the navigation controller 36 based upon EM signals received from the trackers. The navigation controller 36 may analyze the received EM signals to associate relative states thereto. Again, such navigation system 32 examples may have structural configurations that are different than the navigation system 32 configuration shown in FIG. 1.

The navigation system 32 may have any other suitable components or structure not specifically recited herein. Furthermore, any of the techniques, methods, and/or components described above with respect to the navigation system 32 shown may be implemented or provided for any of the other examples of the navigation system 32 described herein. For example, the navigation system 32 may utilize solely inertial tracking or any combination of tracking techniques, and may additionally or alternatively comprise, fiber optic-based tracking, machine-vision tracking, and the like.

Referring to FIG. 7, the robotic system 10 includes a control system 60 that comprises, among other components, the instrument controller 28 and the navigation controller 36. The control system 60 further includes one or more software programs and software modules. The software modules may be part of the program or programs that operate on the instrument controller 28, navigation controller 36, or a combination thereof, to process data to assist with control of the robotic system 10. The software programs and/or modules include computer readable instructions stored in memory 64 on the instrument controller 28, navigation controller 36, or a combination thereof, to be executed by one or more processors 70 of the controllers 28, 36. The memory 64 may be any suitable configuration of memory, such as non-transitory memory, RAM, non-volatile memory, etc., and may be implemented locally or from a remote database. Additionally, software modules for prompting and/or communicating with the user may form part of the program or programs and may include instructions stored in memory 64 on the instrument controller 28, navigation controller 36, or a combination thereof. The user may interact with any of the input devices of the navigation user interface UI or other user interface UI to communicate with the software modules. The user interface software may run on a separate device from the instrument controller 28 and/or navigation controller 36. The instrument 14 may communicate with the instrument controller 28 via a power/data connection. The power/data connection may provide a path for the input and output used to control the instrument 14 based on the position and orientation data generated by the navigation system 32 and transmitted to the instrument controller 28.

The control system 60 may comprise any suitable configuration of input, output, and processing devices suitable for carrying out the functions and methods described herein. The control system 60 may comprise the instrument controller 28, the navigation controller 36, or a combination thereof, and/or may comprise only one of these controllers, or additional controllers. The controllers may communicate via a wired bus or communication network as shown in FIG. 7, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

Instrument

In one exemplary configuration, the instrument 14 is best shown in FIGS. 8-19. The instrument 14 includes the hand-held portion 16 to be held by the user, the tool support 18 movably coupled to the hand-held portion 16 to support the tool 20, the actuator assembly 400 with the plurality of actuators 21, 22, 23 operatively interconnecting the tool support 18 and the hand-held portion 16 to move the tool support 18 in three degrees of freedom relative to the hand-held portion 16, and the constraint assembly 24 having the passive linkage 26 operatively interconnecting the tool support 18 and the hand-held portion 16.

The hand-held portion 16 comprises a grip 72 for being grasped by the user so that the user is able to manually support the instrument 14. The hand-held portion 16 may be configured with ergonomic features such as a grip for a hand of a user to hold, a textured or mixed material coating for preventing a user's hand from slipping when wet and/or bloody. The hand-held portion 16 may include a taper to accommodate users with different hand sizes and contoured to mate with the contours of a user's hand and/or fingers. The hand-held portion 16 also comprises a base 74 to which the grip 72 is attached by one or more fasteners, adhesive, welding, or the like. In the version shown, the base 74 comprises a sleeve 76 having a generally hollow cylindrical shape. Joint supports 77, 78, 79 extend from the sleeve 76. The actuators 21, 22, 23 may be movably coupled to the base 74 at the joint supports 77, 78, 79 via joints described further below.

Figure 12:
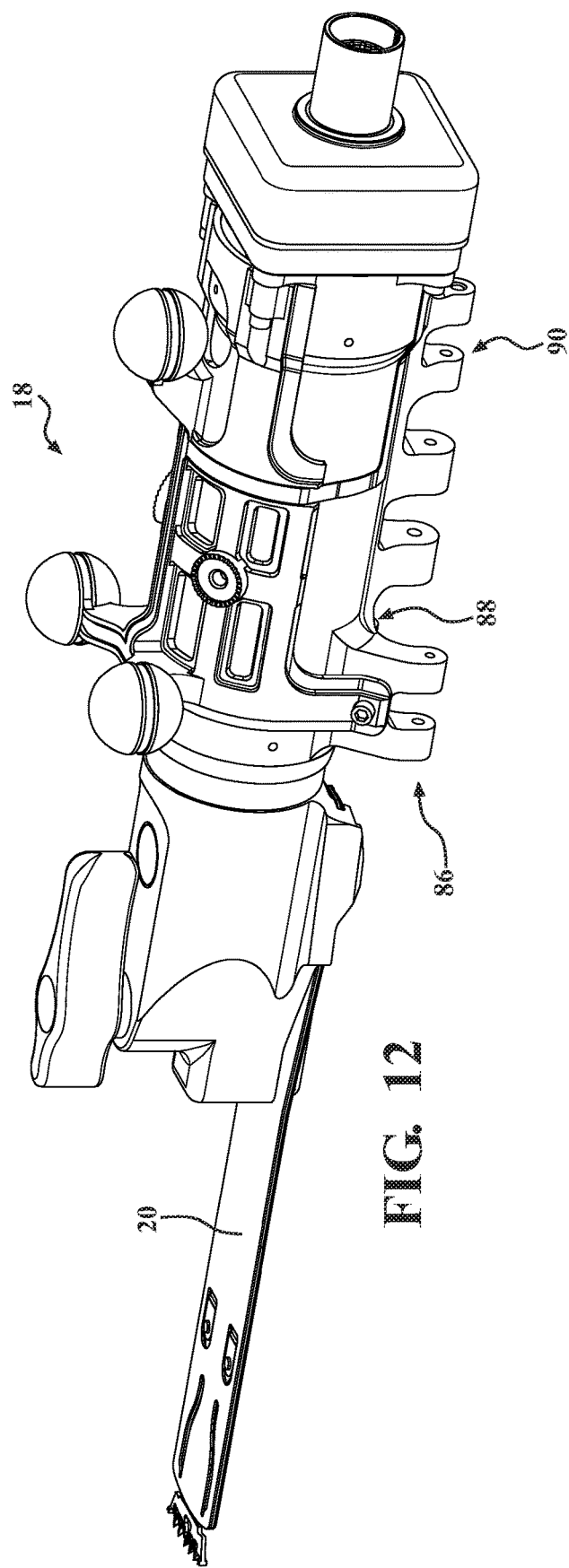
FIG. 12 is a top and rear perspective view of the tool support of the robotic instrument.
Figure 13:
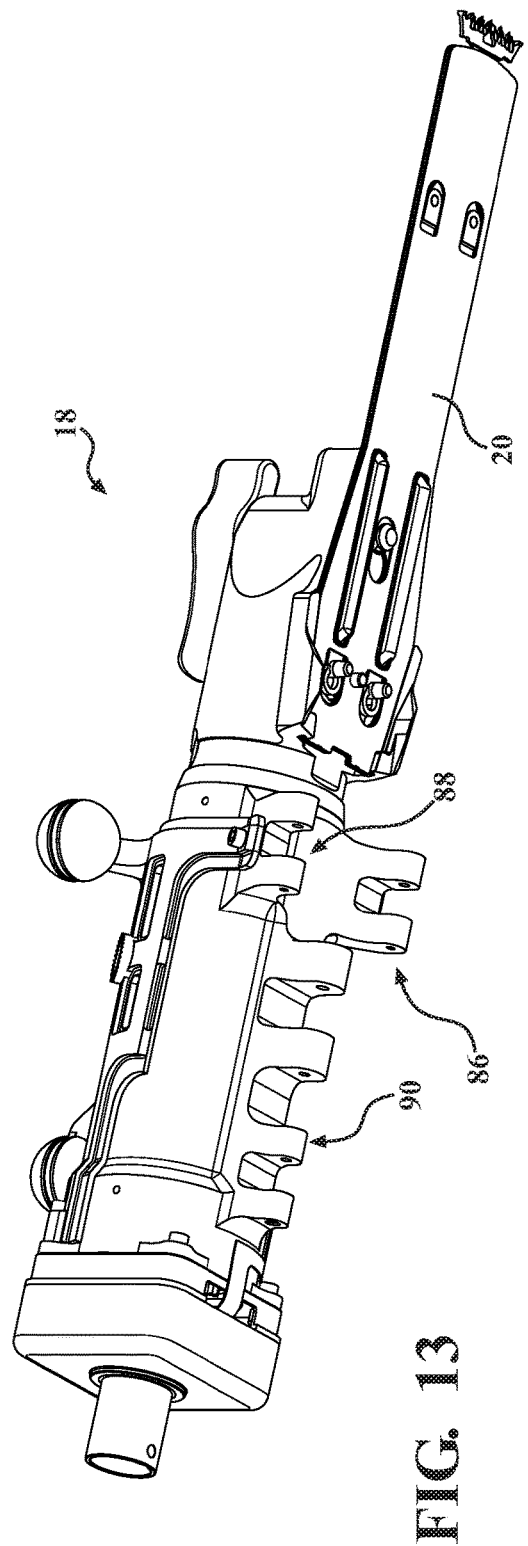
FIG. 13 is a bottom and rear perspective view of the tool support of the robotic instrument.

The tool support 18 comprises a tool support body 80 to which the tracker 52 can be removably mounted via one or more tracker mounts fixed to the tool support 18 at one or more mounting locations 82. The tool 20 is removably coupled to the tool support 18 in the version shown. In particular, the tool support 18 comprises a tool coupler, such as head 84 to which the tool 20 is mounted, as described in U.S. Pat. No. 9,820,753 to Walen et al., incorporated herein by reference. The drive motor M that drives operation of the tool 20 is disposed in the tool support body 80 (e.g., to drive oscillation of the saw blade in some versions). The tool 20 may be attached to and released from the head 84 in the manner disclosed in U.S. Pat. No. 9,820,753 to Walen et al., incorporated herein by reference. As best shown in FIGS. 12 and 13, the tool support 18 also comprises a plurality of actuator mounts 86, 88, 90 at which the actuators 21, 22, 23 are to be movably coupled to the tool support 18 via joints, as described further below. The actuator mounts 86, 88, 90 may comprise brackets, or the like, suitable to mount the actuators 21, 22, 23 such that the tool support 18 is able to move in at least three degrees of freedom relative to the hand-held portion 16.

The actuators 21, 22, 23, in the version shown, comprise electric, linear actuators that extend between the base 74 and the tool support body 80. When actuated, an effective length of the actuator 21, 22, 23 changes to vary a distance between the tool support body 80 and the base 74 along a corresponding axis of the actuator 21, 22, 23. Accordingly, the actuators 21, 22, 23 work in concert to change their effective lengths and move the tool support 18 in at least three degrees of freedom relative to the hand-held portion 16. In the version shown, three actuators 21, 22, 23 are provided, and may be referred to as first, second, and third actuators 21, 22, 23 or front actuators 21, 22, and rear actuator 23. The first, second, and third actuators 21, 22, 23 are adjustable in effective length along a first active axis AA1, a second active axis AA2, and a third active axis AA3 (see FIG. 14). The first, second, and third actuators 21, 22, 23 are independently adjustable in effective length to adjust one or more of a pitch orientation, a roll orientation, and a z-axis translation position of the tool support 18 relative to the hand-held portion 16, as previously described. More actuators may be provided in some examples. The actuators may comprise rotary actuators in some examples. The actuators 21, 22, 23 may comprise linkages having one or more links of any suitable size or shape. The actuators 21, 22, 23 may have any configuration suitable to enable movement of the tool support 18 relative to the hand-held portion 16 in at least three degrees of freedom. For example, in some versions, there may be one front actuator and two rear actuators, or some other arrangement of actuators.

Figure 14:
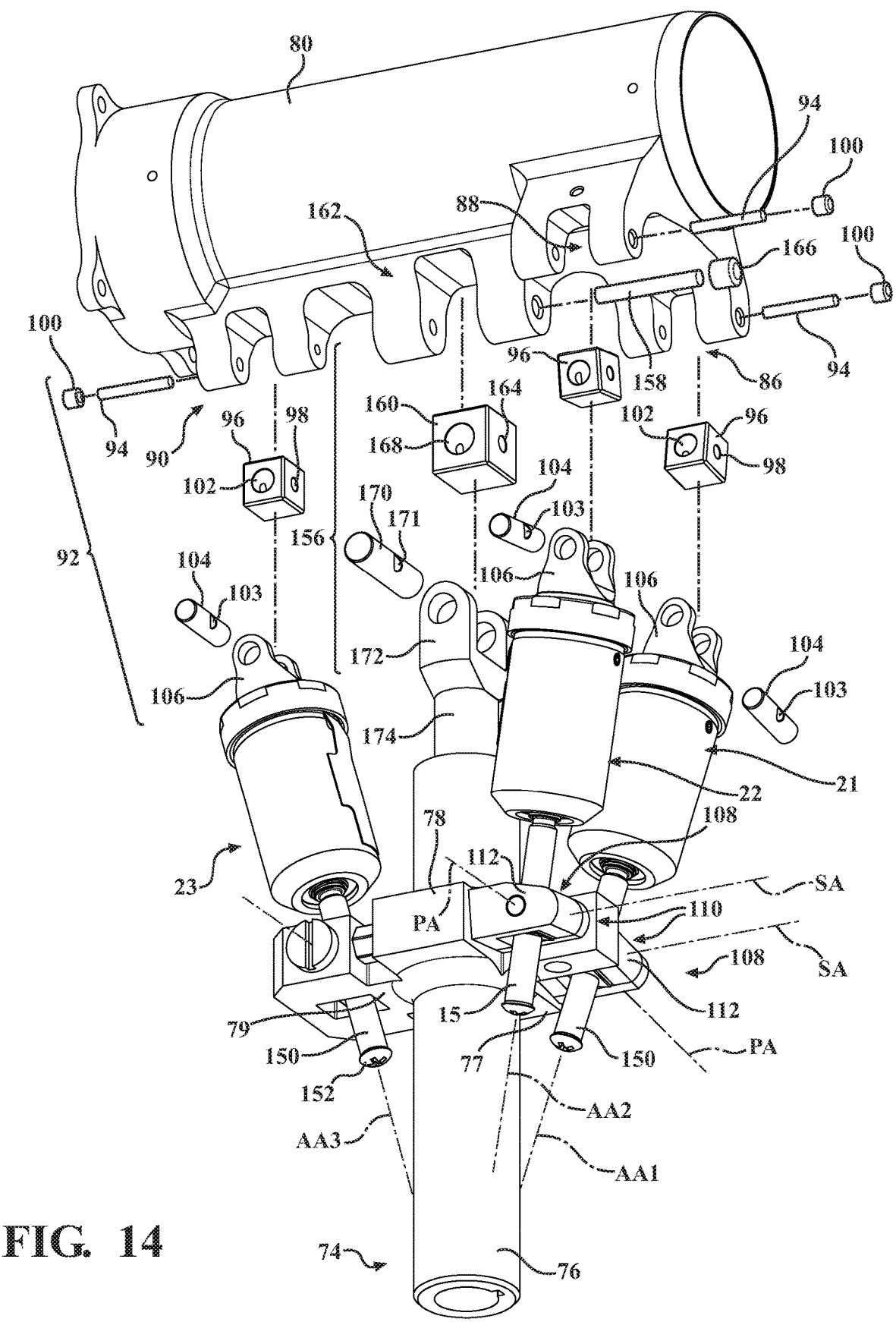
FIG. 14 is an exploded view showing a body of the tool support and associated joint connections to a plurality of actuators.
Figure 16:
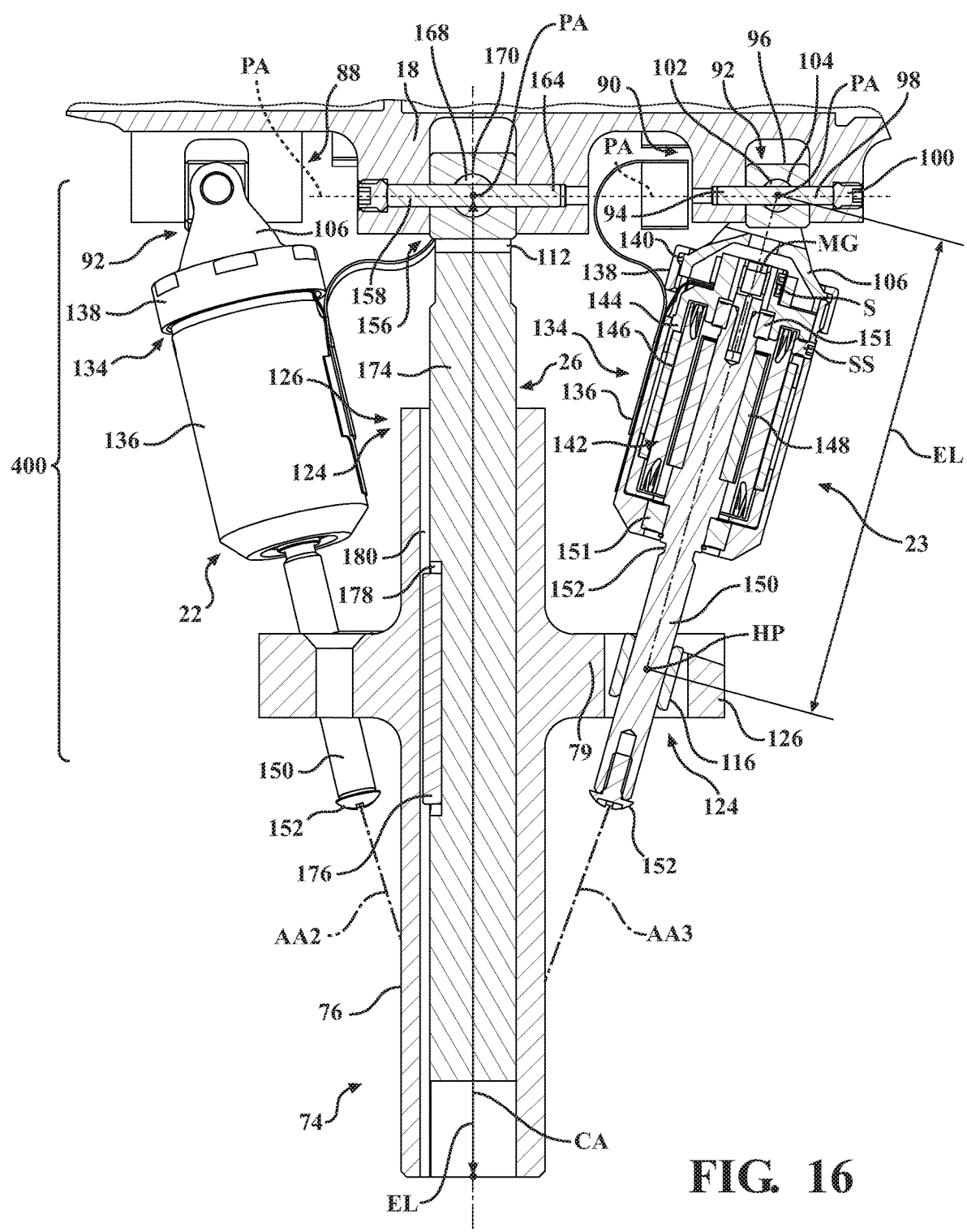
FIG. 16 is a partial cross-sectional view taken generally along the line 16-16 in FIG. 10.
Figure 19:
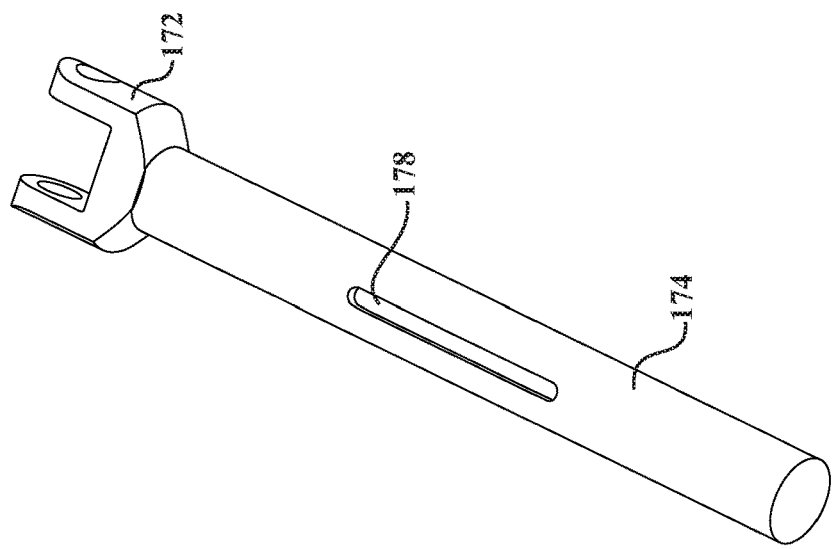
FIG. 19 is a perspective view of a shaft of a passive linkage.
Figure 18:
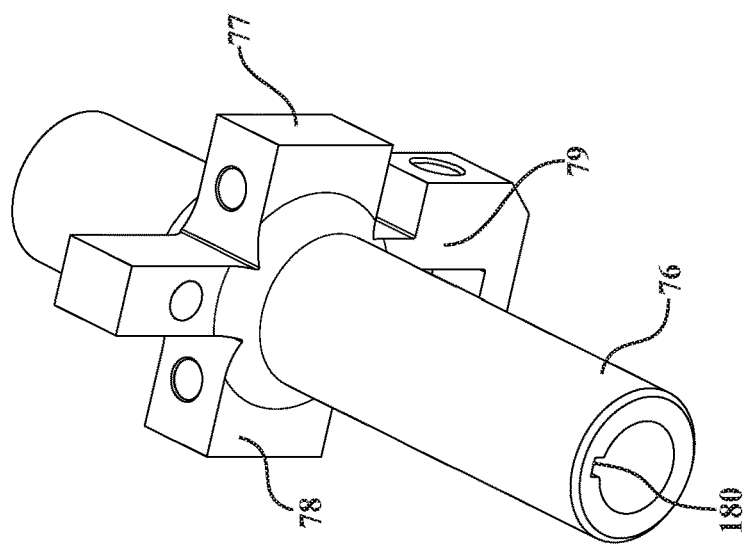
FIG. 18 is a bottom perspective view of the base of the hand-held portion.
Figure 17:
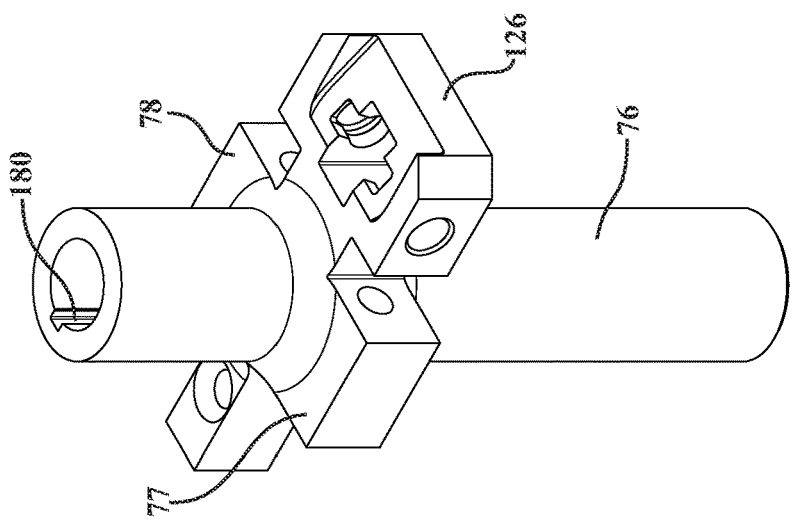
FIG. 17 is a top perspective view of the base of the hand-held portion.
Figure 21:
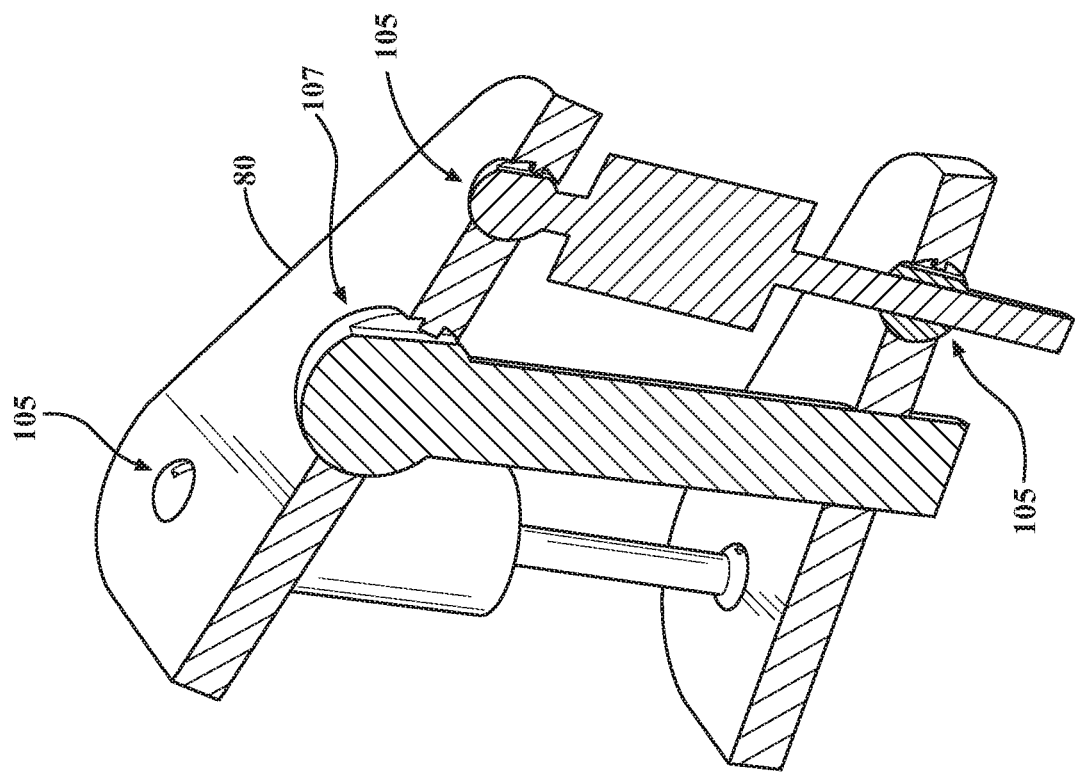
FIG. 21 is a cross-sectional view of the alternative actuator and linkage arrangement.
Figure 20:
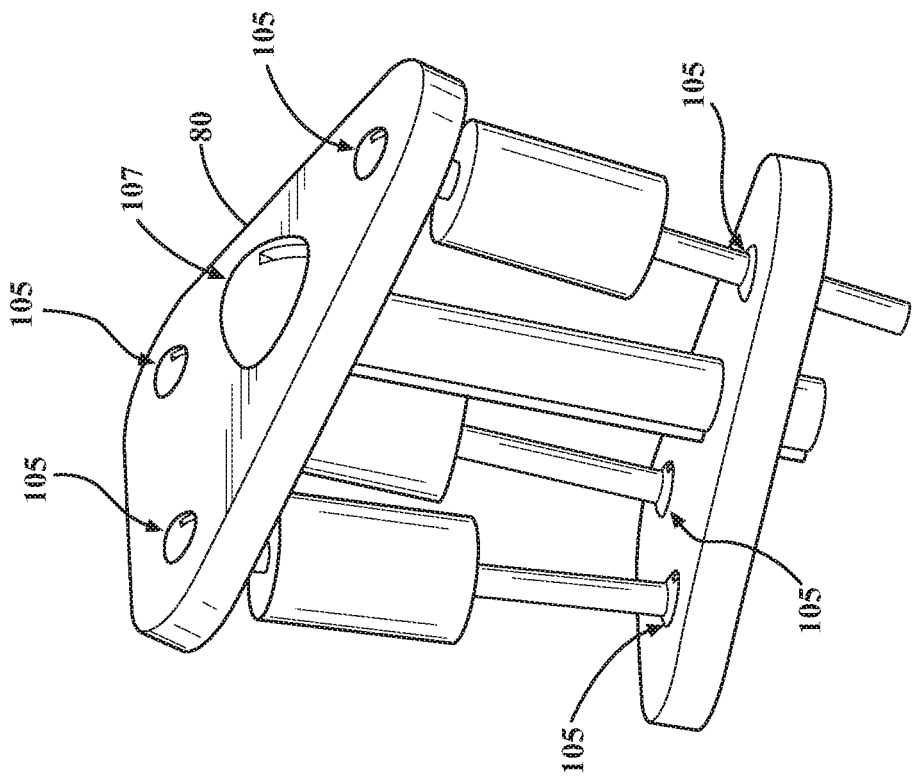
FIG. 20 is a perspective view of an alternative actuator and linkage arrangement.

In this version, the actuators 21, 22, 23 are coupled to the base 74 and the tool support body 80 via a plurality of active joints. The active joints include a set of first active joints 92 that couple the actuators 21, 22, 23 to the tool support body 80 at the actuator mounts 86, 88, 90. In one version, as shown in FIGS. 14 and 16, the first active joints 92 comprises active U-joints. The U-joints comprise first pivot pins 94 and joint blocks 96. The first pivot pins 94 pivotally connect the joint blocks 96 to the actuator mounts 86, 88, 90 via throughbores 98 in the joint blocks 96. Set screws 100 may secure the first pivot pins 94 to the actuator mounts 86, 88, 90. The U-joints may also comprise second pivot pins 104. The joint blocks 96 have crossbores 102 to receive the second pivot pins 104. The second pivot pins 104 have throughbores 103 to receive the first pivot pins 94, such that the first pivot pins 94, the joint blocks 96, and the second pivot pins 104 form a cross of the U-joint. The first pivot pin 94 and the second pivot pin 104 of each U-joint define pivot axes PA that intersect (see FIG. 16). The second pivot pins 104 pivotally connect a pivot yoke 106 of the actuators 21, 22, 23 to the joint blocks 96. As a result, the actuators 21, 22, 23 are able to move in two degrees of freedom relative to the tool support body 80. Other types of active joints are also contemplated, such as active spherical joints 105 comprising balls with slots that receive pins (see, e.g., FIGS. 20 and 21).

Figure 15:
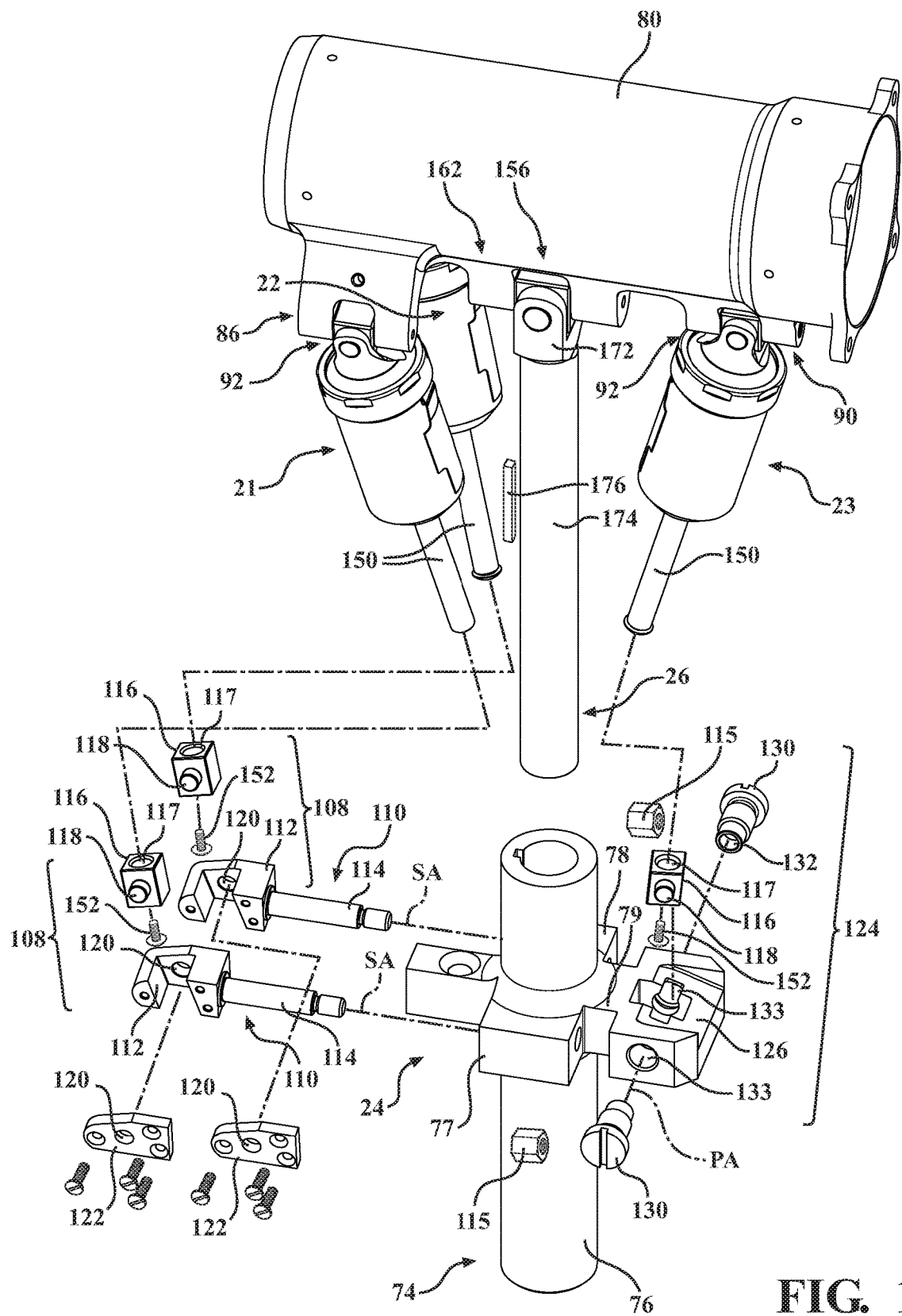
FIG. 15 is an exploded view showing a base of the hand-held portion and associated joint connections to the plurality of actuators.

Referring to FIGS. 14 and 15, the active joints also comprise a set of second active joints 108 coupling the front two actuators 21, 22 to the base 74 of the hand-held portion 16. In the version shown, the second active joints 108 are supported at the joint supports 77, 78. Each of the second active joints 108 comprises a swivel yoke 110 arranged to swivel relative to the base 74 of the hand-held portion 16 about a swivel axis SA. Each swivel yoke 110 has a swivel head 112 and a post 114 extending from the swivel head 112 to pivotally engage the base 74 at one of the joint supports 77, 78. Nuts 115 threadably connect to one end of the posts 114 to trap the posts 114 in the base 74 while allowing the respective swivel yoke 110 to freely rotate within its respective joint support 77, 78.

Each of the second active joints 108 comprises a carrier 116 pivotally coupled to one of the swivel yokes 110. The carriers 116 have internally threaded throughbores 117 to receive lead screws 150 of the front two actuators 21, 22, as described further below. Each of the carriers 116 also comprises opposed trunnions 118 that allow the carriers 116 to pivot relative to the swivel yokes 110 about pivot axes PA (see FIG. 14) by being seated in pockets 120 in the swivel yokes 110. In some versions, for each of the second active joints 108, the swivel axis SA intersects the pivot axis PA to define a single vertex about which the actuators 21, 22 move in two degrees of freedom.

Covers 122 are fastened to the swivel heads 112 and define one of the pockets 120, while the swivel head 112 defines the other pocket 120. During assembly, the carriers 116 are first positioned with one of the trunnions 118 placed in the pocket 120 in the swivel head 112, and the cover 122 is then fastened over the other trunnion 118 such that the carrier 116 is captured between the cover 122 and the swivel head 112 and is able to pivot relative to the swivel yoke 110 via the trunnions 118 and pockets 120. Owing to the configuration of the swivel yokes 110 and the associated carriers 116, i.e., the carriers 116 ability to swivel about the swivel axes SA and pivot about the pivot axes PA, the second active joints 108 allow two degrees of freedom of movement of the front two actuators 21, 22 relative to the base 74. Other joint arrangements between the front two actuators 21, 22 and the base 74 are also possible.

The active joints also comprise a third active joint 124 coupling the rear (third) actuator 23 to the base 74 of the hand-held portion 16. In the version shown, the third active joint 124 is supported at the joint support 79. The third active joint 124 comprises a pivot housing 126 fixed to the joint support 79 of the base 74.

The third active joint 124 comprises a carrier 116 pivotally coupled to the pivot housing 126 via trunnions 118. Fasteners 130 having pockets 132 attach to either side of the pivot housing 126 via throughbores 133 to engage the trunnions 118. The fasteners 130 are arranged such that the carrier 116 is able to pivot via the trunnions 118 being located in the pockets 132 after assembly. The carrier 116 has an internally threaded throughbore 117 to receive a lead screw 150 of the rear actuator 23, as described further below. Owing to the configuration of the pivot housing 126 and associated carrier 116, i.e., the ability of the associated carrier 116 to only pivot about the pivot axis PA (e.g., and not swivel), the third active joint 124 allows only one degree of freedom of movement of the rear actuator 23 relative to the base 74. Other joint arrangements between the rear actuator 23 and the base 74 are also possible.

Referring to FIG. 16, each of the actuators 21, 22, 23 comprises a housing 134. The housing 134 comprises a canister 136 and a cap 138 threadably connected to the canister 136. The pivot yokes 106 that form part of the first active joints 92 are fixed to the housings 134 such that the housings 134 and pivot yokes 106 are able to move together relative to the tool support 18 via the first active joints 92.

The caps 138 capture annular shoulders 140 of the pivot yokes 106 to secure the pivot yokes 106 to the canisters 136.

In some versions, the pivot yokes 106 and canisters 136 comprise one or more alignment features to align each pivot yoke 106 to its respective canister 136 in a predefined, relative orientation. Such alignment features may comprise mating portions, keys/keyways, or the like. During assembly, the pivot yoke 106 may first be secured to the canister 136 in its predefined, relative orientation, and the cap 138 may then be threaded onto the canister 136 (e.g., via mating outer and inner threads) to trap the pivot yoke 106 to the canister 136 at the predefined, relative orientation. This predefined relationship may be helpful in routing and/or aligning the flex circuits FC, preventing rolling of the pivot yoke 106 relative to the canister 136, and/or for other purposes.

Each of the actuators 21, 22, 23 also comprises a motor 142 disposed in each housing 134. The motor 142 has a casing 144 disposed in the housing 134 and a motor winding assembly 146 disposed within the casing 144. The motor winding assembly 146 may also be aligned in a predefined, relative orientation to the canister 136, such as via a set screw SS (see FIG. 16) or other alignment feature, such as those described above. Each motor 142 also has a rotor 148 fixed to the lead screw 150. The lead screw 150 is supported for rotation in the housing 134 by one or more bushings and/or bearings 151. The rotor 148 and associated lead screw 150 are configured to rotate relative to the housing 134 upon selective energization of the motor 142. The lead screws 150 have fine pitch and lead angles to prevent backdriving (i.e., they are self-locking). As a result, a load placed on the tool 20 does not easily back drive the motor 142. In some examples, the lead screws 150 have an 8-36 class 3 thread that results in a lead of from 0.02 to 0.03 inches/revolution. Other thread types/sizes may also be employed.

Each of the actuators 21, 22, 23 may be controlled by a separate motor controller. Motor controllers may be wired separately to the actuators 21, 22, 23, respectively, to individually direct each actuator 21, 22, 23 to a given target position. In some examples, the motor controllers are proportional integral derivative (PID) controllers. In some examples, the motor controllers can be integrated with or form part of the instrument controller 28. For ease of illustration, the motor controllers shall be described herein as being part of the instrument controller 28.

A power source provides, for example, 32 VDC power signals to the motors 142 via the console 33. The 32 VDC signal is applied to the motors 142 through the instrument controller 28. The instrument controller 28 selectively provides the power signal to each motor 142 to selectively activate the motors 142. This selective activation of the motors 142 is what positions the tool 20. The motors 142 may be any suitable type of motor, including brushless DC servomotors, other forms of DC motors, or the like. The power source also supplies power to the instrument controller 28 to energize the components internal to the instrument controller 28. It should be appreciated that the power source can provide other types of power signals such as, for example, 12 VDC, 24 VDC, 40 VDC, etc.

One or more sensors S (see also FIG. 7) transmit signals back to the instrument controller 28 so that the instrument controller 28 can determine a current position of the associated actuator 21, 22, 23 (i.e., a measured position). The levels of these signals may vary as a function of the rotational position of the associated rotor 148. In one implementation, the sensor(s) S may resolve the rotational position of the rotor 148 within a given turn at a high resolution. These sensors S may be Hall-effect sensors that output analog and/or digital signals based on the sensed magnetic fields from the rotor 148, or from other magnets placed on the lead screw 150 (see, e.g., the 2-pole magnet MG in FIG. 16). A low voltage signal, e.g., 5 VDC, for energizing the Hall-effect sensors may be supplied from the motor controller associated with the motor 142 with which the Hall-effect sensors are associated. In some examples, two Hall-effect sensors are disposed in the housing 134 and spaced 90 degrees apart from each other around the rotor 148 to sense rotor position so that the instrument controller 28 is able to determine the position and count incremental turns of the rotor 148 (one such sensor S and magnets MG are shown in FIG. 16). In some versions, the Hall-effect sensors output digital signals representing incremental counts. Various types of motors and sensor arrangements are possible. In some examples, the motors 142 are brushless DC servomotors and two or more internal Hall-effect sensors may be spaced 90 degrees, 120 degrees, or any other suitable spacing from each other around the rotor 148. The sensors S may also comprise absolute or incremental encoders, which may be used to detect a rotational position of the rotor 148 and to count turns of the rotor 148. Other type of encoders may be also used as the one or more sensors. The sensors may be placed at any suitable location on the actuator and its surrounding components suitable to determine the position of each actuator as it is adjusted, such as on the housing, nut, screw, etc. In yet another configuration, sensorless motor control may be utilized. In such an implementation, the position of each rotor may be determined by measuring the motor's back-emf and/or inductance. One suitable example may be found in U.S. Pat. No. 7,422,582, which is hereby incorporated by reference in its entirety.

In some examples, output signals from the Hall-effect sensors are sent to the instrument controller 28. The instrument controller 28 monitors the received signals for changes in their levels. Based on these signals the instrument controller 28 determines rotor position. Rotor position may be considered the degrees of rotation of the rotor 148 from an initial or home position. The rotor 148 can undergo plural 360° rotations. The rotor position can therefore exceed 360°. A scalar value referred to as a count is representative of rotor position from the home position. The rotors 148 rotate in both clockwise and counterclockwise directions. Each time the signal levels of the plural signals (analog or digital) undergo a defined state change, the instrument controller 28 increments or decrements the count to indicate a change in rotor position. For every complete 360° rotation of the rotor 148, the instrument controller 28 increments or decrements the value of the count by a fixed number of counts. In some examples, the count is incremented or decremented between 100 and 3,000 per 360-degree revolution of the rotor 148. In some examples, there are 1,024 positions (counts) per 360-degree revolution of the rotor 148, such as when an incremental encoder is used to monitor rotor position. Internal to the instrument controller 28 is a counter associated with each actuator 21, 22, 23. The counter stores a value equal to the cumulative number of counts incremented or decremented. The count value can be positive, zero or negative. In some versions, the count value defines incremental movement of the rotor 148. Accordingly, the rotors 148 of the actuators 21, 22, 23 may first be moved to known positions, referred to as their home positions (described further below), with the count values being used thereafter to define the current positions of the rotors 148.

As previously described, the carriers 116 have the internally threaded throughbores 117 to threadably receive the lead screws 150 so that each of the lead screws 150 can rotate relative to a corresponding one of the carriers 116 to adjust the effective length of a corresponding one of the plurality of actuators 21, 22, 23 and thereby vary the counts measured by the instrument controller 28. Each of the housings 134 and corresponding carriers 116 are constrained from relative movement in at least one degree of freedom to allow the lead screws 150 to rotate relative to the carriers 116. More specifically, the lead screws 150 are able to rotate relative to the carriers 116 owing to: the pivot yokes 106 being unable to rotate about the associated active axes AA1, AA2, AA3 (i.e., the pivot yokes 106 are limited from such rotational movement by virtue of the configuration of the first active joints 92); and the carriers 116 being unable to rotate about the associated active axes AA1, AA2, AA3 (i.e., the carriers 116 are limited from such rotational movement by virtue of the configuration of the second active joints 108 and the third active joint 124).

Stops 152, such as threaded fasteners and shoulders formed on the lead screws 150, are fixed to the lead screws 150. The stops 152 are sized to abut the carriers 116 at ends of travel of each lead screw 150.

As previously described, the actuators 21, 22, 23 are actively adjustable in effective length to enable movement of the tool support 18 relative to the hand-held portion 16. One example of this effective length is labeled "EL" on the third actuator 23 in FIG. 16. Here, the effective length EL is measured from a center of the associated carrier 116 to a center of the associated first active joint 92. As each actuator 21, 22, 23 is adjusted, the effective length EL changes, by varying how far the lead screw 150 has been threaded into or out of its associated carrier 116 and thereby changing the distance from the center of the associated carrier 116 to the center of the associated first active joint 92. The actuators 21, 22, 23 are adjustable between minimum and maximum values of the effective length EL. The effective length EL of each actuator 21, 22, 23 can be represented/measured in any suitable manner to denote the distance between the tool support 18 and the hand-held portion 16 along the active axes AA1, AA2, AA3 that changes to cause various movements of the tool support 18 relative to the hand-held portion 16.

The constraint assembly 24 works in concert with the actuators 21, 22, 23 to constrain the movement provided by the actuators 21, 22, 23. The actuators 21, 22, 23 provide movement in three degrees of freedom, while the constraint assembly 24 constrains movement in three degrees of freedom. In the version shown, the constraint assembly 24 comprises the passive linkage 26, as well as a passive linkage joint 156 that couples the passive linkage 26 to the tool support 18.

In one version, as shown in FIGS. 14 and 16, the passive linkage joint 156 comprises a passive linkage U-joint. The U-joint comprises a first pivot pin 158 and a joint block 160. The first pivot pin 158 pivotally connects the joint block 160 to a passive linkage mount 162 of the tool support body 80 via a throughbore 164 in the joint block 160. A set screw 166 may secure the first pivot pin 158 to the passive linkage mount 162. The U-joint also comprises a second pivot pin 170. The joint block 160 has a crossbore 168 to receive the second pivot pin 170. The second pivot pin 170 pivotally connects a passive linkage pivot yoke 172 of the passive linkage 26 to the joint block 160. The second pivot pin 170 has a throughbore 171 to receive the first pivot pin 158, such that the first pivot pin 158, the joint block 160, and the second pivot pin 170 form a cross of the U-joint. The first pivot pin 158 and the second pivot pin 170 define pivot axes PA that intersect (see FIG. 16). As a result, the passive linkage 26 is able to move in two degrees of freedom relative to the tool support body 80. Other types of passive linkage joints are also contemplated, such as a passive linkage spherical joint 107 comprising a ball with slot that receives a pin (see, e.g., FIGS. 20 and 21).

The passive linkage 26 comprises a shaft 174 fixed to the passive linkage pivot yoke 172. The passive linkage 26 also comprises the sleeve 76 of the base 74, which is configured to receive the shaft 174 along a constraint axis CA. The passive linkage 26 is configured to allow the shaft 174 to slide axially along the constraint axis CA relative to the sleeve 74 and to constrain movement of the shaft 174 radially relative to the constraint axis CA during actuation of one or more of the actuators 21, 22, 23.

The passive linkage 26 further comprises a key 176 to constrain rotation of the shaft 174 relative to the sleeve 76 about the constraint axis CA. The key 176 is best shown in FIG. 16. The key 176 fits in opposing keyways 178, 180 in the shaft 174 and sleeve 76 to rotationally lock the shaft 174 to the sleeve 76. Other arrangements for preventing relative rotation of the shaft 174 and sleeve 76 are also contemplated, such as an integral key/slot arrangement, or the like. The passive linkage 26 operatively interconnects the tool support 18 and the hand-held portion 16 independently of the actuators 21, 22, 23. The passive linkage is passively adjustable in effective length EL along the constraint axis CA during actuation of one or more of the actuators 21, 22, 23. The sleeve 76, shaft 174, and key 176 represent one combination of links for the passive linkage 26. Other sizes, shapes, and numbers of links, connected in any suitable manner, may be employed for the passive linkage 26.

In the version shown, the passive linkage joint 156 is able to pivot about two pivot axes PA relative to the tool support 18. Other configurations are possible.

Figure 9:
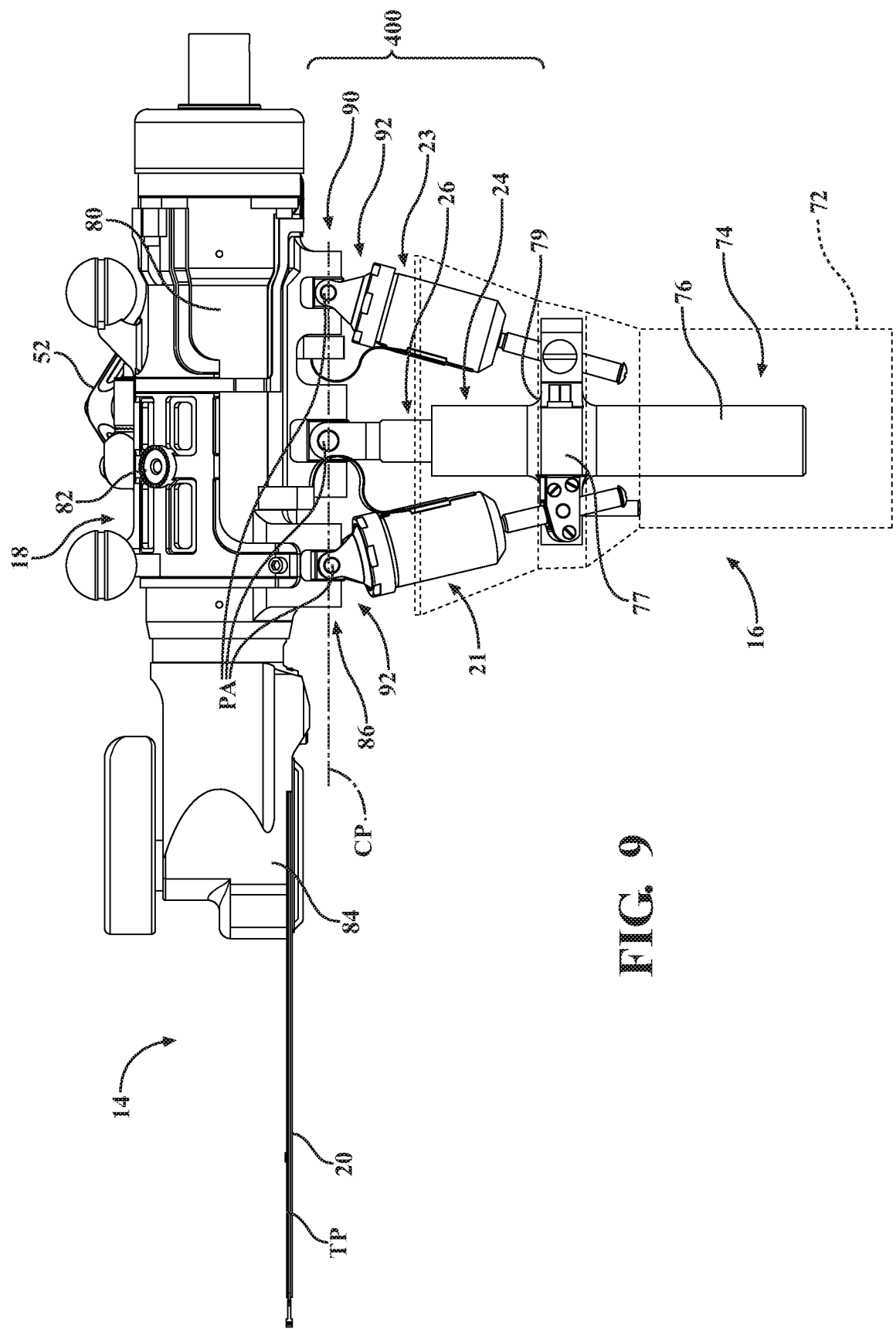
FIG. 9 is a side elevational view of the robotic instrument.

Also, in the version shown, the first active joints 92 and the passive linkage joint 156 define pivot axes PA disposed on a common plane CP (see FIGS. 9 and 11). Non-parallel pivot axes PA, parallel pivot axes PA disposed on different planes, combinations thereof, and/or other configurations, are also contemplated.

In some versions, the head 84 of the tool support 18 is arranged so that the tool 20 is located on a tool plane TP (e.g., blade plane) parallel to the common plane CP when the tool 20 is coupled to the tool support 18 (see FIGS. 9 and 11). In some examples, the tool plane TP is spaced from the common plane CP by 2.0 inches or less, 1.0 inches or less, 0.8 inches or less, or 0.5 inches or less.

Referring to FIGS. 10, 14, and 16, the constraint axis CA and the third active axis AA3 may be located to be coplanar along a vertical center plane VCP throughout actuation of the actuators 21, 22, 23. Other configurations are also contemplated, including those in which the constraint axis CA and the third active axis AA3 are not coplanar.

In the version shown, the actuators 21, 22, 23 are arranged such that the active axes AA1, AA2, AA3 are in a canted configuration relative to the constraint axis CA in all positions of the actuators 21, 22, 23, including when in their home positions. Canting the axes AA1, AA2, AA3 generally tapers the actuator arrangement in a manner that allows for a slimmer and more compact base 74 and associated grip 72. Other configurations are contemplated, including those in which the active axes AA1, AA2, AA3 are not in the canted configuration relative to the constraint axis CA. Such configurations may include those in which the actuator axes AA1, AA2, AA3 are parallel to each other in their home positions.

Further configurations of the actuators, active joints, and constraint assembly are possible. In some versions, the constraint assembly may be absent and the tool support 18 of the instrument 14 may be able to move in additional degrees of freedom relative to the hand-held portion 16. Furthermore, as mentioned above, the actuator assemblies described below may be used.

Virtual Boundaries

Figure 22:
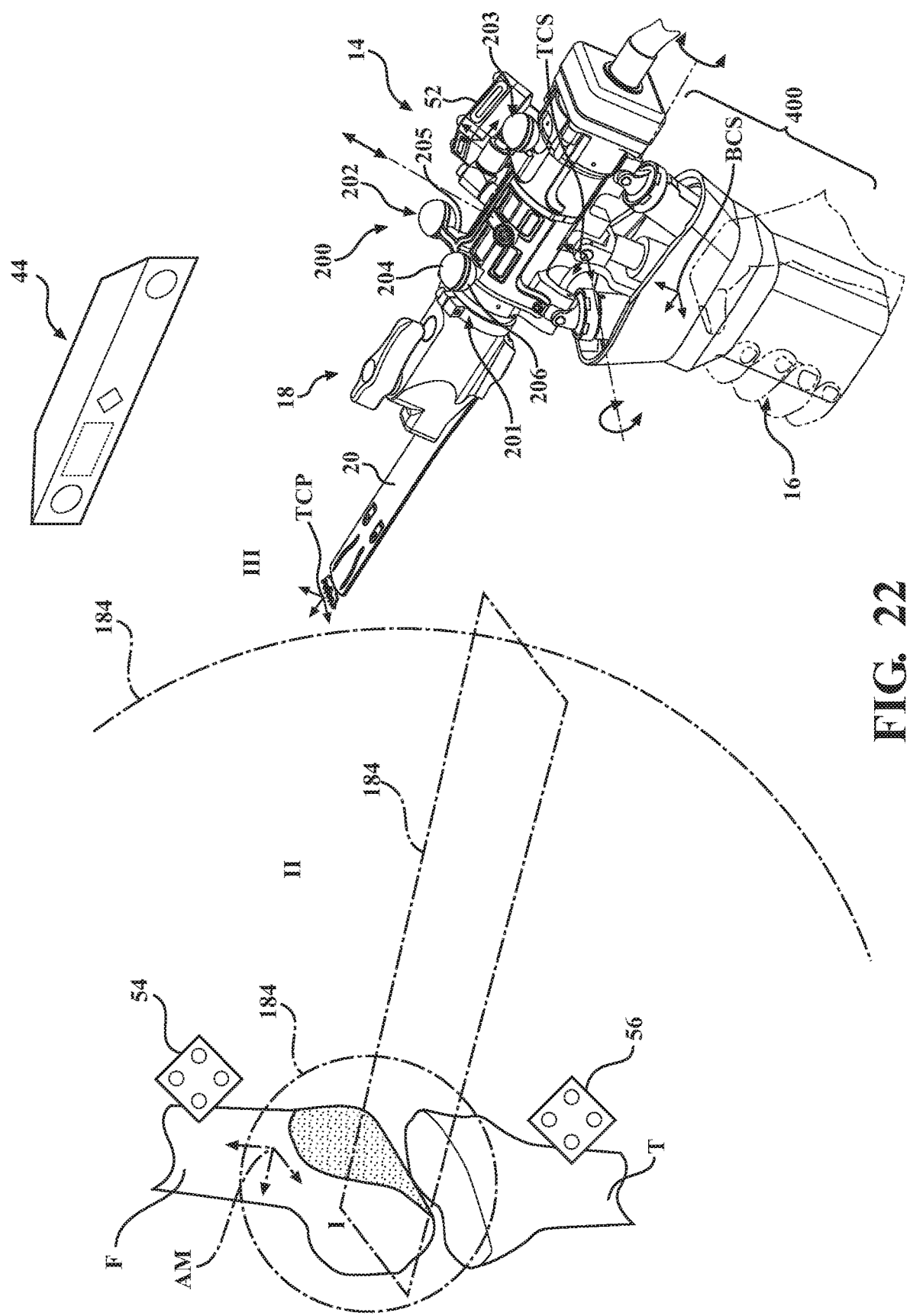
FIG. 22 illustrates various regions in which the robotic instrument is used.

The software employed by the control system 60 to control operation of the instrument 14 includes a boundary generator 182 (see FIG. 7). The boundary generator 182 may be implemented on the instrument controller 28, the navigation controller 36, and/or on other components, such as on a separate controller. The boundary generator 182 may also be part of a separate system that operates remotely from the instrument 14. Referring to FIG. 22, the boundary generator 182 is a software program or module that generates one or more virtual boundaries 184 for constraining movement and/or operation of the instrument 14. In some examples, the boundary generator 182 provides virtual boundaries 184 that define a virtual cutting guide (e.g., a virtual saw cutting guide). Virtual boundaries 184 may also be provided to delineate various operational/control regions as described below. The virtual boundaries 184 may be one-dimensional (1D), two-dimensional (2D), three-dimensional (3D), and may comprise a point, line, axis, trajectory, plane (an infinite plane or plane segment bounded by the anatomy or other boundary), volume or other shapes, including complex geometric shapes. The virtual boundaries 184 may be represented by pixels, point clouds, voxels, triangulated meshes, other 2D or 3D models, combinations thereof, and the like. U.S. Patent Publication No. 2018/0333207 and U.S. Pat. No. 8,898,043 are incorporated by reference, and any of their features may be used to facilitate planning or execution of the surgical procedure.

The virtual boundaries 184 may be used in various ways. For example, the control system 60 may: control certain movements of the tool 20 to stay inside the boundary; control certain movements of the tool 20 to stay outside the boundary; control certain movements of the tool 20 to stay on the boundary (e.g., stay on a point, trajectory, and/or plane); control certain movements of the tool 20 to approach the boundary (attractive boundary) or to be repelled from the boundary (repulsive boundary); and/or control certain operations/functions of the instrument 14 based on a relationship of the instrument 14 to the boundary (e.g., spatial, velocity, etc.). Other uses of the boundaries 184 are also contemplated.

In some examples, one of the virtual boundaries 184 is a desired cutting plane, as shown in FIG. 22. The control system 60 will ultimately function to keep the tool 20 on the desired cutting plane in some versions. The virtual boundary 184 that controls positioning of the tool 20 may also be a volumetric boundary, such as one having a thickness slightly larger than a blade thickness to constrain a saw blade to stay within the boundary and on a desired cutting plane, as shown in FIG. 2. Therefore, the desired cutting plane can be defined by a virtual planar boundary, a virtual volumetric boundary, or other forms of virtual boundary. Virtual boundaries 184 may also be referred to as virtual objects. The virtual boundaries 184 may be defined with respect to an anatomical model AM, such as a 3D bone model (see FIG. 22, which illustrates the anatomical model AM being virtually overlaid on the actual femur F due to their registration). In other words, the points, lines, axes, trajectories, planes, volumes, and the like, that are associated with the virtual boundaries 184 may be defined in a coordinate system that is fixed relative to a coordinate system of the anatomical model AM such that tracking of the anatomical model AM (e.g., via tracking the associated anatomy to which it is registered) also enables tracking of the virtual boundary 184.

The anatomical model AM is registered to the first patient tracker 54 such that the virtual boundaries 184 become associated with the anatomical model AM and associated coordinate system. The virtual boundaries 184 may be implant-specific, e.g., defined based on a size, shape, volume, etc. of an implant and/or patient-specific, e.g., defined based on the patient's anatomy. The virtual boundaries 184 may be boundaries that are created pre-operatively, intra-operatively, or combinations thereof. In other words, the virtual boundaries 184 may be defined before the surgical procedure begins, during the surgical procedure (including during tissue removal), or combinations thereof. The virtual boundaries 184 may be provided in numerous ways, such as by the control system 60 creating them, receiving them from other sources/systems, or the like. The virtual boundaries 184 may be stored in memory for retrieval and/or updating.

In some cases, such as when preparing the femur F for receiving the total knee implant IM (see FIG. 1), the virtual boundaries 184 comprise multiple planar boundaries that can be used to delineate multiple cutting planes (e.g., five cutting planes) for the total knee implant IM, and are associated with a 3D model of the distal end of the femur F. These multiple virtual boundaries 184 can be activated, one at a time, by the control system 60 to constrain cutting to one plane at a time.

The instrument controller 28 and/or the navigation controller 36 track the state of the tool 20 relative to the virtual boundaries 184. In one example, the state of the TCP coordinate system (e.g., pose of the saw blade) is measured relative to the virtual boundaries 184 for purposes of determining target positions for the actuators 21, 22, 23 so that the tool 20 remains in a desired state. In some cases, the control system 60 controls/positions the instrument 14 in a manner that emulates the way a physical handpiece would respond in the presence of physical boundaries/barriers.

Referring back to FIG. 7, two additional software programs or modules run on the instrument controller 28 and/or the navigation controller 36. One software module performs behavior control 186. Behavior control 186 is the process of computing data that indicates the next commanded/desired position and/or orientation (e.g., desired pose) for the tool 20. In some cases, only the desired position of the TCP is output from the behavior control 186, while in some cases, the commanded pose of the tool 20 is output. Output from the boundary generator 182 (e.g., a current position and/or orientation of the virtual boundaries 184 in one or more of the coordinate systems) may feed as inputs into the behavior control 186 to determine the next commanded position of the actuators 21, 22, 23 and/or orientation for the tool 20. The behavior control 186 may process this input, along with one or more other inputs described further below, to determine the commanded pose.

The instrument controller 28 may control the one or more actuators 21, 22, 23 by sending command signals to each actuator 21, 22, 23 to adjust the tool 20 towards a desired pose. The instrument controller 28 may know the entire length that an actuator 21, 22, 23 may adjust the tool support 18 relative to the hand-held portion 16. In some examples, the instrument controller 28 knows the entire length which an actuator 21, 22, 23 is capable of adjusting and may send command signals to the actuators 21, 22, 23 to move a measured distance from position to position. A measured position may be a known position, or a distance between the present location of an actuator 21, 22, 23 and the actuator limits. Each position that the actuator 21, 22, 23 moves to may be a measured distance from a positive limit and a negative limit of actuator travel (i.e. a position between two ends of a lead screw). The instrument controller 28 may command the actuators 21, 22, 23 to and from measured positions as described below.

The instrument controller 28 may send command signals to each actuator 21, 22, 23 to move the actuators 21, 22, 23 from a first position to a commanded position which will place the tool 20 into a desired pose. In some examples, the commanded position may be determined by the instrument controller 28 in conjunction with the navigation system 32 to determine the location of the tool 20 and tool support 18 relative to the hand-held portion 16, patient trackers PT, 54, 56, a virtual object, such as desired cut plane or a combination thereof and send a signal to the actuators 21, 22, 23 to adjust a certain distance or commanded position in order to place the tool 20 into the desired pose. The instrument controller may command the actuator 21, 22, 23 to a position in order to reach the desired adjustment of the tool 20. The instrument controller 28 may control the actuators 21, 22, 23 to linearly move a calculated distance to adjust the tool 20 towards a desired pose. In other examples, such as when absolute encoders are used, the instrument controller may send signals to the actuators 21, 22, 23 to place each actuator 21, 22, 23 into a commanded position based on the known location of the tool support 18 relative to the hand-held portion determined by the absolute encoder. A previously commanded position may be a position which the actuator 21, 22, 23 was adjusted to prior to the current position of the actuator 21, 22, 23. In some examples, the previously commanded position may be a position which the actuators 21, 22, 23 were commanded to in order to adjust the tool 20 towards a desired pose.

In some examples, when one or more of the actuators 21, 22, 23 have reached their limit, the instrument controller 28 may require the hand-held portion 16 to be adjusted in order to bring the tool 20 back into a range where the actuators are capable of adjusting the tool 20 towards the desired pose. In such a case, a simulated commanded position may be used to indicate to a user how to move the hand-held portion 16 in order to bring the tool 20 and actuators 21, 22, 23 back into alignment with the desired pose. A simulated commanded position may be a position determined by the instrument controller 28 in conjunction with navigation data from the navigation system 32 in which the hand-held portion 16 must be moved to adjust the tool 20 towards a desired pose without adjusting the actuators 21, 22, 23. The simulated commanded position works with the guidance array 200, indicators 201, 202, 203, or both to signal to a user that the hand-held portion 16 needs to be moved in particular way to place the tool 20 at the desired pose. In some examples, guidance array 200, indicators 201, 202, 203, or both to signal to a user to move the hand-held portion 16 in the same fashion as if the actuators 21, 22, 23 were adjusting the tool 20, but relies on the user to correct the pose of the tool 20 by manipulating the hand-held portion 16 while the actuators remain in position.

The second software module performs motion control 188. One aspect of motion control 188 is the control of the instrument 14. The motion control 188 receives data defining the next commanded pose from the behavior control 186. Based on these data, the motion control 188 determines the next rotor position of the rotors 148 of each actuator 21, 22, 23 (e.g., via inverse kinematics) so that the instrument 14 is able to position the tool 20 as commanded by the behavior control 186, e.g., at the commanded pose. In other words, the motion control 188 processes the commanded pose, which may be defined in Cartesian space, into actuator positions (such as rotor positions) of the instrument 14, so that the instrument controller 28 can command the motors 142 accordingly, to move the actuators 21, 22, 23 of the instrument 14 to commanded positions, such as commanded rotor positions corresponding to the commanded pose of the tool 20. In one version, the motion control 188 regulates the rotor position of each motor 142 and continually adjusts the torque that each motor 142 outputs to, as closely as possible, ensure that the motor 142 drives the associated actuator 21, 22, 23 to the commanded rotor position.

In some versions, the instrument controller 28, for each actuator 21, 22, 23, determines the difference between a measured position and a commanded position of the rotor 148. The instrument controller 28 outputs a target current (proportional to a torque of the rotor), changing the voltage to adjust the current at the actuator from an initial current to the target current. The target current effectuates a movement of the actuators 21, 22, 23, moving the tool 20 from the measured pose to the commanded pose. This may occur after the commanded pose is converted to joint positions. In one example, the measured position of each rotor 148 may be derived from the sensor S described above, such as an encoder.

The boundary generator 182, behavior control 186, and motion control 188 may be sub-sets of a software program. Alternatively, each may be software programs that operate separately and/or independently in any combination thereof. The term "software program" is used herein to describe the computer-executable instructions that are configured to carry out the various capabilities of the technical solutions described. For simplicity, the term "software program" is intended to encompass, at least, any one or more of the boundary generator 182, behavior control 186, and/or motion control 188. The software program can be implemented on the instrument controller 28, navigation controller 36, or any combination thereof, or may be implemented in any suitable manner by the control system 60.

A clinical application 190 may be provided to handle user interaction. The clinical application 190 handles many aspects of user interaction and coordinates the surgical workflow, including pre-operative planning, implant placement, registration, bone preparation visualization, and post-operative evaluation of implant fit, etc. The clinical application 190 is configured to output to the displays 38. The clinical application 190 may run on its own separate processor or may run alongside the instrument controller 28 and/or the navigation controller 36. In one example, the clinical application 190 interfaces with the boundary generator 182 after implant placement is set by the user, and then sends the virtual boundaries 184 returned by the boundary generator 182 to the instrument controller 28 for execution.

Homing

Prior to treating the anatomy (e.g., prior to cutting the femur F and/or tibia T), and during certain modes of operation described below, a homing procedure may be performed that establishes the home position for the tool 20 by placing each of the actuators 21, 22, 23 at their respective home positions. This process is employed to provide a reference position from which to count the incremental movements of the rotors 148 measured by the sensors S so that the control system 60 is able to determine the current position of the rotors 148. In some versions, when the sensors S are able to measure absolute positions of the rotors 148, then homing may not be necessary. Effectively, the homing process establishes the initial rotor positions (zero position) of the actuators 21, 22, 23. The home position is effectively a position of the rotor 148 that provides the greatest possible travel in each direction along the active axis AA1, AA2, AA3. In some examples, the home position is generally located such that a home point HP of the lead screw 150, centrally disposed halfway between the stops 152, is centrally disposed in the associated carrier 116 (see FIG. 16 which illustrates two of the actuators 22, 23 in their home positions). Even when the homing procedure is not used, such as with absolute encoders, setting the actuators 21, 22, 23 to the home point HP prior to or after executing other modes (such as approach mode, described further below) may be included. The instrument controller 28 may be configured to control the actuators 21, 22, 23 to their home positions between minimum and maximum values of the effective lengths EL of the actuators 21, 22, 23.

When in the home position, the amount of adjustability of the actuators 21, 22, 23 is maximized to keep the tool 20 at a desired pose. Various levels of adjustment are possible depending on the particular geometry and configuration of the instrument 14. In some examples, when all the actuators 21, 22, 23 are in their home positions, the tool 20 may be adjusted in pitch orientation about +/−18° relative to the home position, assuming zero changes in the roll orientation and no z-axis translation. In some examples, when all the actuators 21, 22, 23 are in their home positions, the tool 20 may be adjusted in roll orientation about +/−33° relative to the home position, assuming zero changes in the pitch orientation and no z-axis translation. In some examples, when all the actuators 21, 22, 23 are in their home positions, the tool 20 may be adjusted in z-axis translation about +/−0.37 inches relative to the home position, assuming zero changes in the pitch orientation and roll orientation. The tool 20, of course, may be adjusted in pitch, roll, and z-axis translation simultaneously, sequentially, or combinations thereof during operation.

The homing procedure for each actuator 21, 22, 23 can be carried out sequentially, simultaneously, or in any desired order. In some instances, during the homing procedure, the instrument controller 28 actuates each motor 142. The motor 142 is actuated to rotate its associated lead screw 150 so as to cause relative axial displacement between the lead screw 150 and the associated carrier 116 in each axial direction along the associated active axis AA1, AA2, AA3 until the stops 152 make contact with the carrier 116. Such contact could be determined by additional sensors S, by monitoring current to the motor 142 (e.g., a spike in current beyond a threshold value would indicate a stop 152 has been reached), or the like. For example, the motor 142 may actuate the lead screw 150 until one of the stops 152 engages the carrier 116, at which point the cumulative counts and associated end rotor position is stored. The counter that stores the cumulative counts representative of rotor position may also be set to zero when the first stop 152 is reached, but is not required. The motor 142 may then actuate the lead screw 150 in the opposite direction until the other stop 152 engages the carrier 116. During this time period, the instrument controller 28 monitors the signal(s) from the sensor(s) S to count turns of the rotor 148 until the other end rotor position is reached. The instrument controller 28 maintains the count in the counter that is representative of the total degrees of rotation of the lead screw 150 (e.g., of the shaft thereof)

between the stops 152. The home position is the mean of those counts or the mean rotor position between the stops 152.

In some examples, the instrument controller 28 stores as data the cumulative counts representative of the rotations of the rotor 148 needed to displace the lead screw 150 between the end rotor positions (e.g., between travel limits). The absolute difference between these two counts is calculated. This difference is divided by two. This value represents the number of counts, through which the rotor 148 must be cycled from its current position in order to center the home point HP in the carrier 116 to the home position. For example, in this process, the instrument controller 28 may receive an indication that: at one end rotor position, the count value was 2500; and at the other end rotor position, the count value was −1480. The difference between these count values is 3980. One half this difference is 1990. Thus, the mean count value between end rotor positions can be calculated as −1480+1990=510. This number is referred to as a target position. During the homing process, this target position is a positive or negative number equal to the cumulative count representative of the home position. The instrument controller 28 in turn, applies energization signals to the motor 142 so as to cause the rotor 148 to rotate towards this count representing the home position.

During the resultant rotation of the rotor 148, the changing values of the sensors S result in the output of counts that change the count value stored in the counter. During this step, the instrument controller 28 compares the cumulative count stored in the counter to the count represented by the home position. When these two values are equal, the instrument controller 28 terminates the application of energization signals to motor 142. The instrument controller 28 may also set the counter to zero at the home position. It should be understood that this rotation of the rotor 148 and, by extension, lead screw 150 results in the displacement of the lead screw 150 relative to the carrier 116 to its home position along the active axis AA1, AA2, AA3. Once the actuators 21, 22, 23 are at their home positions, soft stops may be enabled to prevent the stops 152 (e.g., hard stops) from contacting the carrier 116 at the extreme ends of travel. The soft stops may be software enabled stops set at count values just shy of the extreme ends of travel measured during the homing procedure. The soft stops may be values preprogrammed into the software. The soft stops may be a combination of count values and preprogrammed values.

As shown in FIG. 16, each of the actuators 21, 22, 23 have an effective length EL. The effective length EL at the home position may be any suitable length. In some examples, the effective length EL at the home position may be about 2.14 inches and minimum/maximum values of the effective length EL when engaging the hard stops 152 may be about 1.72 and 2.56 inches, respectively. When the soft stops are employed, the minimum/maximum values of the effective length EL may be about 1.78 inches and 2.50 inches, respectively. It should be understood that these values are merely examples, and other values are contemplated.

In some examples, each incremental count associated with the rotation of the rotor 148 that results in the displacement of the rotor 148 toward the carrier 116 is a positive incremental count and each incremental count associated with the rotation of the rotor 148 resulting in the displacement of the rotor 148 away from the carrier 116 is a negative incremental count. The instrument controller 28 thus is able to provide cumulative count data representative of the rotor position.

An initial location of the base coordinate system BCS can be determined based on a known geometric relationship between the tool support coordinate system TCS and the base coordinate system BCS when the actuators 21, 22, 23 are in their home positions or other predetermined position. This relationship changes when the actuators 21, 22, 23 are adjusted and the associated changes can be determined based on the kinematics of the robotic system 10 (e.g., which establishes a dynamic transformation between these coordinate systems). Alternatively, or additionally, another tracker could be attached and fixed with respect to the base coordinate system BCS to directly track a pose of the base coordinate system BCS relative to the tool support coordinate system TCS. Thus, the robotic system 10 knows the position of the tool 20, such as in the home position and its relation to the pose of the hand-held portion 16. Accordingly, when the tool 20 is moved by the user and its pose is tracked using the tool tracker 52, the robotic system 10 also tracks the pose of the hand-held portion 16 and its base coordinate system BCS. In some examples, as a result of prior calibration processes, the position of the tool 20 relative to the tool support 18 is assumed to be known.

Figure 60:
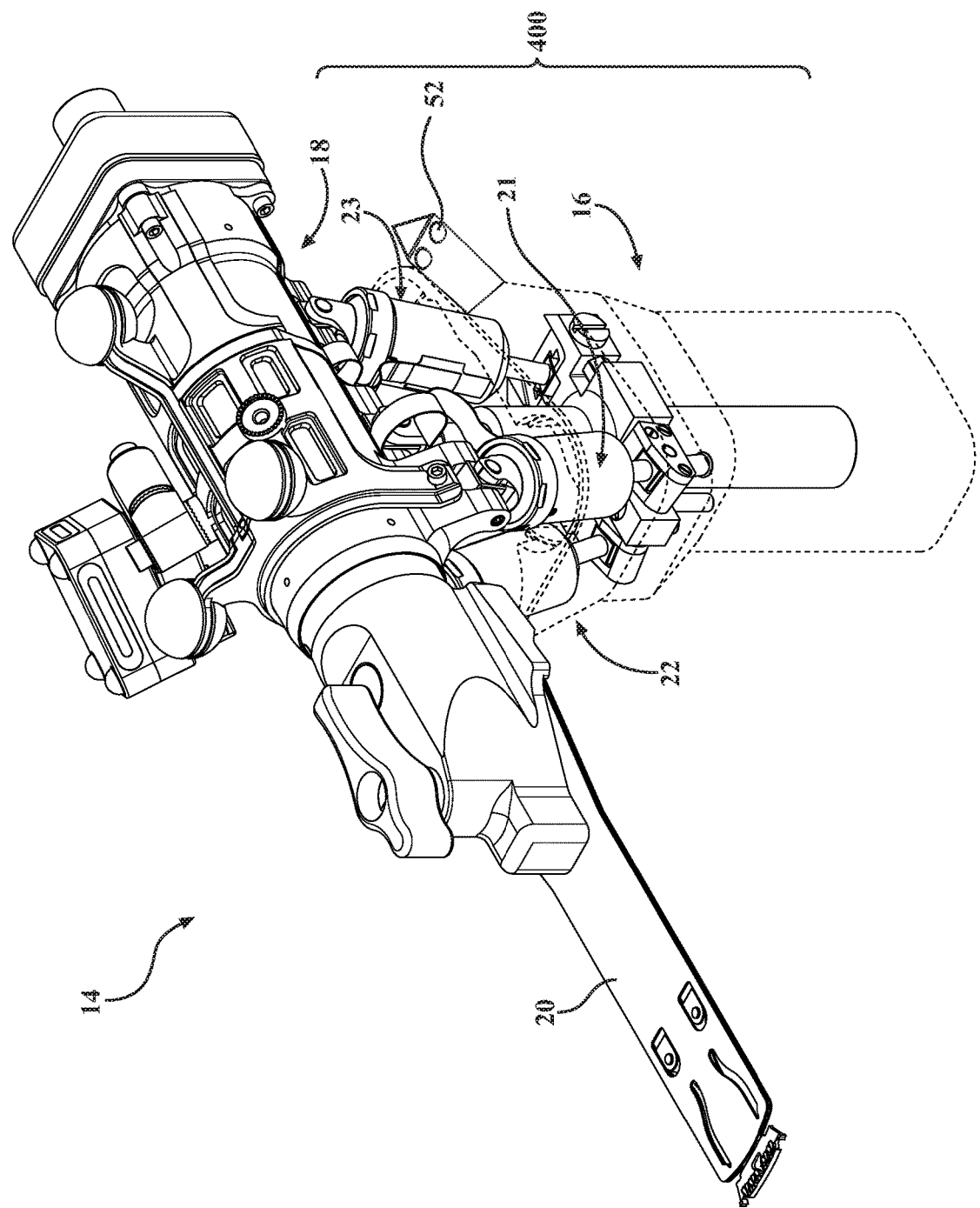
FIG. 60 illustrates a perspective view of an alternative configuration of the robotic instrument.

In some versions, the home position is determined by first determining a pose of the hand-held portion 16 (e.g., of the base coordinate system BCS) relative to the tool support 18 (e.g., relative to the tool support coordinate system TCS) in a common coordinate system by employing a separate tracker fixed to the hand-held portion 16 (see FIG. 60). This spatial relationship between the hand-held portion 16 and the tool support 18 could also be determined by registration using the pointer 57 and known calibration divots on the hand-held portion 16, or via other navigation methods. The current rotor position of each of the actuators 21, 22, 23 can then be derived from this spatial relationship based on the kinematics of the instrument 14. Knowing the current rotor positions, and measuring changes from the current rotor positions using the encoders (and corresponding encoder signals), the instrument controller 28 can thereafter operate each of the actuators 21, 22, 23 until they reach their home positions. The home positions can be stored in the memory of the instrument controller 28.

In essence, the instrument controller 28 uses tracking data obtained by the navigation system 32 from the trackers 52 coupled to tool support 18 and the hand-held portion 16 on the instrument 14 to determine the position of the actuators 21, 22, 23 so that, thereafter, the incremental encoders can operate as absolute encoders.

Once registration, calibration, and homing (if used) are complete, the navigation system 32 is able to determine the spatial pose of the tool 20 with respect to the anatomy (e.g., with respect to the femur F or other target tissue) and the one or more virtual boundaries 184. The instrument 14 is thus ready for boundary constrained treatment of the anatomy (e.g., the instrument 14 is ready for cutting a target volume of material from the femur F). Even if the homing procedure as defined above is not used (e.g. absolute encoders), the actuators 21, 22, 23 may still be set to their home positions prior to or after executing other operating modes, such as approach mode.

After the homing process, control is based on the position and/or orientation data from the navigation controller 36 and the cumulative count data from the instrument controller 28 or other position data of the actuator(s). Control could also be based on user input, such as from a trigger or other input device, such as a footswitch. In some examples, the instrument 28 may operate automatically based on a pose of the tool 20 relative to the anatomy being treated, as described further below.

Control of the instrument 14 takes into account the latest positions and/or orientations of the anatomy (e.g., the femur F) and the instrument 14, which are transmitted from the navigation controller 36 to the instrument controller 28 over the data connection. Using these data, the instrument controller 28 determines the location (i.e., position and/or orientation) of the virtual boundaries 184 in a desired coordinate system. The relative location of the tool 20 (e.g., the TCP) to the virtual boundaries 184 is also computed. The instrument controller 28 updates the navigation system 32 (including the displays 38) with the position and/or orientation of the tool 20 relative to the anatomy to which the tool 20 is to be applied. An indication of the location of the virtual boundaries 184 may also be presented.

The relative location of the tool 20 to the virtual boundaries 184 is evaluated by the instrument controller 28 to determine if action needs to be taken, i.e., moving the tool 20, changing a speed (such as an oscillation speed) of the tool 20, stopping operation of the tool 20, etc. Instructional data packets are sent, for example, to the motor controllers, such as from the console 33 or other component of the instrument controller 28. These instructional data packets include the target positions for the rotors 148 of the motors 142 (or target position of the actuator). Here, each target position may be a positive or negative number representative of a targeted cumulative count for the associated rotor 148. The console 33 or other component of the instrument controller 28 generates and sends these instructional data packets to each motor controller at the rate of one packet every 0.05 to 4 milliseconds. In some examples, each motor controller receives an instructional data packet at least once 0.125 milliseconds. Instrument controller 28 may also selectively regulate a cutting speed of the instrument 14 based on the relative location of the tool 20 to one or more of the virtual boundaries 184. For instance, the drive motor M that controls oscillation of the tool 20 and corresponding cutting, may be disabled by the instrument controller 28 any time the tool 20 is in an undesired relationship to the virtual boundaries 184, e.g., the tool 20 is off a target plane by more than a threshold value.

During use, when the robotic system 10 determines a pose (a current pose) of the tool 20 with the navigation system 32 by virtue of the tracker 52 being located on the tool support 18. The instrument controller 28 may also determine a current position of each of the actuators 21, 22, 23 based on an output encoder signal from the one or more encoders located on each of the actuators 21, 22, 23. Once the current position of each of the actuators 21, 22, 23 is received, the instrument controller 28 may calculate a current pose of the hand-held portion 16 (e.g., a current pose of the base coordinate system BCS with respect to a desired coordinate system, such as the TCP coordinate system using forward kinematics to convert from the actuator positions to the pose (TCP with respect to BCS). Once the instrument controller 28 has the current relative poses of the tool support 18 and the hand-held portion 16 in the desired coordinate system, the instrument controller 28 may then determine a commanded pose of the tool 20 based on the current pose of the tool 20 as determined by the navigation system 32, the current pose of the hand-held portion 16 calculated by the current position of each of the actuators 21, 22, 23, and based on a position and/or orientation of a planned virtual object, subject as a desired cutting plane. The instrument computes a pose (a commanded pose) of TCP with respect to BCS that results in the TCP being on the desired plane or aligned with the planned virtual object. The instrument controller 28 may send command instructions to the actuators 21, 22, 23 to move to a commanded position, thereby changing the pose of the tool support 18 and tool 20. In one example, the commanded pose of the tool 20 is further based on a target cut plane so the instrument controller 28 calculates the current pose of the tool support 18 and the current positions of the actuators 21, 22, 23 in order to determine the current pose of the hand-held portion 16. Once the current pose of the tool support 18, current positions of the actuators 21, 22, 23, and the current pose of the hand-held portion 16 are known, the instrument controller 28 can send command signals to the actuators 21, 22, 23 to adjust the tool support 18 and tool 20 based on the desired plane. The controller computes the commanded pose assuming that, momentarily (during a single iteration) the pose of the hand-held portion (BCS) is stationary relative to patient anatomy. By updating the corresponding poses each time, the actual movement of BCS is adjusted for.

Figure 64:
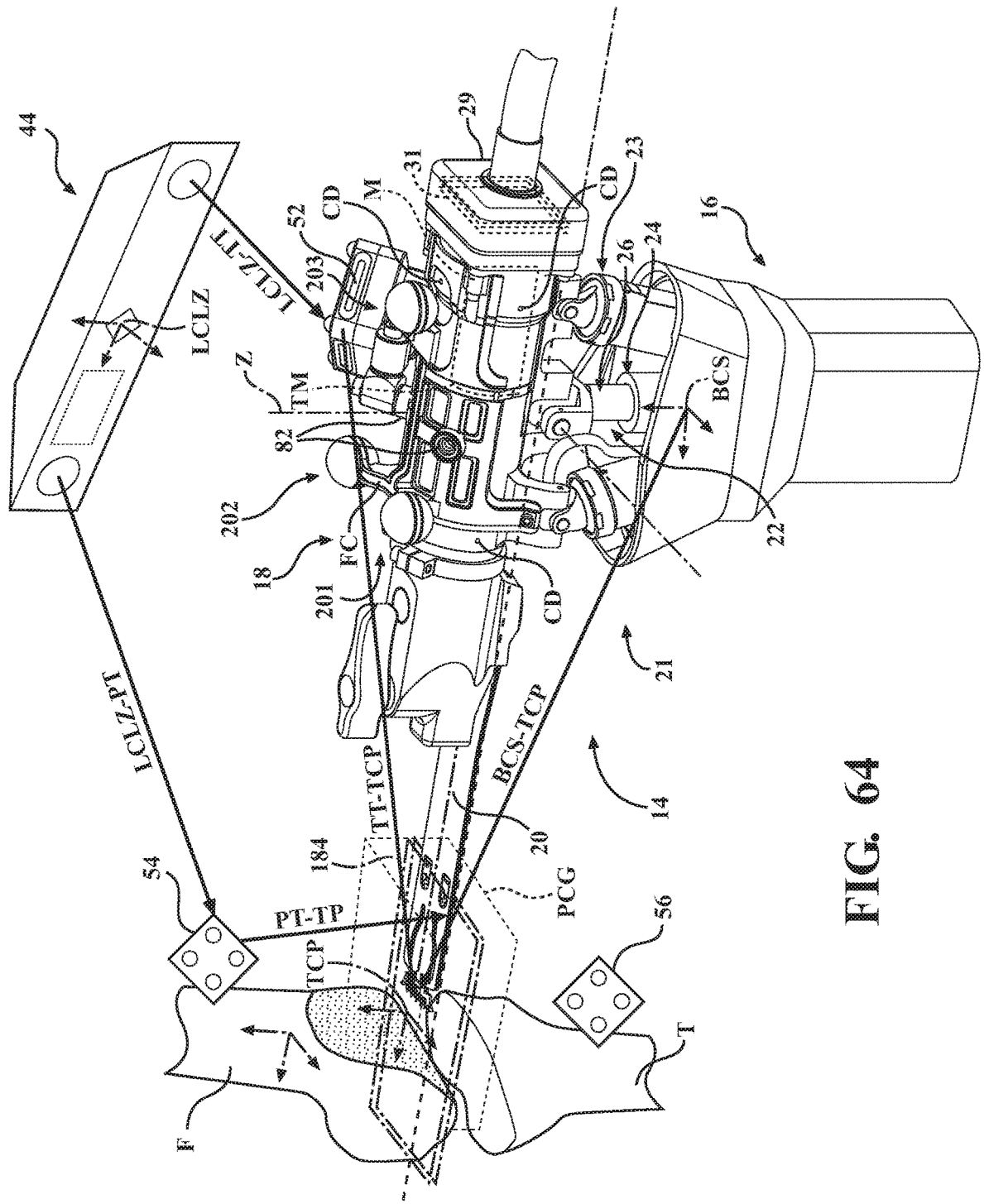
FIG. 64 illustrates a portion of the navigation system relative to the patient anatomy and a surgical robotic instrument.

Turning to FIG. 64, the exemplary control is described with respect to the various transforms. The TCP is determined by tracking the tool 20 with the tracker 52 in LCLZ (LCLZ-TT), and determining a transform between tool tracker 52 and the TCP of the tool 20 (TT-TCP), such as the saw, using registration data. Similarly, the patient is tracked using the patient tracker PT (shown as 54) in the LCLZ (LCLZ-PT). A transform (PT-TP) is determined between the patient tracker PT and each planned virtual object 184 (TP) using registration data and planning information. As described above, a transform between BCS and TCP (BCS-TCP) is computed based on the current positions of each actuator (described above). The transform between BCS and TCP is utilized to relate the various coordinate systems back to the hand-held portion 16, since the commanded pose may be determined relative to the BCS. Conceptually, the commanded pose, is an update to the BCS to TCP transform which results in the TCP being aligned with the planned virtual object 184 (the target plane TP) in this example.

Throughout this description, unless otherwise noted, any instance of pose may be a commanded pose, a current pose, a past pose, or a past commanded pose. While each of these poses may be different from one another, due to the frequency of control, the difference in position and/or orientation between these poses may be minimal in each control iteration.

It should be understood that the combination of position and orientation of an object is referred to as the pose of the object. Throughout this disclosure, it is contemplated that the term pose may be replaced by position and/or orientation and vice-versa to achieve suitable alternatives of the concepts described herein. In other words, any use of the term pose can be replaced with position and any use of the term position may be replaced with pose.

Visual Guidance

Figure 65:
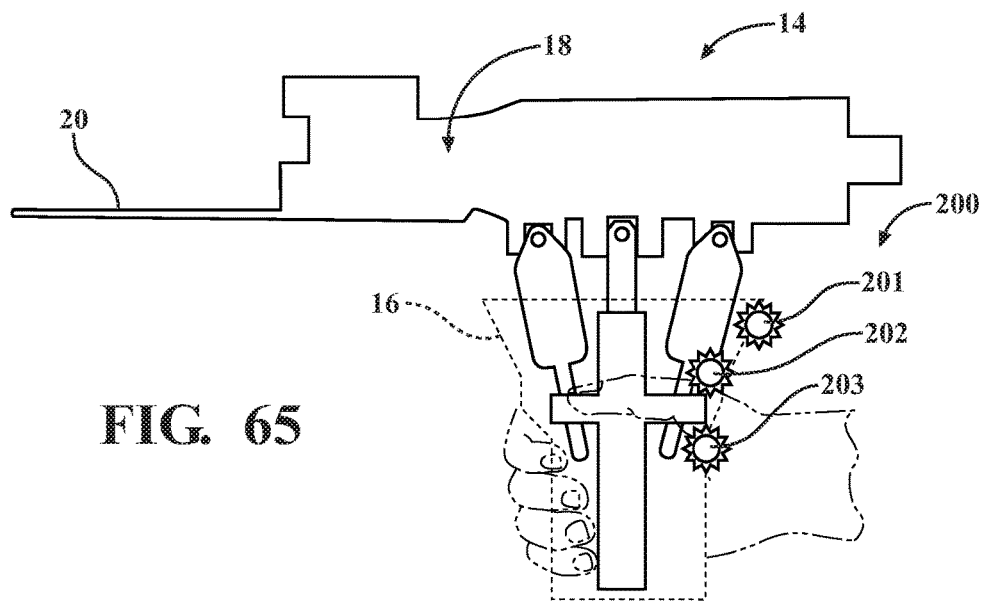
FIG. 65 illustrates the instrument with a guidance array located on the hand-held portion.

As shown in FIG. 22, a guidance array 200 may be coupled to the tool support 18. Additionally, or alternatively, the guidance array 200 could be attached to the hand-held portion 16 such as seen in FIG. 65, or other portion of the instrument 14. In the version shown, the guidance array 200 comprises at least a first visual indicator 201, a second visual indicator 202, and a third visual indicator 203. Each of the visual indicators 201, 202, 203 comprises one or more illumination sources coupled to the instrument controller 28. In some versions, the illumination sources comprise one or more light emitting diodes (e.g., RGB LEDs), which can be operated in different states, e.g., on, off, flashing/blinking at different frequencies, illuminated with different intensities, different colors, combinations thereof, and the like. In the version shown in FIG. 22, each of the visual indicators 201, 202, 203 comprises upper portion and lower portion 204, 206 (upper segment 204; lower segment 206). It is further contemplated that the each of the visual indicators 201, 202, 203 may be divided into more than two portions 204, 206, such as three or more, four or more, or even ten or more portions. For example, each of the visual indicators 201, 202, 203 may be divided into three portions, with each portion including one or more LEDs. The visual indicators 201, 202, 203 may have generally spherical shapes with the upper and lower portions 204, 206 comprising hemispherical, transparent or translucent domes that can be separately controlled/illuminated as desired. It is contemplated that the visual indicators 201, 202, 203 may have a shape other than a sphere such as a cylinder, a ring, a square, a polygon, or any other shape capable of conveying visual cues to a user. One or more light emitting diodes may be associated with each dome. The visual indicators 201, 202, 203 may be fixed via one or more mounting brackets 205 to the tool support 18 or to the hand-held portion 16.

Figure 66:
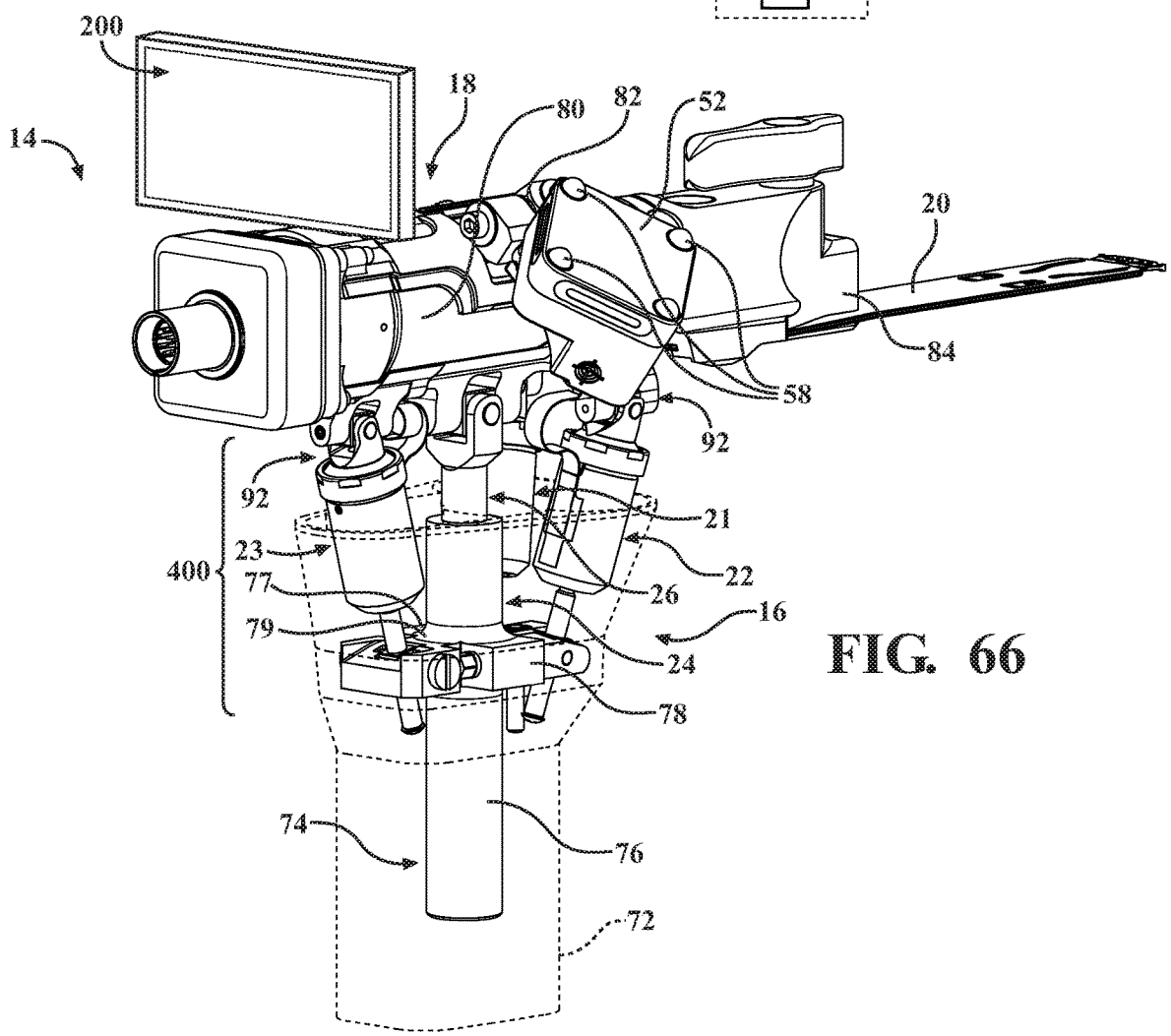
FIG. 66 illustrates the instrument with a guidance array as a display screen.

In some examples, where no guidance array is used, the visual indicators 201, 202, 203 may comprise separate portions of a display screen (See FIG. 66), such as separate regions on a LCD, or LED display mounted to the tool support 18 or the hand-held portion 16 (e.g. FIG. 66). The display screen may also be included as part of the navigation system, in addition or as an alternative to having a display screen mounted to the instrument.

In some configurations, there may be one, two, three, or four portions of the display screen, each corresponding to a different visual indicator. Each portion of the display screen may correspond to a different visual graphic. As described below, each of the visual indicators (or portions of the display screen) may be based on actuator information. In some cases, a single visual indicator may be based on actuator information from two or more actuators. Furthermore, as described throughout, the visual indicator may be used in a first mode indicating where the user should position the tool and a second mode where the visual indicator indicates where the user should position the hand-held portion.

For example, the visual indicator 201, 202, 203 may be configured to output a first indication (a first visual graphic) based on a first commanded position of the first actuator 21, 22, 23 and a second indication (second visual graphic) based on a second commanded position of the first actuator 21, 22, 23, wherein the first indication is different than the second indication, and the first commanded position is different from the second commanded position. As described above, the visual indicator 201, 202, 203 may be controlled based any suitable type of actuator information. In other words, the visual graphics displayed on the display screen may be based on the commanded position, the previous commanded position, a simulated commanded position, a current measured position, a previous measured position, available travel, an actuator limit (such as a hard or soft stop), a distance needed from current position to commanded position, or a combination thereof.

In some configurations, the instrument controller 28 is configured to control illumination of the upper and lower portions 204, 206 such that the upper and lower portions 204, 206 are operated in different states to indicate the direction of desired movement of the tool 20. It is further contemplated that the instrument controller 28 may be configured to control illumination of multiple portions in different states or with different indications. For example, the different states may indicate to the user: (1) how the user should move the hand-held portion 16 to place the tool 20 (e.g., saw blade) at a desired pose (e.g., on a desired cutting plane); or (2) how the user should move the hand-held portion 16 such that the actuators 21, 22, 23 move in a preferred direction, such as closer to their home positions while the control system 60 simultaneously works to keep the tool 20 at the desired pose, as will be described further below.

During some modes of operation, the instrument controller 28 is configured to automatically control/adjust the guidance array 200 (e.g., change states thereof) to visually indicate to the user desired changes in pitch orientation, roll orientation, and z-axis translation of the tool 20 to achieve the desired pose of the tool 20 while the user moves the tool 20 via the hand-held portion 16. In some versions, the guidance array 200 is coupled to the tool support 18 or to the hand-held portion 16 in a way that intuitively represents the plane of the tool 20. For example, since three points define a plane, the three visual indicators 201, 202, 203 may generally represent the plane of the tool 20. In some cases, each of the indicators 201, 202, 203 corresponds to one of the points P1, P2, P3 having a known position relative to the plane of the tool 20 (e.g., located in the tool plane and defined in the TCP coordinate system, the tool support coordinate system TCS, or defined in any other suitable coordinate system). In some versions, the indicators 201, 202, 203 correspond to points P4, P5, P6, respectively, of the tool 20, as shown in FIGS. 23A-23D. Points associated with the visual indicators 201, 202, 203 could be defined at other suitable locations in the plane of the tool 20 or at locations having a known relationship to the plane of the tool 20.

Collectively, the guidance array 200, using the one or more visual indicators 201, 202, 203 may be located and their states controlled to visually indicate to the user desired changes in movement (e.g. amount of travel) to change pitch, roll, and translation of the tool 20, and by extension, desired changes in pitch, roll, and translation of the tool support coordinate system TCS to achieve a desired pose. More specifically, the instrument controller 28 is configured to illuminate the guidance array 200 in a manner that enables the user to distinguish between a desired change in pitch orientation, a desired change in roll orientation, and a desired change in translation. The instrument controller 28 may be configured to illuminate the guidance array 200 or control the display screen in a manner that enables the user to indicate an amount of travel required to move the tool 20 to a desired plane. A desired plane may be a plane or a plane segment. The changes in pitch, roll, and translation are, for example, relative to one or more of the virtual boundaries.

In another configuration, the guidance array 200, using the one or more visual indicators 201, 202, 203 may be located and their states controlled to visually indicate to the user desired changes in movement (e.g. amount of travel) to change pitch, roll, and translation of the hand-held portion 16 and by extension, desired changes in pitch, roll, and translation of the base coordinate system BCS to achieve a desired pose. More specifically, the instrument controller 28 is configured to illuminate the guidance array 200 or display screen in a manner that enables the user to distinguish between a desired change in pitch orientation, a desired change in roll orientation, and a desired change in translation. The instrument controller 28 is configured to illuminate the guidance array 200 in a manner that enables the user to indicate an amount of travel required to move the hand-held portion 16 so that the tool 20 is on a desired plane. The changes in pitch, roll, and translation are, for example, relative to one or more of the virtual boundaries 184.

The instrument controller 28 may switch operation of the guidance array 200 and/or visual indicators 201, 202, 203 (or display screen) from a mode where the guidance array/ visual indicators indicate desired changes in movement of the tool 20 to indicate desired changes in movement of the hand-held portion 16 based on an input signal, such as activation of an input device (e.g. footswitch, trigger, etc.). Alternatively, the instrument controller 28 may be configured to switch between these modes based on the position of the tool 20 and the position of a reference location of bone in a known coordinate system, such as trackers 54, 56, PT. A reference location may be a point, surface, or volume in the coordinate system used to locate the instrument 14 relative a target object. For example, the reference location may be a surface of a bone, a point within a bone, an imaginary or virtual point within the known coordinate system, a volume in the coordinate system, or a combination thereof. The position and/or orientation of the reference location is known with respect to the patient tracker through registration and suitable planning steps.

As described below, the instrument controller 28 may switch modes based on a distance parameter. A distance parameter may be a distance (e.g. how far apart two objects are), magnitude (the direction of the distance relative to one object), or both. In some examples, the instrument controller 28 may switch modes when the distance parameter has a direction away from bone and a magnitude greater than a first threshold value. It should be appreciated that while in the first mode, the instrument controller 28 automatically controls each of the actuators 21, 22, 23 to maintain the tool 20 in a pose relative to a pose of the hand-held portion 16, and wherein in the second mode, the controller automatically controls each of the actuators 21, 22, 23 such that the tool 20 actively moves towards the desired plane relative to the pose of the hand-held portion 16. The automatic switching between modes may provide the user with the type of guidance that is appropriate determined by the proximity to bone and the cut to be made. In other words, as the instrument 14 is close to bone, the guidance array 200 and/or visual indicators 201, 202, 203 operate to provide precise guidance to ensure that the hand-held portion 16 remains positioned in a pose that maximizes the range of motion relative to the desired plane.

In the scheme shown in FIGS. 23A-23D, the first and second visual indicators 201, 202 are located in front of the hand-held portion 16 and on opposing sides of the instrument 14, roughly aligned with the actuators 21, 22, respectively. The third visual indicator 203 is located rearward of the hand-held portion 16, roughly aligned with the actuator 23 and near the rear of the instrument 14, i.e., the first and second visual indicators 201, 202 are located distal to the third visual indicator 203. As shown in FIG. 2, when viewed from above and in the home position, the first and second visual indicators 201, 202 are located forward of the y-axes of the tool support coordinate system TCS and the base coordinate system BCS and on opposing sides of the x-axes of the tool support coordinate system TCS and the base coordinate system BCS. When viewed from above and in the home position, the third visual indicator 203 is located rearward of the y-axes and aligned with the x-axes. In some examples, when in the home position, the tool support 18 defines the vertical central plane VCP through the x-axes, wherein the first and second visual indicators 201, 202 are offset from the vertical central plane VCP on opposing sides of the vertical central plane VCP and the vertical central plane VCP passes through the third visual indicator 203 (see FIG. 11). Other arrangements of the visual indicators 201, 202, 203 are contemplated.

In some examples, referring back to FIGS. 23A-23D, the upper and lower portions 204, 206 can be oriented vertically on directional axes DA parallel to the z-axis of the tool support coordinate system TCS, and different states (e.g., colors, frequencies, intensities, etc.) can be shown in each of the upper and lower portions 204, 206 to indicate an upward/downward direction of desired movement of each visual indicator 201, 202, 203. As a result of this arrangement, for example, when all of the visual indicators 201, 202, 203 are controlled to indicate downward movement is desired, that indicates the user should move their hand downwardly (see arrow in FIG. 23A). The instrument controller 28 may control illumination of the upper portions 204 so that the upper portions 204 are operated in a first state and the lower portions 206 are operated in a second state, different than the first state, to indicate to the user to change the translation position of the tool 20 and/or hand-held portion 16 relative to the virtual boundary 184. In the example shown, a downward direction can be visually indicated by illuminating the upper portions 204 red, while the lower portions 206 are illuminated yellow (e.g., red over yellow indicates the direction is down).

The instrument controller 28 may also be configured to control illumination of the upper portion 204 of the first visual indicator 201 to be operated in a first state and to control illumination of the upper portion 204 of the second visual indicator 202 to be operated in a second state, different than the first state, to indicate to the user to change the roll orientation of the tool 20. Likewise, the instrument controller 28 may be configured to control illumination of the upper portion 204 of the third visual indicator 203 to be operated in a first state and to control illumination of the upper portions 204 of the first and second visual indicators 201, 202 to be operated in a second state, different than the first state, to indicate to the user to change the pitch orientation of the tool 20 relative to the virtual boundary 184. For example, as shown in FIG. 23B, when only slight downward movement and a change in pitch orientation is required (see arrows), the first and second visual indicators 201, 202 can be illuminated to show that they still need to be moved downward slightly, but the third visual indicator 203 can be illuminated differently to show that the rear of the instrument 14 needs to move down further than the front (i.e., a change in pitch is needed). In the example shown, a slight downward direction can be visually indicated by illuminating the upper portions 204 of the first and second visual indicators 201, 202 yellow, while the lower portions 206 are illuminated green (e.g., yellow over green indicates the direction is slightly down). At the same time, the third visual indicator 203 can remain illuminated as in FIG. 23A (e.g., red over yellow) to show that further downward movement is required at the rear, and thus visually and intuitively indicate to the user that the instrument 14 is to be reoriented in pitch.

As shown in FIG. 23C, the instrument controller 28 may be configured to control illumination of the upper and lower portions 204, 206 of the first and second visual indicators 201, 202 such that the upper and lower portions 204, 206 are operated in the same state to indicate that corresponding points (P1, P2 or P4, P5) in the plane of the tool 20 or associated with the plane of the tool 20 are at desired positions (e.g., as indicated by green over green illumination). In other words, the first and second actuators 21, 22 do not require any further actuation to ultimately place the tool 20 on the desired plane. However, as also shown in FIG. 23C, the upper and lower portions 204, 206 of the third visual indicator 203 are still in different states indicating that the rear of the instrument 14 (and corresponding point P3 or P6) still needs to be lowered, albeit less than required in FIG. 23B (as can be indicated by yellow over green illumination as described above). FIG. 23D shows the results of the user slightly moving the rear of the instrument 14 as instructed (in pitch) such that the tool 20 is at the desired pose as indicated by all of the upper and lower portions 204, 206 of the visual indicators 201, 202, 203 operating in the same state (e.g., green over green illumination).

As previously mentioned, each visual indicator 201, 202, 203 of the guidance array 200 (or each portion of a display screen) may be associated with one or more of the actuators 21, 22, 23. In other words, in certain configurations, each visual indicator 201, 202, 203 may be paired with a corresponding one of the actuators 21, 22, 23 such that states of a particular visual indicator 201, 202, 203 directly reflects actuator information about its corresponding actuator 21, 22, 23. It is also contemplated that each visual indicator 201, 202, 203 may be paired with two or more of the actuators 21, 22, 23. In another example, two or more of the actuators 21, 22, 23 may be paired with one or more visual indicators 201, 202, 203. In some cases, states of a particular visual indicator 201, 202, 203 may reflect the amount of movement required for one or more actuators 21, 22, 23 to move its corresponding point (e.g., P1, P2, P3 or P4, P5, P6) to the commanded pose (e.g., desired plane of the tool 20). For example, the illumination scheme of red over yellow, as shown on all the visual indicators 201, 202, 203 in FIG. 23A, indicates that each actuator 21, 22, 23 needs to travel (e.g., retract) a relatively large distance to move their corresponding points to the desired plane, or it may indicate that the desired plane is out of the reach of the actuators 21, 22, 23. More specifically, in some cases, the illumination scheme of red over yellow indicates that the travel distance required to reach the desired plane may be greater than 60%, 65%, 70%, 75%, 80%, or more of an actuator's total available travel (e.g., as measured from the actuator's home position to the hard or soft limits). Other ranges are also contemplated. If the illumination scheme was instead yellow over red, then the actuators 21, 22, 23 need to travel a relatively large distance in the opposite direction (e.g., extend).

Similarly, the illumination scheme of yellow over green, as shown on the visual indicators 201, 202 in FIG. 23B, may indicate that the associated actuators 21, 22 need to move (e.g., retract; elongate) a relatively smaller distance to move their corresponding points to the desired plane. More specifically, in some cases, the illumination scheme of yellow over green indicates that the operational range required to reach the desired plane may be in a range of from 30-80%, 30-75%, 30-70%, 30-65%, 30-60%, 40-80%, 40-75%, 40-70%, 40-65%, 40-60%, 50-80%, 50-75%, 50-70%, 50-65%, or 50-60% of an actuator's total available travel. Other ranges are also contemplated. If the illumination scheme was instead green over yellow, then the actuators 21, 22 need to travel a relatively smaller distance in the opposite direction (e.g., extend).

Figure 23E:
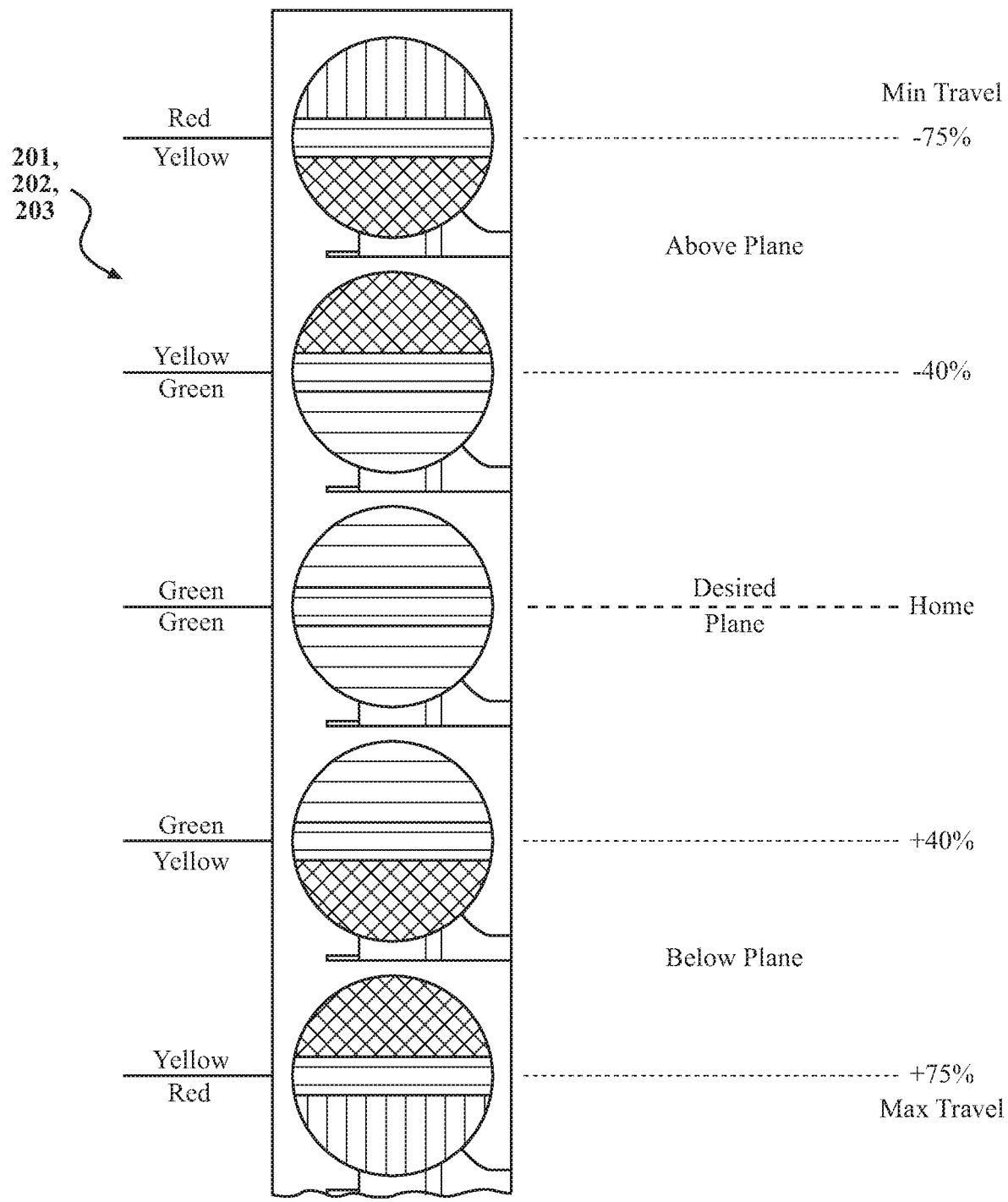
FIG. 23E illustrates an example scheme of states for visual indicators of the guidance array.

The illumination scheme of green over green, as shown on all the visual indicators 201, 202, 203 in FIG. 23D, may indicate that the associated actuators 21, 22, 23 need to travel (e.g., retract or extend) a relatively small distance to move their corresponding points to the desired plane, or it may indicate that the corresponding points are already on the desired plane. More specifically, in some cases, the illumination scheme of green over green indicates that the travel distance required to reach the desired plane may be in a range of from 0-30%, 0-40%, or 0-50% of an actuator's total available travel, in either direction. Other ranges are also contemplated. An example scheme of states for the visual indicators 201, 202, 203, and threshold values for determining when to change the states, is shown in FIG. 23E. In FIG. 23E, a positive (+) percentage of required travel from the home position indicates required movement in extension and a negative (−) percentage of required travel from the home position indicates required movement in retraction. Other threshold values and state changes associated with such threshold values are contemplated. For example, the threshold value could be based on actual distances of required travel (e.g., in millimeters or inches), and/or other suitable parameters.

Each of the visual indicators 201, 202, 203 include at least one illumination source, such as light emitting diodes (LEDs). Each LED can be operated in different states such as on, off, flashing/blinking at different frequencies, illuminated with different intensities/colors, combinations thereof, and the like. In most examples, the visual indicators 201, 202, 203 include a plurality of LEDs, so that each of the visual indicators 201, 202, 203 is capable of producing several colors of light such as green, yellow, and red in each portion of the visual indicator. Each color may be representative of information about one or more of the actuators 21, 22, 23. The colors, frequency, intensity, and/or states of the visual indicators 201, 202, 203 may be tied to one or more actuator information such as a commanded position, a previous commanded position, a simulated commanded position, current position, a previous measured position, available travel, an actuator limit (such as a hard or soft stop), a distance needed from current position to commanded position, or a combination thereof.

In one example, the information about at least one of the actuators 21, 22, 23 may be a commanded position of a first actuator 21, 22, 23 and an available travel of the first actuator 21, 22, 23. The visual indicator may be controlled based on the commanded position of the first actuator to move the tool 20 to and the available travel of the first actuator. For example, a first color may be based on a first range of travel within an operational range of an actuator and a commanded position of that actuator 21, 22, 23, and a second color may be a second range of travel within the operational range of the actuator 21, 22, 23 and a commanded position of that actuator 21, 22, 23, which is different than the first range of travel. A third color representing a third range of travel of the actuator 2, 22, 23 within the available travel may also be included, the third range of travel different than the second range of travel. For example, the first color is red and correlates to the commanded position of the actuator 21, 22, 23 being closest to the outer limits of the available travel, the second color is yellow and correlates to the commanded position of the actuator 21, 22, 23 being farther away from the outer limits of the available travel, and the third color is green indicating that the commanded position of the actuator 21, 22, 23 is far from the limits of the available travel range. In one example, each visual indicator 201, 202, 203 is representative of an actuator 21, 22, 23, displaying a visual cue (e.g. one or more colors; one or more patterns; one or more intensities) needed to move each actuator to a desired location. In another example, the colors associated with the visual indicators 201, 202, 203 are representative of several actuator parameters such that the visual indicators 201, 202, 203 would convey to the user a first color representative of the amount of travel needed to bring at least one actuator 21, 22, 23 to the commanded position, and a second color representative of the direction needed to move the hand-held portion 16 to bring the tool 20 into the operational range of the actuator. As described above, the third color may correspond to the outermost range of available travel (i.e., the least travel remaining available relative to the commanded position, the second color may correspond to the middle range of available travel, and the first color may correspond to the innermost range of available travel (i.e., the most travel remaining available relative to the commanded position). In some examples, when the visual indicators 201, 202, 203 are configured to have an upper portion 204 and a lower portion 206, each of the visual indicators 201, 202, 203 may illuminate both the upper portion 204 and the lower portion 206 in different states to indicate a direction of desired movement of the hand-held portion 16. In some versions, the illumination of the upper and lower portions 204, 206 of the visual indicators 201, 202, 203 may be operated in the same state based on a commanded position and the available travel of the hand-held portion 16.

The guidance array 200, the visual indicators 201, 202, 203 may be configured to visually indicate changes in pitch orientation, roll orientation, z-axis translation, or a combination thereof based on actuator information in a first mode where the guidance array and/or visual indicator is indicating placement of the tool and a second mode where the guidance array 200 and/or visual indicator 201, 202, 203 is indicating placement of the hand-held portion 16. The guidance array 200, the visual indicators 201, 202, 203 may visually indicate the same visual cues based on actuator information in both modes. Alternatively, the guidance array 200, the visual indicators 201, 202, 203 may visually indicate different visual cues based on actuator information in each mode. For example, the visual indicators 201, 202, 203 may be controlled based on available travel and a commanded position of one or more of the actuators 21, 22, 23. In another configuration, each visual indicator 201, 202, 203 may display the position of a corresponding actuator 21, 22, 23 and indicate to the user a corrective movement and/or direction to place the hand-held portion 16 and/or tool 20 on plane. Additionally, and/or alternatively, each visual indicator 201, 202, 203 may display the position of the hand-held portion 16 and indicate to the user a corrective movement and/or direction to place the hand-held portion 16 and/or tool 20 on plane. For example, each of the visual indicators 201, 202, 203, may indicate to a user changes in pitch orientation, roll orientation, z-axis translation, or a combination thereof based on actuator information to adjust the hand-held portion 16.

As described above, the guidance array 200 and/or visual indicators 201, 202, 203 (such as display screen) may be used to guide a user to move the hand-held portion 16 and/or tool 20 to a desired pose (e.g. target plane). In cases where the actuators 21, 22, 23 may not be actively moving the tool 20 towards the desired pose, i.e., changes in pose of the tool 20 may be caused solely by the user moving the hand-held portion 16, then a virtual simulation may be employed to indicate to the user how to move the hand-held portion 16 to achieve a desired pose of the tool 20. This simulation may operate as though the actuators 21, 22, 23 were being actively controlled to achieve the desired pose and therefore, the instrument controller 28 generates a simulated commanded position (not executed) for each of the actuators 21, 22, 23 that may exceed the available travel of one or more of the actuators 21, 22, 23. In this case, the visual indicator 201, 202, 203 may still illuminate red (e.g., for being out of range or close to the limit of the range) indicating to the user that the hand-held portion 16 needs to be moved. In other words, when an actuator 21, 22, 23 needs to be operated to a position near or beyond its limits, this directly indicates to the user that the hand-held portion 16 needs to be moved, i.e., so the hand-held portion 16 is located so that the actuators 21, 22, 23 can operate to place the tool 20 at the desired pose without exceeding the limits. For example, the instrument controller 28 determines a current position of each of the actuators 21, 22, 23 based on an output signal from one or more encoders located on each of the actuators 21, 22, 23. Once the current position of each of the actuators 21, 22, 23 is received, the instrument controller 28 may calculate a current pose of the hand-held portion 16. Once the instrument controller 28 has the current poses of the tool support 18 and the hand-held portion 16, the instrument controller 28 may then determine a commanded pose of the tool 20, hand-held portion 16, or both based on the current pose of the tool 20 and the current pose of the hand-held portion 16 calculated by the current position of each of the actuators 21, 22, 23. The instrument controller 28 may then send command instructions to a user through the visual indicators 201, 202, 203 (through use of the guidance array 200 in some instances) which also correlate to how the user is to move the hand-held portion 16 (i.e. move the entire instrument 14 towards the target plane).

It should be understood that the guidance array and/or visual indicator(s) 201, 202, 203 described throughout may be used with any surgical tool and any actuator configuration of the instrument 14. For example, the guidance array 200, visual indicators 201, 202, 203, or both may be used with the configurations described further below. Furthermore, the guidance array 200 and/or visual indicators 201, 202, 203 may be understood to encompass configurations where the guidance array 200 and/or visual indicators 201, 202, 203 enables the robotic system 10 to indicate an amount of travel required to move the tool 20 and/or the handheld portion 16 to a desired pose, trajectory, orientation, position, plane, or combinations thereof. Any guidance array and/or visual indicators may be used with any configuration of the instrument 14 to signal to a user how to position, move, and/or adjust the instrument 14 in any of the operating modes described throughout the present application. The changes in pitch, roll, and translation are, for example, relative to one or more of the virtual boundaries. The guidance array 200 and/or visual indicator 201, 202, 203 could facilitate positioning of different types of tools, including but not limited to, drill or reamer, a driver (for placement of a screw or a pin), a bur, a pin, a guide tube, etc.

It should be appreciated that other types of feedback could be employed to help guide the user, such as audible, tactile (e.g., vibrations), or the like. For example, the drive motor M could be employed to provide feedback. Other types of visual feedback could also be employed, such as using augmented reality techniques, projecting light onto the anatomy, or the like.

Operation

During operation, the robotic system 10 is initially powered up and the software application for operating the system is started. The trackers 52, 54, 56, PT are initialized and the trackers 52, 54, 56 are placed on the instrument 14 and on the target anatomy (e.g., femur F and tibia T). With the trackers 54, 56 mounted to the anatomy, the anatomy and/or associated images/models are registered to the trackers 54, 56 using known registration techniques. This may require the user to touch certain surfaces or landmarks on the anatomy with the pointer 57. For example, this may require the user to touch several points on the surface of the anatomy while pressing a select button on the pointer 57 or pressing a foot switch of the navigation system 32. This "paints" the points on the surface in the navigation system 32 for matching with the pre-operative and/or intra-operative image/model of the anatomy. The pre-operative image and/ or the intra-operative image/model of the anatomy is loaded in the navigation system 32. The tracked portion of the anatomy is registered to the pre-operative/intra-operative image/model. By extension, this allows the robotic system 10 to, as the anatomy moves, present a graphical representation of the actual position and orientation of the anatomy on the displays 38.

In a calibration/registration procedure, the orientation and location of the tracker 52 is calibrated/registered relative to the tool support 18 by reference to the fixed and known locations of the calibration divots CD or other reference points. In some examples, one or more trackers 52 may be located on the tool support 18, the hand-held portion 16, or both so that the position of the tool support 18 and/or the hand-held portion 16 are tracked by the navigation system 32. In examples in which the tracker 52 is integrated into the instrument 14, then such calibration would be unnecessary since the relative location of the tracker 52 to the tool support 18 is known.

The virtual objects (e.g., virtual boundaries 184) being used to control operation of the instrument 14 are also defined/obtained. Software running on instrument controller 28 (e.g., the boundary generator 182) generates/obtains an initial definition of the virtual objects. The user may have the ability and option to adjust the nature/placement of the virtual objects as may be necessary.

As shown in FIG. 22, in one exemplary configuration, the control system 60 defines various regions at predefined distances and/or positions from the target site and/or anatomy. These are shown as regions I, II, and III. Each of these regions may be defined in the coordinate system associated with the anatomy and/or virtual boundaries 184. In some cases, these regions are defined as spheres or other geometric primitives about the target site and/or the anatomy. In other examples, the regions (and others described below) may be defined with respect to the instrument 14, tool support 18, the hand-held portion 16, the tool 20, the target site/anatomy, or a combination thereof. The control system 60 may control the instrument 14 when the regions defined by the hand-held portion 16, the tool support 18, the tool 20, the target site/anatomy, or a combination thereof approach a specific virtual boundary/virtual cutting guide feature.

In some examples, the instrument controller 28 is coupled to the plurality of actuators 21, 22, 23 and the visual indicators 201, 202, 203 to control their operation in a plurality of modes including: a home mode in which the instrument controller 28 automatically adjusts each of the plurality of actuators 21, 22, 23 to their home position; an approach mode in which the instrument controller 28 indicates the desired movement of the tool 20 to place the tool 20 at the desired pose (e.g., on a desired trajectory or plane) while the plurality of actuators 21, 22, 23 are maintained at their home positions; and an on-target mode in which the tool 20 is generally located at the desired pose and the instrument controller 28 uses the guidance array 200 and its associated visual indicators 201, 202, 203 to indicate the desired movement of the hand-held portion 16 to keep the plurality of actuators 21, 22, 23 within a threshold of their home positions.

Additionally, and/or alternatively, the instrument controller 28 may place the instrument 14 into modes other than homing mode, approach mode, and on-target mode, controlling the visual guidance array, the visual indicators 201, 202, 203, the actuators 21, 22, 23, or a combination thereof to actuate and adjust based on a plurality of inputs.

In another configuration, the instrument controller 28 may operate in a mode to control the guidance array and/or visual indicators to indicate a desired movement of the hand-held portion 16 to place the tool 20 at a desired pose (e.g., on a desired trajectory or plane) based on the pose of the instrument 14 within a region while the plurality of actuators 21, 22, 23 are maintained at a position.

In another example, the instrument controller 28 may operate in a mode to control the guidance array and/or visual indicators to indicate a desired movement of the hand-held portion 16 to place the tool 20 at a desired pose (e.g., on a desired trajectory or plane) based on the pose of the instrument 14 within a region while the plurality of actuators 21, 22, 23 are actively adjusting the tool support 18 and tool 20 relative to the target plane and hand-held portion 16.

In some examples, the instrument controller 28 may operate in a first mode that automatically controls each of the actuators 21, 22, 23 such that the tool support 18 and tool 20 actively moves towards a desired plane relative to the hand-held portion 16 based on the pose of the instrument 14, and automatically switches into a second mode, indicating with the guidance array 200, the visual indicators 201, 202, 203, or both a desired movement of the hand-held portion 16 to place the tool 20 at a desired pose based on the pose of the instrument 14 while the plurality of actuators 21, 22, 23 are maintained at a position. Other modes of operation are also possible.

Additionally, in one example, the controller may configured to control the visual indicator in a first mode to visually indicate changes in pitch orientation, roll orientation, and translation position of the saw blade while the user moves the instrument based on actuator information of the plurality of actuators, the controller further configured to control the visual indicator in a second mode to visually indicate changes in pitch orientation, roll orientation, and translation position of the hand-held portion while the user moves the instrument based on actuator information of the plurality of actuators, the controller configured to switch between the first mode and the second mode based on the position of the tool 20 and the position of the reference location or based on an input signal received from an input device.

The robotic system 10 may activate the home mode to place the instrument 14 in the home position upon start-up, e.g., when the robotic system 10 is initially powered-up, the actuators 21, 22, 23 are placed in their home positions. Even in the absence of completing the entire defined home mode, the actuators 21, 22, 23 may be set in their respective home positions prior to moving.

Figure 24A:
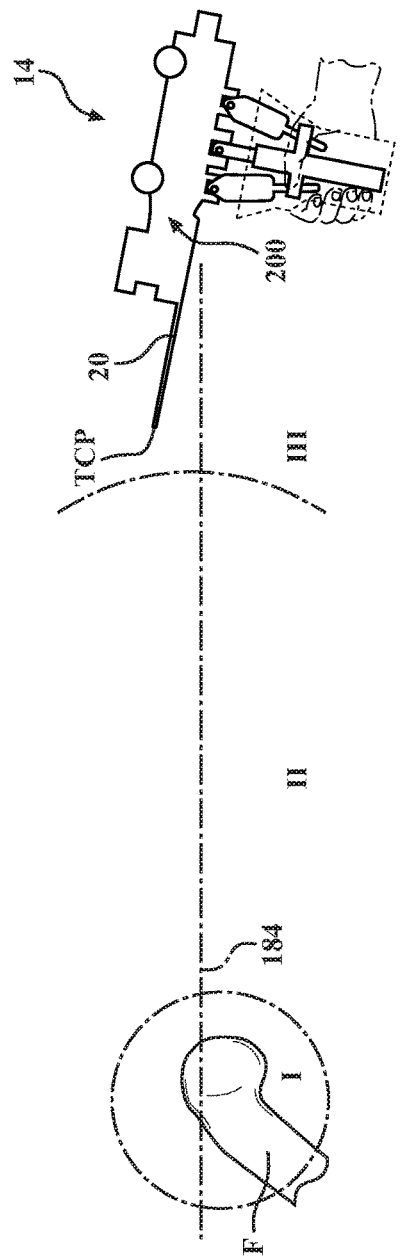
FIGS. 24A-24C illustrate use of the guidance array.

As shown in FIG. 24A, when the TCP of the instrument 14 is located in region III, outside region II, the tool 20 is spaced well away from the anatomy. Region III may also be referred to as the "far away" or "remote" region. As a result, the control system 60 may not yet need to guide the user to place the tool 20 in the desired pose (however, guidance can begin in region III in some versions). In region III, the instrument controller 28 maintains the instrument 14 in the home position, e.g., the instrument controller 28 maintains the target positions of the actuators 21, 22, 23 at their home positions. Generally, operation of the tool 20 is disabled in region III, e.g., the user is unable to activate the drive motor M via trigger, foot switch, or other input device. In some versions, the user may be able to override this disable function to allow the user to perform some treatment when in region III.

It should be appreciated that the phrase 'TCP' of the instrument" has been used interchangeably with the phrase 'position of the saw blade'. Thus, in any instance where the TCP of the instrument/tool is used, it may be substituted with the position of the saw blade and vice-versa. Of course, it is also contemplated that the position of the 'saw blade' may alternatively be a position of a tool of any suitable configuration, such as a drill, bur, guide tube, pin, and the like.

In alternative configurations, the instrument controller 28 may automatically disable the input device, such as a footswitch or trigger, when the instrument 14 is in any region based on the actuator information, such as the operational range of one or more actuator parameters.

Figure 24B:
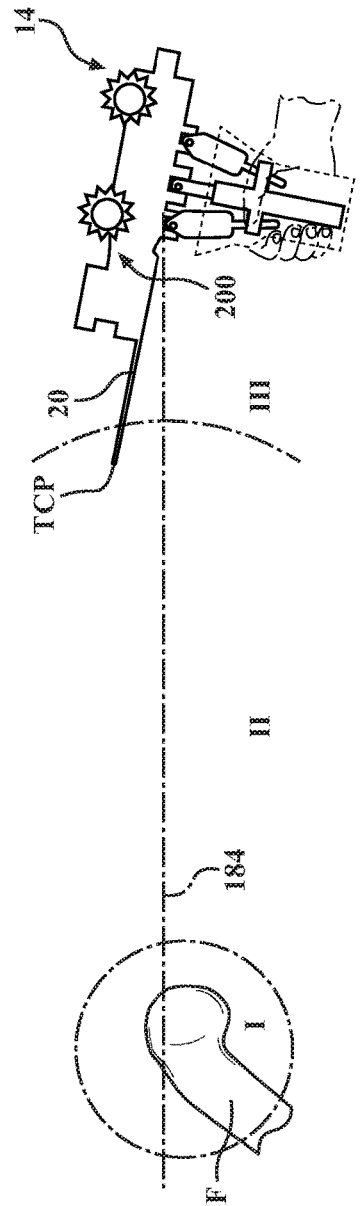
Figure 24C:
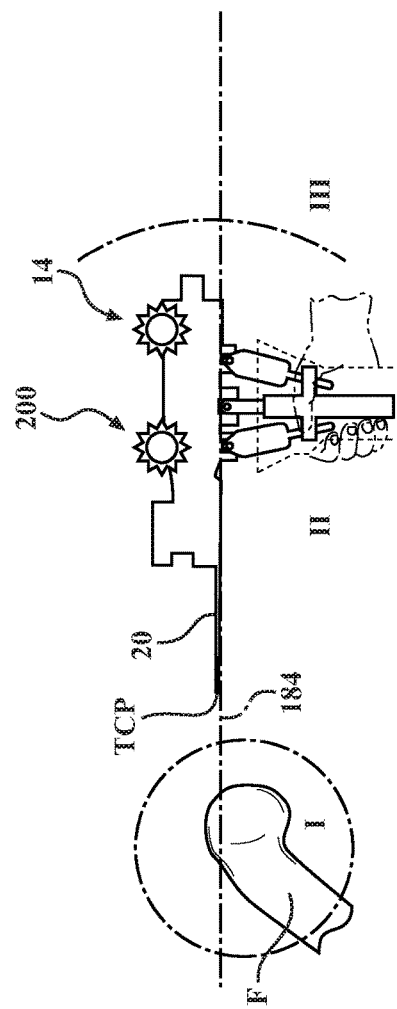

Referring to FIG. 24B, the user advances the tool 20 from region III into region II (e.g., as indicated by a location of the TCP). Region II may also be referred to as the "middle" region. In some versions, when the user advances the tool 20 from region III into region II, the instrument controller 28 automatically activates the approach mode. In the approach mode, the instrument controller 28 controls the guidance array 200 and its associated visual indicators 201, 202, 203 to guide the user to place the tool support 18 and tool 20 in the desired pose (e.g., desired trajectory, plane, etc.), as previously described. Images may also be presented on the navigation displays 38 to indicate the relative location of the instrument 14 to the desired pose. Once the tool 20 is in a threshold distance of the desired pose, which may be indicated when all current cumulative count values are within corresponding threshold count values for each actuator 21, 22, 23, then the instrument controller 28 snaps the tool 20 into the desired pose, as shown in FIG. 24C.

Snapping refers to the behavior control 186 transmitting the desired pose of the tool 20 to the motion control 188, which then generates target rotor positions for the actuators 21, 22, 23 to place the tool 20 at the desired pose. In some versions, snapping occurs when the available travel for each actuator 21, 22, 23 to place the tool 20 at the desired pose is within a threshold, such as within a threshold percentage of available travel, within a threshold distance of available travel, or the like. In some cases, the thresholds are the same as the thresholds associated with the state changes of the visual indicators 201, 202, 203. For instance, once all the visual indicators 201, 202, 203 show green, then the instrument controller 28 snaps the tool 20 into the desired pose by activating each actuator 21, 22, 23 to move as needed so that its corresponding point (e.g., P1, P2, P3 or P4, P5, P6) is in its desired position (e.g., on the tool plane). The speed (velocity) and/or acceleration at which the actuators 21, 22, 23 are operated to perform the snapping operation can be controlled/limited by the control system 60. In some cases, faster accelerations may be desirable to give the user clear haptic feedback when snapping to the desired pose, owing to the associated forces being transmitted through the hand-held portion 16 to the user's hand. Audible and visual feedback are also provided when the actuators 21, 22, 23 snap to the desired pose, owing to all of the actuators 21, 22, 23 being operated simultaneously.

In other versions, the tool 20 may move to the desired pose and then the user may adjust the hand-held portion 16 to a more comfortable position within the threshold value of available travel of actuators 21, 22, 23 to perform a cut while the tool 20 is maintained at its desired position. The user may then select, by activating an input device, such as a button and/or a foot switch, or selecting on a touchscreen, to move into a free-hand mode where the pose of the hand-held portion 16 relative to the pose of the tool 20 is held or frozen in its current spatial relationship. It is contemplated that the held pose of the hand-held portion 16 relative to the pose of the tool 20 changes the virtual threshold value of the actuators 21, 22, 23, restraining actuator movement by to maintain the held pose once the user has selected the free-hand mode. Alternatively, when the free-hand mode is activated, the plurality of actuators 21, 22, 23 may be reset to their home positions.

Figure 25A:
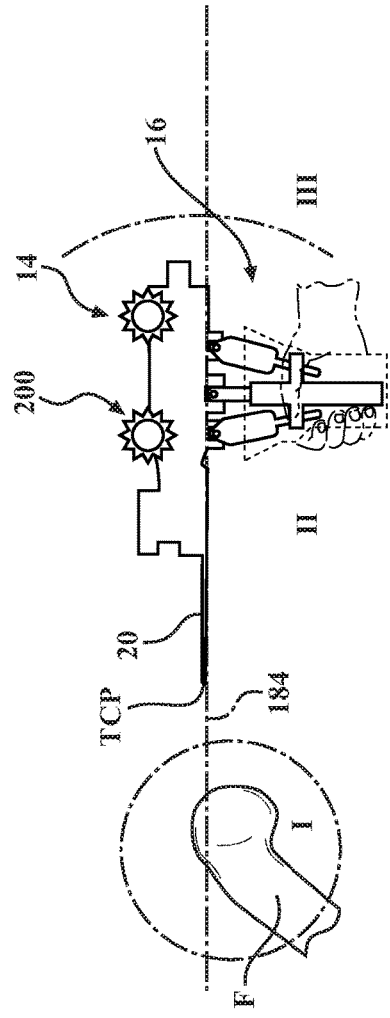
FIGS. 25A-25C illustrate use of the guidance array and adjustment of the plurality of actuators to maintain the tool on a desired plane.
Figure 25B:
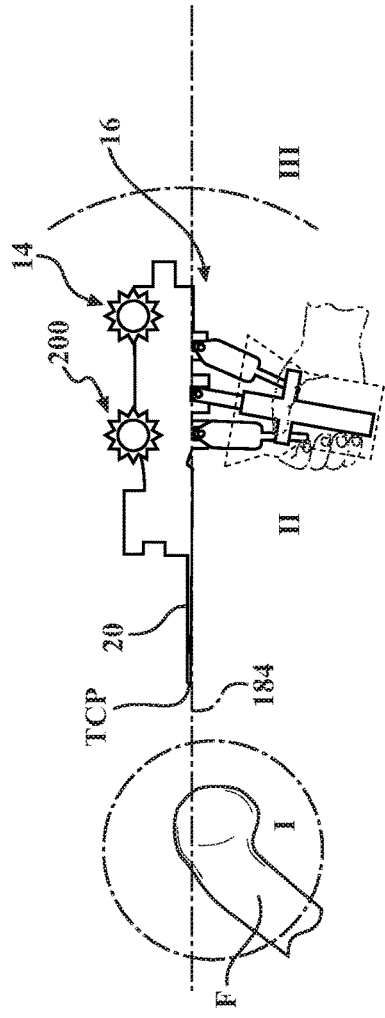
Figure 25C:
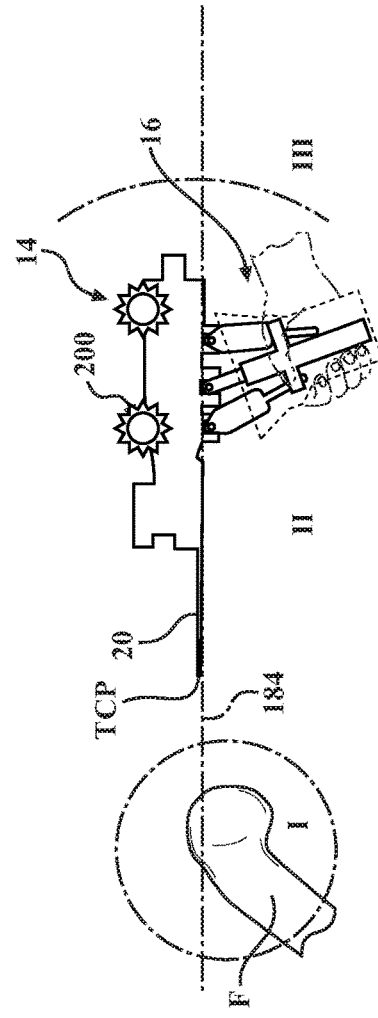

Once the instrument controller 28 snaps the tool 20 into the desired pose, then the on-target mode is activated, as illustrated in FIGS. 25A-25C. In particular, the instrument controller 28 generates a set of target rotor positions to which the rotors 148 integral to the motors 142 must rotate to maintain the tool 20 at the desired pose. In other words, if the user moves the hand-held portion 16 in a manner that causes the tool 20 to move away from its desired pose, this is detected by the navigation system 32. In response to this movement, the instrument controller 28 determines, based on data from the navigation system 32, how far the tool 20 has moved away from the desired pose and compensates for such movement by driving the actuators 21, 22, 23 as needed to bring the tool 20 back to the desired pose. It should be appreciated that such deviations from the desired pose will usually be small, as the instrument controller 28 will be operating at a high frequency (e.g., frame rate) to continuously account for such deviations in substantially real-time.

The target rotor positions are determined based on the relationships between actuation of the actuators 21, 22, 23 and resulting movement (e.g., kinematics). For example, if the desired pose requires z-axis translation relative to the hand-held portion 16, there is a first order relationship between the extent to which the tool 20 will move in the z-axis and the amount of rotation of each rotor 148 (e.g., how many counts are associated with such z-axis movement). There are also relationships between the extent to which the tool 20 will change its pitch orientation in response to actuation of the third actuator 23 alone, or in combination with one or both of the first and second actuators 21, 22. Lastly, there are relationships between the extent to which the tool 20 will change its roll orientation in response to actuation of one or both of the first and second actuators 21, 22, with or without actuation of the third actuator 23. Based on these relationships, the instrument controller 28 determines the target rotor position for each rotor 148 that is required to maintain the desired pose of the tool 20. The instrument controller 28 operates the motors 142 based on these target rotor positions. For example, the console 33 may transmit packets to the motor controllers containing these target rotor positions, and each motor controller may apply appropriate energization signals to the associated motor 142. These energization signals cause the rotation of the rotor 148 that results in the repositioning of the lead screw 150 that displaces the tool support 18/tool 20 as needed to maintain the tool 20 in the desired pose.

The instrument controller 28 may use tracking data from the navigation system 32 to operate the motors 142 based on a location of the hand-held portion 16 relative to the tool support 18, adjusting the actuators 21, 22, 23 to maintain the tool 20 at the desired pose.

FIGS. 25B and 25C illustrate the user moving the hand-held portion 16 in a manner that would otherwise move the tool 20 off the desired pose (compare to FIG. 25A), if not for the actuators 21, 22, 23 compensating for such error to maintain the tool 20 at the desired pose. The time period (e.g., frame rate) in which such detection and compensation occurs can be in the milliseconds, or sub-milliseconds, e.g., 0.5 to 4 milliseconds, or faster. Faster or slower frame rates are also contemplated. Accordingly, the robotic system 10 responds quickly to the tool 20 moving away from its desired pose such that the tool 20 only deviates slightly from the desired pose in any given time period.

Figure 26A:
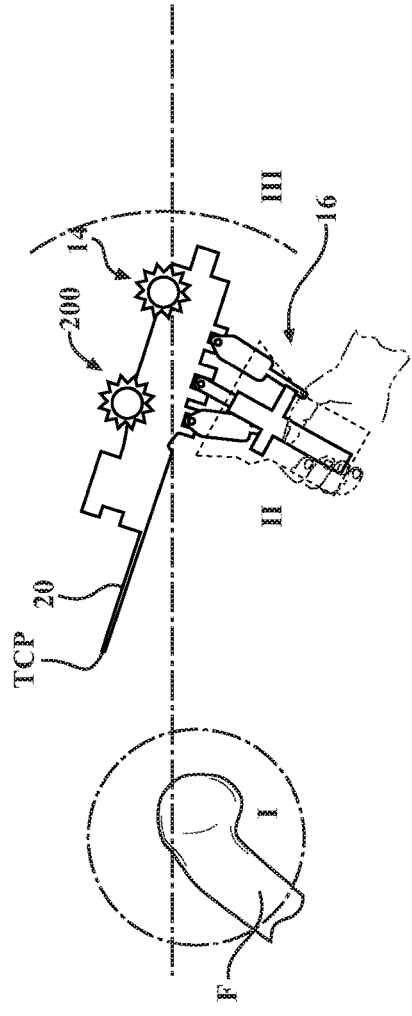
FIGS. 26A-26B illustrate movement of the tool off the desired plane and use of the guidance array to place the tool on the desired plane.
Figure 26B:
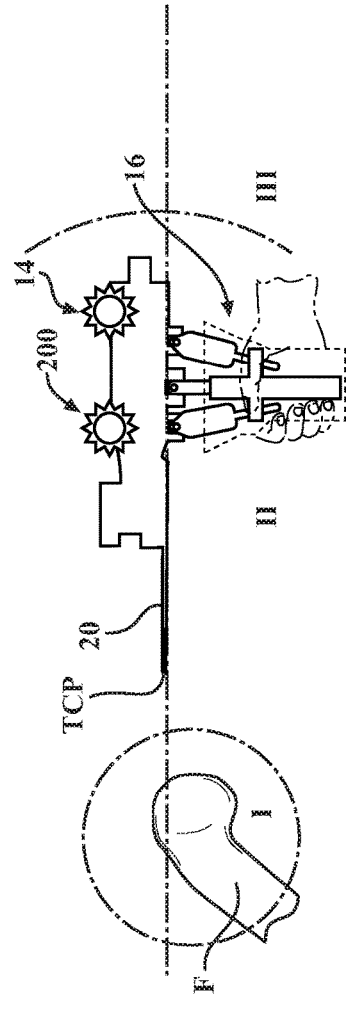

In region II, when the hand-held portion 16 has been moved by the user to a position at which the instrument 14 is unable, through operation of the actuators 21, 22, 23, to keep the tool 20 at the desired pose, as shown in FIG. 26A, the tool 20 unsnaps from the desired pose. More specifically, unsnapping occurs when one or more of the actuators 21, 22, 23 exceed their available travel and can no longer adjust as needed to stay at the desired pose. When unsnapping occurs, the instrument controller 28 exits the on-target mode. The instrument controller 28 then immediately operates in the home mode to re-home the actuators 21, 22, 23. Re-homing of the actuators 21, 22, 23, may be considered part of the unsnapping process. Accordingly, the user is provided with haptic feedback via the re-homing of each of the actuators 21, 22, 23, which transmits forces through the hand-held portion 16 to the user's hand. Audible and visual feedback associated with re-homing the actuators 21, 22, 23 is also provided. Once homing is complete, the instrument controller 28 again operates the guidance array 200 in the approach mode, as previously described, to direct the user as to how to move the hand-held portion 16 to place the tool 20 at the desired pose (FIG. 26B). The instrument controller 28 re-snaps the tool 20 to the desired pose and re-enters the on-target mode once the required travel for all the actuators 21, 22, 23 are again within the predefined thresholds.

The instrument controller 28 also controls operation of the guidance array 200 in the on-target mode, albeit with a slightly different function than in the approach mode. In both the on-target mode and the approach mode, the guidance array 200 is controlled to control the states of the visual indicators 201, 202, 203 to show the user desired movement of the hand-held portion 16 of the instrument 14. As described previously, the actuators 21, 22, 23 are held at the home position or other predetermined position as the user arranges the hand-held portion 16, guided by the visual indicators 201, 202, 203, toward the desired plane. By keeping the actuators 21, 22, 23 at their home position or other predetermined position, a user may find it easier to adjust and line up the tool 20 with the desired plane and instrument pose relative to the target. However, in the on-target mode, the tool 20 is already generally at the desired pose, so the visual guidance is not intended to help place the tool 20 at the desired pose, but instead is intended to guide the user as to how to move the hand-held portion 16 to provide the instrument 14 with sufficient adjustability by keeping the actuators 21, 22, 23 near their home positions or other predetermined position. For example, when in the on-target mode in region II, the user may need to move the hand-held portion 16 upwardly in the z-axis direction to move all the actuators 21, 22, 23 closer to their home positions, while keeping the tool 20 at the desired pose. In other words, the actuators 21, 22, 23 may be nearly fully extended. To accomplish this, the directional indication from the guidance array 200 is upward. In this case, the guidance array 200 is actually guiding the user to move the hand-held portion 16 upward so that the actuators 21, 22, 23 operate toward their home positions to maximize adjustability of the actuators 21, 22, 23. As the user moves the hand-held portion 16 upward, the actuators 21, 22, 23 continue to operate to keep the tool 20 at the desired pose (e.g., on the virtual boundary 184). As a result, the actuators 21, 22, 23 retract, such as retracting toward their home positions. Ideally, when the user reaches region I and starts cutting bone, a maximum amount of travel is available in either direction for each actuator 21, 22, 23. Otherwise, if one or more of the actuators 21, 22, 23 have nearly reached their available travel in either direction, then even slight movements of the hand-held portion 16 may result in the instrument controller 28 being unable to keep the tool 20 at the desired pose, and an inaccurate cut could be made. In some cases, as described further below, when this happens (e.g., when one or more of the actuators 21, 22, 23 have reached a travel limit or threshold) the instrument controller 28 may deactivate/disable the drive motor M, despite whether an input device, such as a trigger or footswitch, is actuated. The instrument controller 28 may automatically switch the instrument 14 between an operational state which the drive motor M can be actuated (e.g. through an input device), and a disabled state which blocks the input signal sent by the input device causing activation of the drive motor M based the pose of the tool 20 in a known coordinate system, the pose of the hand-held portion 16, and the commanded pose of the tool 20. The pose of the hand-held portion 16 may be based on actuator information, such as a measured position of each actuator 21, 22, 23. By controlling the instrument 14 in this manner, the instrument controller 28 is configured to automatically switch between modes when the pose of the tool 20, the pose of the hand-held portion 16, and the commanded pose of the tool 20 are indicative of a condition where the commanded pose of the tool 20 is out of range of the actuators 21, 22, 23. In other words, the actuators 21, 22, 23 are unable to effectively maintain the tool 20 on the desired plane when this condition exists.

In the on-target mode, the visual indicators 201, 202, 203, collectively, represent desired movement of the hand-held portion 16 and corresponding movement of the actuators 21, 22, 23 to keep the tool 20 at the desired pose. For example, when the first visual indicator 201 is operated to indicate that movement of the hand-held portion 16 is needed, the visual indicator 201, 202, 203 is representing that one or more of the actuators 21, 22, 23 is too far away from its home position and the hand-held portion 16 needs to be moved. As another example, if the tool 20 is at the desired pose, but all three of the actuators 21, 22, 23 are nearly fully retracted, i.e., they have reached their maximum available travel in one direction, then the instrument controller 28 will operate the guidance array 200 and/or display screen to instruct the user that the hand-held portion 16 needs to be generally lowered in the z-axis direction so that all the actuators 21, 22, 23 extend toward their home positions.

Alternatively, in some example modes, when the first visual indicator 201 is operated to indicate that movement of the hand-held portion 16 is needed, the visual indicator 201 is representing that one or more of the actuators 21, 22, 23 is outside of the operational range of each actuator 21, 22, 23 relative to a commanded position and the hand-held portion 16 needs to be moved. As another example, if the tool 20 is at the desired pose, but all three of the actuators 21, 22, 23 are nearly fully retracted, i.e., they have reached a limit of the actuator in one direction or are within a certain range of motion within the total available travel, then the instrument controller 28 will operate the visual indicators 201, 202, 203 to instruct the user that the hand-held portion 16 needs to be generally lowered or raised in the z-axis direction so that all the actuators 21, 22, 23 are within their operational range relative to the commanded position.

In some configurations, as a user moves the instrument 14, the instrument controller 28 may change the operating mode of the instrument 14, actively controlling at least one motion parameter of the tool 20 relative to the hand-held portion 16 with a particular control configuration. A motion parameter may be a controlled variable relating to the movement of the tool support relative to the hand-held portion. For example, a motion parameter may be a velocity, an acceleration, a torque, or a combination thereof relating to the movement behavior of the tool support. In some examples, the instrument controller 28 may change values of the motion parameter relating to velocity, acceleration, or both, so that the instrument 14 adjusts the tool support 20 more quickly or more slowly to maintain or each the desired pose of the instrument 14. Velocity may relate to the rate at which the tool support adjusts position in a particular direction. Actuator acceleration may relate to the rate of change of velocity at which the tool support 18 is adjusted relative to the hand-held portion 16 between positions. Such changes may be dependent on: (i) the region in which the TCP is located; (ii) the location of the instrument 14 (e.g., of the TCP) relative to a reference location associated with a bone in a known coordinate system; (iii) a distance parameter; (iv) the pose of the tool support 18 relative to the hand-held portion 16; (v) or a combination thereof. Controlling the acceleration of the tool support may affect the force and/or torque that is used to attract the tool support to the desired plane. The motor current and/or voltage for each actuator may be controlled to adjust the motion parameter of the tool support relative to the hand-held portion.

The distance parameter may be determined by locating with the navigation system 32 the one or more trackers 52 associated with the tool 20, the tool support 18, the hand-held portion 16, or a combination thereof relative to a reference location associated with bone, such as the one or more trackers 54, 56, and determining with the instrument controller 28 the direction, distance, or both of the tool 20, the tool support 18, the hand-held portion 16, or a combination thereof. A distance parameter may be a magnitude, a distance, or both.

The instrument controller 28 may control the actuators 21, 22, 23 to move the tool 20 toward a desired plane at a first value of the motion parameter between the tool 20 and the hand-held portion 16. The instrument controller 28 may then move the tool 20 toward the desired plane at a second value of the motion parameter so that the velocity, acceleration, or both are different between the first value and the second value. For example, as shown in FIGS. 61A and 61B, as a user brings the instrument 14 closer to the reference location associated with the bone, the instrument controller 28, using the distance parameter provided by the navigation system 32, adjusts the one or more motion parameters (e.g. velocity; acceleration) to move the tool 20 relative to the hand-held portion 16 towards the desired plane at varying motion parameter values (i.e., the first value of the motion parameter and the second value of the motion parameter).

By controlling the velocity, acceleration, or both of the tool support relative to the hand-held portion such that the velocity and/or acceleration is relatively low, before the tool 20 is within a distance that is capable of cutting bone (FIG. 61A), the movement may be less abrupt and result in less force/torque to be applied. This may reduce the potentially disorienting effects of moving the actuators 21, 22, 23 to compensate for the pose of the hand-held portion 16 and/or reduce the force on the hand of the user. Then, when the tool is within a distance that is capable of cutting bone (FIG. 61B), the controller acts to control the velocity, acceleration or both of the tool support relative to the hand-held portion such that the velocity and/or acceleration is relatively high, ensuring a precise cut.

Figure 61A:
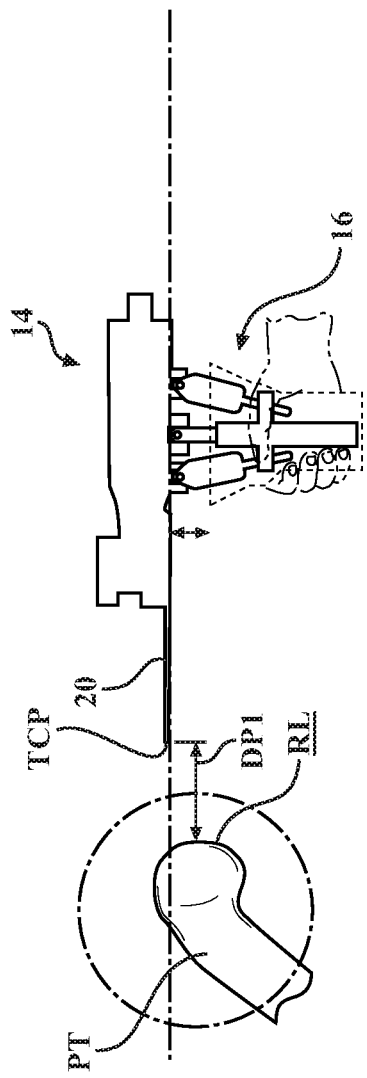
FIGS. 61A and 61B illustrate various regions in which the robotic instrument is used with varying actuator behavior.

With reference to FIG. 61A, when the position of the TCP is spaced from the reference location associated with bone (RL) with a first distance parameter (DP1), the instrument is controlled such that the tool support is moved relative to the handheld portion, e.g., a motion parameter with a first value. This is because the TCP is still a significant distance from the surface of the bone.

Figure 61B:
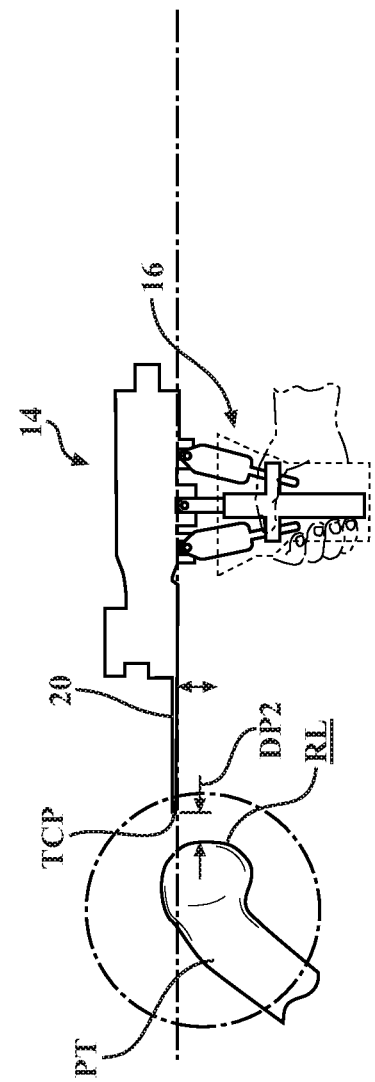

With reference to FIG. 61B, when the position of the TCP is spaced from the reference location associated with bone (RL) with a second distance parameter (DP2), the instrument 14 is controlled such that a motion parameter with a second value is utilized. The first value is lower than the second value. For example, when motion parameter is acceleration the acceleration at the first value is lower than the acceleration for the second value.

By controlling the acceleration of the actuators 21, 22, 23, the instrument controller 28 may function to indicate to the user that a mode transition is taking place. This is because that significant changes in the acceleration of the actuators 21, 22, 23 may change the center of gravity of the instrument 14 and may result in sensations of force being experienced by the user. In one example, by changing the acceleration of the actuators 21, 22, 23 based on the distance parameter or pose of the tool 20 relative to a reference location on the bone, the instrument 14 may provide a force sensation to the user indicative that the actuators 21, 22, 23 are behaving different as the instrument 14 moves closer to the reference location (i.e., the distance parameter has a lower magnitude).

As the instrument changes between modes, states, or both, the guidance array 200, visual indicators 201, 202, 203, the instrument 14, or any portion of the robotic system 10 may include an indicator signaling the transition between the modes, states, or both. The indicator may be a haptic indicator, a visual indicator, an audible indicator, or a combination thereof to inform a user of the transition. For example, a haptic guidance indicator, such as described in U.S. Pat. No. 10,231,790 to Quaid et al., may be used. In another example, an audible indicator, such as change in drive motor M operation, similar to as described in U.S. Pat. No. 9,707,043 to Bozung, may be incorporated. Other indicators are contemplated.

In some configurations, the robotic system 10 is understood as having two primary regions of operation—region IV and region V. When the tool enters region IV, the instrument 14 may be controlled and respond similar to the on-target mode in region I. In region V, the instrument controller 28 may hold the actuators 21, 22, 23 in a particular position while guiding a user through the guidance array 200 to move the hand-held portion 16 of the instrument 14 so that the tool 20 moves toward a target plane with the motor M disabled. Any of the features described with reference to region I may be used with region IV and vice-versa.

In some configurations, the instrument controller 28 may control the velocity, acceleration, or both of the tool support 18 and tool 20 relative to the hand-held portion 16 and may change values of such motion parameters while moving from region V to region IV. This may be accomplished by changing values of one or more motion parameters of the actuators 21, 22, 23 while moving from region V to region IV. Region IV is located immediately adjacent to and encompassing the reference location associated with the bone and region V is the space outside of region IV. In the present example, the one or more values of the motion parameters are adjusted so that as the tool 20 enters region IV, the velocity, acceleration or both of the tool 20 towards the desired plane relative to the hand-held portion 16 is progressively adjusted while the guidance array 200 directs the user to adjust the hand-held portion 16 to stay on target. In other words, as the instrument approaches region IV, the actuators 21, 22, 23 are controlled such that the acceleration of the tool support 18 relative to hand-held portion 16 is greater than when the instrument 14 first entered region V (determined based on the position of the tool 20 relative to the reference location of the bone or based on the computed distance parameter).

While in the on-target mode in region II, the instrument controller 28 may enable operation of the tool 20, e.g., the trigger or foot switch of the user interface UI of the instrument 14 may be operational to allow the user to start/stop operation of the drive motor M. In some cases, the input device merely allows on/off functionality, while the instrument controller 28 automatically controls a speed of the drive motor M. In other versions, the user's input may be taken into account to control the speed of the drive motor M. In some examples, the drive motor M is operational in the on-target mode, but becomes disabled should the tool 20 unsnap from the desired pose.

In some versions, the drive motor M may be disabled until the TCP reaches region I or IV. In some examples, the instrument controller 28 controls the actuators 21, 22, 23 to move the tool 20 towards the desired plane, and further controls a motor parameter of the drive motor M at a first value and a second value, such that the first value is different than the second value. A motor parameter may be a controlled variable of the drive motor M which affects behavior of the tool 20 during different modes. For example, a motor parameter may be a speed (e.g. revolutions per minute (RPM)), a torque, an operation time, a current, an acceleration, or a combination thereof. The instrument controller 28 changes operation from the first value to the second value based on the position of the tool 20 and the position of a reference location associated with bone. In another example, the instrument controller 28 controls the actuators 21, 22, 23 to move the tool 20 towards the desired plane, and further controls a motor parameter of the drive motor M at a first value and a second value, such that the first value is different than the second value. The instrument controller 28 is configured to change operation from the first value to the second value based on the distance parameter. The motor parameter may be a motor speed or a motor torque.

In one implementation, the motor parameter may be a motor speed, and the instrument controller 28 may operate such that the motor speed is controlled at a first speed when the distance parameter has a first magnitude and direction, and a second speed when the distance parameter has a second magnitude and direction, different from the first magnitude. This could be implemented where the first magnitude is 10 cm and the second magnitude is 2 cm, the first motor speed is 0 rpm, the second motor speed is 16000 rpm, and the direction is away from bone. This could also be implemented when the instrument 14 is in a given position relative to a predetermined coordinate system. This may result in activation of the drive motor M only when the instrument 14 is relatively close to the bone to be cut. The first motor speed may be when the motor is stopped, and the second motor speed may be a desired operating speed for the given tool.

Figure 27:
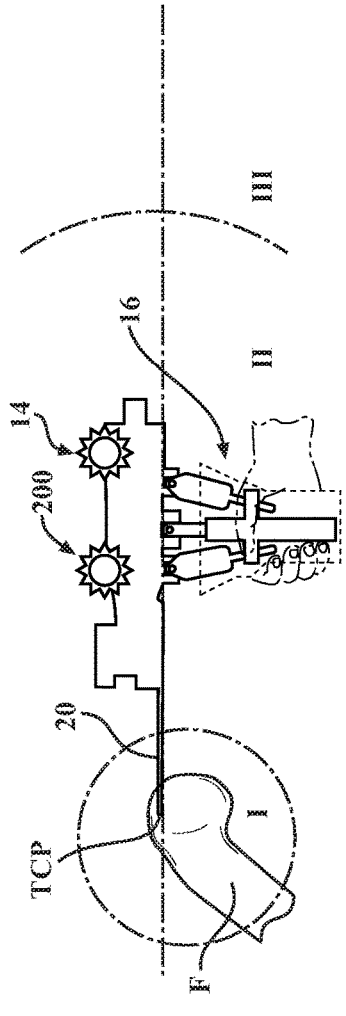
FIG. 27 illustrates use of the robotic instrument to resect bone along the desired plane.

The instrument controller 28 continues to operate the instrument 14 in the on-target mode as the user continues movement of the TCP into region I, ultimately resulting in the distal end of the tool 20 penetrating the surface of the anatomy at the location in which the treatment is to be performed, as shown in FIG. 27. Region I may also be referred to as the "treatment" or "resection" region. In some versions, the drive motor M becomes operational when entering region I so that the user can depress the trigger, foot switch, or other input device to drive the tool 20 to treat (e.g., cut) the tissue. In particular, the instrument controller 28 enables operation of the drive motor M (e.g., the console 33 sends associated instruction packets to the drive motor controller indicating that the drive motor M can be actuated). The user at this time depresses trigger, foot switch, or actuates another input device to actuate the drive motor M. The tool 20 is therefore energized, for example, to resect the tissue at the target site. In some versions, the drive motor M may be controlled directly by the instrument controller 28 without requiring any input from the user, e.g., the tool 20 may be actuated automatically based on being within region I.

In region I, when in the on-target mode, the instrument controller 28 may monitor rotor positions of each of the actuators 21, 22, 23 and disable the drive motor M when any of the actuators 21, 22, 23 reach one their soft stops, hard stops, or any other predefined threshold, such as 90% of the travel to the soft stops. This threshold could be configurable. As described above, the instrument controller 28 may automatically switch the instrument 14 between an operational state which the drive motor M can be actuated (e.g. through an input device), and a disabled state which blocks the input signal sent by the input device causing activation of the drive motor M based the pose of the tool 20 in a known coordinate system, the pose of the hand-held portion 16, and the commanded pose of the tool 20. The pose of the handheld-portion 16 may be based on actuator information, such as a measured position of each actuator 21, 22, 23. By controlling the instrument 14 in this manner, the instrument controller 28 is configured to automatically switch between modes when the pose of the tool 20, the pose of the hand-held portion 16, and the commanded pose of the tool 20 are indicative of a condition where the commanded pose of the tool 20 is out of range of the actuators 21, 22, 23. In other words, the actuators 21, 22, 23 are unable to effectively maintain the tool 20 on the desired plane when this condition exists. Even though the drive motor M may be disabled, the actuators 21, 22, 23 may still operate to maintain the desired pose of the tool 20 to the extent possible.

If the TCP of the tool 20 was in region II when this occurred, then the instrument controller 28 would respond to one of the actuators having reached its limit or threshold by unsnapping the tool 20 from the desired pose and re-homing, but unsnapping the tool 20 from the desired pose may be undesirable in region I, particularly if the tool 20 has already engaged tissue. Instead, in region I, the visual indicators 201, 202, 203 may be placed in a state that signals to the user which of the actuators 21, 22, 23 is outside its acceptable limit/threshold for drive motor M operation (e.g., the visual indicator 201, 202, 203 may begin to blink/flash, change colors, intensity, etc.). Once the user has moved the hand-held portion 16 such that all the actuators 21, 22, 23 can again reach the desired pose (e.g., a threshold amount of travel is available), the visual indicators 201, 202, 203 may resume operation as normal. Of course, unsnapping can still occur in region I in some versions and/or under certain circumstances.

In some versions, once treatment begins (e.g., the tissue is being cut), the drive motor M may continue operating even though one or more of the actuators 21, 22, 23 have reached their operational limit. This may occur, for instance, when cutting into bone and the bone itself provides a suitable cutting guide to continue cutting substantially on the desired plane. In this case, the actuators 21, 22, 23 may be held in their current positions and/or the virtual boundaries 184 may be disabled such that the control system 60 no longer operates to keep the tool 20 at the desired pose. As described above, another potential implementation of this feature would be determining the distance parameter, such as a direction into bone relative to the reference location and a magnitude (i.e. 2 cm, 3 cm, 4 cm into bone) of the tool 20 relative to a reference location on bone. Based on this determination, the instrument controller 28 may controls the actuators 21, 22, 23 such that the tool 20 moves relative to the hand-held portion 16 towards the desired plane at a first value of a motion parameter based on the distance parameter and a second value of the motion parameter based on the distance parameter. The motion parameter may be velocity and may have a first value of greater than 0 (or 1-5 m/s) when the magnitude of the distance parameter is less than 3 cm, and a second value of 0 when the magnitude of the distance parameter is greater than 3 cm, and the direction is into bone.

Figure 63A:
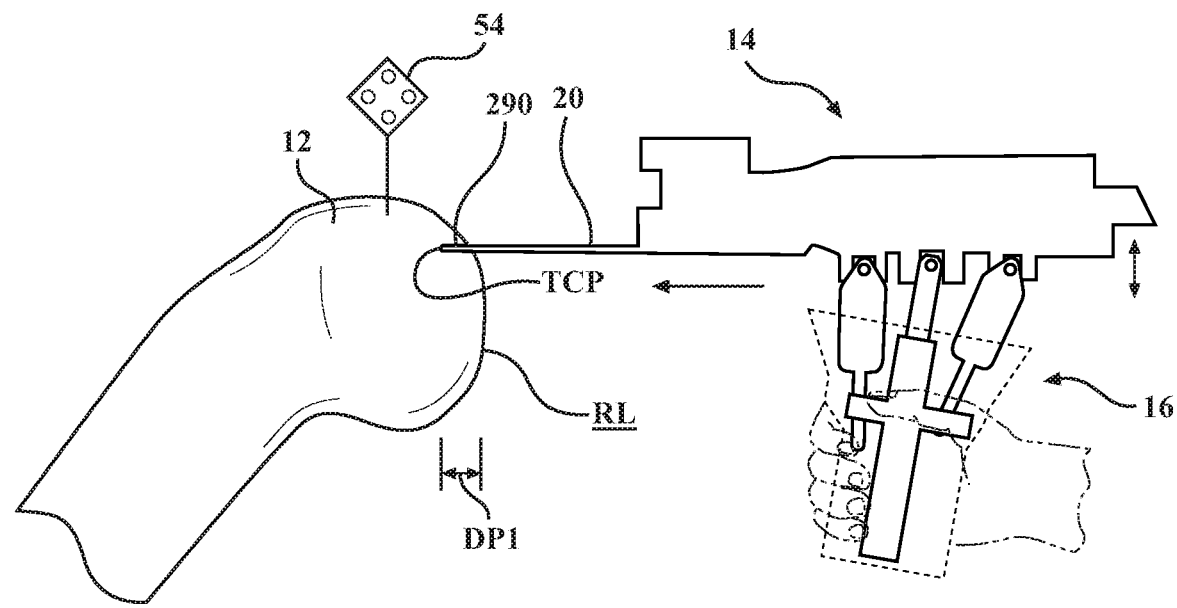
FIGS. 63A and 63B show a schematic view of a robotic instrument performing a cut.
Figure 63B:
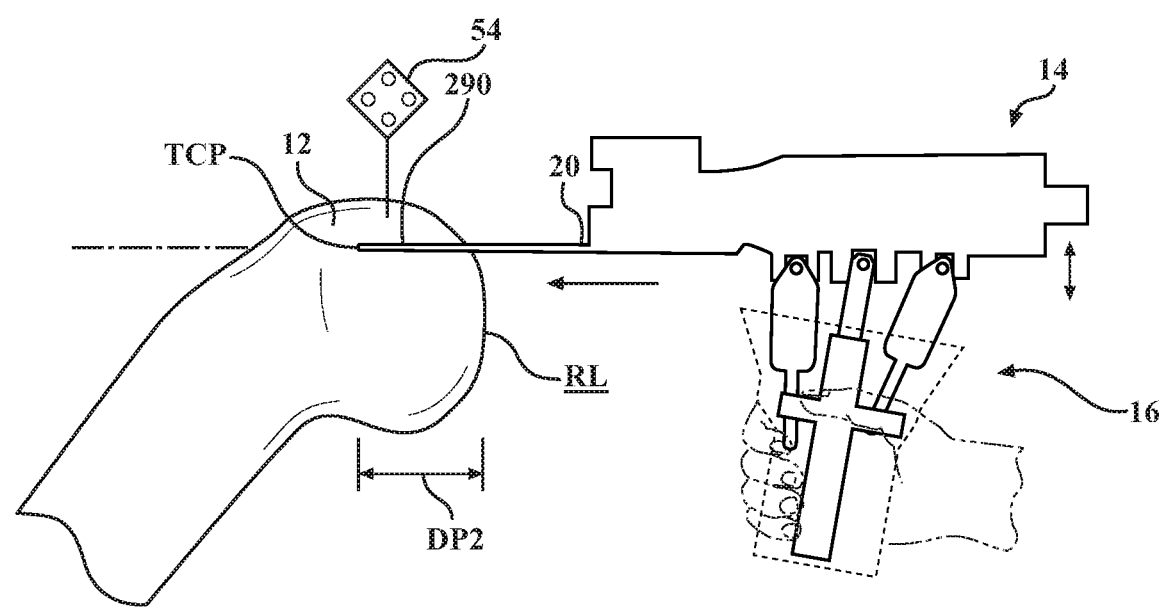

Referring to FIGS. 63A and 63B, once a kerf is established, the instrument controller 28 may automatically adjust values of one or more motion parameters of the tool 20 relative to the hand-held portion 16 as the user cuts the target cut plane which is associated with anatomy of a patient (e.g. bone to be cut). In one example, the motion parameter is acceleration of the tool 20 relative to the hand-held portion 16 as the tool 20 moves towards the desired plane. The instrument controller 28 may change the rate of adjustment of the actuators 21, 22, 23 automatically based on a distance parameter (e.g. direction, magnitude) determined from the pose of the tool 20 (e.g., from the TCP) relative to the reference location associated with the bone. The pose of the tool 20 may be maintained while the guidance array 200 directs the user to move the hand-held portion 16 to maintain or correct to the desired plane.

With reference to FIG. 63A, when the position of the saw blade (TCP) is spaced from the reference location associated with bone (RL) with a first distance parameter (DP1), the instrument is controlled such that the tool support is moved relative to the handheld portion, e.g., a motion parameter with a magnitude greater than zero is used. This is because the kerf has not yet been sufficiently established.

With reference to FIG. 63B, when the position of the saw blade (TCP) is spaced from the reference location associated with bone (RL) with a second distance parameter (DP2), the instrument is controlled such that a motion parameter with a magnitude of zero is utilized or the movement of the tool support relative to the hand-held portion is otherwise stopped. This is because the kerf has been sufficiently established.

Once the tool 20 establishes the kerf, the instrument controller 28 may set the value of the motion parameter to zero, stopping the actuators 21, 22, 23 from adjusting the tool support 18 relative to the hand-held portion 16. Once the tool 20 has established a cut path within the bone, the tool 20 may flex and try to move off course, pushing back onto the hand-held portion 16. The user may perceive this force as a push-back. The sense of "push-back" or "fighting" the hand-held portion is created by the instrument controller 28 controlling the actuators 21, 22, 23 while the tool 20 is in the cutting slot 290. Thus, the only movement that is caused by controlling the actuators to move towards the desired plane is movement of the hand-held portion 16. This means that the instrument controller 28 may cause forces to be applied to the hand-held portion 16, which are then transferred to a user's hand. These forces may result in fatigue and/or discomfort during the cutting process. By changing the motion parameter, the tool 20 may provide less resistance further in the cut. A user may find that by setting the motion parameter value to 0 or by otherwise stopping the movement of the hand-held portion relative to the tool support allows the cut to be finished without struggling against the hand-held portion 16 when the tool 20 is within the cutting slot 290, the cutting slot 290 serving as a natural cut guide (See FIGS. 63A-63B). More particularly, the instrument controller 28 may actively change values of the motion parameter relating to velocity, acceleration, or both so that the further the tool 20 enters into the target anatomy, the actuators 21, 22, 23 adjust towards the target plane with a relatively lower velocity and/or acceleration than the velocity and/or acceleration when the cut was first initiated, eventually stopping actuator movement when the tool 20 is mid cut, utilizing the path cut into the bone as the guide. In other words, the tool support 18 may move with a greater velocity and/or acceleration when the cut is first begun, then the velocity and/or acceleration after the progressed has progressed a threshold distance into bone relative to the reference location. While stopping the actuators 21, 22, 23 from adjusting the tool support 18 was described in terms of setting the motion parameter to zero, it should be appreciated that the actuators 21, 22, 23 may be stopped with other suitable control logic, such as by stopping the motion control aspect of the algorithm or otherwise freezing the position of the plurality of actuators 21, 22, 23.

In some versions, once treatment begins, the instrument controller 28 may restrict the user's ability to place the tool 20 away from the desired pose (e.g., outside or off of the virtual boundary 184). For example, in some implementations, as soon as the navigation system 32 provides any indication that the tool 20 is moving off the desired cutting plane, the instrument controller 28 immediately terminates the application of energization signals to the drive motor M, preventing the tool 20 from gouging the bone, and minimizing soft tissue damage. In some implementations of this feature, the acceptable misalignment of the tool 20 with the desired pose may vary inversely as the depth of the resection increases.

The navigation system 32 may also monitor a depth of the cut. In some versions, when it is determined that that the depth of the cut is between 0.1 and 2.0 mm of a target depth, the instrument controller 28 may cease operation of the drive motor M. In some examples, the instrument controller 28 may not cease operation of the drive motor M, but rely on user-controlled starting, stopping, and/or speed control of the drive motor M. In some configurations, the surface of an anatomical feature to be cut (e.g. surface of a bone) may serve as a reference point, a virtual boundary, or both causing the instrument controller 28 to change operation modes or behavior of: (i) the instrument 14; (ii) one or more actuators 21, 22, 23; (iii) guidance array 200; (iv) one or more visual indicators 201, 202, 203; (v) or a combination thereof. In some examples, the instrument controller 28 controls a motor parameter of the drive motor M at a first value and a second value, such that the first value is different than the second value. The instrument controller 28 changes operation from the first value to the second value based on the position of the tool 20 and the position of a reference location associated with bone, or based on a computed distance parameter. As the tool 20 proceeds into a cut of the bone, the instrument controller 28, using navigation data of the tool 20 relative to the reference location associated with the bone, may activate the drive motor M. Further, the instrument controller 28 may turn off the drive motor M based on the tool 20 has reaching a certain distance parameter value or position relating to the reference point associated with the bone. In some cases, the user may lose feeling of the tool 20 while performing the surgical procedure. By controlling the drive motor M based on the depth of tool 20, the user may be able to control with more accuracy how deep the cut should go, preventing interference with ligaments and arteries located around the cutting area.

In some examples, when the instrument controller 28 changes the operating mode by changing a parameter of the drive motor M, the instrument 14, the input device, the navigation system 32, the instrument controller 28, or a combination thereof may provide an audible indication, a tactile indication, or both that the mode has been changed. In one instance, the input device may be a footswitch, and when the mode of the instrument is changed, controlling the speed of the drive motor M, the footswitch may vibrate. In another example, when the mode is changed speeding up or slowing down the drive motor M, a user may perceive an audible indication such as the motor speed of the drive motor M changing volume, pitch, vibration, or a combination thereof, indicating that the mode of the instrument has changed, such as described in the contents of U.S. Pat. No. 9,707,043 to Bozung.

Any time the user believes that it may be difficult to keep the tool 20 on the desired pose in the on-target mode based on the current treatment progress (e.g., cutting appears to be going off-plane), the user may pull the tool 20 back to region II and away from the desired pose to cause un-snapping and re-homing of the tool 20, and start again in the approach mode. The user may also operate the tool 20 by repeatedly plunging and withdrawing the tool 20 into and out of the anatomy in small reciprocating movements to ensure that the tool 20 stays at the desired pose during the treatment, e.g., to prevent the tool 20 from being caught in a trajectory that will ultimately pull the tool 20 off the desired pose if cutting continues through the bone. In other words, these reciprocating movements of the tool 20 correct for any slight deviations from the desired pose to prevent the tool 20 from being captured in the bone, for example, on a cutting plane that deviates from the desired cutting plane.

In some examples, when the tool 20 is retracted from the current treatment (e.g., cutting) progress, the instrument controller 28 may control each of the plurality of actuators 21, 22, 23 to maintain the tool 20 at a current pose relative to the hand-held portion 16 so that un-snapping and re-homing does not occur. Put another way, the user may retract the tool 20 from a cut and the actuators 21, 22, 23 hold the pose of the tool 20 relative to the hand-held portion 16 despite moving from region to region, so that the user may return to their initial cut with grip and orientation in your hand being the same (see FIGS. 62A-62C). FIG. 62A shows the instrument 14 in Region IV in a pose, and FIG. 62B shows the instrument 14 remaining in the same pose as the instrument 14 is moved into Region V. FIG. 62C depicts the instrument 14 returning to Region IV in the same pose as in FIG. 62A. However, with respect to FIG. 62B, when placed into Region V, any suitable pose could be assumed so long as when the instrument reentered Region IV it assumed the same pose as when it was initially removed from Region IV.

It is contemplated that the current pose is a position other than home, i.e., the controller is capable of maintaining the positions of actuators 21, 22, 23 at a position other than the home position. A user may maintain the actuators at the position to prevent unnecessary actuation and movement, preventing the actuators from generating excessive heat from movement, such as when the instrument 14 is a substantial distance away from the target bone. In some versions, the user may select this tool behavior by actuating an input device, and selecting the free-hand mode where the instrument controller 28 commands a tool pose to be held or frozen in position. Alternatively, in some examples, the instrument controller 28 controls the operation of the instrument 14 in at least a first mode in which the instrument controller 28 automatically controls each of the actuators 21, 22, 23 to maintain a current pose of the tool 20 relative to a pose of the hand-held portion 16, and a second mode in which the controller automatically controls each of the actuators 21, 22, 23 such that the tool 20 actively moves towards the desired plane relative to the pose of the hand-held portion 16. The instrument controller 28 automatically switches from the first mode to the second mode based on the position the tool and the position of a reference location associated with bone in a known coordinate system. It is also contemplated that the instrument controller 28 may control the drive motor M of the instrument 14, automatically switching from a first state where the motor M can be actuated and a second state where the motor M is prevented from actuating based on the position of the reference location associated with the bone and the pose of the tool 20. The instrument controller 28 may automatically switch the instrument 14 from actively controlling the movement of the actuators 21, 22, 23 to the free-hand mode when the tool 20 is removed from a cut based on a pose of the tool 20 and the reference location associated with the bone as determined by the navigation system 32 so that the user may resume the procedure with the same grip about the hand-held portion 16 relative to the tool 20 for—maintaining a comfortable grip, control, convenience, familiarity with anatomy, unexpected anatomy, or a combination thereof. The instrument controller 28 may alternatively be configured to switch modes between the first mode and the second mode based on determine a distance parameter (e.g. distance; magnitude) based on the position of the tool 20 and the position of the reference location associated with the bone. The distance parameter may be a direction, a magnitude, or both. In some cases, when the distance parameter has a direction away from bone and a magnitude greater than a first threshold value, such as 12 cm, the controller may switch to the second mode.

In some versions, the instrument controller 28 may switch between a mode in which the instrument controller 28 automatically controls the actuators 21, 22, 23 such that the tool 20 actively moves towards the desired plane relative to a pose of the hand-held portion 16 and a mode in which the instrument controller 28 automatically controls to maintain the tool 20 in a current pose relative to the pose of the hand-held portion 16. The user may be able to freeze movement of the actuators 21, 22, 23 in a free-hand mode (in any region) to allow the user to perform some treatment (e.g., cutting the patella or other portions of the anatomy). When the actuators 21, 22, 23 are frozen from further movement in the free-hand mode, then the instrument 14 behaves much like a conventional cutting instrument, without any movement of the tool support 18 relative to the hand-held portion 16. The virtual boundaries 184 are also deactivated in the free-hand mode. The free-hand mode may be engaged by any suitable input device of any suitable user input device (e.g., push-button, foot switch, etc.).

Further, it is contemplated that the instrument controller 28, the user, or both may switch the instrument 14 between modes and behaviors manually through an input device, automatically based on navigation data, actuator data, drive motor data, or a combination thereof. In some cases, the user may determine that the instrument should be held in a particular position (the tool support relative to the hand-held portion) and override the instrument controller with an input device.

In some examples, the instrument controller 28 may utilize one or more inputs to determine one or more outputs. The one or more inputs may include a position of the bone determined by a patient tracker 54, 56, such as the reference location, the tool center point TCP of the tool 20 by a tracker 52 on the tool support 18, the pose of the hand-held portion 16, a commanded pose of the tool 20, a distance parameter, actuator information (such as a commanded position, a current position, a past position, etc.), an input signal from a footswitch or touch-screen, or a combination thereof. The one or more outputs of the instrument controller 28 may include changing a motor parameter of the drive motor M, adjusting a motion parameter of the tool support, including changing acceleration or velocity, may turn off the boundary control, hold or freeze the tool 20 and tool support 18 relative to the hand-held portion 16, activate a homing mode, or a combination thereof. Any suitable combination of inputs may be utilized with any suitable output.

It can be appreciated that each of the various modes of operation can be used in combination with any of the other modes of operation. A mode of operation may be any controlled movement, including no movement, determined by the instrument controller 28 and effectuated by the instrument 14. For example, the instrument controller 28 may control the velocity, acceleration, or both which the tool support 18 adjusts the tool 20 and guide a user to a desired pose as described with respect to one or more of FIGS. 24A-24C, FIGS. 25A-25C, FIGS. 26A-26B, FIGS. 61A-61B, FIGS. 62A-62C, FIG. 63A-63B, or a combination thereof. In one example, the control modes described in FIGS. 24A-24C are combined with the control modes of FIGS. 63A-63B so that the instrument 14 is controlled in regions II, II, and I before making the incision in accordance with instrument controls of FIGS. 24A-24C and, once within the kerf, controlled as described with respect to FIGS. 63A-63B. Further, any mode or behavior described such as instrument behavior, actuator behavior, drive motor behavior, or a combination thereof may be combined with any region or location of the instrument 14 relative to itself, the patient, the coordinate system, a virtual location, or a combination thereof.

It should be understood that the guidance array and/or visual indicator(s) 201, 202, 203 described throughout may be used with any surgical tool and any actuator configuration of the instrument 14, with any control mode or behavior control. For example, the guidance array 200, visual indicators 201, 202, 203, or both may be used with any of the control modes and instrument behaviors with the any of the configurations described presently. In one example, the guidance array 200, visual indicators 201, 202, 203, or both may be used the instrument 14 described with respect to the configurations shown in at least FIG. 35, FIG. 45, FIG. 57, FIG. 59, FIG. 60, FIG. 65, FIG. 66, or any configuration of the instrument 14. Furthermore, the guidance array 200 and/or visual indicators 201, 202, 203 may be understood to encompass configurations where the guidance array 200 and/or visual indicators 201, 202, 203 enables the robotic system 10 to indicate an amount of travel required to move the tool 20 and/or the handheld portion 16 to a desired pose, trajectory, orientation, position, plane, or combinations thereof. Any guidance array 200 and/or visual indicators 201, 202, 203 may be used with any configuration of the instrument to signal to a user how to position, move, and/or adjust the instrument 14 in any of the modes described throughout the present application. The changes in pitch, roll, and translation are, for example, relative to one or more of the virtual boundaries. The guidance array 200 and/or visual indicator 201, 202, 203 could facilitate positioning of different types of tools, including but not limited to, drill or reamer, a driver (for placement of a screw or a pin), a bur, a pin, a guide tube, etc.

Figure 28:
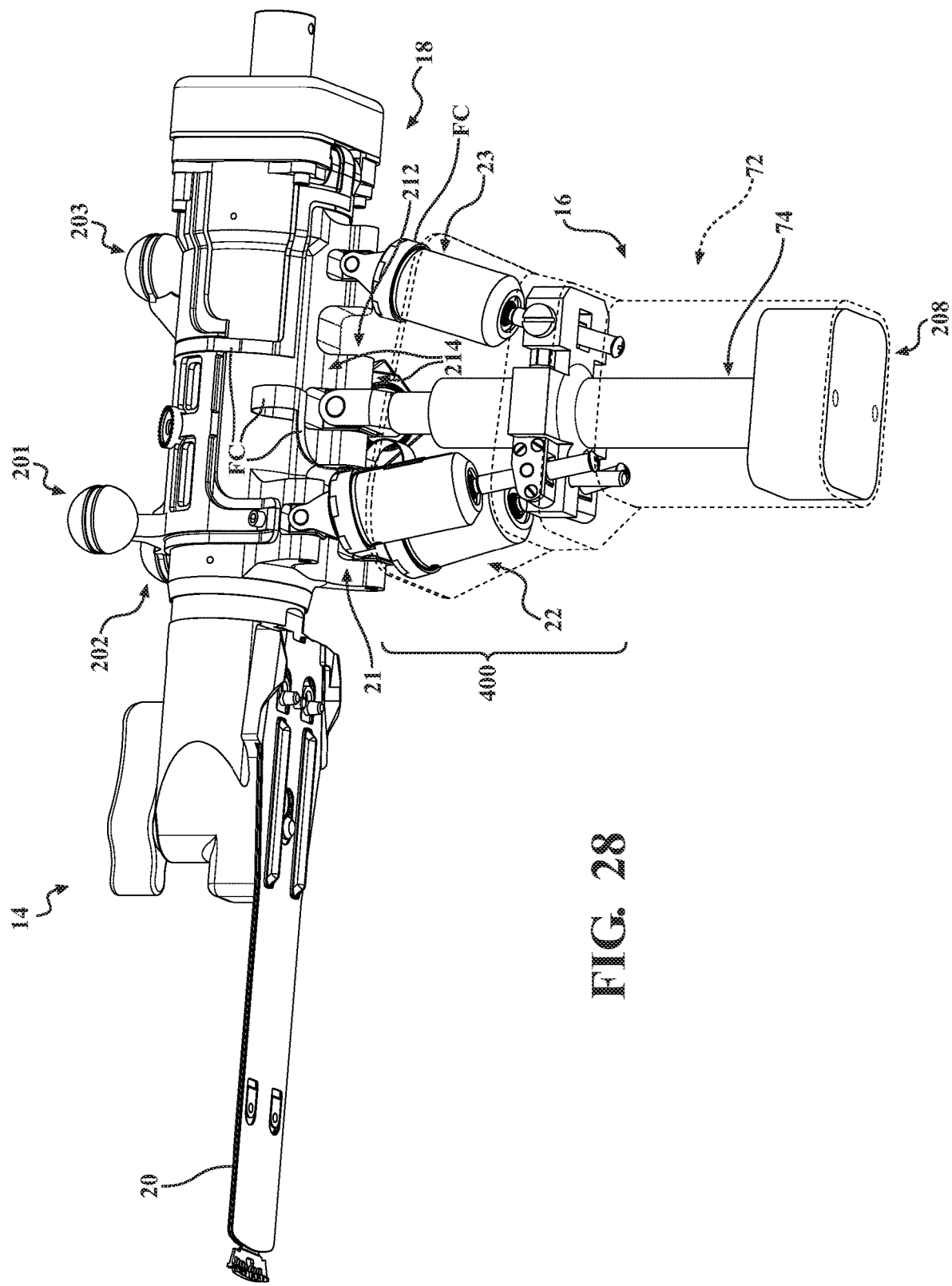
FIG. 28 is a perspective view of another robotic instrument with a grip shown in phantom.
Figure 29:
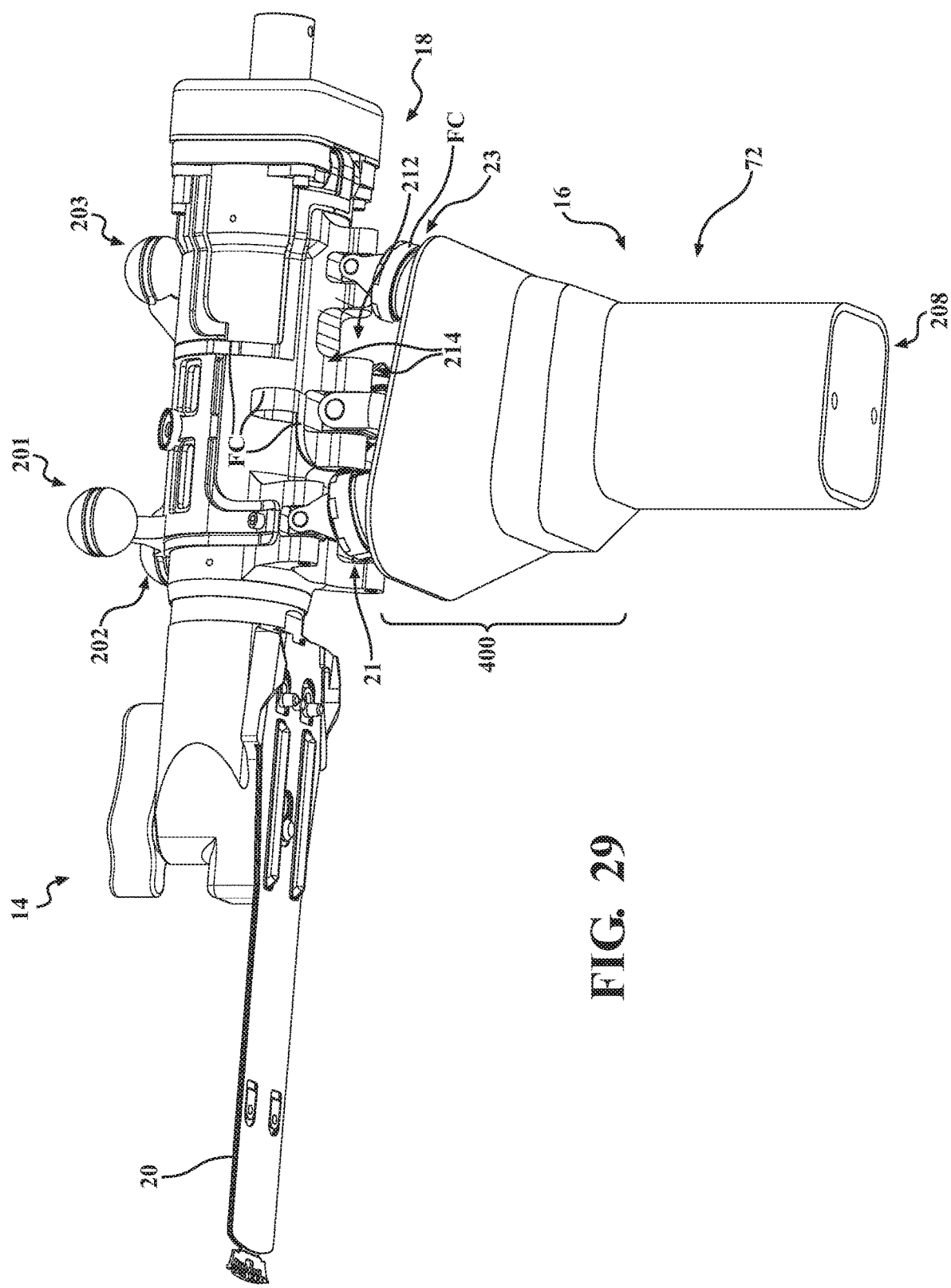
FIG. 29 is another perspective view of the robotic instrument of FIG. 28.

Referring to FIGS. 28 and 29, another version of the robotic instrument 14 is shown. This version is largely the same as previously described. In this version: (1) routing of the flex circuits FC has been slightly modified to account for the range of movement of the actuators 21, 22, 23 about their respective pivots; (2) a weighted end cap 208 has been added to the base 74; and (3) the grip 72 has been modified to account for the alterative routing of the flex circuits FC and the presence of the weighted cap 208.

Routing of the flex circuits FC is best shown in FIG. 29. FIGS. 30 and 31 show the flex circuits FC and the control housing 29 isolated from the remainder of the instrument 14. As shown in FIGS. 30 and 31, the flex circuits FC form part of a flex circuit assembly 210. The flex circuit assembly 210 may comprise multiple, flexible elongated portions (or legs) formed in one-piece or the portions may be formed separately and attached together. The flexible elongated portions may comprise one or more flexible plastic substrates, such as polyimide, transparent conductive polyester film, or the like.

The flex circuit assembly 210 comprises electronic circuits mounted and/or embedded in the flexible plastic substrates. The electronic circuits may include one or more circuits for transmitting data and/or power between the visual indicators 201, 202, 203, and one or more of the circuit boards 31 in the control housing 29. The electronic circuits may also comprise one or more circuits for transmitting data and/or power between the actuators 21, 22, 23, and one or more of the circuit boards 31. The electronic circuits may also comprise one or more circuits for transmitting data and/or power between the sensors S and one or more of the circuit boards 31 (or the sensors S may be considered part of the actuators 21, 22, 23).

Figure 32:
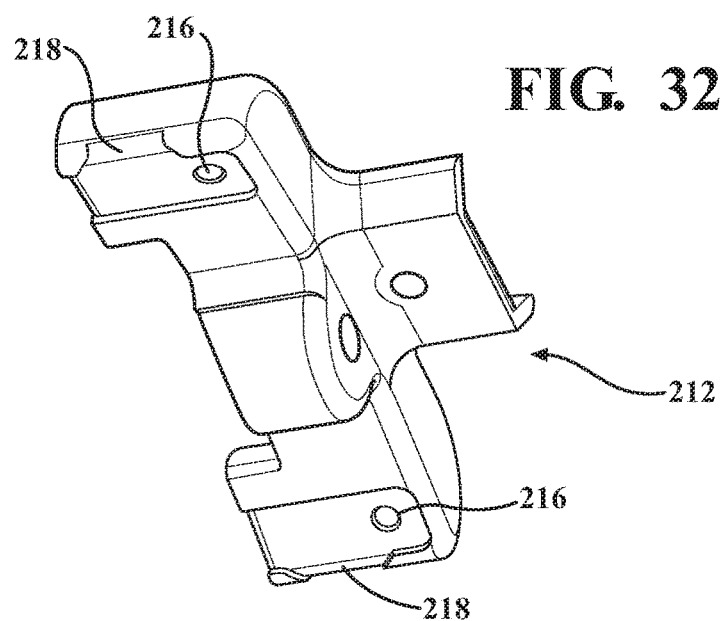
FIG. 32 is a bottom perspective view of a flex circuit support used to anchor portions of the flex circuits shown in FIGS. 30 and 31.

Referring to FIGS. 29 and 32, a flex circuit support 212 is mounted to the tool support 18 via one or more fasteners to anchor two of the flexible elongated portions of the flex circuit assembly 210 that extend to the actuators 21, 22. In particular, the two flexible elongated portions are anchored to the flex circuit support 212 via anchors 214. The anchors 214 act to trap the flexible elongated portions against a surface of the flex circuit support 212. The anchors 214 may comprise fasteners, e.g., screws, etc., or any other suitable form of anchor to hold the flexible elongated portions at the locations shown.

Referring specifically to FIG. 32, the flex circuit support 212 comprises a body defining one or more anchor mounting locations 216 for receiving the anchors 214. The flexible elongated portions that are captured by the anchors 214 comprise openings 220 through which the anchors 214 secure the flexible elongated portions to the body (see openings 220 shown in FIG. 30). The body also defines a pair of notches 218 sized to receive the flexible elongated portions of the flex circuit assembly 210 to guide those flexible elongated portions in a manner that reduces stress on the flexible elongated portions as the actuators 21, 22 move during operation.

Figure 33:
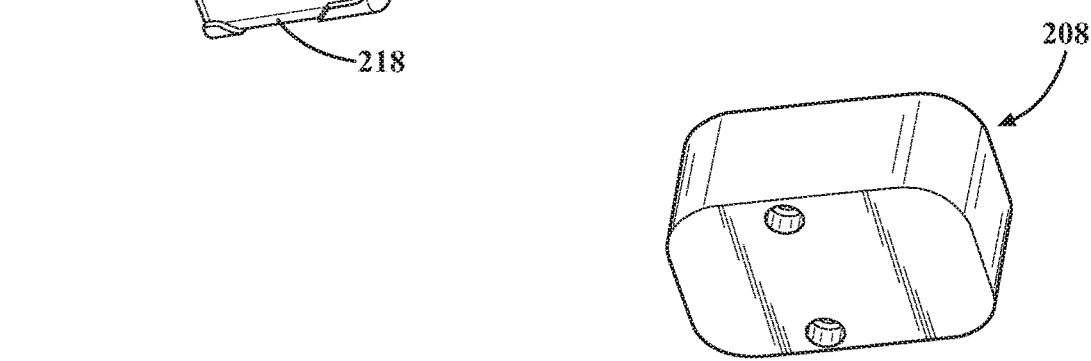
FIG. 33 is a bottom perspective view of a weighted end cap for a hand-held portion of the robotic instrument of FIG. 28.

As shown in FIGS. 28, 29, and 33, the weighted cap 208 may be formed of one or more materials, e.g., plastic, metal, ceramic, combinations thereof, etc. The weighted cap 208 may be sized and/or shaped and have a mass capable of shifting the weight distribution of the instrument 14 to provide suitable balance in the user's hand. The weighted cap 208 may also be designed to address/improve reactionary loads on the user's hand that result from operation of the instrument 14.

Figure 34:
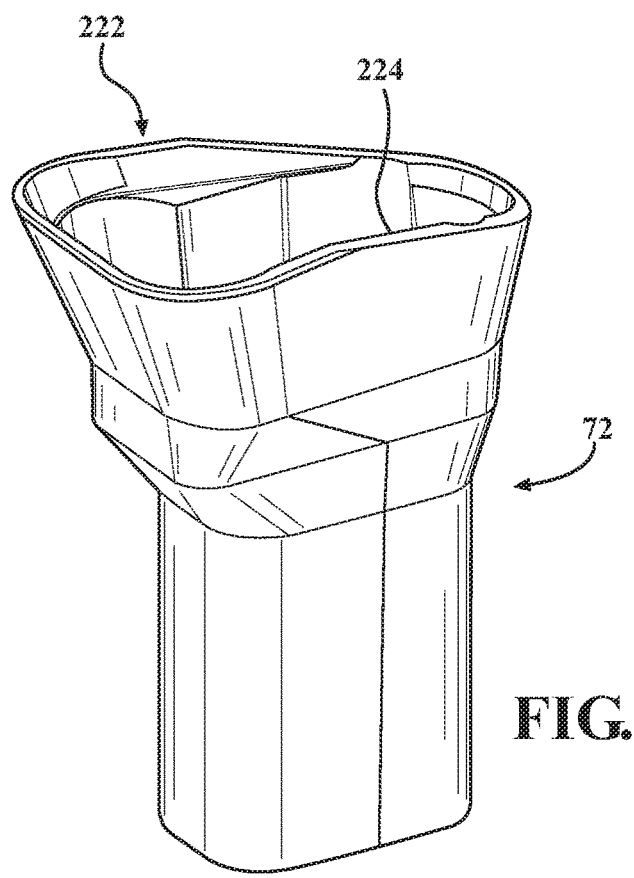
FIG. 34 is a perspective view of the grip of the robotic instrument of FIG. 28.

The grip 72 shown in FIG. 34 is largely the same as the grip 72 previously shown and described except that the top 222 of the grip 72 has an angled declining portion 224 extending toward the rear. The angled declining portion 224 opens the grip 72 in the rear to accommodate the flex circuits FC when the tool support 18 is at certain extreme poses relative to the hand-held portion 16.

Figure 69:
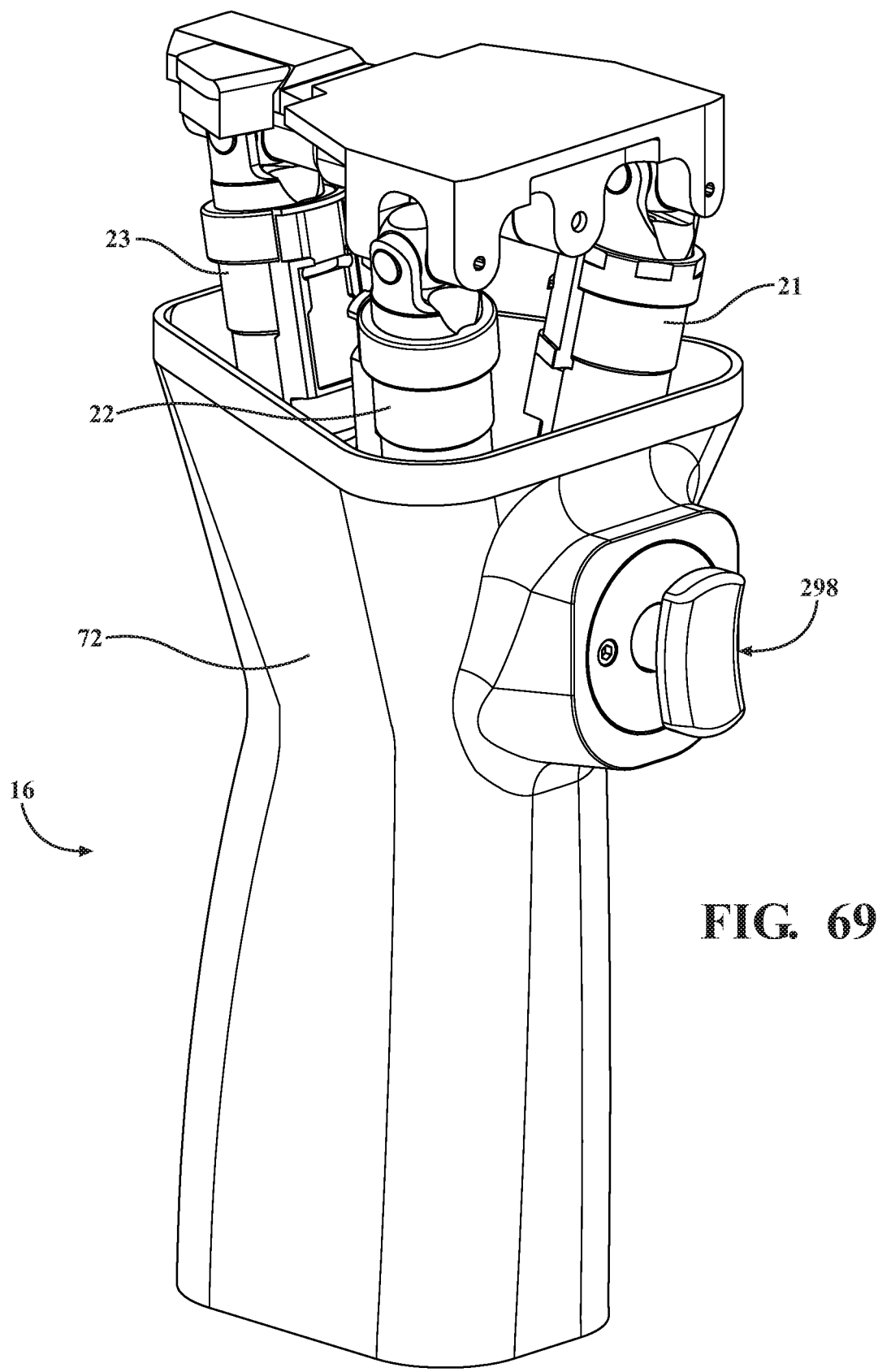
FIG. 69 displays an alternative grip with an input device.

The grip 72 shown in FIG. 69 is substantially similar as the grip 72/hand-held portion 16 shown and described previously, except for the inclusion of an input device 298 configured as a trigger in this depiction. The input device in this configuration is located on the grip 72 to allow a user to selectively send an actuation signal to the instrument controller 28.

Alternative Configurations

Figure 67:
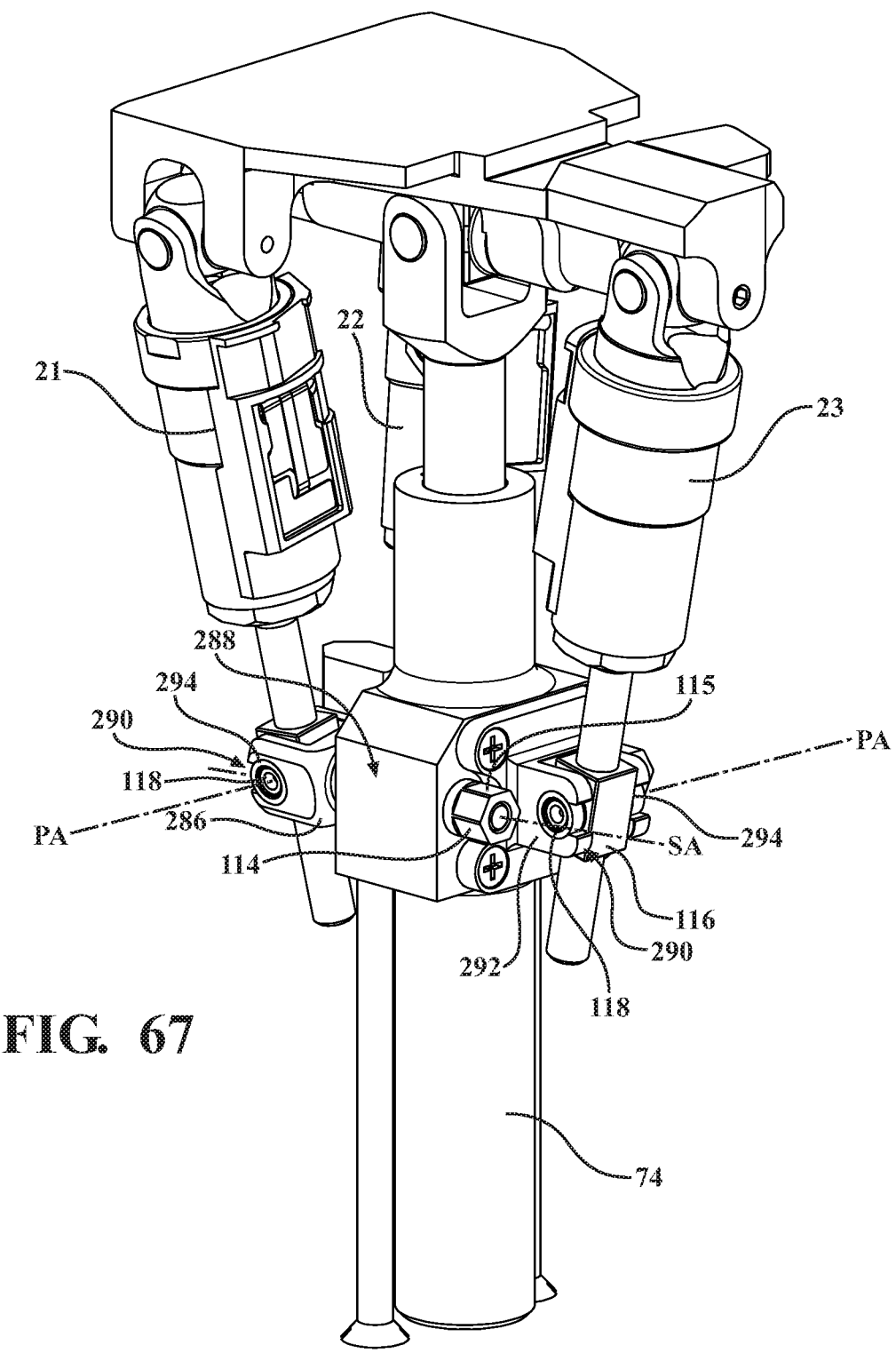
FIG. 67 and FIG. 68 show an alternative configuration for actuator mounting in the hand-held portion.
Figure 68:
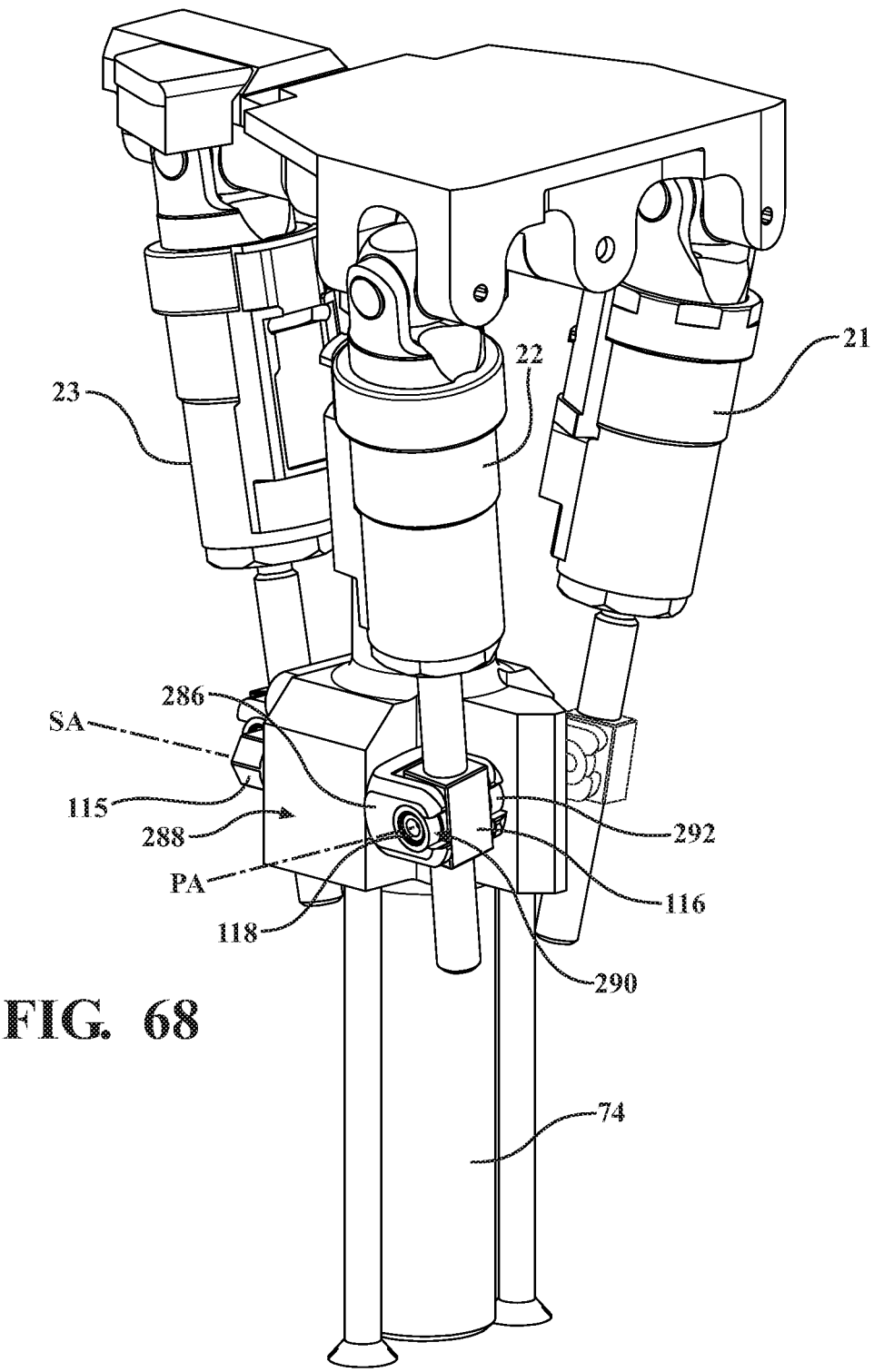

FIGS. 67 and 68 display an alternative configuration for actuator mounting in the hand-held portion 16 with base 74. FIGS. 67 and 68 offer an alternative configurations of the active joints. The active joints may comprise a set of second active joints 108 coupling the front two actuators 21, 22 to the base 74 of the hand-held portion 16. In the version shown, the second active joints 108 are supported at the joint support 288. Each of the second active joints 108 comprises a swivel yoke 110 arranged to swivel relative to the base 74 of the hand-held portion 16. Each swivel yoke 110 has a swivel head 286 and a post 114 extending from the swivel head 286 to pivotally engage the base 74 at the joint support 286. Nuts 115 threadably connect to one end of the posts 114 to trap the posts 114 in the base 74 while allowing the respective swivel yoke 110 to freely rotate within its respective joint support 286.

Each of the second active joints 108 comprises a carrier 116 pivotally coupled to one of the swivel yokes 110. Each of the carriers 116 comprises opposed trunnions 118 that allow the carriers 116 to pivot relative to the swivel yokes 110 about pivot axes PA (see FIG. 14) by being seated in pockets 290 in the swivel yokes 110.

The swivel heads 286 define the pockets 290 configured to receive the trunnions 118. The trunnions 118 of carriers 116 are slid into the pockets 290 so that the trunnions 118 and the carrier 116 is disposed within the swivel head 286. Collars 294 are pressed into to either side of the pivot housing 292 engaging the trunnions 118. The carrier 116 is able to pivot relative to the swivel yoke 110 via the trunnions 118 and pockets 290. Owing to the configuration of the swivel yokes 110 and the associated carriers 116, i.e., the carriers 116 ability to swivel about the swivel axes SA and pivot about the pivot axes PA, the second active joints 108 allow two degrees of freedom of movement of the front two actuators 21, 22 relative to the base 74.

The active joints also comprise a third active joint 124 coupling the rear (third) actuator 23 to the base 74 of the hand-held portion 16. In the version shown, the third active joint 124 is supported at the joint support 79. The third active joint 124 comprises a pivot housing 292 fixed to the joint support 288 of the base 74.

The third active joint 124 comprises a carrier 116 pivotally coupled to the pivot housing 292 via trunnions 118 into pockets 290. Collars 294 are pushed into both sides of the pivot housing 292 engaging the trunnions 118. The collars 294 are arranged such that the carrier 116 is able to pivot via the trunnions 118 being located in pockets 290 of the pivot housing 292 after assembly. Owing to the configuration of the pivot housing 292 and associated carrier 116, i.e., the ability of the associated carrier 116 to only pivot about the pivot axis PA (e.g., and not swivel), the third active joint 124 allows only one degree of freedom of movement of the rear actuator 23 relative to the base 74.

Turning to FIGS. 35-45B, an alternative configuration of the instrument 14 is shown utilizing actuator assembly 400 including actuators 21, 22 and rotary actuator 228, and constraint assembly 24 to connect a hand-held portion 16 to a tool support 18. Actuators 21, 22 are configured to control the height and the pitch of a tool body 80 of the tool support 18 relative to the hand-held portion 16. The rotary actuator assembly 228 is coupled with the tool support 18 to control roll movement of a tool head 84 connected with tool 20, adjusting the cutting plane of tool 20 while the tool body 80 of the tool support 18 and hand-held portion 16 are constrained from rolling relative to each other.

Figure 35:
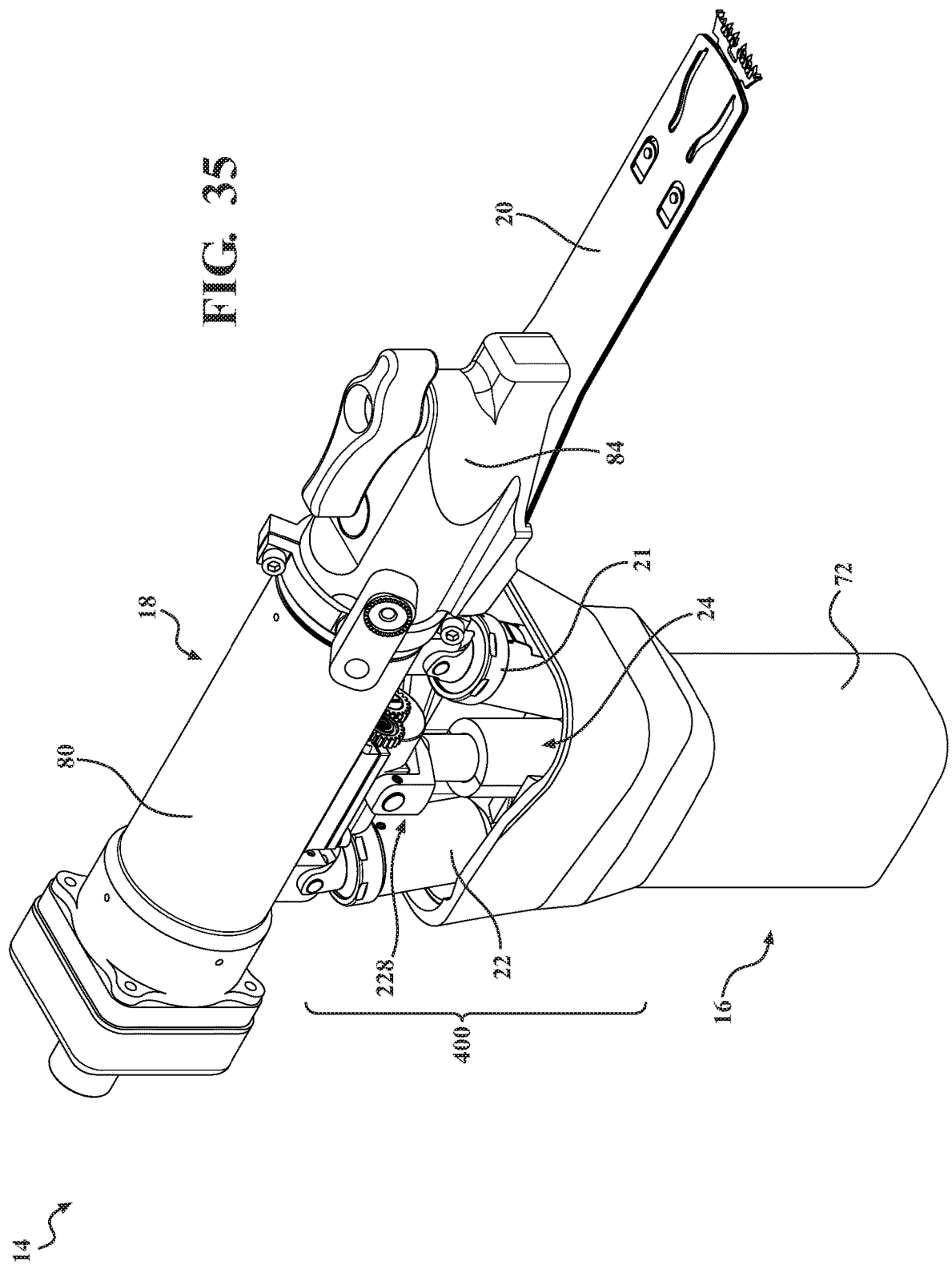
FIG. 35 is a perspective view of an alternative configuration of the robotic instrument.
Figure 36:
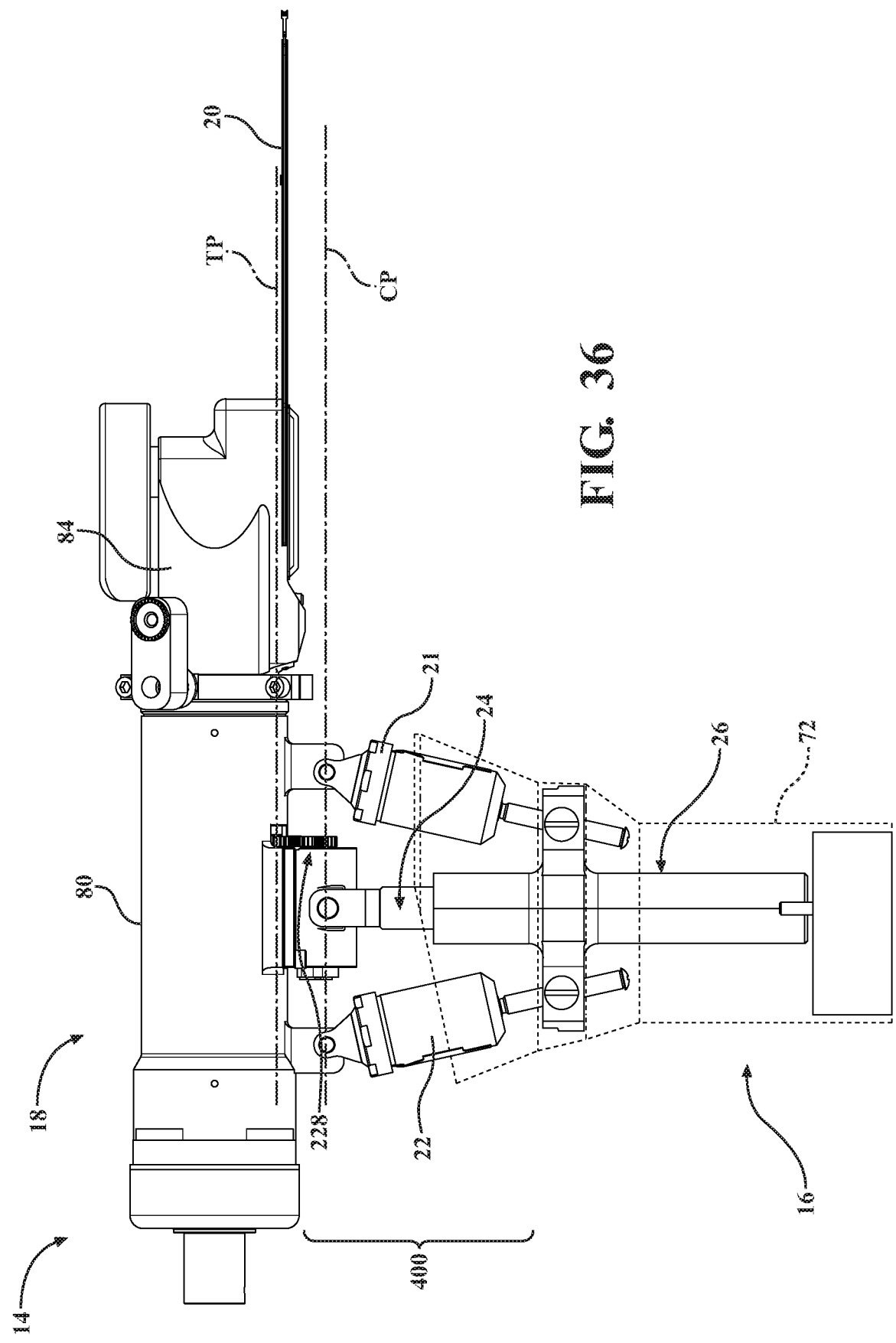
FIG. 36 is a side elevational view of the alternative configuration of the robotic instrument of FIG. 35.

As seen in FIGS. 35-37, the instrument 14 includes the hand-held portion 16 to be held by the user. The hand-held portion 16 may be interchangeably referred to as a hand-holdable body. The hand-holdable body 16 is the portion of the instrument which a user holds and manually supports through gripping the hand-holdable body 16. The hand-holdable body 16 allows the user to move and manipulate the instrument without constraint. The tool support 18 movably coupled to the hand-holdable body 16 to support the tool 20. A first actuator 21 and a second actuator 22 are located between the tool support 18 and the hand-holdable body 16, operatively interconnecting the tool support 18 and the hand-holdable body 16. Actuators 21, 22 are aligned along a longitudinal plane that bisects the hand-holdable body. Actuators 21, 22 are configured to move the tool support 18 in two degrees of freedom, changing the z-axis translation (elevation relative to the hand-held portion 16) and the pitch relative to the hand-holdable body 16. A constraint assembly 24 including a passive linkage 26 is located between the hand-holdable body 16 and the tool support 18, further interconnecting the tool support 18 and the hand-holdable body 16. The constraint assembly 24 is configured to constrain the movement of the tool support 18 to three degrees of freedom relative to the hand-holdable 16.

Figure 38B:
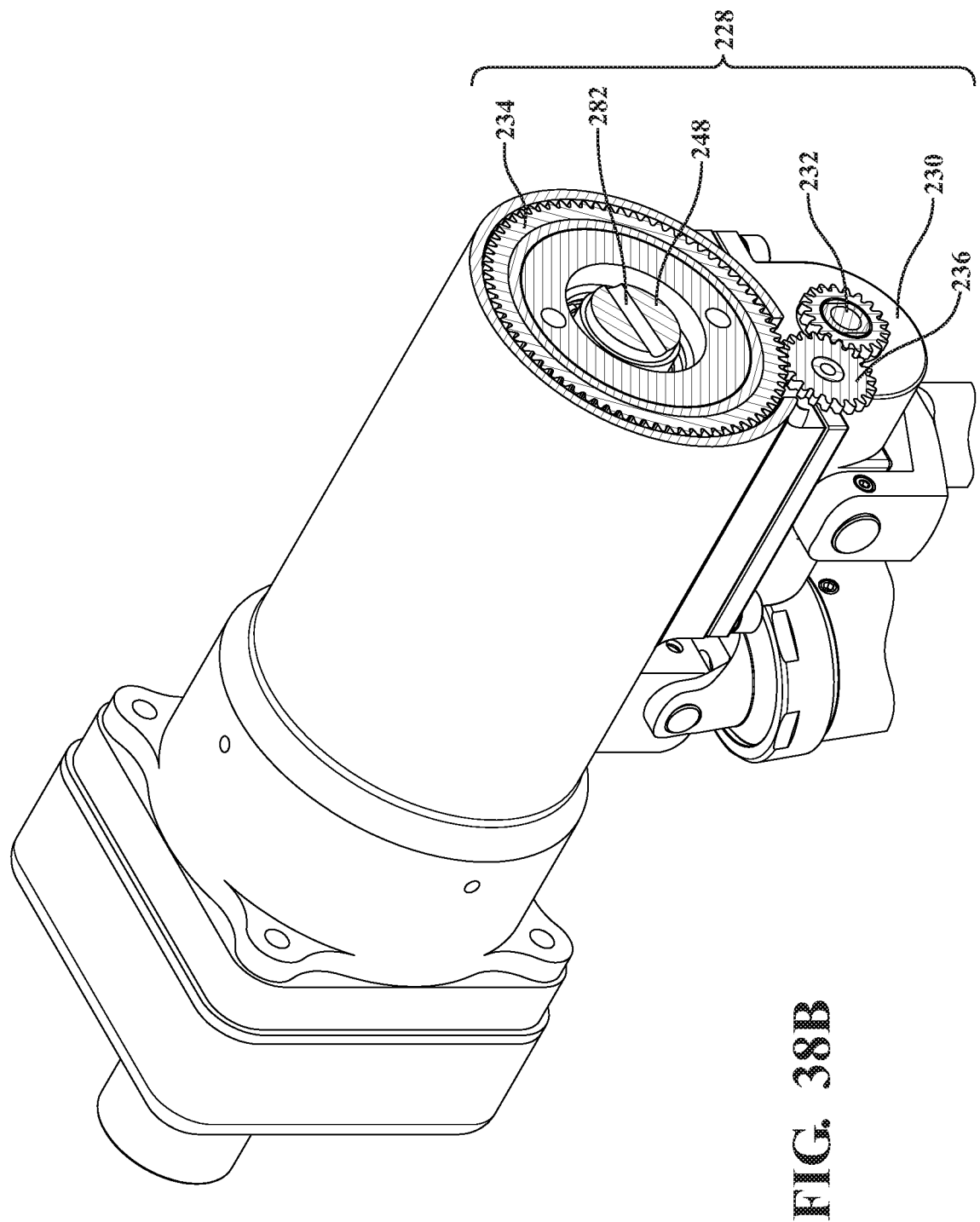
FIG. 38B is a transverse cross-sectional view of the alternative configuration of the robotic instrument of FIG. 35 showing the rotary actuator assembly and a tool support.

The tool support 18 includes a rotary actuator assembly 228 configured to control roll movement of the tool 20 relative to the hand-holdable body 16. FIGS. 38A and 38B depict the rotary actuator assembly 228 including a rotary actuator motor 230, a drive member 232, and a ring gear 234. The rotary actuator motor 230 is in communication with the tool support 18 and may be an electric motor. The drive member 232 is connected to the rotary actuator motor 230 and is configured to be rotated by the rotary actuator motor 230. The drive member 232 may be a gear. The drive member 232 is shown particularly in FIGS. 38A and 38B as a spur gear. The rotary actuator assembly 228 may be configured so that the drive gear 232 directly contacts and rotates the ring gear 234 relative to the tool support 18 and the hand-holdable body 16 when the rotary actuator motor 230 is actuated. The ring gear 234 may be configured as a worm gear connected in communication with the drive member 232 which may be configured as a worm to prevent back driving the tool 20 during operation. As seen in FIG. 38B, the rotary actuator assembly 228 may include one or more intermediate gears 236. The one or more intermediate gears 236 may function to change the drive ratio between the drive gear 232 and the ring gear 234. The one or more intermediate gears 236 may be an idler gear. For example, the one or more intermediate gear 236 may increase the gear ratio between the drive gear 232 and the ring gear 234. The drive gear 232 may be in direct communication with the intermediate gear 236 to rotate the intermediate gear 236 (FIG. 38B). The intermediate gear may be in direct communication with the ring gear 234 so that the ring gear 234 rotates when the rotary actuator motor 230 is actuated.

In the example configuration seen in FIGS. 39A and 39B, the ring gear 234 is integrated with the head 84 of the tool support 18. The tool head 84 may rotate with the ring gear 234, adjusting and controlling the rotational position of the tool 20 (e.g. saw blade). The tool head 84 may rotate about an axis defined by the drive motor M. FIG. 39A depicts the tool support 18 with body 80 and head 84 partially exploded, showing the ring gear 234 on the head 84 and the rotary actuator motor 230, drive gear 232, and intermediate gear 236 in communication with the body 80 of the tool support 18. The head 84 may be configured to engage the tool 20 so that when ring gear 234 is rotated by the rotary actuator motor 230, the head 84 and the tool 20 also rotate, adjusting the roll position of the tool 20 relative to the hand-holdable body 16 and the tool support 18 (e.g. FIGS. 45A and 45B). The head 84 is configured to rotate 360 degrees relative to the hand-holdable body 16 and the tool support 18, positioning the tool 20. The tool head 84 may be connected with the tool support body 80 by an axial retention nut configured to hold the tool head 84 in place. In other configurations, the head 84 may roll 360 degrees or less, 270 degrees or less, 180 degrees or less, 90 degrees or less, or even 50 degrees or less. In further configurations, the tool head 84 may roll 30 degrees or more, 90 degrees or more, 180 degrees or more, 270 degrees or more, or even 360 degrees or more. In some examples, the tool head 84 may have hard stops which prevent the tool head 84 from rotating, limiting the range of rotation of the tool head 84 relative to the tool support 18 and hand-held portion 16.

Figure 38C:
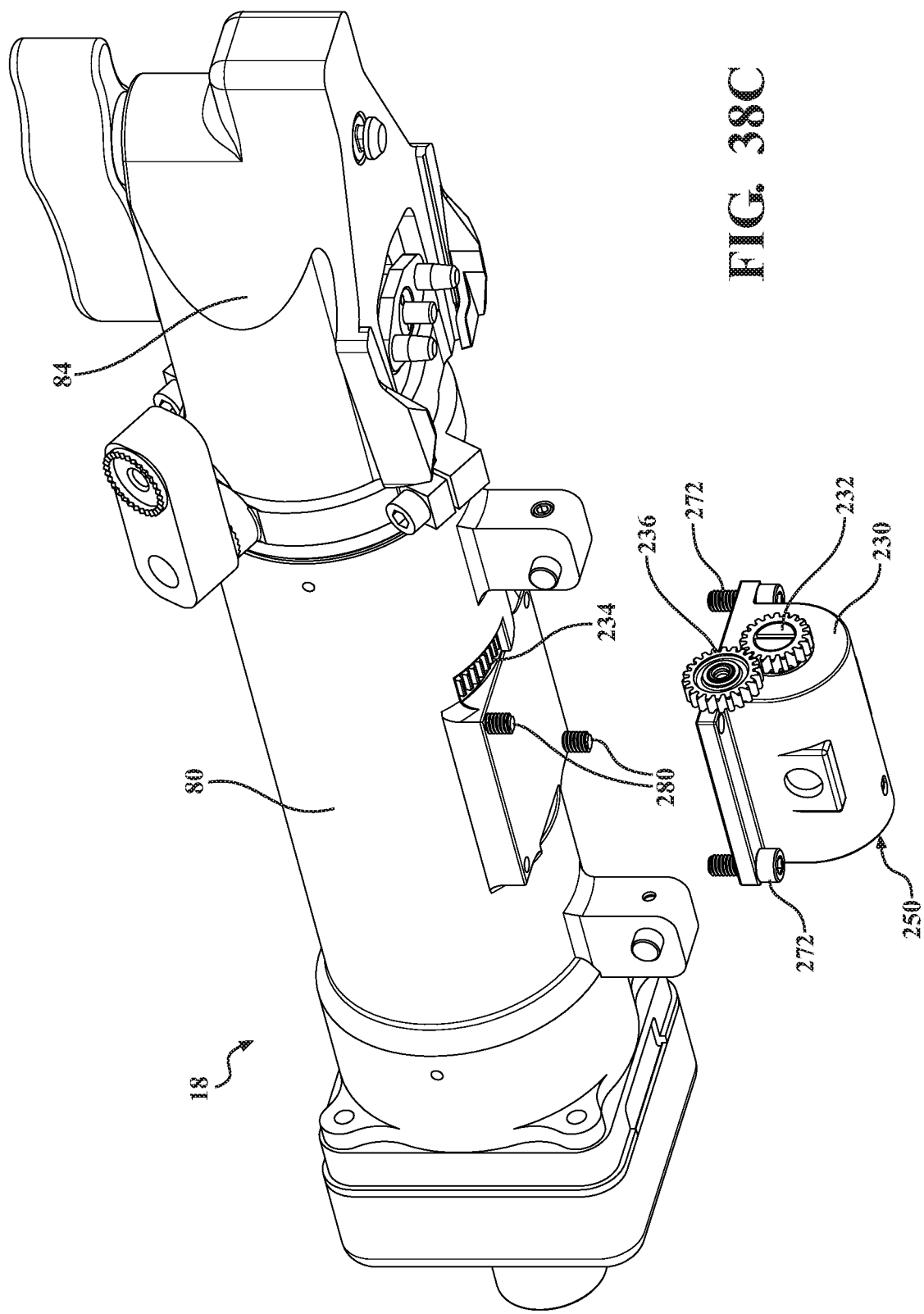
FIG. 38C is a perspective view of the tool support with a rotary actuator motor.

As best seen in FIGS. 38A-38C and 40A-40B, the rotary actuator motor 230 is located below the tool support body 80. The rotary actuator motor 230 is attached with the tool support body 80 and is configured to move with the tool support body 80 as the actuators 21, 22 adjust height and pitch of the tool support body 80 relative to the hand-holdable body 16. The rotary actuator motor is configured to rotate drive gear 232 which is in rotational communication with the ring gear 234 relative to the tool support body 80. The rotary actuator motor rotates the drive gear and, subsequently, the ring gear 234 which is connected with the tool head 84, causing the ring gear 234 and tool head 84 to rotate relative to the tool support body 80. In some configurations, the rotary actuator motor 230 may be integrated into the tool support body 80. In some configurations, the rotary actuator may include an absolute encoder. In another example, such as in FIG. 38C, the rotary actuator motor 230 is a separate unit which is attached to the tool support body 80. For example, FIG. 38C shows a partially exploded view of the tool support body 80 and the rotary actuator motor 230. The rotary actuator motor 230 incudes a housing 250. The rotary actuator motor 230 is attached to the tool support body 80 by fasteners 272 disposed through the rotary actuator motor housing 250 which are received in the tool support body 80, however, other means of attachment, such as adhesive, welding, or the like are contemplated. FIG. 38C shows fasteners 272 at opposite, diagonal corners of the rotary actuator motor 230 for attaching the rotary actuator motor to the tool support. Alignment pins 280 corresponding to opposite corners of the rotary actuator motor 230 are disposed in the tool support body 80, easing the attachment of the rotary actuator motor 230 to the tool support body 80 and alignment with the ring gear 234. The rotary actuator motor 230 includes a housing 250. The housing 250 of the rotary actuator motor 230 may function to provide passive linkage mounts 254 for the passive linkage 26, which will be described further below.

Prior to treating the anatomy (e.g., prior to cutting the femur F and/or tibia T), and during certain modes of operation described below, a homing procedure may be performed that establishes the home position for the rotary actuator 228 may include a homing process similar to actuators 21, 22 (described above) to position the tool head 84 and tool 20. The process provides a reference position from which to count the incremental movements of the drive gear 232, ring gear 234, or both measured by a sensor so that the control system 60 is able to determine the current position of the tool head 84 and tool 20. In some versions, when the sensor is able to measure absolute positions of the drive gear 232, ring gear 234, or both, then homing may not be necessary. In some other configurations, the initial position of the tool head 84 may be determined through other methods. For example, a pointer 57 may be used with calibration divots CD in the tool head 84 and/or in the tool 20 for determining the position of the tool head 84 and tool 20 relative to the tool support 18, the hand-holdable body 16, the tool tracker 52, the patient tracker 54, 56, PT, or a combination thereof.

Figure 43:
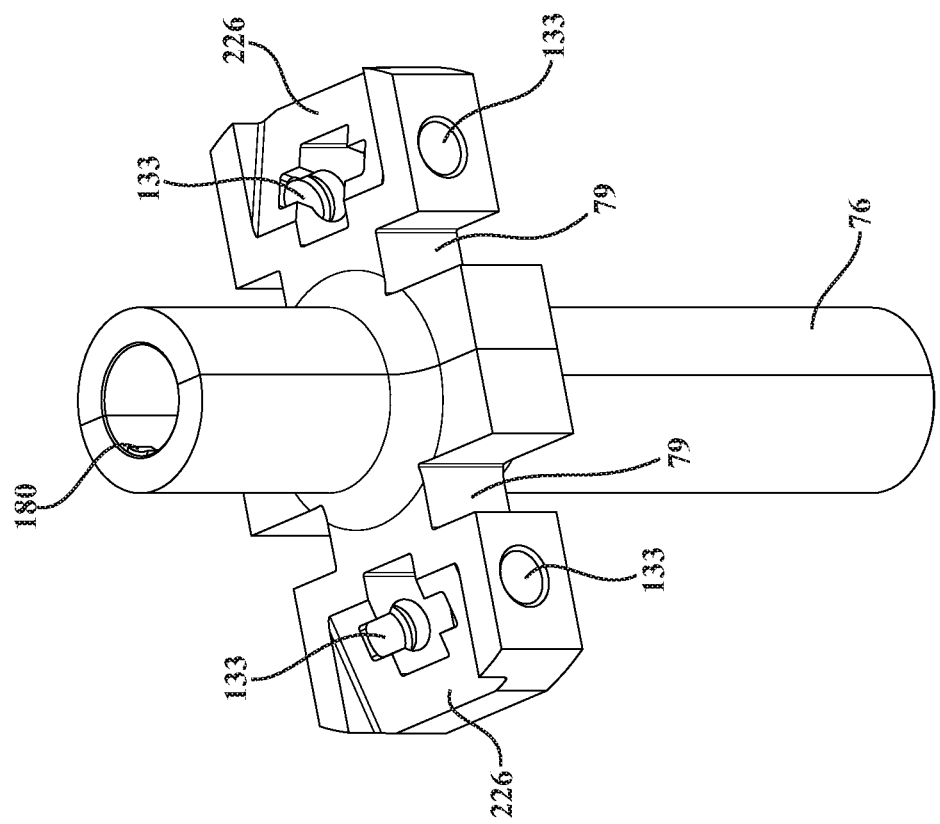
FIG. 43 is a top perspective view of the base of the hand-held portion.

FIGS. 35-37 depict the hand-holdable body 16 connect via actuators 21, 22 and passive linkage 26 to the tool support body 80 of the tool support 18. The hand-holdable body 16 comprises a grip 72 for being grasped by the user so that the user is able to manually support the instrument 14. The hand-holdable body 16 also comprises a base 74 to which the grip 72 is attached by one or more fasteners, adhesive, welding, or the like. In the version shown, the base 74 comprises a sleeve 76 having a generally hollow cylindrical shape. Pivot housings 126, 226 extend from the sleeve 76 (FIGS. 42 and 43). The actuators 21, 22, are movably coupled to the base 74 at the pivot housings 126, 226 described further below.

The tool 20 is removably coupled to the tool support 18 in the configuration shown in FIGS. 35-45. In particular, the head 84 may be removably connected with the tool 20 as described in U.S. Pat. No. 9,820,753 to Walen et al., incorporated herein by reference.

The drive motor M that drives operation of the tool 20 is disposed in the tool support body 80 (e.g., to drive oscillation of the saw blade in some versions). FIGS. 39A and 39B show the tool support 18 and head 84 with ring gear 234. The tool support 18 may incorporate a drive motor M and other driving components shown in U.S. Pat. No. 9,820,753 to Walen et al., to drive oscillating motion of the blade assembly. The drive motor M includes a drive member 248 extending therefrom, configured to spin with the output of the motor M. The driven member 248 extends distally from motor M. The driven member 248 includes a slot 282 that is configured to receive driven shaft 252 of the head 84 so that the driven member 248 receives the driven shaft 252. When the driven member 248 receives the driven shaft 252 in the slot 282 of the driven member 248, the driven member 248 and the driven shaft 252 rotate together when the motor M is activated. The rotational movement of drive motor M rotates driven member 248, which, in turn, rotates driven shaft 252, powering the tool 20. The head 84 rotates with the ring gear 234 adjusting the rotational position of the head 84 and the tool 20 when the rotary actuator 228 is actuated, independent of the activation of the drive motor M. The drive motor M may be configured to remain stationary as the tool 20 and head 84 are rotated by the ring gear 234 of the rotary actuator assembly 228. In another configuration, the drive motor M may be configured to rotate with the ring gear 234 of the rotary actuator assembly 228. The tool 20 may be attached to and released from the head 84 in the manner disclosed in U.S. Pat. No. 9,820,753 to Walen et al., incorporated herein by reference.

Figure 40A:
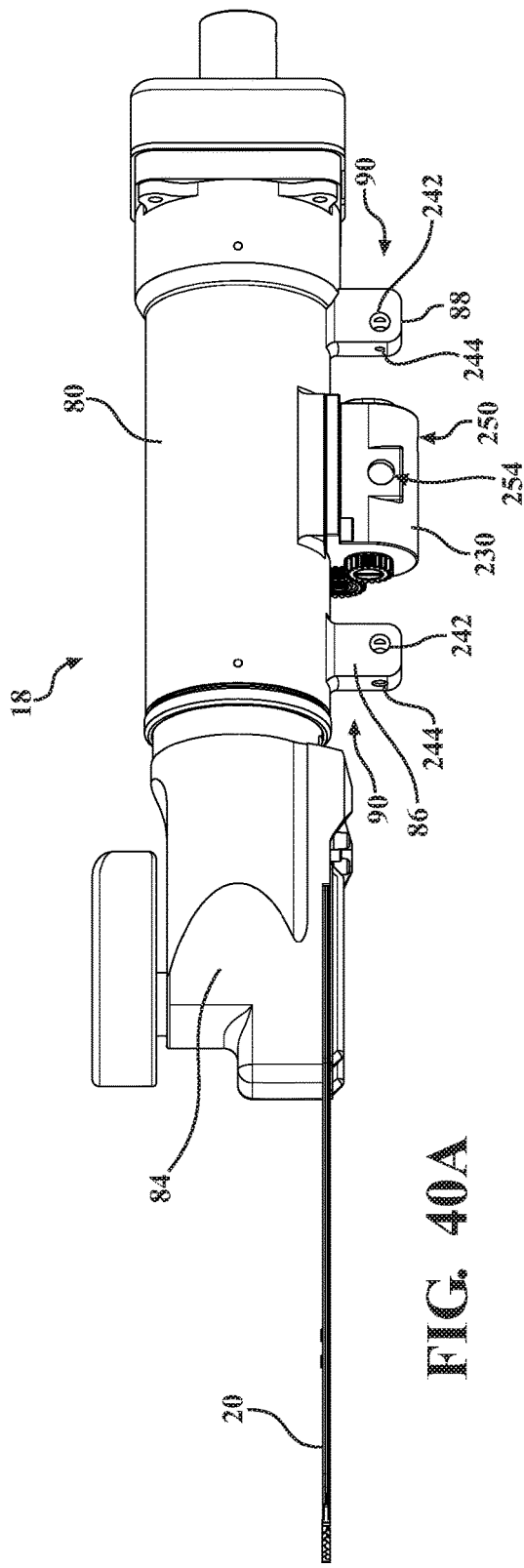
FIGS. 40A and 40B are perspective views of the tool support of the robotic instrument of FIG. 35.
Figure 40B:
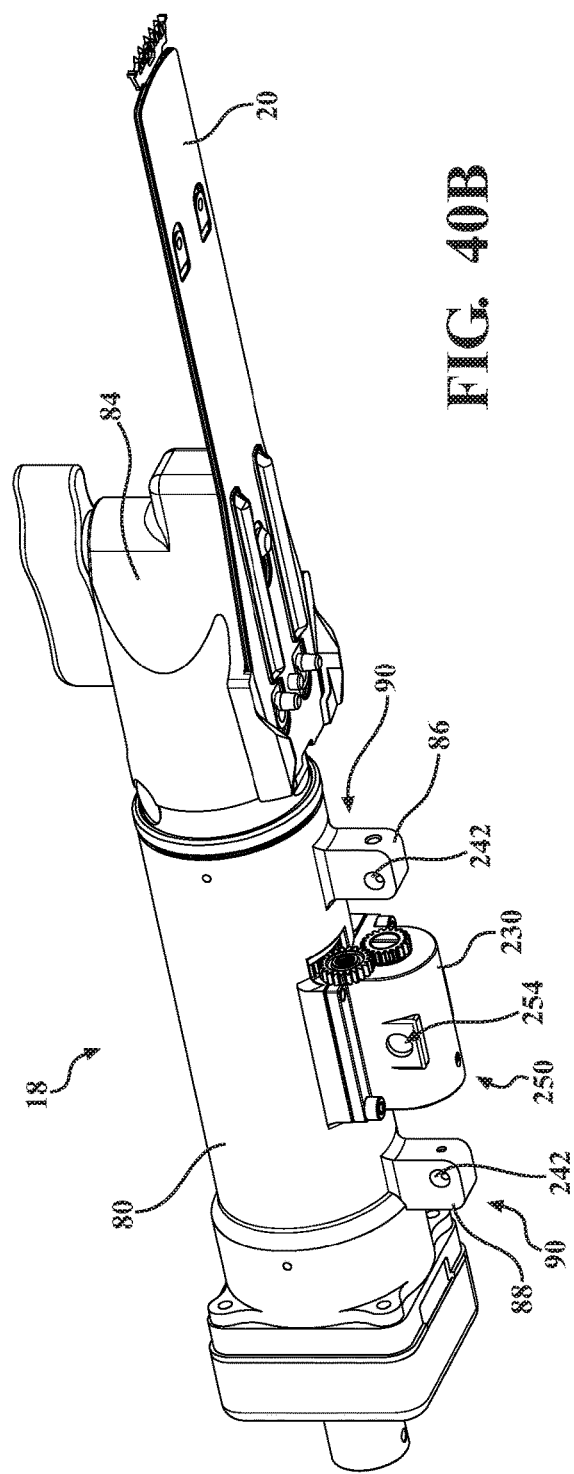

As best shown in FIGS. 40A and 40B, the tool support 18 also comprises a plurality of actuator mounts 86, 88 at which the actuators 21, 22 are to be movably coupled to the tool support 18 via pivot mounts, as described further below. The actuator mounts 86, 88 may comprise brackets, or the like, suitable to mount the actuators 21, 22 such that the tool support 18 is able to move in two degrees of freedom (i.e. z-axis translation and pitch) relative to the hand-held portion 16.

As can be seen in FIGS. 36 and 37, the actuators 21, 22 comprise electric, linear actuators that extend between the base 74 and the tool support body 80. When actuated, an effective length (previously described with respect to FIG. 16) of the actuator 21, 22 changes to vary a distance between the tool support body 80 and the base 74 along a corresponding axis of the actuator 21, 22. Accordingly, the actuators 21, 22 work in concert to change their effective lengths and move the tool support 18 in at least two degrees of freedom (pitch and z-axis translation) relative to the hand-holdable body 16. In the version shown, two actuators 21, 22 are provided, and may be referred to as first and second linear actuators 21, 22 or front actuator 21 and rear actuator 22. The first and second actuators 21, 22 are adjustable in effective length along a first active axis AA1 and a second active axis AA2 (see FIG. 41). The first and second actuators 21, 22 are independently adjustable in effective length to adjust one or more of a pitch orientation, a z-axis translation position, or both of the tool support 18 relative to the hand-holdable body 16, as previously described. The actuators 21, 22 in combination with the rotary actuator assembly 228 are configured to adjust the tool 20 in at least three degrees of freedom, including roll about a longitudinal axis of the tool support 18, relative to the hand-holdable body 16. More actuators may be provided in some examples. The actuators 21, 22 may comprise linkages having one or more links of any suitable size or shape. The actuator assembly 400 with actuators 21, 22 and rotary actuator assembly 228 may have any configuration suitable to enable movement of the tool 20 relative to the hand-holdable body 16 in at least three degrees of freedom.

Figure 41:
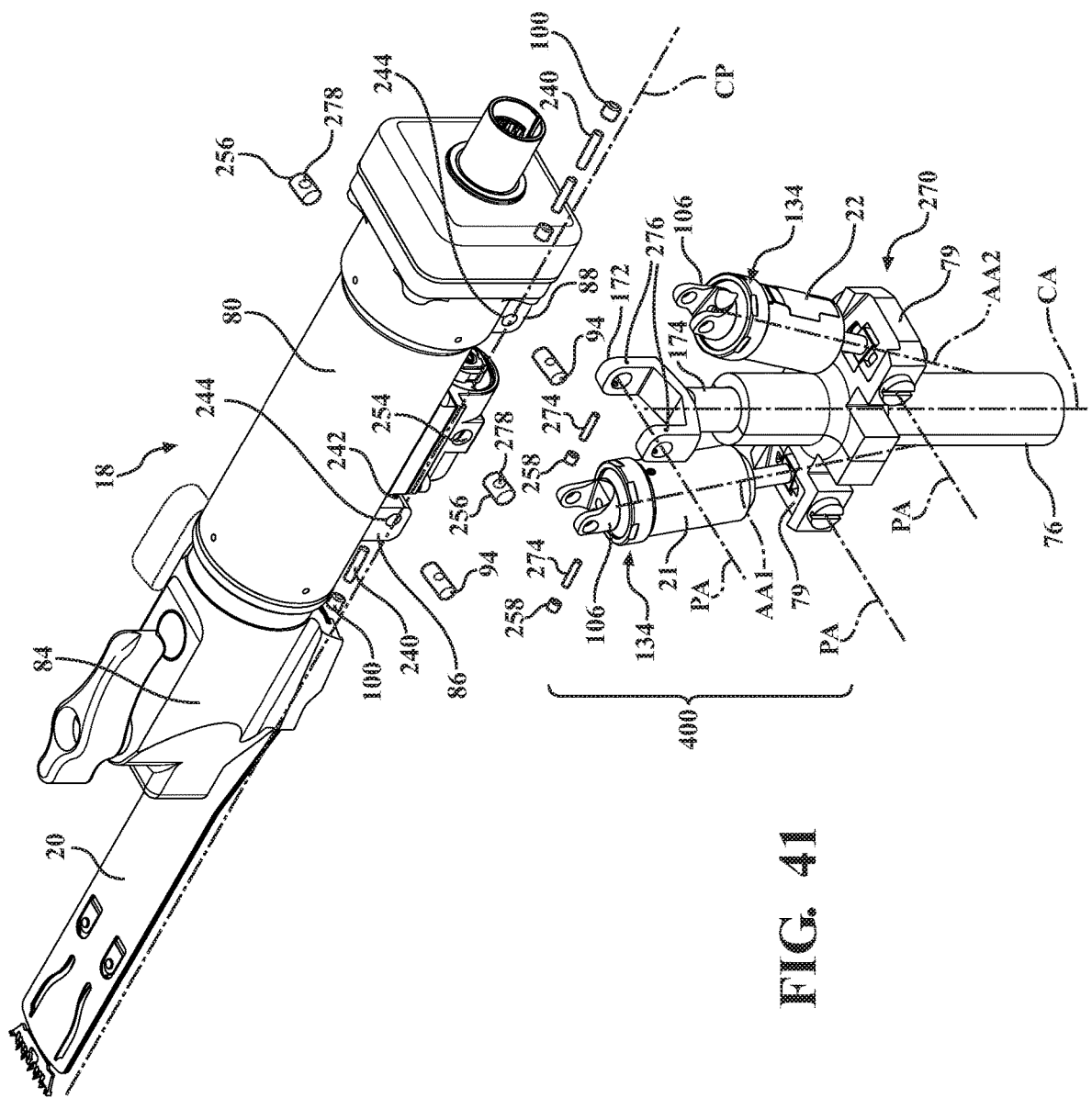
FIG. 41 is an exploded view showing a body of the tool support and associated joint connections to a plurality of actuators.

FIGS. 36, 37 and 38A show actuators 21, 22 coupled to the base 74 and the tool support body 80 via a plurality of active joints. The active joints include a set of first active joints 92 that couple the actuators 21, 22 to the tool support body 80 at the actuator mounts 86, 88. In one version, as shown in FIGS. 41 and 42, the first active joints 92 comprises active pivot joints. The pivot joints comprise pivot pins 94. The pivot pins 94 pass through actuator mounts 86, 88 and pivot yokes 106 located on actuators 21, 22, pivotally connecting the actuators 21, 22 to the actuator mounts 86, 88. Set screws 100 may secure lock pins 240 transversely through the first pivot pins 94 to the actuator mounts 86, 88.

In the configuration shown in FIG. 41, the actuators 21, 22 (along with the passive linkage 26) are constrained to pivot in one direction, restraining the tool support 18 and the hand-holdable body 16 from rotating and rolling relative to each other, while allowing the tool support 18 to be vertically translated and pitched. The actuator mounts 86, 88 have throughbores 242 to receive the lock pins 240. The first pivot pins 94 have crossbores 244 to receive the lock pins 240, such that the first pivot pins 94 and the lock pins 240 intersect, clocking the first pivot pins 94 relative to the actuator mounts 86, 88. As a result, the actuators 21, 22 are able to elevate and pivot relative to the tool support body 80.

The actuators 21, 22 are movably coupled to the base 74 at the pivot housings 126, 226 forming lower active joints 246, 270 coupling the front actuator 21 and the rear actuator 22 to the base 74 of the hand-holdable body 16. The lower active joints 246, 270 are supported at the joint supports 79. The lower active joints 246, 270 comprises pivot housings 126, 226 fixed to the joint supports 79 of the base 74.

The lower active joints 246, 270 each comprises a carrier 116 pivotally coupled to the pivot housings 126, 226 via trunnions 118. Fasteners 130 having pockets 132 attach to either side of the pivot housings 126, 226 via throughbores 133 to engage the trunnions 118. The fasteners 130 are arranged such that the carrier 116 is able to pivot via the trunnions 118 being located in the pockets 132 after assembly. The carrier 116 has an internally threaded throughbore 117 to receive a lead screw 150 of the actuators 21, 22, as described further below. Owing to the configuration of the pivot housing 126, 226 and associated carrier 116, i.e., the ability of the associated carrier 116 to only pivot about the pivot axis PA (e.g., and not swivel), the lower active joints 246, 270 allow only one degree of freedom of movement of the actuators 21, 22 relative to the base 74. Other joint arrangements between the actuators 21, 22 and the base 74 are also possible. Further, the design and functionality of actuators 21, 22 present in FIGS. 35-45 are the same as the actuators 21, 22 presented earlier in FIGS. 1-34. Additionally, actuators 21, 22, in addition to the rotary actuator assembly 228 are controlled, powered and sensed in a similar fashion as described in FIGS. 1-34.

As previously described above, the carriers 116 have the internally threaded throughbores 117 to threadably receive the lead screws 150 so that each of the lead screws 150 can rotate relative to a corresponding one of the carriers 116 to adjust the effective length of a corresponding one of the plurality of actuators 21, 22 and thereby vary the counts measured by the instrument controller 28. Each of the housings 134 and corresponding carriers 116 are constrained from relative movement in at least one degree of freedom to allow the lead screws 150 to rotate relative to the carriers 116 (see FIG. 16). More specifically, the lead screws 150 are able to rotate relative to the carriers 116 owing to: the pivot yokes 106 being unable to rotate about the associated active axes AA1, AA2 (i.e., the pivot yokes 106 are limited from such rotational movement by virtue of the configuration of the first active joints 92); and the carriers 116 being unable to rotate about the associated active axes AA1, AA2 (i.e., the carriers 116 are limited from such rotational movement by virtue of the configuration of the second active joints 246, 270).

Stops 152, such as threaded fasteners and shoulders formed on the lead screws 150, are fixed to the lead screws 150. The stops 152 are sized to abut the carriers 116 at ends of travel of each lead screw 150.

As previously described above, the actuators 21, 22 are actively adjustable in effective length (described above in at least FIG. 16) to enable movement of the tool support 18 relative to the hand-held portion 16. As each actuator 21, 22 is adjusted by varying how far the lead screw 150 has been threaded into or out of its associated carrier 116 and thereby changing the distance from the center of the associated carrier 116 to the center of the associated first active joint 92. The actuators 21, 22 are adjustable between minimum and maximum values of the effective length. The effective length of each actuator 21, 22 can be represented/measured in any suitable manner to denote the distance between the tool support 18 and the hand-held portion 16 along the active axes AA1, AA2 that changes to cause various movements of the tool support 18 relative to the hand-holdable body 16.

The constraint assembly 24 works in concert with the actuators 21, 22 to constrain the movement provided by the actuators 21, 22. The actuators 21, 22 provide movement in two degrees of freedom, while the constraint assembly 24 constrains movement in three degrees of freedom. In the version shown, the constraint assembly 24 comprises the passive linkage 26, as well as a passive linkage joint 156 that couples the passive linkage 26 to the tool support 18.

In the configuration shown in FIGS. 41 and 42, the constraint assembly is attached to the tool support 18 by a passive linkage joint 156. The passive linkage joint 156 includes passive linkage mounts 254 on the tool support 18 and passive linkage pivot yoke 172. A pair of pivot pins 256 pivotally connects the passive linkage pivot yoke 172 of the passive linkage 26 to the passive linkage mounts 254 of the tool support 18, located on the housing 250 of the rotary actuator motor 230. As can be seen in FIGS. 38C and 40A-42, a housing 250 of the rotary actuator motor 230 of the rotary actuator assembly 228 is attached with the tool support body 80. The passive linkage 26 is mounted via the passive linkage yoke 172 to the housing 250 of the rotary motor 230 by the pair of pivot pins 256. The pair of pivot pins 256 are held in place by pins 274 which are disposed through bores 276, 278 in the passive linkage yoke 172 and pivot pins 256, respectively and secured by screw locks 258, holding the pivot pins 256 axial aligned with the passive linkage yoke 172. As a result of connection with the tool support 18, the passive linkage 26 is able to elevate when actuators 21, 22 are actuated, as well as pivot to accommodate different angles of pitch relative to the tool support body 80.

The passive linkage 26 comprises a shaft 174 fixed to the passive linkage pivot yoke 172. The passive linkage 26 also comprises the sleeve 76 of the base 74, which is configured to receive the shaft 174 along a constraint axis CA. The passive linkage 26 is configured to allow the shaft 174 to slide axially along the constraint axis CA relative to the sleeve 74 and to constrain movement of the shaft 174 radially relative to the constraint axis CA during actuation of one or more of the actuators 21, 22.

Figure 44:
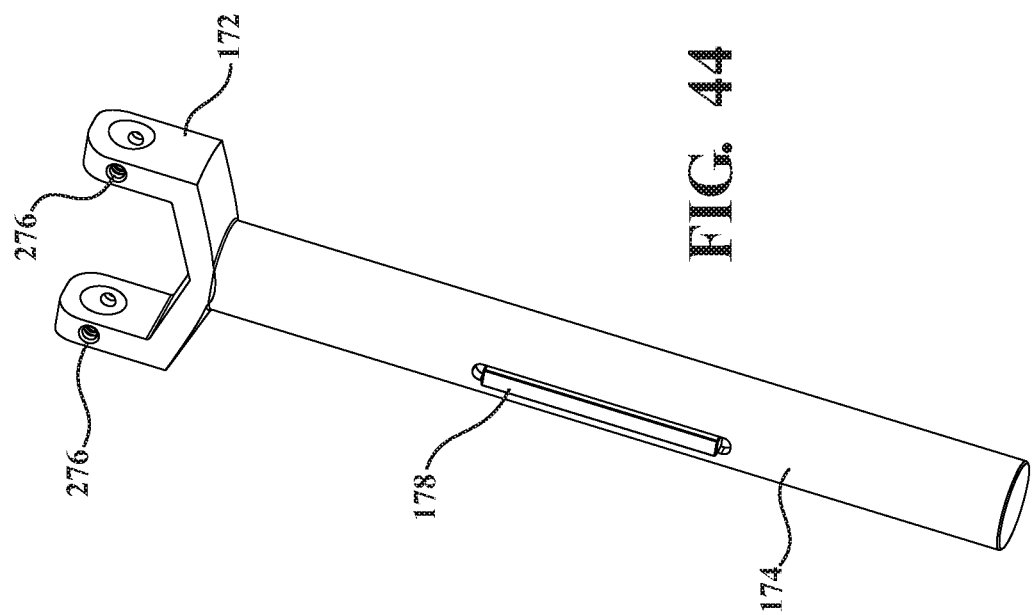
FIG. 44 is a perspective view of a shaft of a passive linkage.

The passive linkage 26 further comprises a key 176 to constrain rotation of the shaft 174 relative to the sleeve 76 about the constraint axis CA. The key 176 is best shown in FIG. 44. The key 176 fits in opposing keyways 178, 180 in the shaft 174 and sleeve 76 to rotationally lock the shaft 174 to the sleeve 76. Other arrangements for preventing relative rotation of the shaft 174 and sleeve 76 are also contemplated, such as an integral key/slot arrangement, or the like. The passive linkage 26 operatively interconnects the tool support 18 and the hand-holdable body 16 independently of the actuators 21, 22. The passive linkage is passively adjustable in effective length along the constraint axis CA during actuation of one or more of the actuators 21, 22. The sleeve 76, shaft 174, and key 176 represent one combination of links for the passive linkage 26. Other sizes, shapes, and numbers of links, connected in any suitable manner, may be employed for the passive linkage 26. The passive linkage joint 156 is able to pivot about a single pivot axis PA relative to the tool support 18. The first active joints 92 and the passive linkage joint 156 define pivot axes PA disposed on a common plane CP (see FIGS. 41 and 42). Non-parallel pivot axes PA, parallel pivot axes PA disposed on different planes, combinations thereof, and/or other configurations, are also contemplated.

As can be seen in FIG. 36, the head 84 of the tool support 18 is arranged so that the tool 20 is located on a tool plane TP (e.g., blade plane) parallel to the common plane CP when the tool 20 is coupled to the tool support 18. In some examples, the tool plane TP is spaced from the common plane CP by 2.0 inches or less, 1.0 inches or less, 0.8 inches or less, or 0.5 inches or less.

In the version shown, the actuators 21, 22 are arranged such that the active axes AA1, AA2 are in a canted configuration relative to the constraint axis CA in all positions of the actuators 21, 22, including when in their home positions. Canting the axes AA1, AA2 generally tapers the actuator arrangement in a manner that allows for a slimmer and more compact base 74 and associated grip 72. Other configurations are contemplated, including those in which the active axes AA1, AA2 are not in the canted configuration relative to the constraint axis CA. Such configurations may include those in which the actuator axes AA1, AA2 are parallel to each other in their home positions.

Figure 45A:
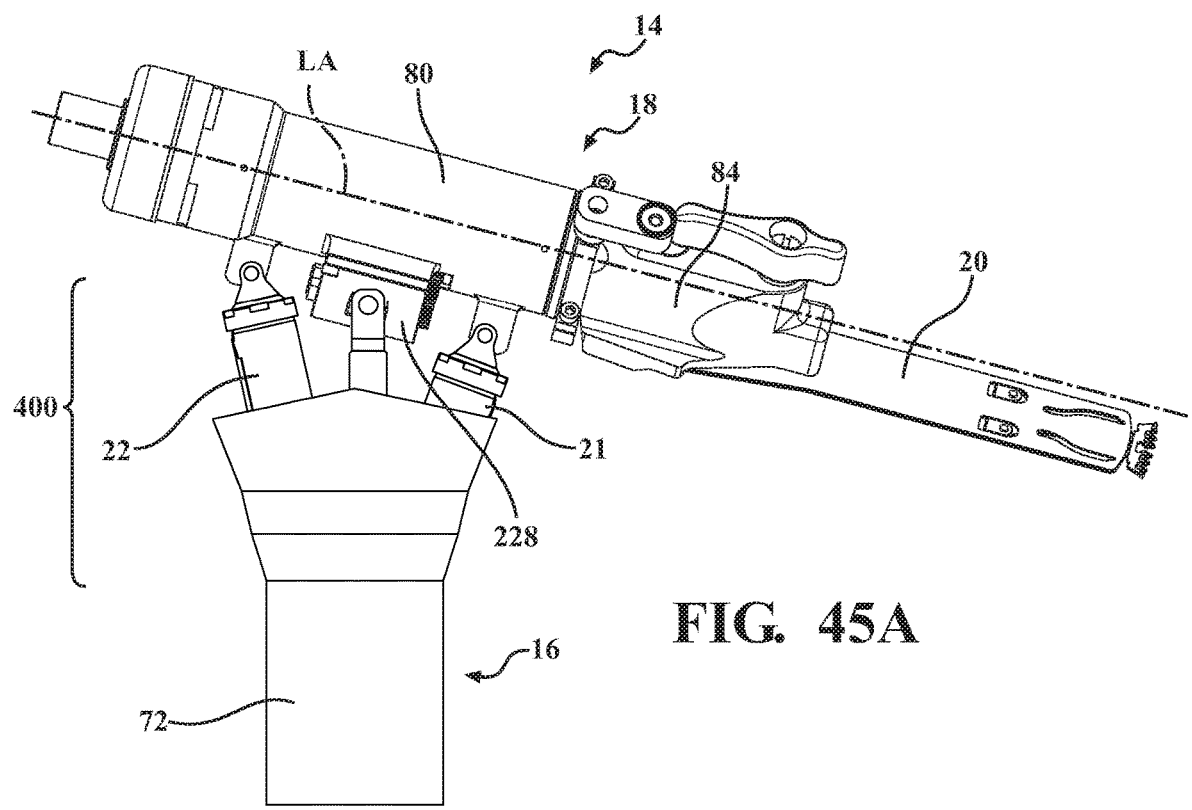
FIGS. 45A and 45B show a perspective view of the robotic instrument of FIG. 35 showing different actuation positions of the tool support and the head.
Figure 45B:
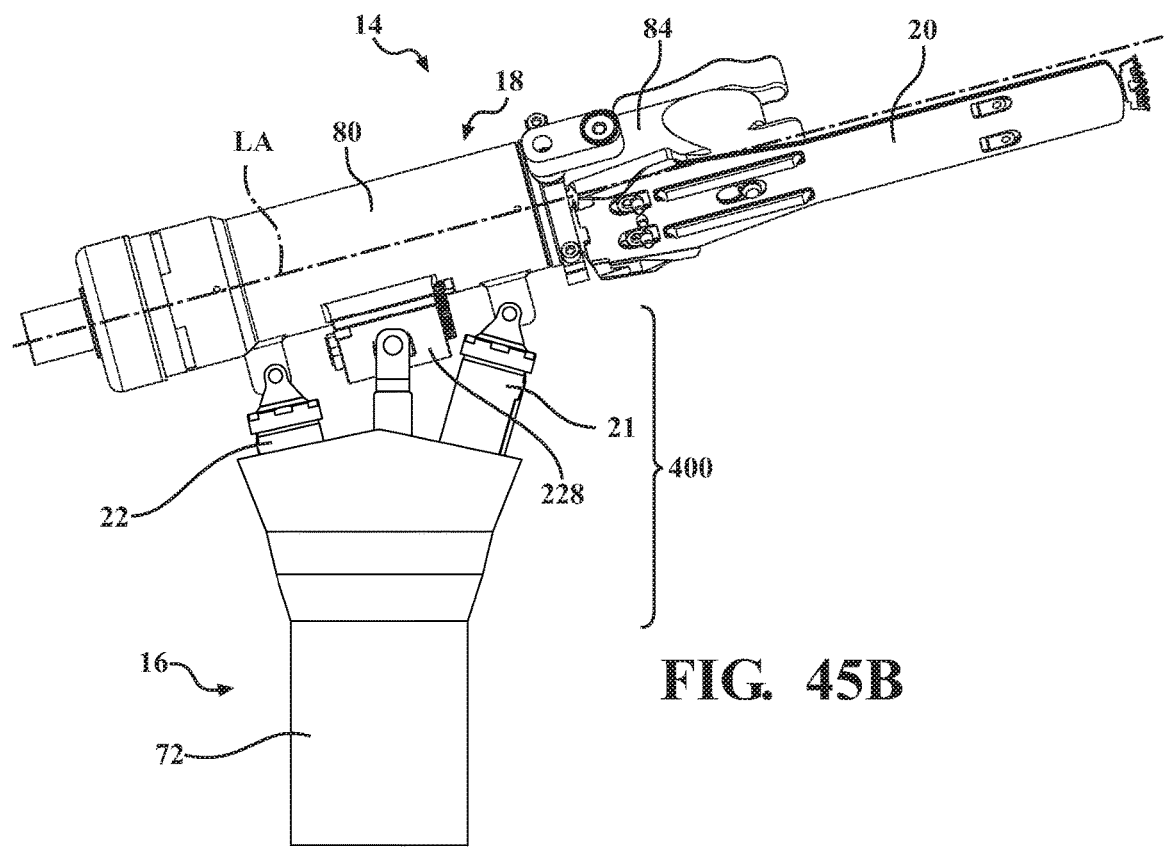

FIGS. 45A and 45B depict the surgical instrument in different states of actuation. FIG. 45A shows the surgical instrument with the distal actuator 21 with its lead screw 150 fully threaded into the carrier 116. The proximal actuator 22 is shown with the lead screw 150 extended, pushing the proximal end of the tool support 18 vertically, pitching distal end of the tool support 18 downward. The tool head 84 holding tool 20 is shown rotated about the longitudinal axis of the tool support 18. Similarly, FIG. 45B shows the proximal actuator 22 with its lead screw 150 fully threaded into the carrier 116. The distal actuator 21 is shown with the lead screw 150 extended, pushing the distal end of the tool support 18 vertically, pitching the distal end of the tool support 18 upward. The tool head 84 and tool are shown rotated in the opposite direction as shown in FIG. 45A about the longitudinal axis of the tool support 18.

An alternative configuration of the instrument 14 is best shown in FIGS. 46-56C. The instrument 14 includes a hand-holdable body 16 to be held by the user, a tool support 18 movably coupled to the hand-holdable body 16 to support a tool 20, an actuator assembly 400 including a plurality of actuators 21, 22, 260 operatively interconnecting the tool support 18 and the hand-holdable body 16 to move the tool support 18 in three degrees of freedom relative to the hand-holdable body 16. Actuator 260 is a primary elevation actuator controlling the z-axis translation, configured to support and carry secondary actuators 21 and 22. Actuator 260 translates in the z-axis direction, moving the tool support 18 and the secondary actuators relative to the hand-holdable body 16. The secondary actuators 21, 22 are configured to adjust the pitch and roll of the tool support 18 relative to the elevation actuator 260 and the hand-holdable body 16. As the elevation actuator 260 moves the tool support 18 and the secondary actuators 21, 22 away from the hand-holdable body, the secondary actuators have a greater range of motion.

Figure 46:
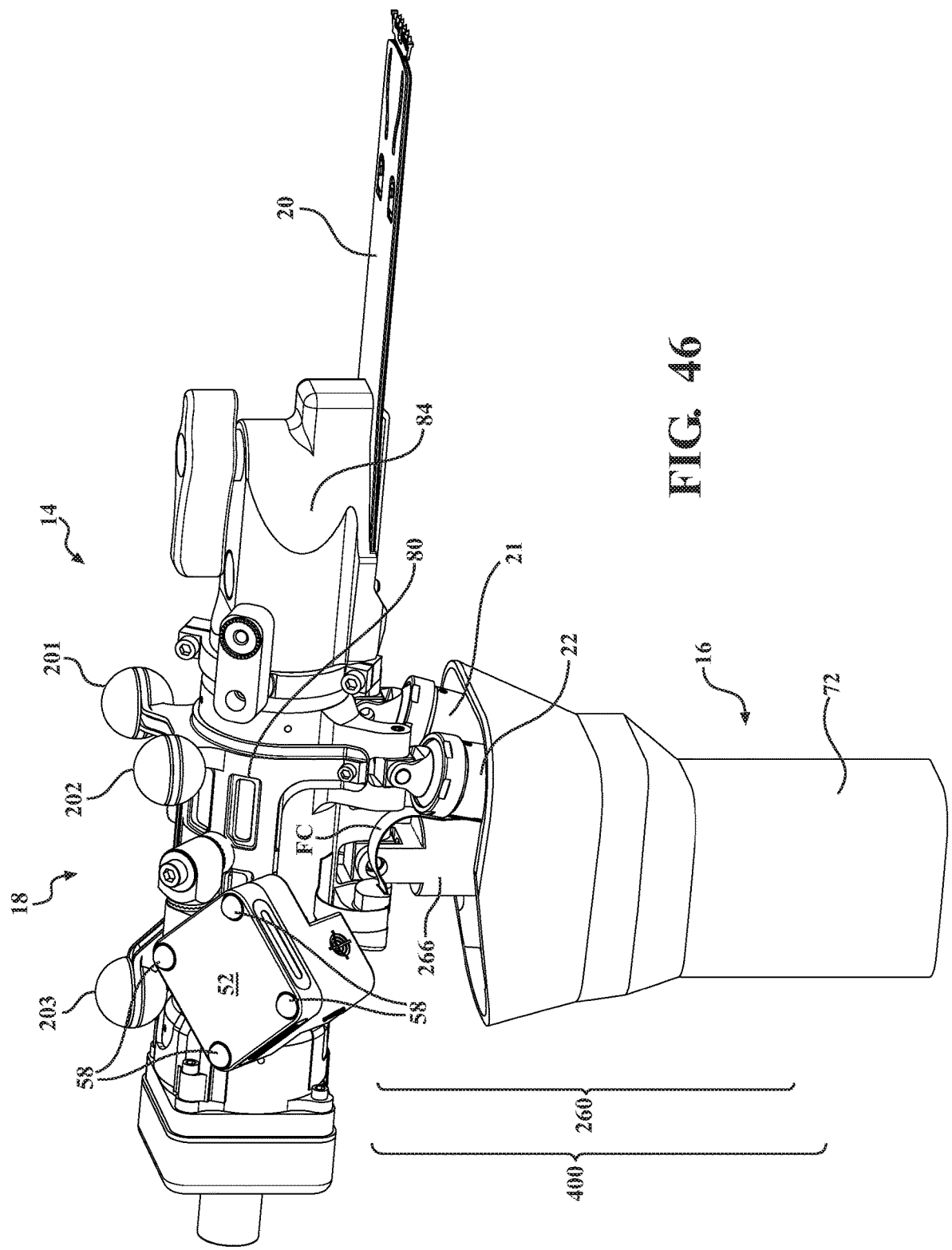
FIG. 46 is a perspective view of an alternative configuration of the robotic instrument.
Figure 47:
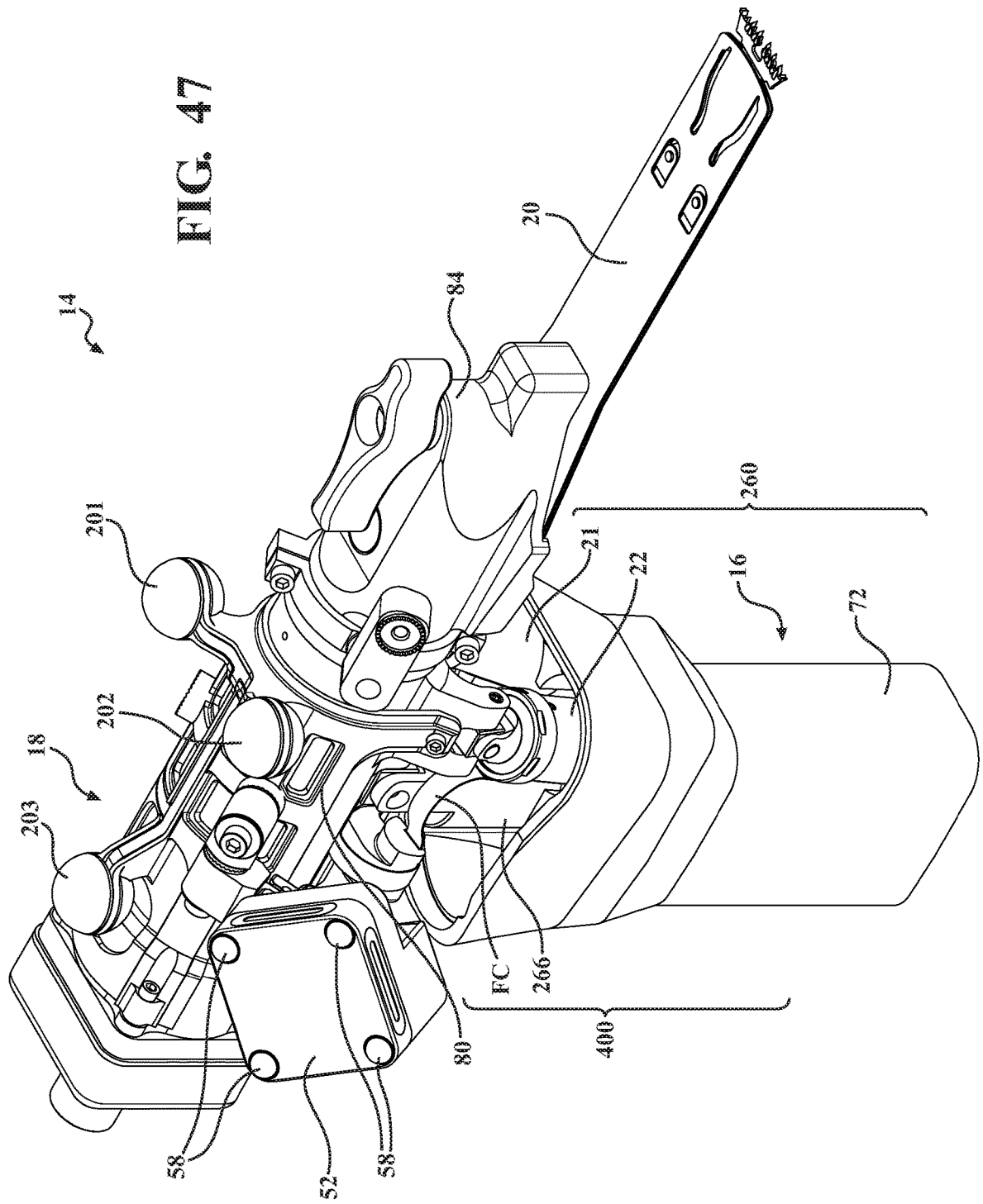
FIG. 47 is a front perspective view of the robotic instrument of FIG. 46.
Figure 48:
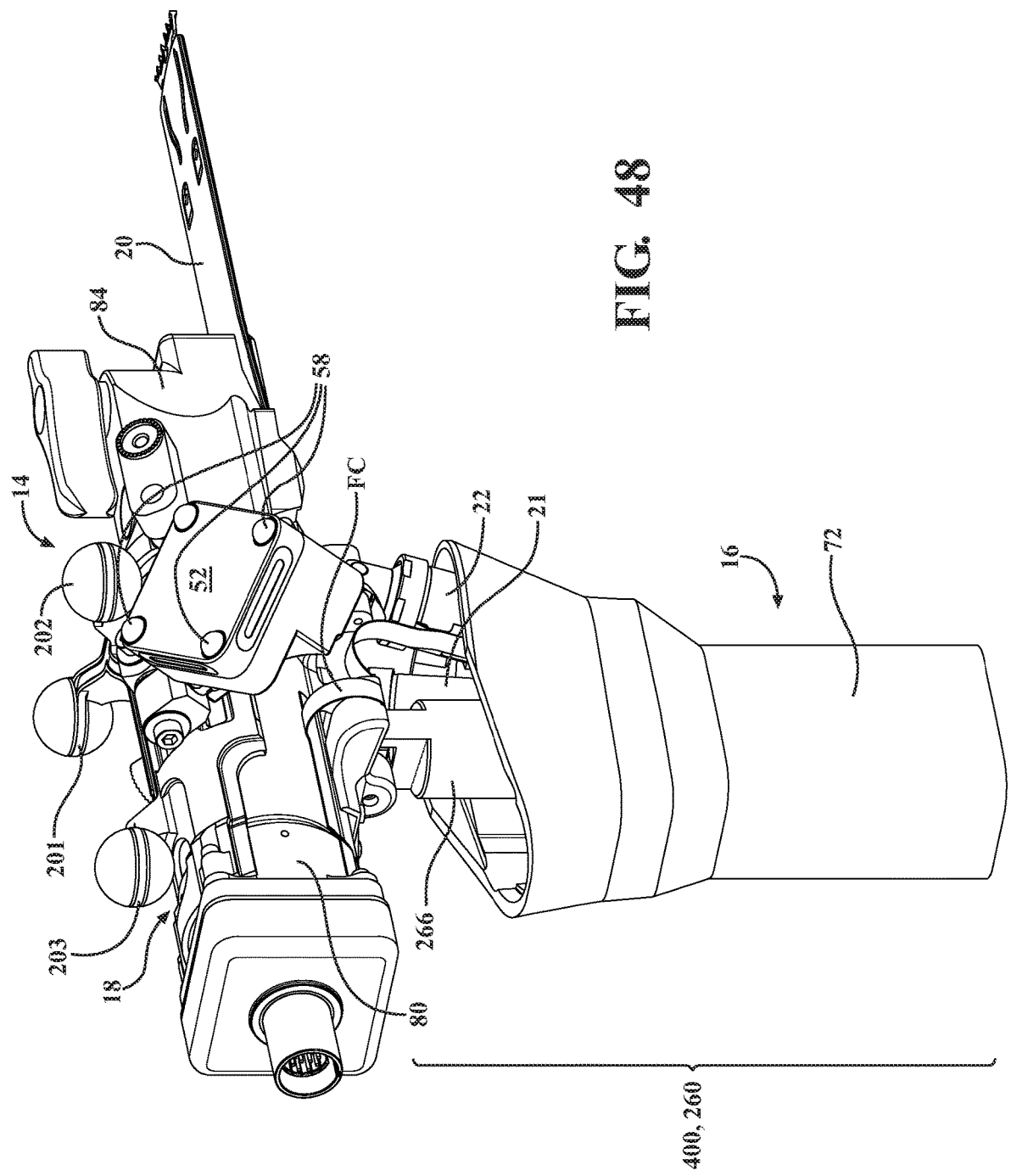
FIG. 48 is a rear perspective view of the robotic instrument of FIG. 46.

Turning to FIGS. 46-48, the hand-holdable body 16 comprises a grip 72 for being grasped by the user so that the user may manually support and freely move the instrument 14. The hand-holdable body 16 may be configured as a pistol grip. The hand-holdable body 16 also comprises a base 74 to which the grip 72 is attached by one or more fasteners, adhesive, welding, or the like.

FIGS. 46-48 depict a front, a side, and a rear perspective view of the surgical instrument 14 with the elevation actuator assembly 260 coupled to the tool support. The elevation actuator assembly is operatively coupled with the tool support 18 and the secondary actuators 21, 22, such that when the elevation actuator assembly 260 is actuated and translates vertically, the tool support 18 and the secondary actuators 21, 22 are also translated vertically.

Figure 49:
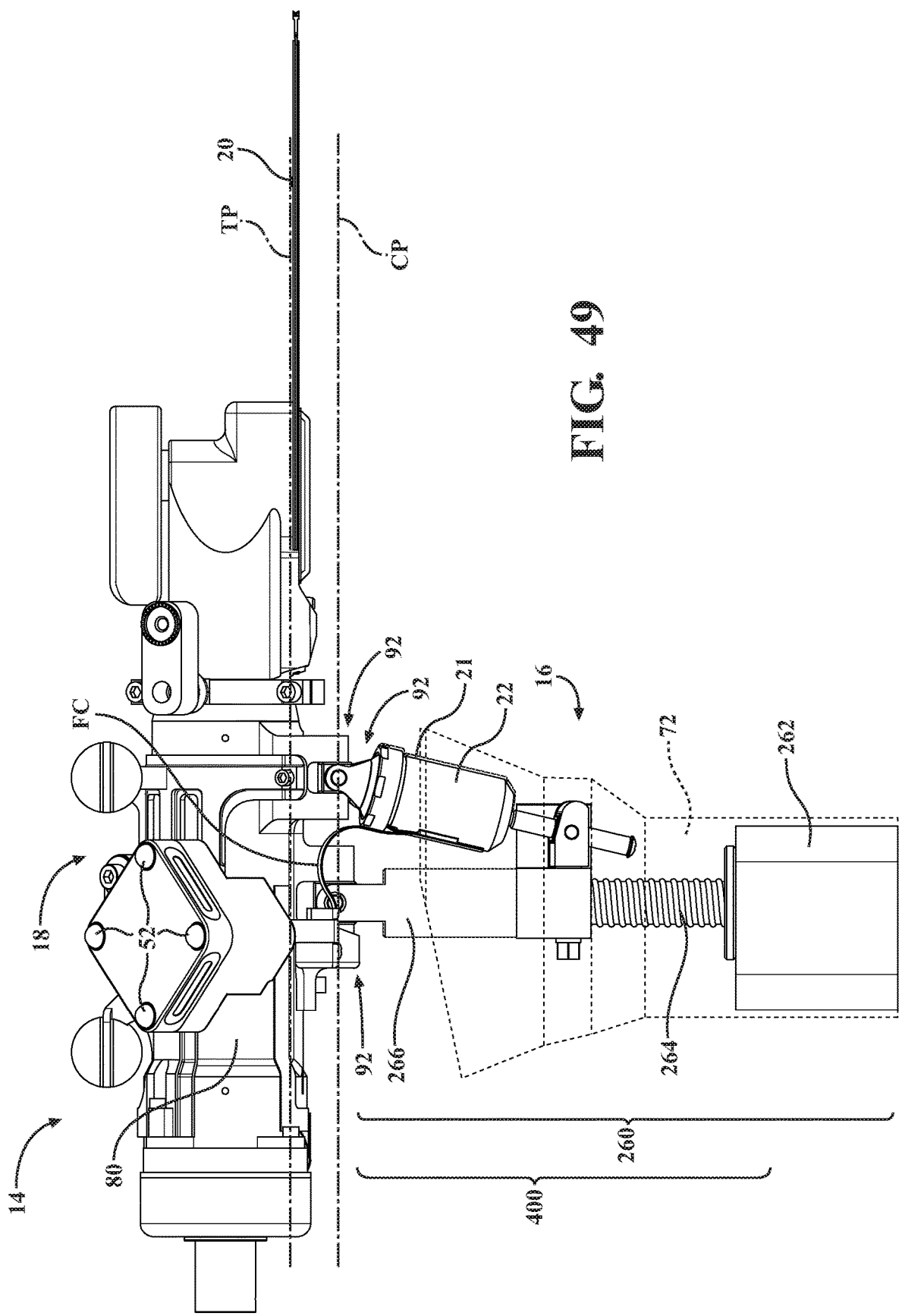
FIG. 49 is a side view of the robotic instrument of FIG. 46 with an actuator assembly including an elevation actuator.
Figure 50:
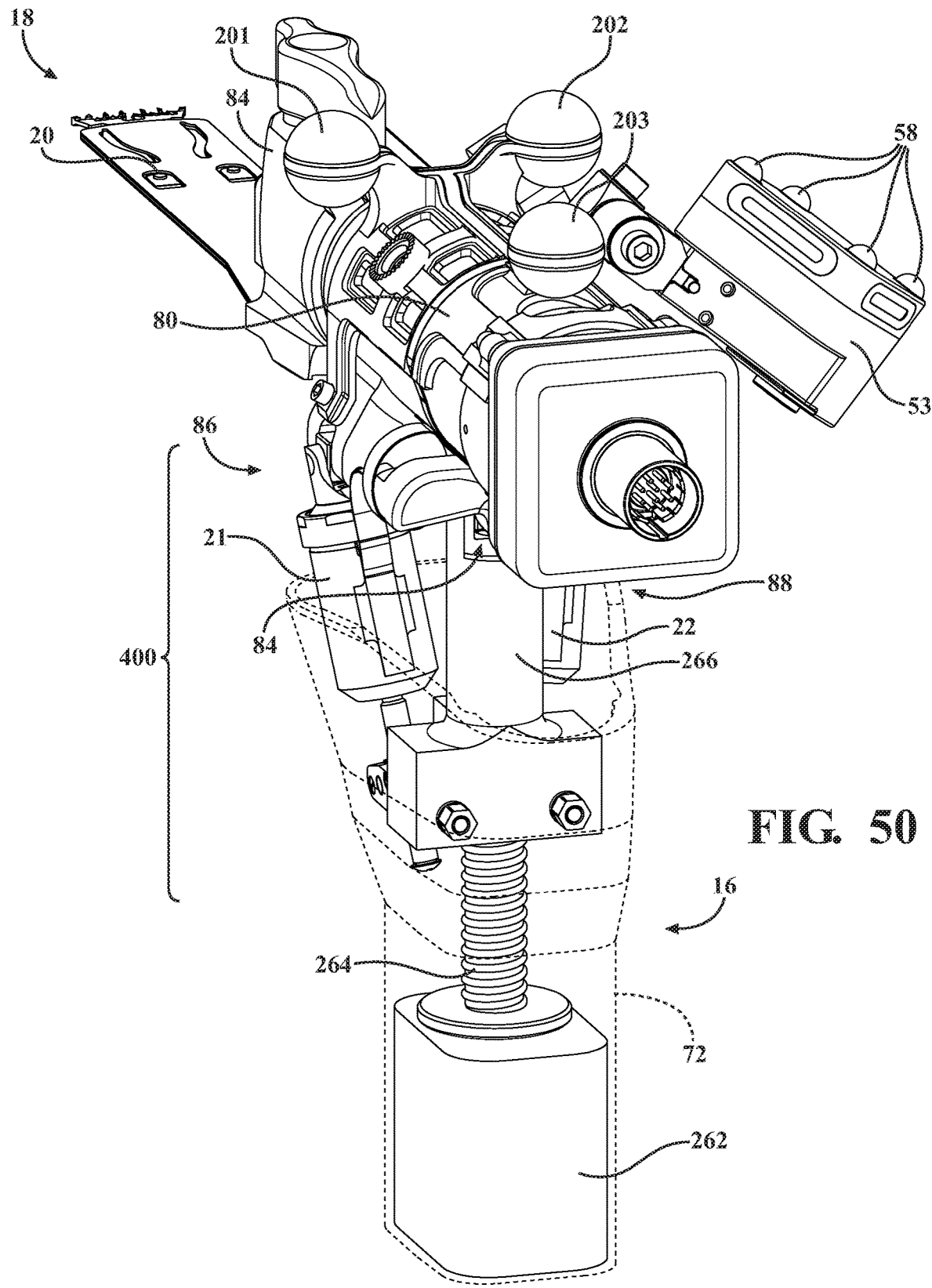
FIG. 50 is a rear perspective view of the robotic instrument of FIG. 46.

Turning to FIG. 49, the base 74 includes the elevation actuator 260 connecting the hand-holdable body 16 with the tool support 18. The tool support 18 is connected with the hand-holdable body 16 by the elevation actuator 260 and secondary actuators 21, 22. The tool support 18 comprises a tool support body 80 to which the tracker 52 can be removably mounted via one or more tracker mounts fixed to the tool support 18. The tool 20 is removably coupled to the tool support 18 in the version shown. In particular, the tool support 18 comprises a tool coupler, such as head 84 to which the tool 20 is mounted, as described in U.S. Pat. No. 9,820,753 to Walen et al., incorporated herein by reference. The drive motor M that drives operation of the tool 20 is disposed in the tool support body 80 (e.g., to drive oscillation of the saw blade in some versions). The tool 20 may be attached to and released from the head 84 in the manner disclosed in U.S. Pat. No. 9,820,753 to Walen et al., incorporated herein by reference.

The elevation actuator 260, as best seen in FIGS. 54A and 54B, comprises a base motor 262, a drive screw 264, and carriage 266 having a generally hollow cylindrical shape. The carriage 266 is threaded to receive the drive screw 264, which is driven by the base motor 262. The carriage 266 is keyed and/or guided to the hand-holdable body 16, allowing the carriage 266 to translate along the drive screw 264 without rotating the carriage 266 relative to the hand-holdable body 16 and the tool support 18. The carriage 266 includes joint supports 77, 78 for connecting the secondary actuators 21, 22 to the carriage.

Figure 55C:
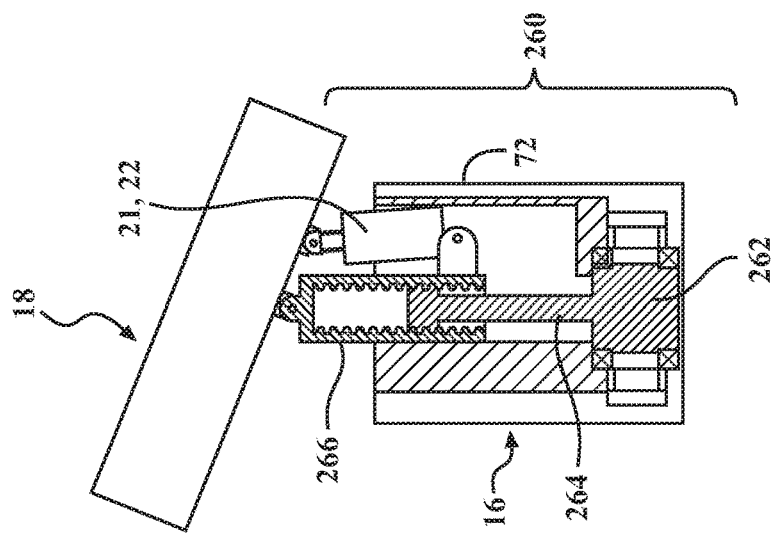
FIGS. 55A-55C are schematic views of the actuator assembly moving the tool support relative a hand-holdable body.
Figure 55B:
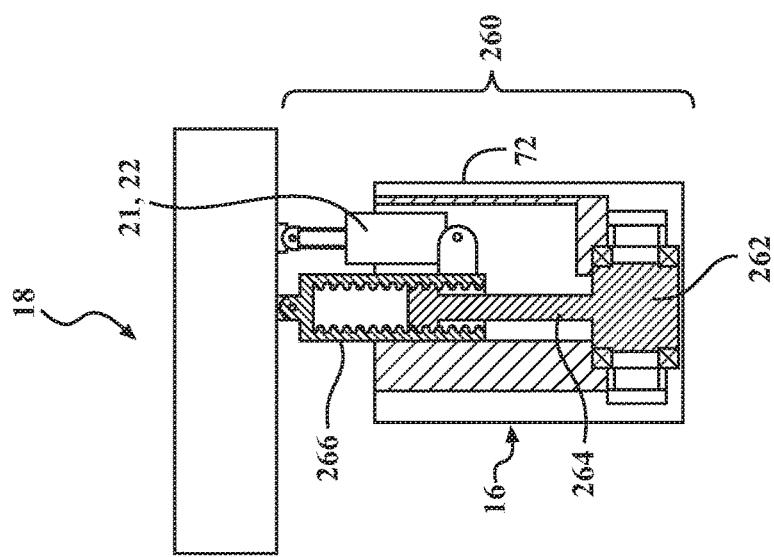
Figure 55A:
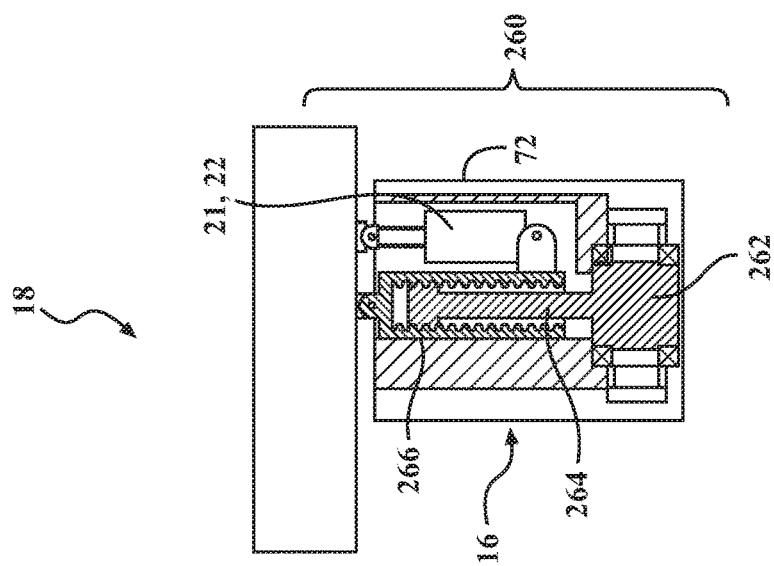

The elevation actuator assembly 260 is movable between a retracted position at which the tool support 18 is adjacent to the hand-holdable body 16 and an extended position at which the tool support 18 is spaced away from the hand-holdable body 16 (as can be seen in FIGS. 55A-55B). The elevation actuator 260 is arranged to move both the tool support 18 and the secondary actuators 21, 22 relative to the hand-holdable body 16 in one degree of freedom. The secondary actuators 21, 22 in conjunction with the elevation actuator 260 are configured to move the tool support 18 in three degrees of freedom relative to the hand-holdable body 16. More actuators may be provided in some examples. The secondary actuators 21, 22 have a greater translation length when the elevation actuator is fully extended position at which the tool support 18 is spaced away from the hand-holdable body 16 (FIG. 55C). The secondary actuators 21, 22 may comprise rotary actuators in some examples. The secondary actuators 21, 22 may comprise linkages having one or more links of any suitable size or shape. The secondary actuators 21, 22 may have any configuration suitable to enable movement of the tool support 18 relative to the hand-holdable body 16 and the carriage 266 in at least two degrees of freedom. For example, in some versions there may be two rear secondary actuators, or some other arrangement of actuators.

Figure 52:
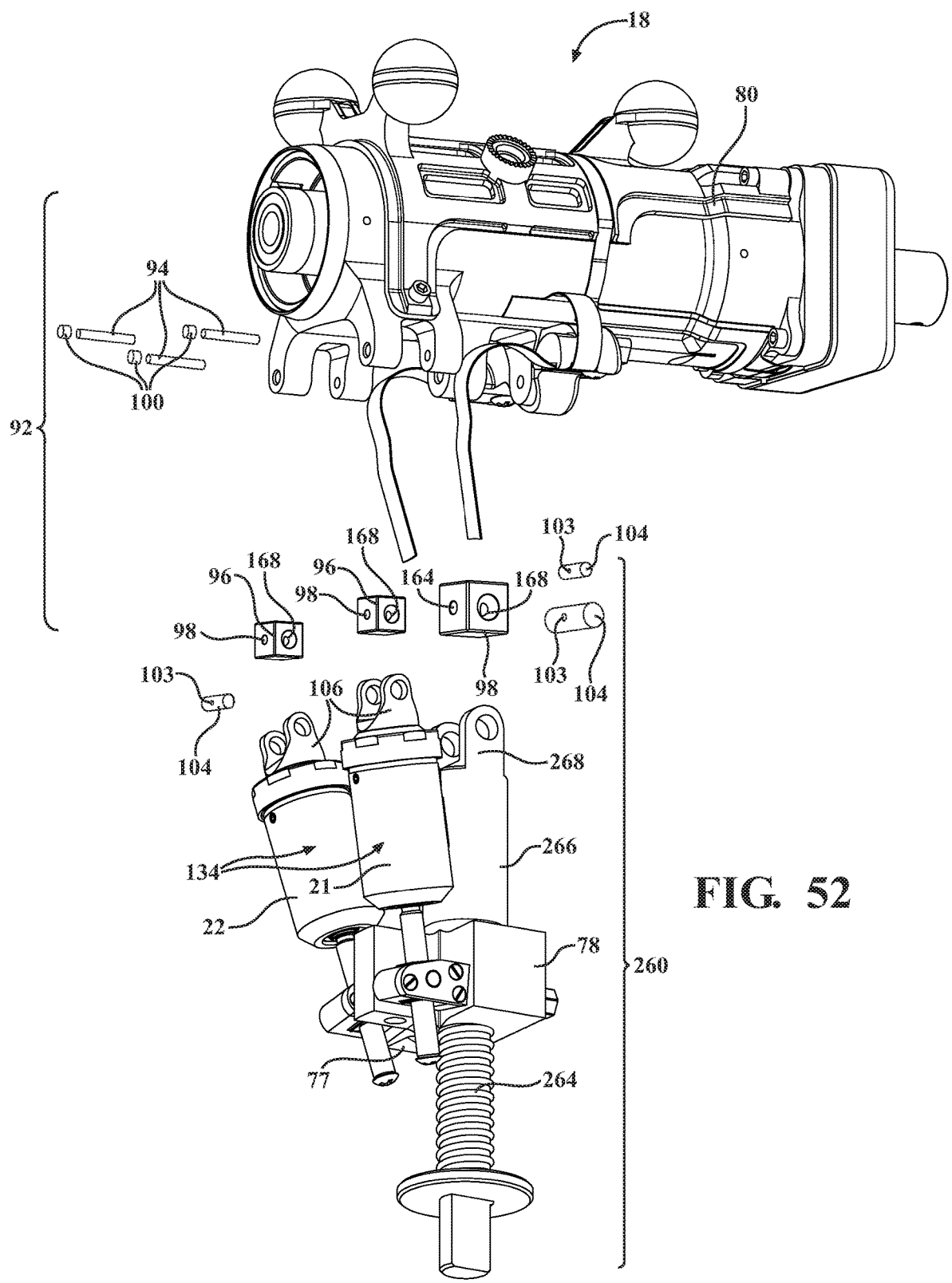
FIG. 52 is an exploded view showing a body of the tool support and associated joint connections to the elevation actuator.

The tool support 18, as shown in FIGS. 52 and 53A-53B, includes a plurality of actuator mounts 86, 88, 90 at which the actuators 21, 22, 260 are to be movably coupled to the tool support 18 via joints, as described further below. The actuator mounts 86, 88, 90 may comprise brackets, or the like, suitable to mount the actuators 21, 22, 260 such that the tool support 18 is able to move in three degrees of freedom relative to the hand-holdable body 16.

FIGS. 53A and 53B depict the secondary actuators 21, 22 as electric, linear actuators that extend between the carriage 266 and the tool support body 80. When actuated, an effective length of the actuator 21, 22 changes to vary a distance between the tool support body 80 and the carriage 266 along a corresponding axis of the actuator 21, 22. Accordingly, the secondary actuators 21, 22 work in concert to change their effective lengths and move the tool support 18 in at least two degrees of freedom relative to the hand-holdable body 16 and the carriage 266 (e.g. roll, pitch, or both). Actuators 21, 22 are provided, and may be referred to as secondary actuators 21, 22 or pitch/roll actuators 21, 22. The secondary actuators 21, 22 each have a stroke length which is less than the stroke length of the elevation actuator 260. The secondary actuators 21, 22 are adjustable in effective length along a first active axis AA1, and a second active axis AA2, respectively (see FIG. 53A, 54A). The elevation actuator 260 is adjustable in effective length along a third active axis AA3 where the carriage 266 translates along the drive screw 264 upon actuation of the base motor 262. The secondary actuators 21, 22 are independently adjustable in effective length to adjust one or more of a pitch orientation, a roll orientation, or both of the tool support 18 relative to the hand-holdable body 16 and the carriage 266, as previously described.

The carriage 266 of the elevation actuator 260 and the secondary actuators 21, 22 are coupled to the tool support body 80 via a plurality of active joints. The active joints include a set of first active joints 92 that couple the carriage 266 and the secondary actuators 21, 22 to the tool support body 80 at the actuator mounts 86, 88, 90. In one version, as shown in FIG. 52, the first active joints 92 comprises active U-joints. The U-joints comprise first pivot pins 94 and joint blocks 96. The first pivot pins 94 pivotally connect the joint blocks 96 to the actuator mounts 86, 88, 90 via throughbores 98 in the joint blocks 96. Set screws 100 may secure the first pivot pins 94 to the actuator mounts 86, 88, 90. The U-joints may also comprise second pivot pins 104. The joint blocks 96 have crossbores 102 to receive the second pivot pins 104. The second pivot pins 104 have throughbores 103 to receive the first pivot pins 94, such that the first pivot pins 94, the joint blocks 96, and the second pivot pins 104 form a cross of the U-joint. The first pivot pin 94 and the second pivot pin 104 of each U-joint define pivot axes that intersect. The second pivot pins 104 pivotally connect a pivot yokes 106, 268 to the joint blocks 96. As a result, the carriage 266 and secondary actuators 21, 22 are able to move in three degrees of freedom relative to the tool support body 80. Other types of active joints are also contemplated.

Referring now to FIG. 53B, the active joints also comprise a set of second active joints 108 coupling the secondary actuators 21, 22 to the carriage 266. In FIG. 53B, the second active joints 108 are supported at the joint supports 77, 78. Each of the second active joints 108 comprises a swivel yoke 110 arranged to swivel relative to the carriage 266 and the hand-holdable body 16 about a swivel axis SA. Each swivel yoke 110 has a swivel head 112 and a post 114 extending from the swivel head 112 to pivotally engage the carriage 266 at one of the joint supports 77, 78. Nuts 115 threadably connect to one end of the posts 114 to trap the posts 114 in the carriage 266 while allowing the respective swivel yoke 110 to freely rotate within its respective joint support 77, 78.

As seen in FIG. 53B, each of the second active joints 108 comprises a carrier 116 pivotally coupled to one of the swivel yokes 110. The carriers 116 have internally threaded throughbores 117 to receive lead screws 150 of the front two actuators 21, 22, as described further below. Each of the carriers 116 also comprises opposed trunnions 118 that allow the carriers 116 to pivot relative to the swivel yokes 110 about pivot axes PA by being seated in pockets 120 in the swivel yokes 110. In some versions, for each of the second active joints 108, the swivel axis SA intersects the pivot axis PA to define a single vertex about which the actuators 21, 22 move in two degrees of freedom.

Covers 122 are fastened to the swivel heads 112 and define one of the pockets 120, while the swivel head 112 defines the other pocket 120. During assembly, the carriers 116 are first positioned with one of the trunnions 118 placed in the pocket 120 in the swivel head 112, and the cover 122 is then fastened over the other trunnion 118 such that the carrier 116 is captured between the cover 122 and the swivel head 112 and is able to pivot relative to the swivel yoke 110 via the trunnions 118 and pockets 120. Owing to the configuration of the swivel yokes 110 and the associated carriers 116, i.e., the carriers 116 ability to swivel about the swivel axes SA and pivot about the pivot axes PA, the second active joints 108 allow two degrees of freedom of movement of the front two actuators 21, 22 relative to the base 74. Other joint arrangements between the front two actuators 21, 22 and the carriage 266 are also possible.

Stops 152, such as threaded fasteners and shoulders formed on the lead screws 150, are fixed to the lead screws 150. The stops 152 are sized to abut the carriers 116 at ends of travel of each lead screw 150.

The actuators 21, 22 are substantially similar to the actuators described with respect to FIG. 16, described above. Each of the actuators 21, 22, 260 may be controlled by a separate motor controller. Motor controllers may be wired separately to the actuators 21, 22, 260, respectively, to individually direct each actuator 21, 22, 260 to a given target position. In some examples, the motor controllers are proportional integral derivative (PID) controllers. In some examples, the motor controllers can be integrated with or form part of the instrument controller. For ease of illustration, the motor controllers shall be described herein as being part of the instrument controller 28 (FIG. 7). The elevation actuator 260 and secondary actuators are controlled, sensed, and powered in a substantially similar manner as the configurations described and displayed above and in FIGS. 1-34.

As previously described, the carriers 116 have the internally threaded throughbores 117 to threadably receive the lead screws 150 so that each of the lead screws 150 can rotate relative to a corresponding one of the carriers 116 to adjust the effective length of a corresponding one of the secondary actuators 21, 22 and thereby vary the counts measured by the instrument controller 28. Each of the housings 134 and corresponding carriers 116 are constrained from relative movement in at least one degree of freedom to allow the lead screws 150 to rotate relative to the carriers 116. More specifically, the lead screws 150 are able to rotate relative to the carriers 116 owing to: the pivot yokes 106 being unable to rotate about the associated active axes AA1, AA2 (i.e., the pivot yokes 106 are limited from such rotational movement by virtue of the configuration of the first active joints 92); and the carriers 116 being unable to rotate about the associated active axes AA1, AA2 (i.e., the carriers 116 are limited from such rotational movement by virtue of the configuration of the second active joint 108).

As previously described, the actuators 21, 22, 260 are actively adjustable in effective length (previously described in relation to FIG. 16) to enable movement of the tool support 18 relative to the hand-holdable body 16. As each actuator 21, 22, 260 is adjusted, the effective length changes, by varying how far the lead screw 150, 264 has been threaded into or out of its associated carrier 116, 266 and thereby changing the distance from the center of the associated carrier 116, 266 to the center of the associated active joint 92. The actuators 21, 22, 260 are adjustable between minimum and maximum values of the effective length. The effective length of each actuator 21, 22, 260 can be represented/measured in any suitable manner to denote the distance between the tool support 18 and the hand-holdable body 16 along the active axes AA1, AA2, AA3 that changes to cause various movements of the tool support 18 relative to the hand-holdable body 16.

Continuing with FIG. 49, the head 84 of the tool support 18 is arranged so that the tool 20 is located on a tool plane TP (e.g., blade plane) parallel to the common plane CP when the tool 20 is coupled to the tool support 18. In some examples, the tool plane TP is spaced from the common plane CP by 2.0 inches or less, 1.0 inches or less, 0.8 inches or less, or 0.5 inches or less.

In FIGS. 52, 53A and 53B, the actuators 21, 22, 260 are arranged such that the active axes AA1, AA2 are in a canted configuration relative to active axis AA3 in all positions of the secondary actuators 21, 22, including when in their home positions. Canting the axes AA1, AA2 generally tapers the actuator arrangement in a manner that allows for a slimmer and more compact carriage 266 and associated grip 72. Other configurations are contemplated, including those in which the active axes AA1, AA2 are not in the canted configuration relative to the third active axis AA3. Such configurations may include those in which the actuator axes AA1, AA2, AA3 are parallel to each other in their home positions.

FIGS. 49 and 55A-C show the secondary actuators 21, 22 disposed toward the distal end of the tool support 18, away from where a user's hand would grip the hand-holdable body 16, nearly eliminating the risk of the user's hand, particularly the webbing between the thumb and index finger, from contacting the actuators 21, 22 during operation. Additionally, the base motor 262 is located in the base of the hand-holdable body 16 and the secondary actuators 21, 22 located toward the distal end, the instrument 14 offering thermal management by placing the actuators away in separate locations.

FIGS. 55A-55C depict a schematic view of the instrument 14 with the tool support 18 moving relative to the hand-holdable body 16 via the elevation actuator 260 and secondary actuators 21, 22. FIG. 55A shows the elevation actuator 260 in the retracted position, keeping the tool support 18 adjacent to the hand-holdable 16. FIG. 55B depicts the elevation actuator in the extended position, placing the tool support 18 away from the hand-holdable body 16. FIG. 55C shows secondary actuators 21, 22 adjusting the tool support 18 in a pitched orientation. In this example, the secondary actuators 21, 22 are retracted pitching the tool support 18 and tool 20 downward.

Figure 56C:
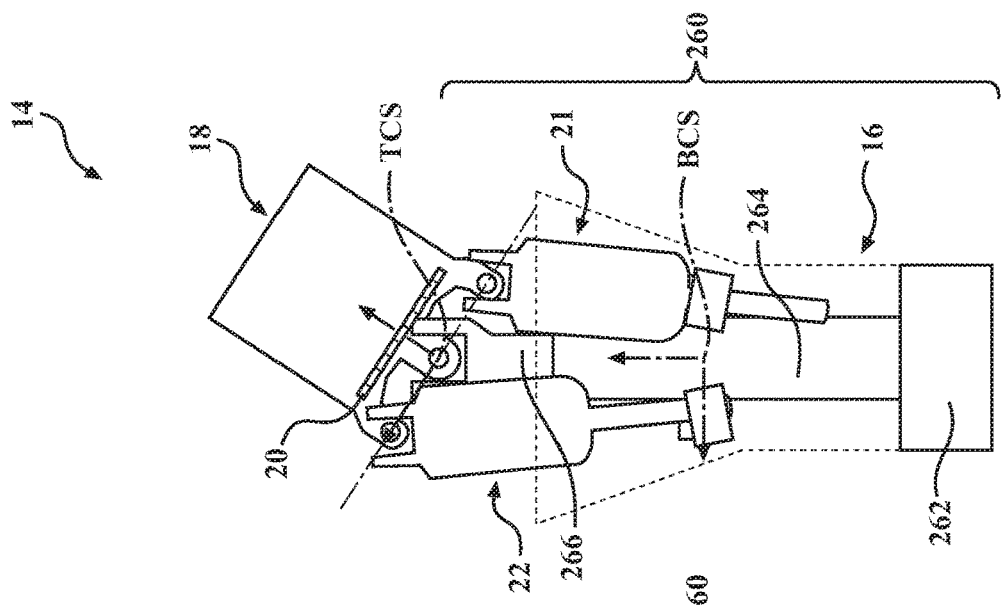
FIGS. 56A-56C show the secondary actuators adjusting the roll of the tool support relative to the hand-holdable body.
Figure 56B:
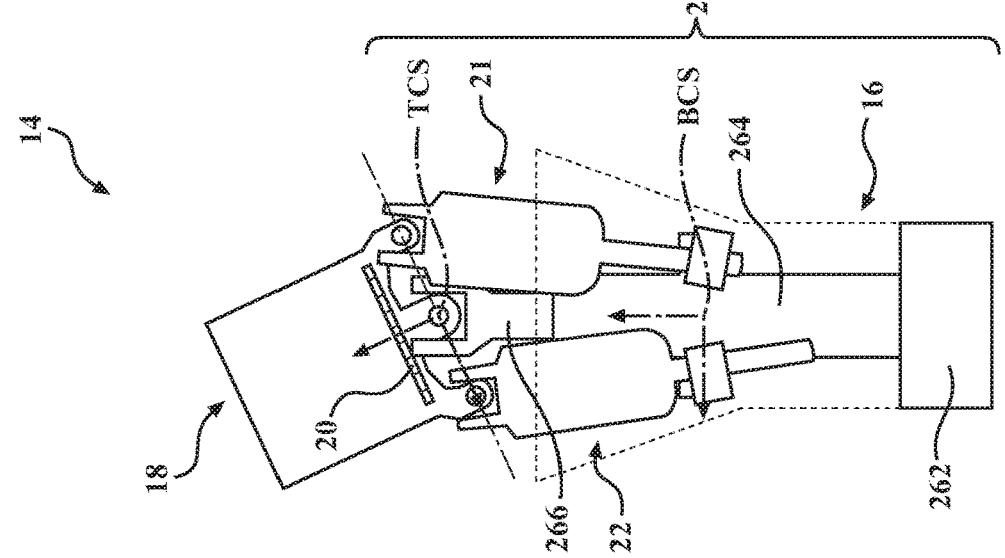
Figure 56A:
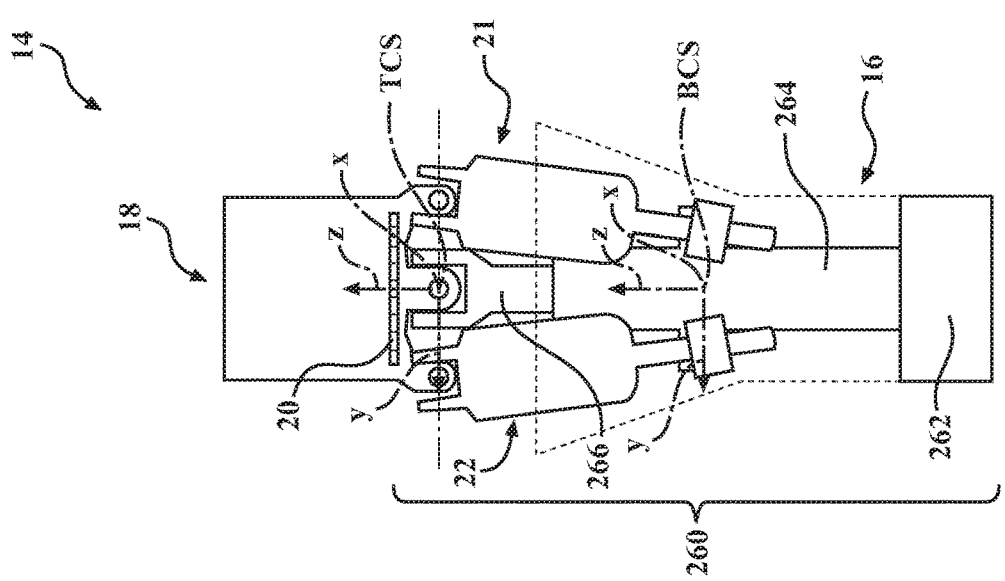

FIGS. 56A-56C show the secondary actuators 21, 22 are shown in different states of actuations. In FIG. 56A, the secondary actuators 21, 22 are both in the home position, maintaining the tool 20 on a level plane. FIG. 56B shows secondary actuator 22 in the retracted position and secondary actuator 21 in the extended position, changing the roll of the tool support 18 and tool 20. Similarly, FIG. 56C shows secondary actuator 21 is retracted and secondary actuator 22 is in the extended position, rolling the tool support 18 and tool 20 in the opposite direction than FIG. 56B.

FIG. 57 shows a perspective view of an alternative configuration of the robotic instrument 14 configured to be used as a modular tool system 300. The instrument of FIG. 57 depicts a substantially similar instrument to the configurations discussed above with an actuator assembly 400 including a plurality of actuators 21, 22, 23 and a constraint assembly 24. The instrument 14 is configured to move in at least three degrees of freedom (e.g. pitch, roll, elevation). The instrument 14 is configured as a modular tool system to be used with a plurality of modular tool heads. The modular tool system 300 is configured to removably attach and swap different modular tool heads (302, 304, 306, 308) into the instrument 14 to perform different functions during surgery. The tool support body 80 includes a receiving portion 332 (e.g. a collet) to receive a plurality of modular tool heads 302, 304, 306, 308 as discussed further below. The receiving portion 332 includes a lock feature 316 for receiving and securing the plurality of modular heads 302, 304, 306, 308. The receiving portion 332 includes a drive receiver 318 connected to an output of motor M which is configured to provide rotational power, when necessary, to one or more of the modular tool heads 302, 308.

FIGS. 58A-58D depict perspective views of the multiple modular tool attachments for use with the robotic instrument 14 of FIG. 57. Each of the modular tool heads 302, 304, 306, 308 shown in FIGS. 58A-58D each include a connecting portion 326 for connecting and inserting into the receiving portion of instrument 14 shown in FIG. 57. Each connection portion 326 includes a lock 314 which is configured to engage the locking feature 316 of the receiving portion 332. The connecting portion 326 of each of the modular tool heads 302, 304, 306, 308 may be configured to be aligned and inserted into the receiving portion 332 of instrument 14. Each of the tool heads 302, 304, 306, 308 may be locked into the receiving portion 332 of the instrument 14. One of ordinary skill in the art would appreciate that any suitable locking configurations and/or methods are contemplated.

FIG. 58A depicts a modular saw head 302 configured to be received by the instrument 14 of FIG. 57. The modular saw head 302 includes a shaft 310 configured to be received by the shaft receiver 318 located in the instrument 14 of FIG. 57. The shaft receiver 318 is connected with motor M to provide a rotational force to the shaft 310, powering the modular saw head 302. The modular saw head 302 includes a transmission 312 for converting the rotational movement of the shaft 310 into another type of movement (e.g. oscillation; orbital; etc.) at the tool mount 320. The tool mount 320 is configured to receive a tool for performing surgical procedures.

Figure 58B:
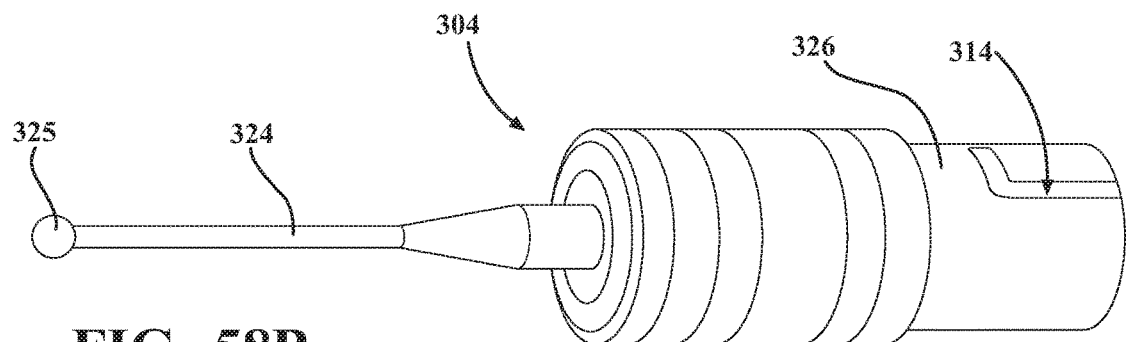

Similar to FIG. 58A, FIG. 58B depicts a modular pointer 304. The modular probe 304 is configured to be received by the instrument 14 of FIG. 57. The modular probe 304 includes a longitudinally extending stem 324 with a rounder tip 325. The modular probe 304 is configured to be used with the navigation system 32 to ascertain a surface and/or an area of surgical interest. The modular probe 304 may be used to register surgical devices, the patient, or both with the navigation system 32. The modular probe 304 is configured to be removably connected with the instrument 14.

Figure 58C:
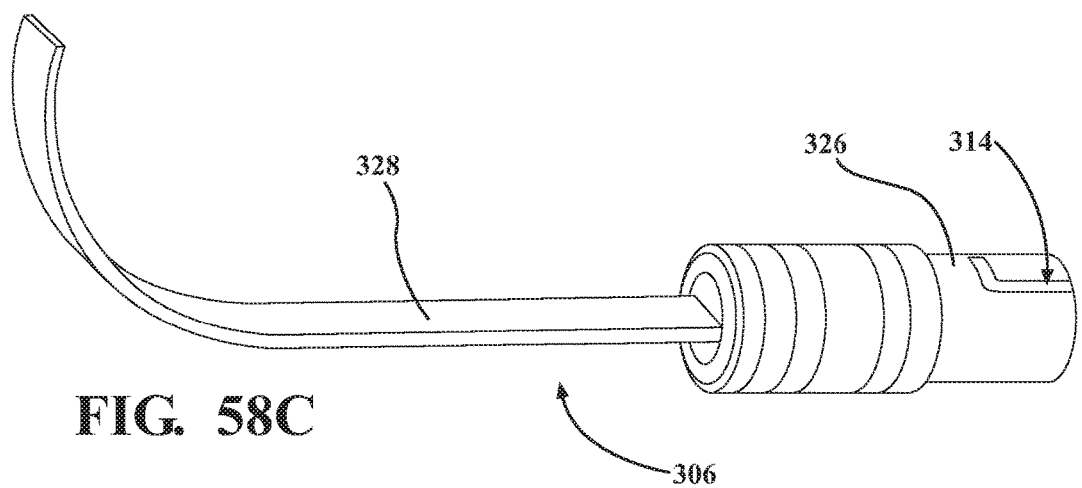

FIG. 58C depicts modular osteotome 306 for use with the instrument 14 of FIG. 57. The modular osteotome 306 includes a connecting portion 326 for attaching with the instrument 14 and a chisel portion 328 extending from the connecting portion 326. The modular osteotome 306 is shown with a curved chisel portion 328, however other shapes, curves, and lengths are considered.

Figure 58D:
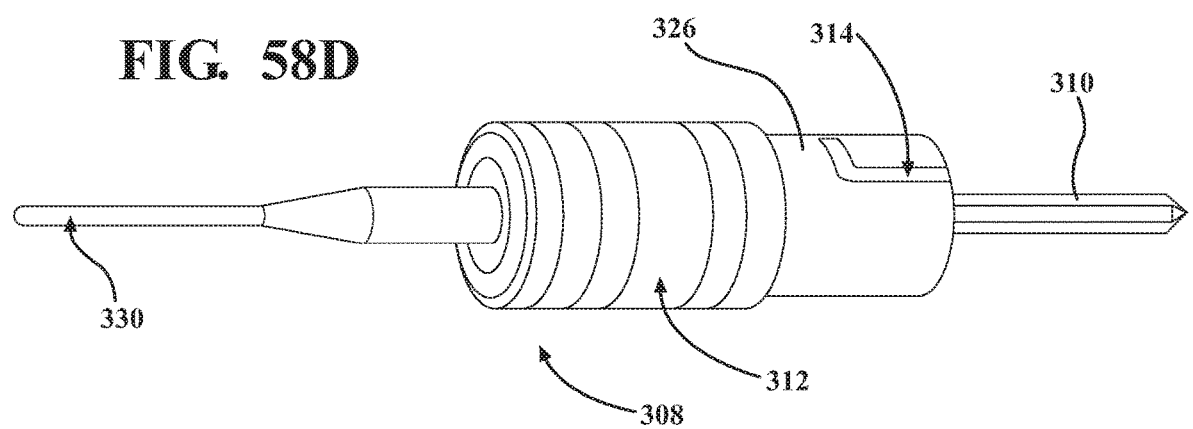

FIG. 58D illustrated a modular drill head 308 for use with the instrument 14 of FIG. 57. The modular drill head 308 includes a shaft 310 configured to be received by the shaft receiver 318 located in the instrument 14 of FIG. 57. The shaft receiver 318 is connected with motor M to provide a rotational force to the shaft 310, powering the modular drill head 308. The modular drill head 308 includes a transmission 312 in the connecting portion 326 which includes a system to increase or decrease the rotational speed and torque provided by motor M, changing the rotational speed and torque of the drill head 330. Any of the above mentioned tools may be directly fixed to the tool support 18, and/or removably coupled with the tool support.

Figure 59:
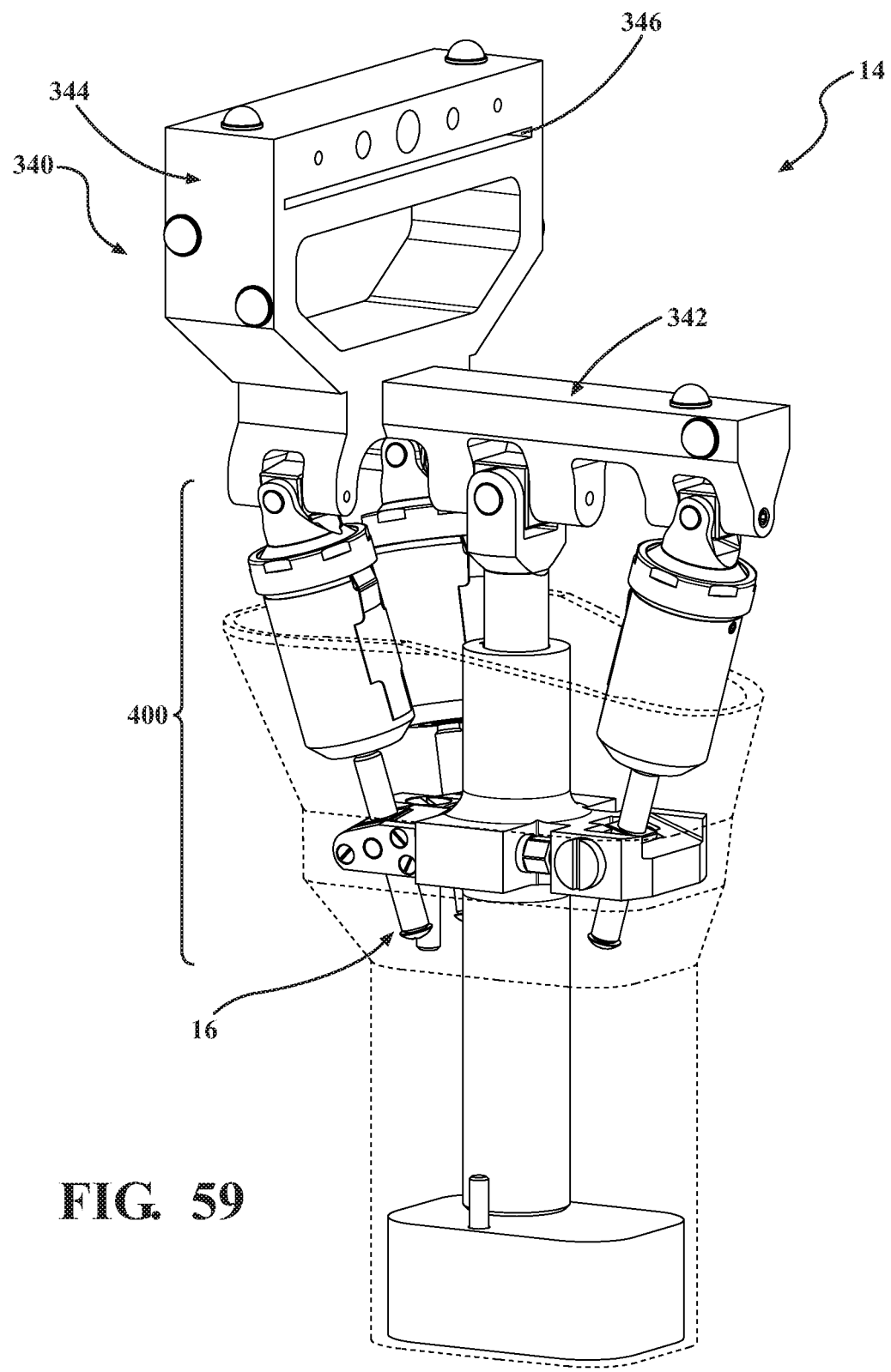
FIG. 59 is a perspective view of a robotic instrument configured as a cut guide.

FIG. 59 is a perspective view of a robotic instrument 14 configured as a cut guide 340. In this configuration, the tool support body is configured as a cut guide 340 that is adjustable in at least three degrees of freedom via the actuators 21, 22, 23 (e.g. pitch, roll, elevation). The cut guide 340 is configured to be used with a surgical device during a surgical procedure, such as a saw. The robotic instrument communicates with the control system and the navigation system to direct a user to position the cut guide 340 for selective surgical cuts without the need for attaching the guide to the anatomical object that is being operated on. The cut guide 340 includes a body 342 which is connected with the actuators 21, 22, 23 and the constraint assembly 24, and a jig 344 extending from the body 342. The jig 344 includes a blade opening 346 that is configured to restrain a saw blade to a selected cut plane, preventing the saw from deviating away from the desired cut area.

In this application, including the definitions below, the term "controller" may be replaced with the term "circuit." The term "controller" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller(s) may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various configurations the controller may actually communicate via a communications system. The communications system includes physical and/or virtual networking equipment such as hubs, switches, routers, and gateways. In some configurations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various configurations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 10182-2008 (commonly called "VHDL"). The hardware description language may be used to manufacture and/or program a hardware circuit. In some configurations, some or all features of a controller may be defined by a language, such as IEEE 1666-2005 (commonly called "SystemC"), that encompasses both code, as described below, and hardware description.

The various controller programs may be stored on a memory circuit. The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SENSORLINK, and Python®.

Clauses Section i. A hand-held robotic system for use with a tool, the system comprising: an instrument comprising a hand-held portion to be held by a user and a tool support coupled to the hand-held portion to support the tool; a guidance array coupled to the instrument and controllable to visually indicate to the user desired changes in pitch orientation, roll orientation, and translation of the tool to achieve a desired pose; and a controller coupled to the guidance array and configured to automatically adjust the guidance array to visually indicate the desired changes in pitch orientation, roll orientation, and translation while the user moves the tool.

ii. A hand-held robotic system for use with a tool, the system comprising: an instrument comprising a hand-held portion to be held by a user and a tool support coupled to the hand-held portion to support the tool; a guidance array coupled to the instrument and arranged to represent a plane of the tool, the guidance array being controllable to visually indicate to the user desired changes in pitch orientation, roll orientation, and translation of the tool to achieve a desired pose; and a controller coupled to the guidance array to control operation of the guidance array.

iii. The hand-held robotic system of clause ii, wherein the controller is configured to operate the guidance array in a manner that enables the user to distinguish between a desired change in pitch orientation, a desired change in roll orientation, and a desired change in translation.

iv. The hand-held robotic system of clause ii, wherein the guidance array comprises a first visual indicator, a second visual indicator, and a third visual indicator, each of the visual indicators comprising one or more illumination sources coupled to the controller.

v. The hand-held robotic system of clause iv, wherein each of the visual indicators comprises upper and lower portions, the controller configured to control illumination of the upper and lower portions such that the upper and lower portions are operated in different states to indicate the direction of desired movement of the plane of the tool.

vi. The hand-held robotic system of clause v, wherein the controller is configured to control illumination of the upper and lower portions such that the upper and lower portions are operated in the same state to indicate that a corresponding point is at a desired position.

vii. The hand-held robotic system of clause v, wherein the visual indicators are arranged to represent the plane of the tool.

viii. The hand-held robotic system of clause vii, wherein the tool support defines a central plane, wherein the first and second visual indicators are offset from the central plane on opposing sides of the central plane and the central plane passes through the third visual indicator.

ix. The hand-held robotic system of clause viii, wherein the controller is configured to control illumination of the upper and lower portions to indicate to the user desired changes in one or more of the pitch orientation, roll orientation, and translation position of the tool relative to the desired pose.

x. The hand-held robotic system of clause viii, wherein the controller is configured to control illumination of the upper portions to be operated in a first state, and to control illumination of the lower portions to be operated in a second state, different than the first state, to indicate to the user to change the translation position of the tool.

xi. The hand-held robotic system of clause viii, wherein the controller is configured to control illumination of the upper portion of the third visual indicator to be operated in a first state and to control illumination of the upper portions of the first and second visual indicators to be operated in a second state, different than the first state, to indicate to the user to change the pitch orientation of the tool.

xii. The hand-held robotic system of clause viii, wherein the controller is configured to control illumination of the upper portion of the first visual indicator to be operated in a first state and to control illumination of the upper portion of the second visual indicator to be operated in a second state, different than the first state, to indicate to the user to change the roll orientation of the tool.

xiii. The hand-held robotic system of clause iv, wherein the visual indicators are disposed along the tool support such that the first and second visual indicators are located distally relative to the third visual indicator.

xiv. The hand-held robotic system of clause iv, wherein each of the visual indicators has a spherical shape with upper and lower hemispherical portions capable of being operated in different states.

xv. The hand-held robotic system of clause ii, comprising a tracker mount fixed to the tool support to removably receive a navigation tracker separate from the guidance array.

xvi. A hand-held robotic system for use with a tool, the robotic system comprising: a hand-held portion to be held and supported by a user; a tool support movably coupled to the hand-held portion to support the tool; a plurality of actuators operatively interconnecting the tool support and the hand-held portion to move the tool support in three degrees of freedom relative to the hand-held portion to place the tool on a desired trajectory or plane, each of the plurality of actuators being adjustable between maximum and minimum positions and having a home position between the maximum and minimum positions; and visual indicators associated with the plurality of actuators to indicate desired movement of the hand-held portion; and a controller coupled to the visual indicators to control operation of the visual indicators to indicate the desired movement of the hand-held portion.

xvii. A hand-held robotic system comprising: a hand-held portion to be held by a user; a tool support movably coupled to the hand-held portion to support the tool; a plurality of actuators operatively interconnecting the tool support and the hand-held portion to move the tool support in three degrees of freedom relative to the hand-held portion to place the tool on a desired trajectory or plane, each of the plurality of actuators being adjustable between maximum and minimum positions and having a home position between the maximum and minimum positions; visual indicators associated with the plurality of actuators to indicate desired movement of the hand-held portion; and a controller coupled to the plurality of actuators and the visual indicators to control operation in a plurality of modes including a home mode in which the controller automatically adjusts each of the plurality of actuators to their home position, an approach mode in which the controller indicates the desired movement of the tool to place the tool on the desired trajectory or plane while the plurality of actuators are at their home positions, and an on-target mode in which the tool is generally located on the desired trajectory or plane and the controller indicates the desired movement of the hand-held portion to maintain the tool on the desired trajectory or plane.

xviii. A method of initializing a hand-held robotic system for use, the method comprising: providing an instrument comprising a hand-held portion to be held by a user and a blade support coupled to the hand-held portion to support the saw blade, with a plurality of actuators operatively interconnecting the blade support and the hand-held portion to move the blade support in three degrees of freedom relative to the hand-held portion, with each of the plurality of actuators including an encoder configured to output an encoder output signal; determining a pose of the hand-held portion in a known coordinate system at a first time; obtaining an encoder signal for each of the plurality of actuators at the first time; and determining a home position based on the pose of the hand-held portion and the encoder signal.

xix. A method of guiding movement of an instrument having a hand-held portion to be held by a user and a tool support coupled to the hand-held portion to support a tool, a guidance array coupled to the instrument and arranged to represent a plane of the tool, the method comprising the steps of: visually indicating to the user desired changes in pitch orientation, roll orientation, and translation of the tool to achieve a desired pose.

xx. A method of guiding movement of a robotic instrument, the robotic instrument having a hand-held portion to be held by a user, a tool support movably coupled to the hand-held portion to support a tool, a plurality of actuators operatively interconnecting the tool support and the hand-held portion to move the tool support in three degrees of freedom relative to the hand-held portion to place the tool on a desired trajectory or plane, and visual indicators associated with the plurality of actuators, the method comprising the steps of: controlling operation of the robotic instrument in a plurality of modes including: a home mode in which the controller automatically adjusts each of the plurality of actuators to a home position between maximum and minimum positions; and an approach mode in which the controller indicates a desired movement of the tool to place the tool on the desired trajectory or plane while the plurality of actuators are at their home positions; and an on-target mode in which the tool is generally located on the desired trajectory or plane and the controller indicates the desired movement of the hand-held portion to maintain the tool on the desired trajectory or plane.

xxi. A robotic surgical instrument comprising: a hand-holdable body to be held by a user; a tool support movably coupled to the hand-holdable body; a tool coupler supported by the tool support; a plurality of actuators to move the tool support in a plurality of degrees of freedom relative to the hand-holdable body, the plurality of actuators including: a pair of linear actuators operatively interconnecting the tool support and the hand-holdable body with each of the pair of linear actuators having a first portion connected to the hand-holdable body and a second portion connected to the tool support, the pair of linear actuators being arranged to control elevation and pitch of the tool support relative to the hand-holdable body; and a rotary actuator arranged to control roll movement of the tool coupler relative to the tool support and the hand-holdable body.

xxii. The surgical instrument of clause xxi further including a constraint assembly having a passive linkage operatively interconnecting the tool support and the hand-holdable body, the passive linkage being coupled to the tool support and the hand-holdable body in a manner configured to constrain movement of the tool support relative to the hand-holdable body in three degrees of freedom.

xxiii. The surgical instrument of clause xxii, wherein the pair of linear actuators comprise a first actuator adjustable in effective length along a first axis, a second actuator adjustable in effective length along a second axis.

xxiv. The surgical instrument of clause xxiii, wherein the passive linkage is adjustable in effective length along a constraint axis, the constraint axis being coplanar along a center plane throughout actuation of the plurality of actuators.

xxv. The surgical instrument of clause xxiv, wherein the linear actuators are pivotally coupled to the tool support and pivotally coupled to the hand-holdable body such that the linear actuators are able to pivot relative to the tool support and the hand-holdable body during actuation.

xxvi. The surgical instrument of clause xxiv, wherein a first actuator of the pair of linear actuators and a second actuator of the pair of linear actuators are independently adjustable in effective length to adjust a pitch and elevation orientation of the tool support relative to the hand-holdable body.

xxvii. The surgical instrument of clause xxiii, wherein the rotary actuator includes a motor and a housing.

xxviii. The surgical instrument of clause xxvii, wherein the constraint assembly is pivotally coupled to the housing of the rotary actuator, connecting the constraint assembly to the tool support.

xxix. The surgical instrument of clause xxii, wherein the rotary actuator is connected with the tool support and the tool coupler, the rotary actuator being configured to rotate the tool coupler 360 degrees relative to the tool support and the hand-holdable body.

xxx. The surgical instrument of clause xxii, wherein the pair of linear actuators are aligned along a longitudinal plane that bisects the hand-holdable body.

xxxi. The surgical instrument of clause xxix, wherein the rotary actuator comprises a motor with a drive member rotatably connected to a ring gear.

xxxii. The surgical instrument of clause xxxi wherein the drive member of the motor is a worm and the ring gear is configured as a worm gear.

xxxiii. The surgical instrument of clause xxxi, wherein the drive member of the motor is a spur gear.

xxxiv. The surgical instrument of clause xxiii, wherein the spur gear is rotatably connected to an idler gear which is rotatably connected with the ring gear.

xxxv. The surgical instrument of clause xxxi, wherein the ring gear and the tool coupler are arranged such that when the rotary actuator is activated, the ring gear and the tool coupler rotate together.

xxxvi. The surgical instrument of clause xxxv, wherein the tool support includes an accessory motor to drive motion of the tool coupler.

xxxvii. The surgical instrument of clause xxxvi, wherein the tool coupler includes a working end and the accessory motor is configured to actuate the working end of the tool coupler, wherein the rotary actuator is configured to rotate the tool coupler independently from the accessory motor.

xxxviii. The surgical instrument of clause xxxvi, wherein the tool coupler includes a transmission coupled to the accessory motor to convert rotational motion from the accessory motor into oscillating motion of the tool.

xxxix. The surgical instrument of clause xxxvii, wherein the working end of the tool coupler is attached to a saw blade, so that when the accessory motor is activated, the saw blade oscillates.

xl. The surgical instrument of clause xxxix, wherein the tool coupler is configured to rotate as the accessory motor is activated, rotating the tool coupler and saw blade while the saw blade oscillates, changing a cutting plane of the saw blade.

xli. The surgical instrument of clause xxxi, wherein the motor of the rotary actuator is disposed along a plane of the tool support.

xlii. The surgical instrument of clause xxxvi, wherein the tool coupler includes a working end and the accessory motor is configured to rotate the working end of the tool coupler, wherein the rotary actuator is configured to rotate the tool coupler and the accessory motor together.

xliii. A robotic surgical instrument for use with a surgical tool, the surgical instrument comprising: a hand-holdable body to be held by a user; a tool support movably coupled to the hand-holdable body to support the tool; a plurality of actuators to move the tool support in a plurality of degrees of freedom relative to the hand-holdable body, the plurality of actuators including: an elevation actuator with a first portion connected to the hand-holdable body and a second portion connected to the tool support; and a pair of secondary actuators, each of the pair of secondary actuators including an actuator portion operatively connected to the elevation actuator and a support portion operatively connected to the tool support such that each of the pair of secondary actuators is arranged to effectively operate between the elevation actuator and the tool support to move the tool support relative to the elevation actuator; wherein the elevation actuator is arranged to move both the tool support and the secondary actuators relative to the hand-holdable body in one degree of freedom.

xliv. The surgical instrument of clause xliii, wherein each of the plurality of actuators is actively adjustable in effective length.

xlv. The surgical instrument of clause xliii, wherein the secondary actuators are operable independent of the elevation actuator to control pitch and roll of the tool support.

xlvi. The surgical instrument of clause xliv wherein the elevation actuator is movable between a retracted position at which the tool support is adjacent to the hand-holdable body and an extended position at which the tool support is spaced away from the hand-holdable body; wherein the pair secondary actuators have greater translation length in the extended position relative to the retracted position since a distance between the hand-holdable body and the tool support is greater in the extended position.

xlvii. The surgical instrument of clause xliii, wherein the elevation actuator has a first stroke length and each of the secondary actuators has a second stroke length that is less than the first stroke length.

xlviii. The surgical instrument of clause xliii, wherein the hand-holdable portion includes a proximal end and a distal end, the elevation actuator is located between the proximal end and the distal end of the hand-holdable portion, and the secondary actuators are located distal to the elevation actuator.

xlix. The surgical instrument of clause xliii, wherein the pair of secondary actuators comprises a first actuator adjustable in effective length along a first active axis, a second actuator adjustable in effective length along a second active axis; and wherein the elevation actuator is adjustable in effective length along a third active axis.

l. The surgical instrument of clause xliv, including a controller coupled to the plurality of actuators to control adjustment of the plurality of actuators to define a virtual saw cutting guide.

li. The surgical instrument of clause 1, wherein the controller is configured to control the plurality of actuators to return to a home position between a minimum value and a maximum value of the effective lengths of the actuators.

lii. The surgical instrument of clause li, wherein the controller is configured to control a pitch orientation, a roll orientation, and a translation position of the tool support relative to the hand-holdable body to define the virtual saw cutting guide.

liii. The surgical instrument of clause 1, wherein the controller comprises a control housing mounted to the tool support and a control board located inside the control housing.

liv. The surgical instrument of clause 1, wherein a motor to drive motion of the tool is connected with the tool support comprises.

lv. A hand-held robotic system for use with a surgical tool, the system comprising: an instrument comprising a hand-held portion to be held and supported by a user; a tool support movably coupled to the hand-held portion to support the surgical tool; a plurality of actuators operatively interconnecting the tool support and the hand-held portion to move the tool support in three degrees of freedom relative to the hand-held portion to place the surgical tool at a desired position, pose or orientation; and a visual indicator to indicate desired movement of the hand-held portion; and a controller coupled to the plurality of actuators to control adjustment of the plurality of actuators to maintain the surgical tool at the desired position, pose, or orientation, the controller coupled to the visual indicator, the controller configured to control the visual indicator to visually indicate changes in pitch orientation, roll orientation, and translation position while the user moves the instrument based on actuator information of the plurality of actuators.

lvii. A hand-held robotic system for use with a saw blade, the system comprising: an instrument comprising; a hand-held portion to be held by a user and a blade support coupled to the hand-held portion to support the saw blade; a plurality of actuators operatively interconnecting the blade support and the hand-held portion to move the blade support in three degrees of freedom relative to the hand-held portion; a first tracker coupled to the blade support, a second tracker coupled to the hand-held portion; a navigation system comprising a localizer, the localizer configured to determine a pose of the first tracker and the second tracker to determine a pose of the saw blade and a pose of the hand-held portion; and a controller operable to determine a commanded pose of the saw blade based on the pose of the saw blade, the pose of the hand-held portion, and a desired pose of the saw blade, and the controller is operable to control one or more of the plurality of actuators to move towards the commanded pose.

lviii. The hand-held robotic system of clause lvii, wherein the controller is operable to control one or more of the plurality of actuators to move towards the commanded pose further based on minimum and maximum positions of the plurality of actuators.

Several configurations have been discussed in the foregoing description. However, the configurations discussed herein are not intended to be exhaustive or limit the teachings to any particular form. The terminology which has been used is intended to be in the nature of words of description rather than of limitation. Many modifications and variations are possible in light of the above teachings which may be practiced otherwise than as specifically described.

The invention claimed is:

1. A hand-held robotic instrument for use with a tool to perform surgery, the robotic instrument comprising:

a hand-held portion to be held by a user;
a tool support movably coupled to the hand-held portion to support the tool;
a plurality of actuators operatively interconnecting the tool support and the hand-held portion to move the tool support in three degrees of freedom relative to the hand-held portion, each of the plurality of actuators being actively adjustable in effective length; and
a constraint assembly having a passive linkage operatively interconnecting the tool support and the hand-held portion, the passive linkage being coupled to the tool support and the hand-held portion in a manner configured to constrain movement of the tool support relative to the hand-held portion in three degrees of freedom.

2. The robotic instrument of claim 1, wherein the passive linkage operatively interconnects the tool support and the hand-held portion independently of the plurality of actuators, the passive linkage being passively adjustable in effective length.

3. The robotic instrument of claim 2, wherein the constraint assembly comprises a passive linkage joint coupling the passive linkage to the tool support.

4. The robotic instrument of claim 3, wherein the passive linkage joint comprises a passive linkage U-joint or a passive linkage spherical joint.

5. The robotic instrument of claim 3, wherein the passive linkage comprises a shaft and a sleeve configured to receive the shaft along a constraint axis, the passive linkage being configured to allow the shaft to slide axially along the constraint axis relative to the sleeve and to constrain movement of the shaft radially relative to the constraint axis during actuation of one or more of the plurality of actuators.

6. The robotic instrument of claim 5, wherein the passive linkage comprises a key to constrain rotation of the shaft relative to the sleeve about the constraint axis.

7. The robotic instrument of claim 5, wherein each of the plurality of actuators is disposed along an active axis, the active axes configured to be arranged in a canted configuration relative to the constraint axis.

8. The robotic instrument of claim 7, comprising a plurality of first active joints coupling the plurality of actuators to the tool support.

9. The robotic instrument of claim 8, wherein each of the plurality of first active joints comprises an active U-joint or an active spherical joint.

10. The robotic instrument of claim 9, wherein the first active joints and the passive linkage joint define parallel pivot axes disposed on a common plane.

11. The robotic instrument of claim 10, wherein the tool support comprises a tool coupler arranged so that the tool is located on a tool plane parallel to the common plane when the tool is removably coupled to the tool support.

12. The robotic instrument of claim 9, comprising a second active joint coupling two of the plurality of actuators to the hand-held portion and a third active joint coupling one of the plurality of actuators to the hand-held portion and wherein each of the second active joints comprises a swivel yoke arranged to swivel relative to the hand-held portion about a swivel axis and the third active joint comprises a pivot housing fixed to the hand-held portion.

13. The robotic instrument of claim 12, wherein each of the plurality of actuators comprises a lead screw, the carriers configured to threadably receive the lead screws so that each of the lead screws can rotate relative to a corresponding one of the carriers to adjust the effective length of a corresponding one of the plurality of actuators.

14. The robotic instrument of claim 13, wherein each of the plurality of actuators comprises a motor having a rotor fixed to one of the lead screws, and each of the plurality of actuators comprises a housing, the rotor being configured to rotate relative to the housing, and wherein each of the first active joints comprises a pivot yoke extending from a corresponding one of the housings.

15. The robotic instrument of claim 14, wherein each of the housings and corresponding carrier are constrained from relative movement in a first degree of freedom to allow the lead screws to rotate relative to the carriers.

16. The robotic instrument of claim 14, wherein the plurality of actuators comprises a first actuator adjustable in effective length along a first active axis, a second actuator adjustable in effective length along a second active axis, and a third actuator adjustable in effective length along a third active axis, wherein the passive linkage is adjustable in effective length along a constraint axis, the constraint axis and the third active axis being coplanar along a center plane throughout actuation of the plurality of actuators.

17. A hand-held robotic instrument for use with a saw blade in performing surgery, the robotic instrument comprising:
a hand-held portion to be held by a user;
a blade support movably coupled to the hand-held portion to support the saw blade;
a plurality of actuators operatively interconnecting the blade support and the hand-held portion to move the blade support in three degrees of freedom relative to the hand-held portion;
a constraint assembly operatively interconnecting the blade support and the hand-held portion to constrain movement of the blade support relative to the hand-held portion in three degrees of freedom; and
a controller coupled to the plurality of actuators to control adjustment of the plurality of actuators to maintain the saw blade along a plane.

18. The robotic instrument of claim 17, wherein the plurality of actuators comprises a first actuator adjustable in effective length along a first active axis, a second actuator adjustable in effective length along a second active axis, a third actuator adjustable in effective length along a third active axis, and a passive linkage adjustable in effective length along a constraint axis.

19. The robotic instrument of claim 17, wherein the blade support comprise a motor to drive motion of the saw, wherein the blade support comprises a transmission coupled to the motor to convert rotary motion from the motor into oscillating motion of the saw.

20. The robotic instrument of claim 17, further comprising a tracker mount fixed to the blade support to removably receive a navigation tracker.

21. The robotic instrument of claim 17, wherein the robotic instrument weighs less than 6 lbs.

22. A robotic surgical instrument comprising:
a hand-holdable body to be held by a user;
a tool support movably coupled to the hand-holdable body;
a tool coupler supported by the tool support;
a plurality of actuators to move the tool support in a plurality of degrees of freedom relative to the hand-holdable body, the plurality of actuators including:
a pair of linear actuators operatively interconnecting the tool support and the hand-holdable body with each of the pair of linear actuators having a first portion connected to the hand-holdable body and a second portion connected to the tool support, the pair of linear actuators being arranged to control elevation and pitch of the tool support relative to the hand-holdable body; and
a rotary actuator arranged to control roll movement of the tool coupler relative to the tool support and the hand-holdable body.

23. A robotic surgical instrument for use with a surgical tool, the surgical instrument comprising:
a hand-holdable body to be held by a user;
a tool support movably coupled to the hand-holdable body to support the tool;
a plurality of actuators to move the tool support in a plurality of degrees of freedom relative to the hand-holdable body, the plurality of actuators including:
an elevation actuator with a first portion connected to the hand-holdable body and a second portion connected to the tool support; and
a pair of secondary actuators, each of the pair of secondary actuators including an actuator portion operatively connected to the elevation actuator and a support portion operatively connected to the tool support such that each of the pair of secondary actuators is arranged to effectively operate between the elevation actuator and the tool support to move the tool support relative to the elevation actuator;
wherein the elevation actuator is arranged to move both the tool support and the secondary actuators relative to the hand-holdable body in one degree of freedom.

* * * * *